US008168617B2

(12) United States Patent
Jandeleit et al.

(10) Patent No.: US 8,168,617 B2
(45) Date of Patent: May 1, 2012

(54) COMPLEX PANTOIC ACID ESTER NEOPENTYL SULFONYL ESTER CYCLIZATION RELEASE PRODRUGS OF ACAMPROSATE, COMPOSITIONS THEREOF, AND METHODS OF USE

(75) Inventors: Bernd Jandeleit, Menlo Park, CA (US); Yunxiao Li, Sunnyvale, CA (US); Mark A. Gallop, Santa Clara, CA (US); Noa Zerangue, Belmont, CA (US); Peter A. Virsik, Portola Valley, CA (US); Wolf-Nicolas Fischer, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 868 days.

(21) Appl. No.: 12/205,031

(22) Filed: Sep. 5, 2008

(65) Prior Publication Data

US 2009/0076147 A1   Mar. 19, 2009

Related U.S. Application Data

(60) Provisional application No. 60/970,924, filed on Sep. 7, 2007, provisional application No. 61/061,059, filed on Jun. 12, 2008.

(51) Int. Cl.
*A61K 31/66* (2006.01)
*A61K 31/255* (2006.01)
*C07F 9/02* (2006.01)
*C07C 309/04* (2006.01)

(52) U.S. Cl. ............. 514/119; 514/517; 558/45; 558/48

(58) Field of Classification Search ........................ None
See application file for complete search history.

(56) References Cited

U.S. PATENT DOCUMENTS

| | | | |
|---|---|---|---|
| 4,199,601 | A | 4/1980 | Durlach |
| 4,355,043 | A | 10/1982 | Durlach |
| 5,073,641 | A | 12/1991 | Bundgaard et al. |
| 5,596,095 | A | 1/1997 | Roberts et al. |
| 5,716,961 | A | 2/1998 | Sands |
| 5,952,389 | A | 9/1999 | Fogel |
| 6,265,437 | B1 | 7/2001 | Berthelon et al. |
| 6,294,583 | B1 | 9/2001 | Fogel |
| 6,391,922 | B1 | 5/2002 | Fogel |
| 6,514,524 | B1 | 2/2003 | Saslawski et al. |
| 6,689,816 | B2 | 2/2004 | Fogel |
| 7,351,740 | B2 | 4/2008 | Zerangue et al. |
| 2002/0013366 | A1 | 1/2002 | Fogel |
| 2002/0119912 | A1 | 8/2002 | Fogel |
| 2003/0158254 | A1 | 8/2003 | Zerangue et al. |
| 2004/0102525 | A1 | 5/2004 | Kozachuk |
| 2005/0148673 | A1 | 7/2005 | Harbut et al. |
| 2006/0063802 | A1 | 3/2006 | Guitton et al. |
| 2006/0128802 | A1 | 6/2006 | Fogel |

FOREIGN PATENT DOCUMENTS

| | | |
|---|---|---|
| DE | 3019350 | 11/1989 |
| WO | WO 96/18609 | 6/1996 |
| WO | WO 2007/032720 | 3/2007 |

OTHER PUBLICATIONS

Online "http://www.medilexicon.com/drugs/campral.php" accessed Nov. 7, 2009.*
Church, Andrew J. and Giovannoni, Gavin "Poststreptococcal movement disorders" in Neuroimmunology in Clinical Practice Eds. Bernadette Kalman and Thomas H. Brannagan III Blackwell: 2008 Chapter 21, 240-250.*
Fodstad et. al. "Intractable singultus: a diagnostic and therapeutic challenge" British Journal of Neurosurgery 1993, 7, 255-262.*
Kalviainen, R. "Clinical picture of EPM1-Unverricht-Lundborg disease" Epilepsia, 49(4):549-556, 2008.*
Adam, Octavian R. "Symptomatic Treatment of Huntington Disease" Neurotherapeutics: The Journal of the American Society for Experimental NeuroTherapeutics Apr. 2008, vol. 5, 181-197.*
Bernardy, et al., Prostaglandins and congeners. 20. synthesis of prostaglandins via conjugate addition of lithium trans-1-alkenyltrialkylalanate reagents. A novel reagent for conjugate 1,4-additions. *J. Org. Chem* 1979, 44, 1438-47.
Breton, et al., Acetylation of unsymmetrical diols in the presence of Al2O3. *Tetrahedron Lett.* 1997, 38, 3825-28.
Bundgaard Ed., "Design of prodrugs," Elsevier Science Publishers, Netherlands, 1985.
Chen, et al., Synthesis of functional olefin copolymers with controllable topologies using a chain-walking catalyst. *J. Am. Chem. Soc*, 2003, 125, 6697-6704.
U.S. Appl. No. 12/252,167, filed Oct. 15, 2008, Yunxiao, et al.
De Kimpe, et al., Synthesis of 3-halopyrroles. *Tetrahedron* 1997, 53, 3693-3706.
De La Mora, et al., Synthesis of tricyclic-2-aminoindoles by intramolecular 1,3-dipolar cycloaddition of 1-ω-azidoalkylindoles. *Tetrahedron Lett.* 2001, 42, 5351-53.
Effenberger, et al., Enzyme catalyzed addition of hydrocyanic acid to substituted pivalaldehydes-a novel synthesis of (R)-pantolactone¹. *Tetrahedron: Asymmetry* 1995, 6, 271-82.
Ezquerra, et al., Stereoselective double alkylation of ethyl N-boc-pyroglutamate. *J. Org. Chem.* 1994, 59, 4327-31.
Flynn et al., A mild two-step method for the hydrolysis/methanolysis of secondary amides and lactams. *J. Org. Chem.* 1983, 48, 2424-26.
Flynn et al., Intramolecular Wittig cyclization: a novel route to previously unknown 3-thia and 3-sulfinyl analogues of testosterone. *J. Org. Chem.* 1983, 48(22), 4125-27.
Gassman, et al., A general procedure for the base-promoted hydrolysis of hindered esters at ambient temperatures. *J. Org. Chem.* 1979, 42, 918-20.
Hashimoto, et al., the total synthesis of (±)-forskolin. *J. Am. Chem. Soc.* 1988, 110, 3670-72.

(Continued)

*Primary Examiner* — Paul A Zucker
(74) *Attorney, Agent, or Firm* — Dorsey & Whitney LLP

(57) ABSTRACT

Pantoic acid ester neopentyl sulfonyl ester prodrugs of acamprosate, pharmaceutical compositions comprising such prodrugs, and methods of using such prodrugs and compositions thereof for treating diseases are disclosed. In particular, acamprosate prodrugs exhibiting enhanced oral bioavailability and methods of using acamprosate prodrugs to treat neurodegenerative disorders, psychotic disorders, mood disorders, anxiety disorders, somatoform disorders, movement disorders, substance abuse disorders, binge eating disorder, cortical spreading depression related disorders, tinnitus, sleeping disorders, multiple sclerosis, and pain are disclosed.

25 Claims, No Drawings

OTHER PUBLICATIONS

Ishii et al., Lactone synthesis by a,ω-diols with hydrogen peroxide catalyzed by heteropoly acids combined with cetylpyridinium chloride. *J. Org. Chem.*, 1988, 53, 5549-52.

Marschner, et al., Synthesis of all stereoisomeric carbapentofuranoses. *J. Org. Chem.* 1995, 60, 5224-35.

Miyashita, et al., Pyridinium p-toluenesulfonate. A mild and efficient catalyst for the tetrahydropyranylation of alcohols. *J. Org. Chem.* 1977, 42, 3772-74.

Mullis et al., Regiospecificity of reactions of epoxides and oxetanes with trimethylsilyl cyanide. *J. Org. Chem.* 1982, 47, 2873-75.

Nagarajan, et al., Chemistry of naturally occurring polyamines. 11. Unsaturated spermidine and spermine derivatives. *J. Org. Chem.* 1987, 52, 5044-46.

Nicolaou, et al., Total synthesis of the tumor-associated Le family of glycosphingolipids. *J. Am.Chem Soc.* 1990, 112, 3693-95.

Nishimura, et al., Palladium(II)-catalyzed oxidation of alcohols to aldehydes and ketones by molecular oxygen. *J. Org. Chem.*, 1999, 64, 6750-55.

Ozerov et al., Synthesis and pharmacological activity of 2-dimethoxyphosphinylethyl esters of N-acylated neuroactive amino acids, *Pharm. Chem. J.*, (1993) 27(5), pp. 338-342.

Pappo, et al., Osmium tetroxide-catalyzed periodate oxidation of olefinic bonds. *J. Org. Chem.* 1956, 21, 478-79.

Pillard, et al., A stereospecific synthesis of (±) α-conhydrine and (±) β-conhydrine. *Tetrahedron Lett.* 1984, 25, 1555-56.

Pirrung, et al., A convenient procedure for the deprotection of silylated nucleosides and nucleotides using triethylamine trihydrofluoride. *Bioorg. Med. Chem. Lett.* 1994, 4(11), 1345-46.

Scheinmann et al., A convenient synthesis of a novel γ-aminobutyric acid analogue: 4-amino-2,2-dimethylbutanoic acid. *J. Chem. Res.* (S) 1993, 414-415.

Srikrishna and Kumar, Claisen rearrangement based methodology for the spiroannulation of a cyclopentane ring. Formal total synthesis of (±)-acorone and isoacorones. *Tetrahedron* 2000, 56, 8189-95.

Trudeau, et al., Rh-catalyzed enantioselective diboration of simple alkenes: reaction development and substrate scope. *J. Org. Chem.* 2005, 70, 9538-44.

Wei, et al., A new efficient synthesis of taxol A-ring synthon via two aldol condensations. *Tetrahedron* 1998, 54, 12623-30.

International Search Report in PCT/US2008/075444 (3 pages).
International Search Report in PCT/US2008/075453 (3 pages).
International Search Report in PCT/US2008/075462 (3 pages).
International Search Report in PCT/US2008/075472 (3 pages).
U.S. Appl. No. 12/204,961, filed Sep. 5, 2008, Jandeleit et al.
U.S. Appl. No. 12/204,080, filed Sep. 5, 2008, Jandeleit et al.
U.S. Appl. No. 12/205,275, filed Sep. 5, 2008, Jandeleit et al.
U.S. Appl. No. 12/225,167, filed Oct. 15, 2008, Jandeleit et al.

Abbott et al., The formalin test: scoring properties of the first and second phases of the pain response in rats. *Pain* 1995, 60, 91-102.

Azevedo and Figueiredo, Tinnitus treatment with acamprosate: a double-blind study. *Rev Bras Otorrinolaringol* 2005, 71(5), 618-23.

Bauer and Brozoski, Assessing tinnitus and prospective tinnitus therapeutics using a psychophysical animal model. *J Assoc Res Otolarynology* 2001, 2(1), 54-64.

Bauer and Brozoski, Effect of gabapentin on the sensation and impact of tinnitus. *Laryngoscope* 2006, 116(5), 675-81.

Bello and Hajnal, Acute methylphenidate treatments reduce sucrose intake in restricted-fed bingeing rats. *Brain Res Bulletin* 2006, 70, 422-29.

Buda-Levin et al., Baclofen reduces fat intake under binge-type conditions. *Physiology & Behavior* 2005, 86, 176-84.

Bundgaard in "A Textbook of Drug Design and Development," Krogsgaard-Larsen and Bundgaard Eds., Harwood Academic, Philadelphia, 1991, pp. 113-192.

Chapman et al., Anticonvulsant activity of two metabotropic glutamate group I antagonists selective for the mGlu5 receptor: 2-methyl-6-(phenylethynyl)-pyridine (MPEP), and (E)-6-methyl-2-styryl-pyridine (SIB 1893). *Neuropharmacology* 2000, 39, 1567-74.

Correll et al., Subanesthetic ketamine infusion therapy: a retrospective analysis of a novel therapeutic approach to complex regional pain syndrome. *Pain Med* 2004, 5(3), 263-75.

Daoust, et al., Acamprosate modulates synaptosomal GABA transmission in chronically alcoholised rats. *Pharmacol. Biochem. Behav.* 1992, 41, 669-74.

De Azevedo et al., 109$^{th}$ Meeting and OTO Expo of the Am. Acad. Otolaryngology—Head and Neck Foundation, Los Angeles, CA, Sep. 25-28, 2005.

De Witte et al., Neuroprotective and abstinence-promoting effects of acamprosate—elucidating the mechanism of action. *CNS Drugs* 2005, 19(6), 517-37.

Eisenberg et al., Effect of early administration of the N-methyl-D-aspartate receptor antagonist amantadine on the development of postmastectomy pain syndrome: a prospective pilot study. *J Pain* 2007, 8(3), 223-9.

Fabbrini et al., Levodpa-induced dyskinesias. *Movement Disorders* 2007, 22(10), 1379-1389.

Goetz et al., Sarizotan as a treatment for dyskinesias in Parkinson's disease: a double blind placebo-controlled trial. *Movement Disorders* 2007, 22(2), 179-86.

Han et al., the effect of acamprosate on alcohol and food craving in patients with alcohol dependence. *Drug Alcohol Dependence* 2008, 93, 279-83.

Heilig and Egli, Pharmacological treatment of alcohol dependence: target symptoms and target mechanisms. *Pharmacology & Therapeutics* 2006, 111, 855-76.

Jensen et al., Transient lower esophageal sphincter relaxations in dogs are inhibited by a metabotropic glutamate receptor 5 antagonist. *Eur J Pharmacology* 2005, 519, 154-57.

Johnson and Ait-Daoud, Neuropharmacological treatments for alcoholism: scientific basis and clinical findings. *Psychopharmacology* 2000, 149(4), 327-44.

Kast and Altschuler, Consideration of acamprosate for treatment of amyotrophic lateral sclerosis. *Med Hypotheses* 2007, 69(4), 836-837.

Killestein et al., Glutamate inhibition in MS: the neuroprotective properties of riluzole. *J Neurol Sci* 2005, 233(1-2), 113-15.

Kornhuber and Quack, Cerebrospinal fluid and serum concentrations of the N-methyl-D-aspartate (NMDA) receptor antagonist memantine in man. *Neruosci Lett* 1995, 195(2), 137-39.

Lea and Faden, Metabotropic glutamate receptor subtype 5 antagonists MPEP and MTEP. *CNS Drug Rev* 2006, 12(2), 149-66.

Lipton, Failures and successes of NMDA receptor antagonists: molecular basis for the use of open-channel blockers like memantine in the treatment of acute and chronic neurological insults. *NeuroRx* 2004, 1(1), 101-10.

Más-Serrano et al., Kinetic study of acamprosate absorption in rat small intestine. *Alcohol Alcohol* 2000, 35(4), 324-30.

Mcgeehan and Olive, Attenuation of cocaine-induced reinstatement of cocaine conditioned place preference by acamprosate. *Behav Pharmacol* 2006, 17(4), 363-7.

Mela et al., Antagonism of metabotropic glutamate receptor type 5 attenuates L-DPA-induced dyskinesia and its molecular and neurochemical correlates in a rat model of Parkinson's disease. *J Neurochemistry* 2007, 101, 483-497.

Menniti et al., CP-101,606, and NR2B subunit selective NMDA receptor antagonist, inhibits NMDA and injury induced c-fos expression and cortical spreading depression in rodents. *Neuropharmacology* 2000, 39, 1147-55.

Molina-Hernandez et al., Antidepressant-like and anxiolytic-like actions of the mGlu5 receptor antagonist MTEP, microinjected into lateral septal nuclei of male Wistar rats. *Prog Neuro-Psychopharmacology Biolog Psychiatry* 2006, 30, 1129-35.

Murman et al., Cognitive, behavioral, and motor effects of the NMDA antagonist ketamine in Huntington's disease. *Neurology* 1997, 49(1), 153-61.

Nozaki-Taguchi et al., Vincristine-induced allodynia in the rat. *Pain* 2001, 93, 69-76.

Overman et al., Acamprosate for the adjunctive treatment of alcohol dependence. *Annals Pharmacotherapy.* 2003, 37, 1090-99.

Paille et al., Double-blind randomized multicentre trial of acamprosate in maintaining abstinence from alcohol. *Alcohol Alcohol* 1995, 30, 239-47.

Papot et al., Design of selectively activated anticancer prodrugs: elimination and cyclization strategies. *Curr Med Chem—Anti-Cancer Agents*, 2002, 2, 155-85.

Paz et al., Glutamatergic dysfunction in schizophrenia: from basic neuroscience to clinical psychopharmacology. *Eur Neuropsychopharmacology* 2008, prepublication No. NEUSPY-10085, 14 pages.

Peeters et al., Effects of pan- and subtype-selective N-methyl-D-aspartate receptor antagonists on cortical spreading depression in the rat: therapeutic potential for migraine. *J Pharmacology and Experimental Therapeutics* 2007, 321(2), 564-72.

Pelc et al., Efficacy and safety of acamprosate in the treatment of detoxified alcohol-dependent patients. A 90-day placebo-controlled dose-finding study. *Br. Psychiatry* 1997, 171, 73-77.

Pud et al., The NMDA receptor antagonist amantadine reduces surgical neuropathic pain in cancer patients: a double blind, randomized, placebo controlled trial. *Pain* 1998, 75(2-3), 349-54.

Rabben et al., Prolonged analgesic effect of ketamine, an N-methyl-D-aspartate receptor inhibitor, inpatients with chronic pain. *J Pharmacol Exp Ther* 1999, 289(2), 1060-1066.

Rammes et al., The anti-craving compound acamprosate acts as a weak NMDA-receptor antagonist, but modulates NMDA-receptor subunit expression similar to memantine and MK-801. *Neuropharmacology* 2001, 40, 749-60.

Riedel et al., Fear conditioning-induced time- and subregion-specific increase in expression of mGlu5 receptor protein in rat hippocampus. *Neuropharmacology* 2000, 39, 1943-51.

Roberts et al., Neopentyl ester protecting groups for arylsulfonic acids. *Tetrahedron Lett* 1997, 38(3), 355-58.

Saivin et al., Clinical pharmacokinetics of acamprosate. *Clin Pharmacokinet* 1998, 35, 331-45.

Santos et al., Cyclization-activated prodrugs, synthesis, reactivity and toxicity of dipeptide esters of paracetamol. *Bioinorganic & Medicinal Chemistry Letters*, 2005, 15, 1595-98.

Scott et al., Acamprosate—a review of its use in the maintenance of abstinence in patients with alcohol dependence. *CNS Drugs* 2005, 19(5), 445-64.

Shan et al., Prodrug strategies based on intramolecular cyclization reactions. *J Pharm Sciences* 1997, 86(7), 765-67.

Sindrup and Jensen, Efficacy of pharmacological treatments of neuropathic pain: an update and effect related to mechanism of drug action. *Pain* 1999, 83, 389-400.

Staner et al., Effects of acamprosate on sleep during alcohol withdrawal: a double-blind placebo-controlled polysomnographic study in alcohol-dependent subjects. *Alcohol Clin Exp Res* 2006, 30(9), 1492-9.

Storto et al., Insulin secretion is controlled by mGlu5 metabotropic glutamate receptors. *Molecular Pharmacology* 2006, 69(4), 1234-41.

Teng and Demetrio, Memantine may acutely improve cognition and have a mood stabilizing effect in treatment-resistant bipolar disorder. *Rev Bras Psiquiatr* 2006, 28(3), 251-6.

Zarate et al., an open-label trial of riluzole in patients with treatment-resistant major depression. *Am J Psychiatry* 2004, 161, 171-4.

Zarate et al., an open-label trial of the glutamate-modulating agent riluzole in combination with lithium for the treatment of bipolar depression. *Biol Psychiatry* 2005, 57, 430-2.

Zornoza et al., Pharmacology of acamprosate: an overview. *CNS Drug Reviews*, 2003, 9(4), 359-74.

\* cited by examiner

COMPLEX PANTOIC ACID ESTER NEOPENTYL SULFONYL ESTER CYCLIZATION RELEASE PRODRUGS OF ACAMPROSATE, COMPOSITIONS THEREOF, AND METHODS OF USE

This application claims the benefit under 35 U.S.C. §119 (e) of U.S. Provisional Application Ser. Nos. 60/970,924 filed Sep. 7, 2007, and 61/061,059 filed Jun. 12, 2008, each of which is incorporated by reference in its entirety.

FIELD

Disclosed herein are pantoic acid ester neopentyl sulfonyl ester prodrugs of acamprosate that exhibit enhanced oral bioavailability, pharmaceutical compositions comprising such prodrugs, and methods of using such prodrugs and compositions thereof for treating diseases. In particular, acamprosate prodrugs exhibiting enhanced oral bioavailability and methods of using acamprosate prodrugs to treat neurodegenerative disorders, psychotic disorders, mood disorders, anxiety disorders, somatoform disorders, movement disorders, substance abuse disorders, binge eating disorder, cortical spreading depression related disorders, sleeping disorders, tinnitus, multiple sclerosis, and pain.

BACKGROUND

Prodrugs are derivatized forms of drugs that following administration are converted or metabolized to an active form of the drug in vivo. Prodrugs are used to modify one or more aspects of the pharmacokinetics of a drug in a manner that enhances the therapeutic efficacy of a drug. For example, prodrugs are often used to enhance the oral bioavailability of a drug. To be therapeutically effective, drugs exhibiting poor oral bioavailability may require frequent dosing, large administered doses, or may need to be administered by other than oral routes, such as intravenously. In particular, many drugs with sulfonic acid groups exhibit poor oral bioavailability.

Intramolecular cyclization prodrug strategies have been used to modify the pharmacokinetics of drugs (Bundgaard in "A Textbook of Drug Design and Development," Krogsgaard-Larsen and Bundgaard Eds., Harwood Academic, Philadelphia, 1991, pp. 113-192; Bungaard and Nielsen, U.S. Pat. No. 5,073,641; Santos et al., *Bioorganic & Medicinal Chemistry Letters*, 2005, 15, 1595-1598; Papot et al., *Curr Med Chem—Anti-Cancer Agents*, 2002, 2, 155-185; and Shan et al., *J Pharm Sciences* 1997, 86(7), 765-767). Intramolecular cyclization release prodrug strategies have been applied to drugs containing sulfonic acid functional groups. Prodrugs comprising a substituted neopentyl sulfonate ester derivative in which the neopentyl group is removed in vivo by unmasking a nucleophilic heteroatom bonded to a substituted neopentyl moiety followed by intramolecular cyclization to generate the parent drug in the sulfonic acid or sulfonic acid salt form have been described (Roberts and Patch, U.S. Pat. No. 5,596,095; and Roberts et al., *Tetrahedron Lett* 1997, 38(3), 355-358). In such prodrugs the nucleophilic heteroatom can be nitrogen or oxygen and the nitrogen or oxygen nucleophile can be masked with any amine or alcohol protecting group, respectively, capable of being deprotected in vivo. Roberts and Patch also disclose that the masked nucleophilic group can be a carboxylic ester, e.g., —OCOR where R can be aryl, substituted aryl, heteroaryl, $C_{1-8}$ alkyl, arylalkyl, or heteroarylalkyl. However, Roberts and Patch do not provide biological or pharmacological data to indicate which if any of the substituted neopentyl sulfonate esters release the prodrug in vivo and would therefore be useful for enhancing the oral bioavailability of the corresponding drug.

3-(Acetylamino)propylsulfonic acid (also referred to as N-acetylhomotaurine), acamprosate,

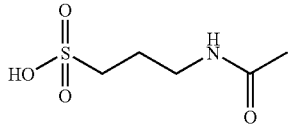

is a derivative of homotaurine, a naturally occurring structural analog of γ-aminobutyric acid (GABA) that appears to affect multiple receptors in the central nervous system (CNS). As an antiglutamatergic agent, acamprosate is believed to exert a neuropharmacological effect as an antagonist of N-methyl-D-aspartate (NMDA) receptors. The mechanism of action is believed to include blocking of the $Ca^{2+}$ channel to slow $Ca^{2+}$ influx and reduce the expression of c-fos, leading to changes in messenger RNA transcription and the concomitant modification to the subunit composition of NMDA receptors in selected brain regions (Zornoza et al., *CNS Drug Reviews*, 2003, 9(4), 359-374; and Rammes et al., *Neuropharmacology* 2001, 40, 749-760). In addition, acamprosate may block $GABA_B$ receptors (Daost, et al., *Pharmacol Biochem Behav.* 1992, 41, 669-74; and Johnson et al., *Psychopharmacology* 2000, 149, 327-344). Similar mechanisms are believed to be associated with the activity of other glutamate modulators such as riluzole, N-acetylcysteine, β-lactams, amantadine, lamictal, memantine, neramexane, remacemide, ifenprodil, and dextromethorphan.

Other diseases or disorders known to be associated with modulation of NMDA activity and for which modulators of NMDA receptor activity are clinically useful include psychotic disorders such as schizophrenia and schizoaffective disorder; mood disorders such as anxiety disorders including posttraumatic stress disorder and obsessive-compulsive disorder, depression, mania, bipolar disorder; and somatoform disorders such as somatization disorder, conversion disorder, hypochondriasis, and body dysmorphic disorder; movement disorders such as Tourette's syndrome, focal dystonia, Huntington's disease, Parkinson's disease, Syndeham's chorea, systemic lupus erythematosus, drug-induced movement disorders, tardive dyskinesia, blepharospasm, tic disorder, and spasticity; substance abuse disorders such as alcohol abuse disorders, narcotic abuse disorders, and nicotine abuse disorders; cortical spreading depression related disorders such as migraine, cerebral damage, epilepsy, and cardiovascular; sleeping disorders such as sleep apnea; multiple sclerosis; and neurodegenerative disorders such as Parkinson's disease, Huntington's disease, Alzheimer's disease, and amyotrophic lateral sclerosis. Recently, acamprosate has been found to be effective in treating tinnitus, or noise originating in the ear, a common disorder (de Azevedo et al., 109th Meeting and OTO EXPO of the Am. Acad. Otolaryngology—Head and Neck Foundation, Los Angeles, Calif., Sep. 25-28, 2005; Azevedo et al, *Rev. Bras. Otorrinolaringol. Engl. Ed.*, 2005, 71, 618-623; and Azevedo et al., WO 2007/082561 A2). Acamprosate analogs (Berthelon et al., U.S. Pat. No. 6,265,437) and salt forms of acamprosate analogs (Durlach, U.S. Pat. No. 4,355,043) are also reported to have therapeutic potential.

There is also evidence that acamprosate may interact with excitatory glutamatergic neurotransmission in general and as an antagonist of the metabotropic glutamate receptor subtype 5 (mGluR5) in particular (De Witte et al., *CNS Drugs* 2005, 19(6), 517-37). The glutamatergic mechanism of action of acamprosate may explain the effects of acamprosate on alcohol dependence and suggests other activities such as in neuroprotection. Dysregulation of the mGluR5 receptor has been implicated in a number of diseases and mGluR5 antagonists have been shown to be effective in treating depression, pain, anxiety disorders, alcohol abuse disorders, drug abuse disorders, nicotine abuse disorders, neurodegenerative disorders such as Parkinson's disease, diabetes, schizophrenia, and gastrointestinal reflux disease.

Acamprosate is a polar molecule that lacks the requisite physicochemical characteristics for effective passive permeability across cellular membranes. Intestinal absorption of acamprosate is mainly by passive diffusion and to a lesser extent by an active transport mechanism such as via an amino acid transporter (Más-Serrano et al., *Alcohol* 2000, 4(3); and 324-330; Saivin et al., *Clin Pharmacokinet* 1998, 35, 331-345). As a consequence, the oral bioavailability of acamprosate in humans is only about 11%. The mean elimination half-life of acamprosate following intravenous infusion (15 min) is 3.2±0.2 h. Efforts to enhance the gastrointestinal absorption and oral bioavailability of acamprosate include co-administrating the drug with polyglycolysed glycerides (Saslawski et al., U.S. Pat. No. 6,514,524). Acamprosate prodrugs exhibiting enhanced absorption from the lower gastrointestinal tract have the potential to increase the oral bioavailability of the drug and to facilitate administration of acamprosate using sustained release oral dosage forms.

SUMMARY

Thus, there is a need for new prodrugs of acamprosate with demonstrated enhanced oral bioavailability. In particular, masked carboxylate neopentylsulfonate ester prodrugs of acamprosate that exhibit enhanced absorption throughout the gastrointestinal tract and especially in the large intestine/colon and hence that are suitable for sustained release oral formulations, can enhance the convenience (by reducing the dose and dosing frequency), efficacy, and side effect profile of acamprosate.

In a first aspect, compounds of Formula (I) are provided:

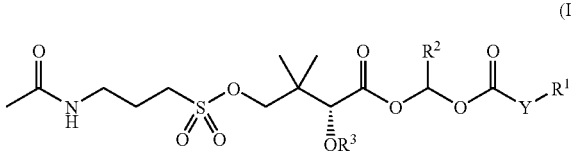

(I)

or a pharmaceutically acceptable salt thereof, wherein:

Y is chosen from —O— and a bond;

$R^1$ is chosen from $C_{1-6}$ alkyl, substituted $C_{1-6}$ alkyl, $C_{3-6}$ cycloalkyl, substituted $C_{3-6}$ cycloalkyl, phenyl, substituted phenyl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{3-6}$ heterocycloalkyl, substituted $C_{3-6}$ heterocycloalkyl, $C_{5-6}$ heteroaryl, substituted $C_{5-6}$ heteroaryl, $C_{4-12}$ heterocycloalkylalkyl, substituted $C_{4-12}$ heterocycloalkylalkyl, $C_{6-12}$ heteroarylalkyl, substituted $C_{6-12}$ heteroarylalkyl, and —$(CH^{R6})_n$—OPO(OH)$_2$ wherein n is chosen from 1, 2, and 3, and each $R^6$ is independently chosen from hydrogen and methyl;

$R^2$ is chosen from hydrogen, $C_{1-6}$ alkyl, substituted $C_{1-6}$ alkyl, $C_{3-6}$ cycloalkyl, substituted $C_{3-6}$ cycloalkyl, phenyl, and substituted phenyl; and $R^3$ is chosen from hydrogen, —PO(OH)$_2$, and —C(O)$R^4$ wherein $R^4$ is $C_{1-4}$ alkyl.

In a second aspect, pharmaceutical compositions are provided comprising at least one pharmaceutically acceptable excipient and at least one compound of Formula (I) or a pharmaceutically acceptable salt thereof.

In a third aspect, methods of treating a disease in a patient are provided comprising administering to a patient in need of such treatment a therapeutically effective amount of a compound of Formula (I) or a pharmaceutically acceptable salt thereof. In certain embodiments, the disease is chosen from a neurodegenerative disorder, a psychotic disorder, a mood disorder, an anxiety disorder, a somatoform disorder, a movement disorder, a substance abuse disorder, binge eating disorder, a cortical spreading depression related disorder, tinnitus, a sleeping disorder, multiple sclerosis, and pain.

DETAILED DESCRIPTION

Definitions

A dash ("-") that is not between two letters or symbols is used to indicate a point of bonding to a moiety or substituent. For example, —CONH$_2$ is attached through the carbon atom.

"Alkyl" by itself or as part of another substituent refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group can have from 1 to 20 carbon atoms, in certain embodiments, from 1 to 10 carbon atoms, in certain embodiments from 1 to 8 carbon atoms, in certain embodiments, from 1 to 6 carbon atoms, in certain embodiments from 1 to 4 carbon atoms, and in certain embodiments, from 1 to 3 carbon atoms.

"Alkoxy" by itself or as part of another substituent refers to a radical —$OR^{31}$ where $R^{31}$ is chosen from alkyl, heteroalkyl, cycloalkyl, heterocycloalkyl, cycloalkylalkyl, heterocycloalkylalkyl, aryl, heteroaryl, arylalkyl, and heteroarylalkyl, as defined herein. Examples of alkoxy groups include, but are not limited to, methoxy, ethoxy, propoxy, butoxy, cyclohexyloxy, and the like. In certain embodiments, an alkoxy group is $C_{1-18}$ alkoxy, in certain embodiments, $C_{1-12}$ alkoxy, in certain embodiments, $C_{1-8}$ alkoxy, in certain embodiments, $C_{1-6}$ alkoxy, in certain embodiments, $C_{1-4}$ alkoxy, and in certain embodiments, $C_{1-3}$ alkoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), and in certain embodiments, from 6 to 10 carbon atoms ($C_{6-10}$).

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{7-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$.

"AUC" is the area under a curve representing the concentration of a compound or metabolite thereof in a biological fluid in a patient as a function of time following administration of the compound to the patient. In certain embodiments provided by the present disclosure, the compound is a prodrug of Formula (I) the drug is acamprosate. Examples of biological fluids include plasma, blood, and cerebrospinal fluid. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the present disclosure, an AUC for acamprosate or metabolite thereof may be determined by measuring over time the concentration of acamprosate or metabolite thereof in the plasma, blood, or other biological fluid or tissue of a patient following administration of a corresponding prodrug of Formula (I) to the patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"$C_{max}$" is the maximum concentration of a drug in the plasma or blood of a patient following administration of a dose of the drug or prodrug to the patient.

"$T_{max}$" is the time to the maximum (peak) concentration ($C_{max}$) of a drug in the plasma or blood of a patient following administration of a dose of the drug or prodrug to the patient.

"Compounds" of Formula (I)-(II) disclosed herein include any specific compounds within these formulae. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to those skilled in the art.

Compounds of Formula (I)-(II) include optical isomers of compounds of Formula (I)-(II), racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example, a chiral high-pressure liquid chromatography (HPLC) column. In addition, compounds of Formula (I)-(II) include Z- and E-forms (or cis- and trans-forms) of compounds with double bonds.

Compounds of Formula (I)-(II) may also exist in several tautomeric forms including the enol form, the keto form, and mixtures thereof. Accordingly, the chemical structures depicted herein encompass all possible tautomeric forms of the illustrated compounds. Compounds of Formula (I)-(II) also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds as referred to herein may be free acid, salts, hydrated, solvated, or N-oxides. Thus, when reference is made to compounds of the present disclosure, such as compounds of Formula (I)-(II), it is understood that a compound also implicitly refers to free acid, salts, solvates, hydrates, N-oxides, and combinations of any of the foregoing. Certain compounds may exist in multiple crystalline, cocrystalline, or amorphous forms. Compounds of Formula (I)-(II) include pharmaceutically acceptable solvates of the free acid or salt form of any of the foregoing, hydrates of the free acid or salt form of any of the foregoing, as well as crystalline forms of any of the foregoing.

Compounds of Formula (I)-(II) may be solvates. The term "solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) indicates the point of bonding of the partial structure to the rest of the molecule.

"Cycloalkyl" by itself or as part of another substituent refers to a saturated or partially unsaturated cyclic alkyl radical. Where a specific level of saturation is intended, the nomenclature "cycloalkanyl" or "cycloalkenyl" is used. Examples of cycloalkyl groups include groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, $C_{3-10}$ cycloalkyl or in certain embodiments, $C_{3-8}$ cycloalkyl. Cycloalkyl includes nonaromatic fused ring systems.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$. In certain embodiments, a cycloalkylalkyl group is $C_{4-18}$ cycloalkylalkyl.

The "(1S)-diastereomer" of a compound of Formula (I) refers to a compound in c=which the stereochemical configuration of the acetal carbon is (S). The "(1R)-diastereomer" of a compound of Formula (I) refers to a compound in c=which the stereochemical configuration of the acetal carbon is (R).

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . "

"Halogen" refers to a fluoro, chloro, bromo, or iodo group. In certain embodiments, halogen is fluoro, and in certain embodiments, halogen is chloro.

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{37}$, =N—N=, —N=N—, —N—N—NR$^{37}$—, —PR$^{37}$—, —P(O)$_2$—, —POR$^{37}$—, —O—P(O)$_2$—, —SO—, —SO$_2$—, —Sn(R$^{37}$)$_2$—, and the like, where each R$^{37}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{5-12}$ heteroaryl, substituted $C_{5-12}$ heteroaryl, $C_{6-18}$ heteroarylalkyl, or substituted $C_{6-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each R$^{37}$ is independently chosen from hydrogen and $C_{1-3}$ alkyl. In certain embodiments, a heteroatomic group is chosen from —O—, —S—, —NH—, —N(CH$_3$)—, and —SO$_2$—.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and 5- to 14-membered bicyclic rings containing one or more, for example, from 1 to 4, or in certain embodiments, from 1 to 3, heteroatoms chosen from N, O, and S, with the remaining ring atoms being carbon, wherein at least one of the rings is an aromatic ring, and wherein at least one heteroatom is present in the at least one aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. In certain embodiments, a heteroaryl group is $C_{5-12}$ heteroaryl, $C_{5-10}$ heteroaryl, and in certain embodiments, $C_{5-6}$ heteroaryl. The ring of a $C_{5-10}$ heteroaryl has from 4 to 9 carbon atoms, with the remainder of the atoms in the ring being heteroatoms.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, in certain embodiments from 5- to 10-membered heteroaryl, and in certain embodiments from 5- to 8-heteroaryl. In certain embodiments heteroaryl groups are those derived from thiophene, pyrrole, benzothiophene, benzofuran, indole, pyridine, quinoline, imidazole, oxazole, or pyrazine.

"Heteroarylalkyl" by itself or as part of another substituent refers to an acyclic alkyl radical in which one of the hydrogen atoms bonded to a carbon atom, is replaced with a heteroaryl group. Typically a terminal or sp³ carbon atom is the atom replaced with the heteroaryl group. Where specific alkyl moieties are intended, the nomenclature "heteroarylalkanyl," "heteroarylalkenyl," and "heterorylalkynyl" is used. In certain embodiments, a heteroarylalkyl group is a 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl, and in certain embodiments, 6- to 14-membered heteroarylalkyl, e.g., the alkanyl, alkenyl, or alkynyl moiety of the heteroarylalkyl is 1- to 4-membered and the heteroaryl moiety is a 5- to 12-membered heteroaryl. In certain embodiments, a heteroarylalkyl group is $C_{6-18}$ heteroarylalkyl and in certain embodiments, $C_{6-10}$ heteroarylalkyl.

"Heterocycloalkyl" by itself or as part of another substituent refers to a saturated or partially unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. Heterocycloalkyl includes nonaromatic heterocycloalkyl fused ring systems. In certain embodiments, a heterocycloalkyl group is a $C_{3-12}$ heterocycloalkylalkyl, $C_{3-10}$ heterocycloalkylalkyl, and in certain embodiments $C_{3-8}$ heterocycloalkyalkyl.

"Heterocycloalkyalkyl" by itself or as part of another substituent refers to an acyclic alkyl radical in which one of the hydrogen atoms bonded to a carbon atom, is replaced with a heterocycloalkyl group as defined herein. In certain embodiments, a heterocycloalkylalkyl group is a $C_{4-18}$ heterocycloalkylalkyl, $C_{4-12}$ heterocycloalkylalkyl, and in certain embodiments $C_{4-10}$ heterocycloalkyalkyl.

"Metabolic intermediate" refers to a compound that is formed in vivo by metabolism of a parent compound and that further undergoes reaction in vivo to release an active agent. Compounds of Formula (I) are protected carboxylate nucleophile prodrugs of acamprosate that are metabolized in vivo to provide the corresponding metabolic intermediates of Formula (II). Metabolic intermediates of Formula (II) undergo nucleophilic cyclization to release acamprosate and one or more reaction products. It is desirable that the reaction products or metabolites thereof not be toxic.

"Neopentyl" refers to a radical in which a methylene carbon is bonded to a carbon atom, which is bonded to three non-hydrogen substituents. Examples of non-hydrogen substituents include carbon, oxygen, nitrogen, and sulfur. In certain embodiments, each of the three non-hydrogen substituents is carbon. In certain embodiments, two of the three non-hydrogen substituents is carbon, and the third non-hydrogen substituent is chosen from oxygen and nitrogen. In certain embodiments, a neopentyl group has the structure:

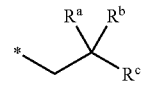

where $R^a$ and $R^b$ are independently chosen from $C_{1-4}$ alkyl, substituted $C_{1-4}$ alkyl, $C_{1-4}$ alkoxy, and substituted $C_{1-4}$ alkoxy; or $R^3$ and $R^4$ together with the carbon to which they are bonded form a ring chosen from a $C_{3-10}$ cycloalkyl, substituted $C_{3-10}$ cycloalkyl, $C_{3-10}$ heterocycloalkyl, and substituted $C_{3-10}$ heterocycloalkyl ring; and $R^c$ is chosen from carbon, nitrogen, and oxygen. In certain embodiments, each of $R^a$ and $R^b$ is methyl; and $R^c$ is chosen from carbon, nitrogen, and oxygen. In certain embodiments, each of $R^a$ and $R^b$ is methyl; and $R^c$ is carbon; in certain embodiments, nitrogen; and in certain embodiments, oxygen.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π (pi)-electron system characteristic of aromatic systems and a number or out-of-plane π (pi)-electrons corresponding to the Hückel rule (4n+1). Examples of heteroatoms to replace the carbon atoms include, but are not limited to, N, P, O, S, and Si, etc. In certain embodiments, a heteroatom is chosen from N, O, and S. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, pharmaceutically acceptable addition salts include metal salts such as sodium, potassium, aluminum, calcium, magnesium and zinc salts, and ammonium salts such as isopropylamine, diethylamine, and diethanolamine salts. In certain embodiments, a pharmaceutically acceptable salt is the hydrochloride salt. In certain embodiments, a pharmaceutically acceptable salt is the sodium salt. Pharmaceutically acceptable salts may be prepared by the skilled chemist, by treating, for example, a compound of Formula (I) with an appropriate base in a suitable solvent, followed by crystallization and filtration.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to at least one compound of Formula (I) and at least one pharmaceutically acceptable vehicle with which the at least one compound of Formula (I) is administered to a patient.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug. For example, referring to compounds of Formula (I), the promoiety is bonded to the drug, acamprosate, via the sulfonic acid functional group of acamprosate. Compounds of Formula (I) are prodrugs of acamprosate that can be metabolized within a patient's body to release acamprosate.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for a prodrug of Formula (I), the drug is acamprosate (1) and the promoiety has the structure:

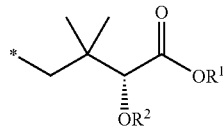

where $R^1$ and $R^2$ are is defined herein.

"Protecting group" refers to a grouping of atoms, which when attached to a reactive group in a molecule masks, reduces, or prevents that reactivity. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Salt" refers to a chemical compound consisting of an assembly of cations and anions. Salts of a compound of the present disclosure include stoichiometric and non-stoichiometric forms of the salt. In certain embodiments, because of its potential use in medicine, salts of a compound of Formula (I) are pharmaceutically acceptable salts.

"Substituted" refers to a group in which one or more hydrogen atoms are independently replaced with the same or different substituent group(s). Examples of substituent groups include, but are not limited to, -M, $—R^{60}$, $—O^-$, $=O$, $—OR^{60}$, $—SR^{60}$, $—S^-$, $=S$, $—NR^{60}R^{61}$, $=NR^{60}$, $—CF_3$, $—CN$, $—OCN$, $—SCN$, $—NO$, $—NO_2$, $=N_2$, $—N_3$, $—S(O)_2 O^-$, $—S(O)_2OH$, $—S(O)_2R^{60}$, $—OS(O_2)O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $—NR^{62}C(NR^{63})NR^{60}R^{61}$, and $—C(NR^{62})NR^{60}R^{61}$ where M is halogen; $R^{60}$, $R^{61}$, $R^{62}$, and $R^{63}$ are independently chosen from hydrogen, alkyl, alkoxy, cycloalkyl, heterocycloalkyl, aryl, and heteroaryl, or $R^{60}$ and $R^{61}$ together with the nitrogen atom to which they are bonded form a ring chosen from a heterocycloalkyl ring. In certain embodiments, $R^{60}$, $R^{61}$, $R^{62}$, and $R^{63}$ are independently chosen from hydrogen, $C_{1-6}$ alkyl, $C_{1-6}$ alkoxy, $C_{3-12}$ cycloalkyl, $C_{3-12}$ heterocycloalkyl, $C_{6-12}$ aryl, and $C_{6-12}$ heteroaryl. In certain embodiments, each substituent group is independently chosen from halogen, $—OH$, $—CN$, $—CF_3$, $=O$, $—NO_2$, $C_{1-3}$ alkoxy, $C_{1-3}$ alkyl, $—COOR^{64}$ wherein $R^{64}$ is chosen from hydrogen and $C_{1-3}$ alkyl, and $—N(R^{65})_2$ wherein each $R^{65}$ is independently chosen from hydrogen and $C_{1-3}$ alkyl. In certain embodiments, each substituent group is independently chosen from halogen, $—OH$, $—CN$, $—CF_3$, $—OCF_3$, $=O$, $—NO_2$, $C_{1-6}$ alkoxy, $C_{1-6}$ alkyl, $—COOR^{26}$, $—N(R^{27})_2$, and $—CON(R^{28})_2$; wherein each of $R^{26}$, $R^{27}$, and $R^{28}$ is independently chosen from hydrogen and $C_{1-6}$ alkyl.

In certain embodiments, each substituent group is independently chosen from halogen, —OH, —CN, —CF₃, ═O, —NO₂, C₁₋₃ alkoxy, C₁₋₃ alkyl, —COOR¹² wherein R¹² is chosen from hydrogen and C₁₋₃ alkyl, and —N(R¹²)₂ wherein each R¹² is independently chosen from hydrogen and C₁₋₃ alkyl. In certain embodiments, each substituent group is independently chosen from halogen, —OH, —CN, —CF₃, —OCF₃, ═O, —NO₂, C₁₋₆ alkoxy, C₁₋₆ alkyl, —COOR¹², —N(R¹²)₂, and —CONR¹²₂; wherein each R¹² is independently chosen from hydrogen and C₁₋₆ alkyl. In certain embodiments, each substituent group is chosen from C₁₋₄ alkyl, —OH, and —NH₂.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of any disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease or disorder even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

Certain embodiments provide a compound of Formula (I):

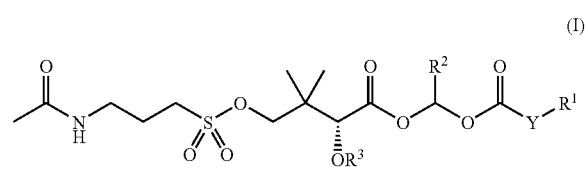

or a pharmaceutically acceptable salt thereof, wherein:

Y is chosen from —O— and a bond;

R¹ is chosen from C₁₋₆ alkyl, substituted C₁₋₆ alkyl, C₃₋₆ cycloalkyl, substituted C₃₋₆ cycloalkyl, phenyl, substituted phenyl, C₄₋₁₂ cycloalkylalkyl, substituted C₄₋₁₂ cycloalkylalkyl, C₇₋₁₂ arylalkyl, substituted C₇₋₁₂ arylalkyl, C₁₋₆ heteroalkyl, substituted C₁₋₆ heteroalkyl, C₃₋₆ heterocycloalkyl, substituted C₃₋₆ heterocycloalkyl, C₅₋₆ heteroaryl, substituted C₅₋₆ heteroaryl, C₄₋₁₂ heterocycloalkylalkyl, substituted C₄₋₁₂ heterocycloalkylalkyl, C₆₋₁₂ heteroarylalkyl, substituted C₆₋₁₂ heteroarylalkyl, and —(CH^{R6})ₙ—OPO(OH)₂ wherein n is chosen from 1, 2, and 3, and each R⁶ is independently chosen from hydrogen and methyl;

R² is chosen from hydrogen, C₁₋₆ alkyl, substituted C₁₋₆ alkyl, C₃₋₆ cycloalkyl, substituted C₃₋₆ cycloalkyl, phenyl, and substituted phenyl; and R³ is chosen from hydrogen, —PO(OH)₂, and —C(O)R⁴ wherein R⁴ is C₁₋₄ alkyl.

In certain embodiments of a compound of Formula (I), each substituent group is independently chosen from halogen, —OH, C₁₋₄ alkyl, C₁₋₄ alkoxy, and —N(R⁵)₂ wherein each R⁵ is independently chosen from hydrogen and C₁₋₂ alkyl.

In certain embodiments of a compound of Formula (I), each substituent group is independently chosen from halogen, —OH, and C₁₋₄ alkyl. In certain embodiments of a compound of Formula (I), each substituent group is independently chosen from —OH, C₁₋₄ alkyl, and C₁₋₄ alkoxy.

In certain embodiments of a compound of Formula (I), R¹ is chosen from C₁₋₆ alkyl, substituted C₁₋₆ alkyl, C₅₋₆ cycloalkyl, substituted C₅₋₆ cycloalkyl, phenyl, substituted phenyl, C₆₋₁₂ cycloalkylalkyl, substituted C₆₋₁₂ cycloalkylalkyl, C₇₋₁₂ arylalkyl, substituted C₇₋₁₂ arylalkyl, C₁₋₆ heteroalkyl, substituted C₁₋₆ heteroalkyl, C₅₋₆ heterocycloalkyl, substituted C₅₋₆ heterocycloalkyl, C₅₋₆ heteroaryl, substituted C₅₋₆ heteroaryl, C₆₋₁₂ heterocycloalkylalkyl, substituted C₆₋₁₂ heterocycloalkylalkyl, C₆₋₁₂ heteroarylalkyl, substituted C₆₋₁₂ heteroarylalkyl, and —(CH^{R6})ₙ—OPO(OH)₂, wherein n is chosen from 1, 2 and 3, and each R⁶ is independently chosen from hydrogen and methyl.

In certain embodiments of a compound of Formula (I), R¹ is chosen from C₁₋₄ alkyl, substituted C₁₋₄ alkyl, C₅₋₆ cycloalkyl, substituted C₅₋₆ cycloalkyl, phenyl, substituted phenyl, C₆₋₁₀ cycloalkylalkyl, substituted C₆₋₁₀ cycloalkylalkyl, C₇₋₁₀ arylalkyl, substituted C₇₋₁₀ arylalkyl, C₁₋₄ heteroalkyl, substituted C₁₋₄ heteroalkyl, C₅₋₆ heterocycloalkyl, substituted C₅₋₆ heterocycloalkyl, C₅₋₆ heteroaryl, substituted C₅₋₆ heteroaryl, C₆₋₁₀ heterocycloalkylalkyl, substituted C₆₋₁₀ heterocycloalkylalkyl, C₆₋₁₀ heteroarylalkyl, substituted C₆₋₁₀ heteroarylalkyl, and —(CH^{R6})ₙ—OPO(OH)₂, wherein n is chosen from 1, 2 and 3, and each R⁶ is independently chosen from hydrogen and methyl. In certain embodiments of a compound of Formula (I), Y is —O—; and $R^1$ is chosen from $C_{1-4}$ alkyl, substituted $C_{1-4}$ alkyl, $C_{5-6}$ cycloalkyl, substituted $C_{5-6}$ cycloalkyl, phenyl, substituted phenyl, $C_{6-10}$ cycloalkylalkyl, substituted $C_{6-10}$ cycloalkylalkyl, $C_{7-10}$ arylalkyl, substituted $C_{7-10}$ arylalkyl, $C_{1-4}$ heteroalkyl, substituted $C_{1-4}$ heteroalkyl, $C_{5-6}$ heterocycloalkyl, substituted $C_{5-6}$ heterocycloalkyl, $C_{5-6}$ heteroaryl, substituted $C_{5-6}$ heteroaryl, $C_{6-10}$ heterocycloalkylalkyl, substituted $C_{6-10}$ heterocycloalkylalkyl, $C_{6-10}$ heteroarylalkyl, substituted $C_{6-10}$ heteroarylalkyl, and —$(CH^{R6})_n$—OPO(OH)$_2$, wherein n is chosen from 1, 2 and 3, and each $R^6$ is independently chosen from hydrogen and methyl. In certain embodiments of a compound of Formula (I), Y is a bond; and $R^1$ is chosen from $C_{1-4}$ alkyl, substituted $C_{1-4}$ alkyl, $C_{5-6}$ cycloalkyl, substituted $C_{5-6}$ cycloalkyl, phenyl, substituted phenyl, $C_{6-10}$ cycloalkylalkyl, substituted $C_{6-10}$ cycloalkylalkyl, $C_{7-10}$ arylalkyl, substituted $C_{7-10}$ arylalkyl, $C_{1-4}$ heteroalkyl, substituted $C_{1-4}$ heteroalkyl, $C_{5-6}$ heterocycloalkyl, substituted $C_{5-6}$ heterocycloalkyl, $C_{5-6}$ heteroaryl, substituted $C_{5-6}$ heteroaryl, $C_{6-10}$ heterocycloalkylalkyl, substituted $C_{6-10}$ heterocycloalkylalkyl, $C_{6-10}$ heteroarylalkyl, substituted $C_{6-10}$ heteroarylalkyl, and —$(CH^{R6})_n$—OPO(OH)$_2$, wherein n is chosen from 1, 2 and 3, and each $R^6$ is independently chosen from hydrogen and methyl.

In certain embodiments of a compound of Formula (I), $R^1$ is chosen from $C_{1-4}$ alkyl, $C_{5-6}$ cycloalkyl, phenyl, $C_{6-10}$ cycloalkylalkyl, $C_{7-10}$ arylalkyl, $C_{1-4}$ heteroalkyl, $C_{5-6}$ heteroaryl, $C_{6-10}$ heterocycloalkylalkyl, $C_{6-10}$ heteroarylalkyl, and —$(CH^{R6})_n$—OPO(OH)$_2$, wherein n is chosen from 1, 2 and 3, and each $R^6$ is independently chosen from hydrogen and methyl.

In certain embodiments of a compound of Formula (I), $R^1$ is chosen from $C_{1-6}$ alkyl, cycloalkyl, phenyl, $C_{6-12}$ cycloalkylalkyl, $C_{7-12}$ arylalkyl, $C_{1-6}$ heteroalkyl, $C_{5-6}$ heterocycloalkyl, $C_{5-6}$ heteroaryl, $C_{6-12}$ heterocycloalkylalkyl, $C_{6-12}$ heteroarylalkyl, and —$(CH^{R6})_n$—OPO(OH)$_2$, wherein n is chosen from 1, 2 and 3, and each $R^6$ is independently chosen from hydrogen and methyl.

In certain embodiments of a compound of Formula (I), $R^1$ is chosen from $C_{1-4}$ alkyl, phenyl, substituted phenyl, benzyl, substituted benzyl, cyclohexyl, substituted cyclohexyl, and —$(CH^{R6})_n$—OPO(OH)$_2$, wherein n is chosen from 1, 2 and 3, and each $R^6$ is independently chosen from hydrogen and methyl.

In certain embodiments of a compound of Formula (I), $R^1$ is chosen from methyl, ethyl, n-propyl, isopropyl, n-butyl, isobutyl, sec-butyl, tert-butyl, phenyl, o-tolyl, benzyl, cyclohexyl, and —$(CH^{R6})_n$—OPO(OH)$_2$, wherein n is chosen from 1, 2 and 3, and each $R^6$ is independently chosen from hydrogen and methyl.

In certain embodiments of a compound of Formula (I), $R^1$ is chosen from $C_{1-6}$ alkyl, benzyl, phenyl, cyclohexyl, hydroxymethyl, 3-hydroxy-2,2-dimethylpropyl, and —CH$_2$—OPO(OH)$_2$ In certain embodiments of a compound of Formula (I), $R^1$ is —$(CH^{R6})_n$—OPO(OH)$_2$ and n is 1; in certain embodiments, n is 2; and in certain embodiments, n is 3.

In certain embodiments of a compound of Formula (I), $R^2$ is chosen from hydrogen, $C_{1-4}$ alkyl, phenyl, and cyclohexyl. In certain embodiments of a compound of Formula (I), $R^2$ is chosen from hydrogen, methyl, ethyl, n-propyl, and isopropyl. In certain embodiments of a compound of Formula (I), $R^2$ is chosen from methyl, ethyl, n-propyl, and isopropyl. In certain embodiments of a compound of Formula (I) wherein $R^2$ is chosen from methyl, ethyl, n-propyl, and isopropyl; the stereochemistry of the carbon atom to which $R^2$ is bonded is of the S-configuration. In certain embodiments of a compound of Formula (I) wherein $R^2$ is chosen from methyl, ethyl, n-propyl, and isopropyl; the stereochemistry of the carbon atom to which $R^2$ is bonded is of the R-configuration. In certain embodiments of a compound of Formula (I) wherein $R^2$ is chosen from methyl, ethyl, n-propyl, and isopropyl; $R^3$ is hydrogen, and in certain embodiments, $R^3$ is —PO(OH)$_2$.

In certain embodiments of a compound of Formula (I), $R^2$ is chosen from $C_{1-6}$ alkyl, substituted $C_{1-6}$ alkyl, $C_{3-6}$ cycloalkyl, substituted $C_{3-6}$ cycloalkyl, phenyl, and substituted phenyl; and the stereochemistry of the carbon atom to which $R^2$ is bonded is of the (S)-configuration.

In certain embodiments of a compound of Formula (I), $R^2$ is chosen from $C_{1-6}$ alkyl, substituted $C_{1-6}$ alkyl, $C_{3-6}$ cycloalkyl, substituted $C_{3-6}$ cycloalkyl, phenyl, and substituted phenyl; and the stereochemistry of the carbon atom to which $R^2$ is bonded is of the (R)-configuration.

In certain embodiments of a compound of Formula (I), $R^3$ is chosen from hydrogen and —PO(OH)$_2$. In certain embodiments of a compound of Formula (I), $R^3$ is hydrogen, and in certain embodiments $R^3$ is —PO(OH)$_2$.

In certain embodiments of a compound of Formula (I), $R^3$ is chosen from hydrogen and —C(O)$R^4$ wherein $R^4$ is $C_{1-4}$ alkyl. In certain embodiments of a compound of Formula (I), $R^3$ is hydrogen; and in certain embodiments $R^3$ is —C(O)$R^4$ wherein $R^4$ is $C_{1-4}$ alkyl.

In certain embodiments of a compound of Formula (I), Y is —O—; $R^1$ is chosen from $C_{1-4}$ alkyl, phenyl, substituted phenyl, benzyl, substituted benzyl, cyclohexyl, substituted cyclohexyl, and —$(CH^{R6})_n$—OPO(OH)$_2$, wherein n is chosen from 1, 2 and 3, and each $R^6$ is independently chosen from hydrogen and methyl; $R^2$ is chosen from hydrogen, $C_{1-4}$ alkyl, phenyl, and cyclohexyl; and is chosen from hydrogen and —PO(OH)$_2$. In certain embodiments of a compound of Formula (I), Y is a bond; $R^1$ is chosen from $C_{1-4}$ alkyl, phenyl, substituted phenyl, benzyl, substituted benzyl, cyclohexyl, substituted cyclohexyl, and —$(CH^{R6})_n$—OPO(OH)$_2$, wherein n is chosen from 1, 2 and 3; $R^2$ is chosen from hydrogen, $C_{1-4}$ alkyl, phenyl, and cyclohexyl; and is chosen from hydrogen and —PO(OH)$_2$.

In certain embodiments of a compound of Formula (I), Y is —O—; $R^1$ is chosen from methyl, ethyl, n-propyl, isopropyl, n-butyl, isobutyl, sec-butyl, tert-butyl, phenyl, o-tolyl, benzyl, cyclohexyl, and —$(CH^{R6}_2)_n$—OPO(OH)$_2$; $R^2$ is chosen from hydrogen, methyl, ethyl, n-propyl, isopropyl, cyclohexyl, and phenyl; and $R^3$ is chosen from hydrogen and —PO(OH)$_2$. In certain embodiments of a compound of Formula (I), Y is a bond; $R^1$ is chosen from methyl, ethyl, n-propyl, isopropyl, n-butyl, isobutyl, sec-butyl, tert-butyl, phenyl, o-tolyl, benzyl, cyclohexyl, and —$(CH^{R6})_n$—OPO(OH)$_2$, wherein n is chosen from 1, 2 and 3; $R^2$ is chosen from hydrogen, methyl, ethyl, n-propyl, isopropyl, cyclohexyl, and phenyl; and $R^3$ is chosen from hydrogen and —PO(OH)$_2$.

In certain embodiments of a compound of Formula (I), Y is —O—; and in certain embodiments Y is a bond.

In certain embodiments of a compound of Formula (I), the compound is chosen from:

acetyloxymethyl(2R)-4-{[3-(acetylamino)propyl]sulfonyloxy}-2-hydroxy-3,3-dimethylbutanoate;

propanoyloxymethyl(2R)-4-{[3-(acetylamino)propyl]sulfonyloxy}-2-hydroxy-3,3-dimethylbutanoate;

butanoyloxymethyl(2R)-4-{[3-(acetylamino)propyl]sulfonyloxy}-2-hydroxy-3,3-dimethylbutanoate;

(2-methylpropanoyloxy)methyl(2R)-4-{[3-(acetylamino)propyl]sulfonyloxy}-2-hydroxy-3,3-dimethylbutanoate;

((2R)-4-{[3-(acetylamino)propyl]sulfonyloxy}-2-hydroxy-3,3-dimethylbutanoyloxy)methyl pentanoate;
(3-methylbutanoyloxy)methyl(2R)-4-{[3-(acetylamino)propyl]sulfonyloxy}-2-hydroxy-3,3-dimethylbutanoate;
(2,2-dimethylpropanoyloxy)methyl(2R)-4-{[3-(acetylamino)propyl]sulfonyloxy}-2-hydroxy-3,3-dimethylbutanoate;
cyclohexylcarbonyloxymethyl(2R)-4-{[3-(acetylamino)propyl]sulfonyloxy}-2-hydroxy-3,3-dimethylbutanoate;
phenylcarbonyloxymethyl(2R)-4-{[3-(acetylamino)propyl]sulfonyloxy}-2-hydroxy-3,3-dimethylbutanoate;
3-pyridylcarbonyloxymethyl(2R)-4-{[3-(acetylamino)propyl]sulfonyloxy}-2-hydroxy-3,3-dimethylbutanoate;
(2-phenylacetyloxy)methyl(2R)-4-{[3-(acetylamino)propyl]sulfonyloxy}-2-hydroxy-3,3-dimethylbutanoate;
methoxycarbonyloxymethyl(2R)-4-{[3-(acetylamino)propyl]sulfonyloxy}-2-hydroxy-3,3-dimethylbutanoate;
ethoxycarbonyloxymethyl(2R)-4-{[3-(acetylamino)propyl]sulfonyloxy}-2-hydroxy-3,3-dimethylbutanoate;
propoxycarbonyloxymethyl(2R)-4-{[3-(acetylamino)propyl]sulfonyloxy}-2-hydroxy-3,3-dimethylbutanoate;
butoxycarbonyloxymethyl(2R)-4-{[3-(acetylamino)propyl]sulfonyloxy}-2-hydroxy-3,3-dimethylbutanoate;
(methylethoxycarbonyloxy)methyl(2R)-4-{[3-(acetylamino)propyl]sulfonyloxy}-2-hydroxy-3,3-dimethylbutanoate;
(2-methylpropoxycarbonyloxy)methyl(2R)-4-{[3-(acetylamino)propyl]sulfonyloxy}-2-hydroxy-3,3-dimethylbutanoate;
cyclohexyloxycarbonyloxymethyl(2R)-4-{[3-(acetylamino)propyl]sulfonyloxy}-2-hydroxy-3,3-dimethylbutanoate;
phenoxycarbonyloxymethyl(2R)-4-{[3-(acetylamino)propyl]sulfonyloxy}-2-hydroxy-3,3-dimethylbutanoate;
[2-(ethoxycarbonyl)phenoxycarbonyloxy]methyl(2R)-4-{[3-(acetylamino)propyl]sulfonyloxy}-2-hydroxy-3,3-dimethylbutanoate;
acetyloxyethyl(2R)-4-{[3-(acetylamino)propyl]sulfonyloxy}-2-hydroxy-3,3-dimethylbutanoate;
propanoyloxyethyl(2R)-4-{[3-(acetylamino)propyl]sulfonyloxy}-2-hydroxy-3,3-dimethylbutanoate;
butanoyloxyethyl(2R)-4-{[3-(acetylamino)propyl]sulfonyloxy}-2-hydroxy-3,3-dimethylbutanoate;
(2-methylpropanoyloxy)ethyl(2R)-4-{[3-(acetylamino)propyl]sulfonyloxy}-2-hydroxy-3,3-dimethylbutanoate;
((2R)-4-{[3-(acetylamino)propyl]sulfonyloxy}-2-hydroxy-3,3-dimethylbutanoyloxy)ethyl pentanoate;
(3-methylbutanoyloxy)ethyl(2R)-4-{[3-(acetylamino)propyl]sulfonyloxy}-2-hydroxy-3,3-dimethylbutanoate;
(2,2-dimethylpropanoyloxy)ethyl(2R)-4-{[3-(acetylamino)propyl]sulfonyloxy}-2-hydroxy-3,3-dimethylbutanoate;
cyclohexylcarbonyloxyethyl(2R)-4-{[3-(acetylamino)propyl]sulfonyloxy}-2-hydroxy-3,3-dimethylbutanoate;
phenylcarbonyloxyethyl(2R)-4-{[3-(acetylamino)propyl]sulfonyloxy}-2-hydroxy-3,3-dimethylbutanoate;
3-pyridylcarbonyloxyethyl(2R)-4-{[3-(acetylamino)propyl]sulfonyloxy}-2-hydroxy-3,3-dimethylbutanoate;
(2-phenylacetyloxy)ethyl(2R)-4-{[3-(acetylamino)propyl]sulfonyloxy}-2-hydroxy-3,3-dimethylbutanoate;
methoxycarbonyloxyethyl(2R)-4-{[3-(acetylamino)propyl]sulfonyloxy}-2-hydroxy-3,3-dimethylbutanoate;
ethoxycarbonyloxyethyl(2R)-4-{[3-(acetylamino)propyl]sulfonyloxy}-2-hydroxy-3,3-dimethylbutanoate;
propoxycarbonyloxyethyl(2R)-4-{[3-(acetylamino)propyl]sulfonyloxy}-2-hydroxy-3,3-dimethylbutanoate;
butoxycarbonyloxyethyl(2R)-4-{[3-(acetylamino)propyl]sulfonyloxy}-2-hydroxy-3,3-dimethylbutanoate;
(methylethoxycarbonyloxy)ethyl(2R)-4-{[3-(acetylamino)propyl]sulfonyloxy}-2-hydroxy-3,3-dimethylbutanoate;
(2-methylpropoxycarbonyloxy)ethyl(2R)-4-{[3-(acetylamino)propyl]sulfonyloxy}-2-hydroxy-3,3-dimethylbutanoate;
cyclohexyloxycarbonyloxyethyl(2R)-4-{[3-(acetylamino)propyl]sulfonyloxy}-2-hydroxy-3,3-dimethylbutanoate;
phenoxycarbonyloxyethyl(2R)-4-{[3-(acetylamino)propyl]sulfonyloxy}-2-hydroxy-3,3-dimethylbutanoate;
[2-(ethoxycarbonyl)phenoxycarbonyloxy]ethyl(2R)-4-{[3-(acetylamino)propyl]sulfonyloxy}-2-hydroxy-3,3-dimethylbutanoate;
acetyloxypropyl(2R)-4-{[3-(acetylamino)propyl]sulfonyloxy}-2-hydroxy-3,3-dimethylbutanoate;
propanoyloxypropyl(2R)-4-{[3-(acetylamino)propyl]sulfonyloxy}-2-hydroxy-3,3-dimethylbutanoate;
butanoyloxypropyl(2R)-4-{[3-(acetylamino)propyl]sulfonyloxy}-2-hydroxy-3,3-dimethylbutanoate;
(2-methylpropanoyloxy)propyl(2R)-4-{[3-(acetylamino)propyl]sulfonyloxy}-2-hydroxy-3,3-dimethylbutanoate;
((2R)-4-{[3-(acetylamino)propyl]sulfonyloxy}-2-hydroxy-3,3-dimethylbutanoyloxy)propyl pentanoate;
(3-methylbutanoyloxy)propyl(2R)-4-{[3-(acetylamino)propyl]sulfonyloxy}-2-hydroxy-3,3-dimethylbutanoate;
(2,2-dimethylpropanoyloxy)propyl(2R)-4-{[3-(acetylamino)propyl]sulfonyloxy}-2-hydroxy-3,3-dimethylbutanoate;
cyclohexylcarbonyloxypropyl(2R)-4-{[3-(acetylamino)propyl]sulfonyloxy}-2-hydroxy-3,3-dimethylbutanoate;
phenylcarbonyloxypropyl(2R)-4-{[3-(acetylamino)propyl]sulfonyloxy}-2-hydroxy-3,3-dimethylbutanoate;
3-pyridylcarbonyloxypropyl(2R)-4-{[3-(acetylamino)propyl]sulfonyloxy}-2-hydroxy-3,3-dimethylbutanoate;
(2-phenylacetyloxy)propyl(2R)-4-{[3-(acetylamino)propyl]sulfonyloxy}-2-hydroxy-3,3-dimethylbutanoate;
methoxycarbonyloxypropyl(2R)-4-{[3-(acetylamino)propyl]sulfonyloxy}-2-hydroxy-3,3-dimethylbutanoate;
ethoxycarbonyloxypropyl(2R)-4-{[3-(acetylamino)propyl]sulfonyloxy}-2-hydroxy-3,3-dimethylbutanoate;
propoxycarbonyloxypropyl(2R)-4-{[3-(acetylamino)propyl]sulfonyloxy}-2-hydroxy-3,3-dimethylbutanoate;
butoxycarbonyloxypropyl(2R)-4-{[3-(acetylamino)propyl]sulfonyloxy}-2-hydroxy-3,3-dimethylbutanoate;
(methylethoxycarbonyloxy)propyl(2R)-4-{[3-(acetylamino)propyl]sulfonyloxy}-2-hydroxy-3,3-dimethylbutanoate;
(2-methylpropoxycarbonyloxy)propyl(2R)-4-{[3-(acetylamino)propyl]sulfonyloxy}-2-hydroxy-3,3-dimethylbutanoate;
cyclohexyloxycarbonyloxypropyl(2R)-4-{[3-(acetylamino)propyl]sulfonyloxy}-2-hydroxy-3,3-dimethylbutanoate;
phenoxycarbonyloxypropyl(2R)-4-{[3-(acetylamino)propyl]sulfonyloxy}-2-hydroxy-3,3-dimethylbutanoate;
[2-(ethoxycarbonyl)phenoxycarbonyloxy]propyl(2R)-4-{[3-(acetylamino)propyl]sulfonyloxy}-2-hydroxy-3,3-dimethylbutanoate;
acetyloxybutyl(2R)-4-{[3-(acetylamino)propyl]sulfonyloxy}-2-hydroxy-3,3-dimethylbutanoate;
propanoyloxybutyl(2R)-4-{[3-(acetylamino)propyl]sulfonyloxy}-2-hydroxy-3,3-dimethylbutanoate;
butanoyloxybutyl(2R)-4-{[3-(acetylamino)propyl]sulfonyloxy}-2-hydroxy-3,3-dimethylbutanoate;
(2-methylpropanoyloxy)butyl(2R)-4-{[3-(acetylamino)propyl]sulfonyloxy}-2-hydroxy-3,3-dimethylbutanoate;
((2R)-4-{[3-(acetylamino)propyl]sulfonyloxy}-2-hydroxy-3,3-dimethylbutanoyloxy)butyl pentanoate;
(3-methylbutanoyloxy)butyl(2R)-4-{[3-(acetylamino)propyl]sulfonyloxy}-2-hydroxy-3,3-dimethylbutanoate;

(2,2-dimethylpropanoyloxy)butyl(2R)-4-{[3-(acetylamino)propyl]sulfonyloxy}-2-hydroxy-3,3-dimethylbutanoate;
cyclohexylcarbonyloxybutyl(2R)-4-{[3-(acetylamino)propyl]sulfonyloxy}-2-hydroxy-3,3-dimethylbutanoate;
phenylcarbonyloxybutyl(2R)-4-{[3-(acetylamino)propyl]sulfonyloxy}-2-hydroxy-3,3-dimethylbutanoate;
3-pyridylcarbonyloxybutyl(2R)-4-{[3-(acetylamino)propyl]sulfonyloxy}-2-hydroxy-3,3-dimethylbutanoate;
(2-phenylacetyloxy)butyl(2R)-4-{[3-(acetylamino)propyl]sulfonyloxy}-2-hydroxy-3,3-dimethylbutanoate;
methoxycarbonyloxybutyl(2R)-4-{[3-(acetylamino)propyl]sulfonyloxy}-2-hydroxy-3,3-dimethylbutanoate;
ethoxycarbonyloxybutyl(2R)-4-{[3-(acetylamino)propyl]sulfonyloxy}-2-hydroxy-3,3-dimethylbutanoate;
propoxycarbonyloxybutyl(2R)-4-{[3-(acetylamino)propyl]sulfonyloxy}-2-hydroxy-3,3-dimethylbutanoate;
(methylethoxycarbonyloxy)butyl(2R)-4-{[3-(acetylamino)propyl]sulfonyloxy}-2-hydroxy-3,3-dimethylbutanoate;
butoxycarbonyloxybutyl(2R)-4-{[3-(acetylamino)propyl]sulfonyloxy}-2-hydroxy-3,3-dimethylbutanoate;
(2-methylpropoxycarbonyloxy)butyl(2R)-4-{[3-(acetylamino)propyl]sulfonyloxy}-2-hydroxy-3,3-dimethylbutanoate;
cyclohexyloxycarbonyloxybutyl(2R)-4-{[3-(acetylamino)propyl]sulfonyloxy}-2-hydroxy-3,3-dimethylbutanoate;
phenoxycarbonyloxybutyl(2R)-4-{[3-(acetylamino)propyl]sulfonyloxy}-2-hydroxy-3,3-dimethylbutanoate;
[2-(ethoxycarbonyl)phenoxycarbonyloxy]butyl(2R)-4-{[3-(acetylamino)propyl]sulfonyloxy}-2-hydroxy-3,3-dimethylbutanoate;
1-acetyloxy-2-methylpropyl(2R)-4-{[3-(acetylamino)propyl]sulfonyloxy}-2-hydroxy-3,3-dimethylbutanoate;
2-methyl-1-propanoyloxypropyl(2R)-4-{[3-(acetylamino)propyl]sulfonyloxy}-2-hydroxy-3,3-dimethylbutanoate;
1-butanoyloxy-2-methylpropyl(2R)-4-{[3-(acetylamino)propyl]sulfonyloxy}-2-hydroxy-3,3-dimethylbutanoate;
2-methyl-1-(2-methylpropanoyloxy)propyl(2R)-4-{[3-(acetylamino)propyl]sulfonyloxy}-2-hydroxy-3,3-dimethylbutanoate;
1-((2R)-4-{[3-(acetylamino)propyl]sulfonyloxy}-2-hydroxy-3,3-dimethylbutanoyloxy)-2-methylpropyl pentanoate;
2-methyl-1-(3-methylbutanoyloxy)propyl(2R)-4-{[3-(acetylamino)propyl]sulfonyloxy}-2-hydroxy-3,3-dimethylbutanoate;
1-(2,2-dimethylpropanoyloxy)-2-methylpropyl(2R)-4-{[3-(acetylamino)propyl]sulfonyloxy}-2-hydroxy-3,3-dimethylbutanoate;
1-cyclohexylcarbonyloxy-2-methylpropyl(2R)-4-{[3-(acetylamino)propyl]sulfonyloxy}-2-hydroxy-3,3-dimethylbutanoate;
2-methyl-1-phenylcarbonyloxypropyl(2R)-4-{[3-(acetylamino)propyl]sulfonyloxy}-2-hydroxy-3,3-dimethylbutanoate;
2-methyl-1-(3-pyridylcarbonyloxy)propyl(2R)-4-{[3-(acetylamino)propyl]sulfonyloxy}-2-hydroxy-3,3-dimethylbutanoate;
2-methyl-1-(2-phenylacetyloxy)propyl(2R)-4-{[3-(acetylamino)propyl]sulfonyloxy}-2-hydroxy-3,3-dimethylbutanoate;
1-methoxycarbonyloxy-2-methylpropyl(2R)-4-{[3-(acetylamino)propyl]sulfonyloxy}-2-hydroxy-3,3-dimethylbutanoate;
1-ethoxycarbonyloxy-2-methylpropyl(2R)-4-{[3-(acetylamino)propyl]sulfonyloxy}-2-hydroxy-3,3-dimethylbutanoate;
2-methyl-1-propoxycarbonyloxypropyl(2R)-4-{[3-(acetylamino)propyl]sulfonyloxy}-2-hydroxy-3,3-dimethylbutanoate;
2-methyl-1-(methylethoxycarbonyloxy)propyl(2R)-4-{[3-(acetylamino)propyl]sulfonyloxy}-2-hydroxy-3,3-dimethylbutanoate;
1-butoxycarbonyloxy-2-methylpropyl(2R)-4-{[3-(acetylamino)propyl]sulfonyloxy}-2-hydroxy-3,3-dimethylbutanoate;
2-methyl-1-(2-methylpropoxycarbonyloxy)propyl(2R)-4-{[3-(acetylamino)propyl]sulfonyloxy}-2-hydroxy-3,3-dimethylbutanoate;
1-cyclohexyloxycarbonyloxy-2-methylpropyl(2R)-4-{[3-(acetylamino)propyl]sulfonyloxy}-2-hydroxy-3,3-dimethylbutanoate;
2-methyl-1-phenoxycarbonyloxypropyl(2R)-4-{[3-(acetylamino)propyl]sulfonyloxy}-2-hydroxy-3,3-dimethylbutanoate;
1-[2-(ethoxycarbonyl)phenoxycarbonyloxy]-2-methylpropyl(2R)-4-{[3-(acetylamino)propyl]sulfonyloxy}-2-hydroxy-3,3-dimethylbutanoate;
acetyloxycyclohexylmethyl(2R)-4-{[3-(acetylamino)propyl]sulfonyloxy}-2-hydroxy-3,3-dimethylbutanoate;
cyclohexylpropanoyloxymethyl(2R)-4-{[3-(acetylamino)propyl]sulfonyloxy}-2-hydroxy-3,3-dimethylbutanoate;
butanoyloxycyclohexylmethyl(2R)-4-{[3-(acetylamino)propyl]sulfonyloxy}-2-hydroxy-3,3-dimethylbutanoate;
cyclohexyl(2-methylpropanoyloxy)methyl(2R)-4-{[3-(acetylamino)propyl]sulfonyloxy}-2-hydroxy-3,3-dimethylbutanoate;
((2R)-4-{[3-(acetylamino)propyl]sulfonyloxy}-2-hydroxy-3,3-dimethylbutanoyloxy)cyclohexylmethyl pentanoate;
cyclohexyl(3-methylbutanoyloxy)methyl(2R)-4-{[3-(acetylamino)propyl]sulfonyloxy}-2-hydroxy-3,3-dimethylbutanoate;
(2,2-dimethylpropanoyloxy)cyclohexylmethyl(2R)-4-{[3-(acetylamino)propyl]sulfonyloxy}-2-hydroxy-3,3-dimethylbutanoate;
cyclohexylcyclohexylcarbonyloxymethyl(2R)-4-{[3-(acetylamino)propyl]sulfonyloxy}-2-hydroxy-3,3-dimethylbutanoate;
cyclohexylphenylcarbonyloxymethyl(2R)-4-{[3-(acetylamino)propyl]sulfonyloxy}-2-hydroxy-3,3-dimethylbutanoate;
cyclohexyl-3-pyridylcarbonyloxymethyl(2R)-4-{[3-(acetylamino)propyl]sulfonyloxy}-2-hydroxy-3,3-dimethylbutanoate;
cyclohexyl(2-phenylacetyloxy)methyl(2R)-4-{[3-(acetylamino)propyl]sulfonyloxy}-2-hydroxy-3,3-dimethylbutanoate;
cyclohexyl[2-(ethoxycarbonyl)phenoxycarbonyloxy]methyl(2R)-4-{[3-(acetylamino)propyl]sulfonyloxy}-2-hydroxy-3,3-dimethylbutanoate;
cyclohexylphenoxycarbonyloxymethyl(2R)-4-{[3-(acetylamino)propyl]sulfonyloxy}-2-hydroxy-3,3-dimethylbutanoate;
cyclohexylcyclohexyloxycarbonyloxymethyl(2R)-4-{[3-(acetylamino)propyl]sulfonyloxy}-2-hydroxy-3,3-dimethylbutanoate;
cyclohexyl(2-methylpropoxycarbonyloxy)methyl(2R)-4-{[3-(acetylamino)propyl]sulfonyloxy}-2-hydroxy-3,3-dimethylbutanoate;
butoxycarbonyloxycyclohexylmethyl(2R)-4-{[3-(acetylamino)propyl]sulfonyloxy}-2-hydroxy-3,3-dimethylbutanoate;

cyclohexyl(methylethoxycarbonyloxy)methyl (2R)-4-{[3-(acetylamino)propyl]sulfonyloxy}-2-hydroxy-3,3-dimethylbutanoate;
cyclohexylpropoxycarbonyloxymethyl(2R)-4-{[3-(acetylamino)propyl]sulfonyloxy}-2-hydroxy-3,3-dimethylbutanoate;
cyclohexylethoxycarbonyloxymethyl(2R)-4-{[3-(acetylamino)propyl]sulfonyloxy}-2-hydroxy-3,3-dimethylbutanoate;
cyclohexylmethoxycarbonyloxymethyl(2R)-4-{[3-(acetylamino)propyl]sulfonyloxy}-2-hydroxy-3,3-dimethylbutanoate;
acetyloxyphenylmethyl(2R)-4-{[3-(acetylamino)propyl]sulfonyloxy}-2-hydroxy-3,3-dimethylbutanoate;
phenylpropanoyloxymethyl(2R)-4-{[3-(acetylamino)propyl]sulfonyloxy}-2-hydroxy-3,3-dimethylbutanoate;
butanoyloxyphenylmethyl(2R)-4-{[3-(acetylamino)propyl]sulfonyloxy}-2-hydroxy-3,3-dimethylbutanoate;
(2-methylpropanoyloxy)phenylmethyl(2R)-4-{[3-(acetylamino)propyl]sulfonyloxy}-2-hydroxy-3,3-dimethylbutanoate;
((2R)-4-{[3-(acetylamino)propyl]sulfonyloxy}-2-hydroxy-3,3-dimethylbutanoyloxy)phenylmethyl pentanoate;
(3-methylbutanoyloxy)phenylmethyl(2R)-4-{[3-(acetylamino)propyl]sulfonyloxy}-2-hydroxy-3,3-dimethylbutanoate;
(2,2-dimethylpropanoyloxy)phenylmethyl(2R)-4-{[3-(acetylamino)propyl]sulfonyloxy}-2-hydroxy-3,3-dimethylbutanoate;
cyclohexylcarbonyloxyphenylmethyl(2R)-4-{[3-(acetylamino)propyl]sulfonyloxy}-2-hydroxy-3,3-dimethylbutanoate;
phenylphenylcarbonyloxymethyl(2R)-4-{[3-(acetylamino)propyl]sulfonyloxy}-2-hydroxy-3,3-dimethylbutanoate;
phenyl-3-pyridylcarbonyloxymethyl(2R)-4-{[3-(acetylamino)propyl]sulfonyloxy}-2-hydroxy-3,3-dimethylbutanoate;
phenyl(2-phenylacetyloxy)methyl(2R)-4-{[3-(acetylamino)propyl]sulfonyloxy}-2-hydroxy-3,3-dimethylbutanoate;
methoxycarbonyloxyphenylmethyl(2R)-4-{[3-(acetylamino)propyl]sulfonyloxy}-2-hydroxy-3,3-dimethylbutanoate;
ethoxycarbonyloxyphenylmethyl(2R)-4-{[3-(acetylamino)propyl]sulfonyloxy}-2-hydroxy-3,3-dimethylbutanoate;
phenylpropoxycarbonyloxymethyl(2R)-4-{[3-(acetylamino)propyl]sulfonyloxy}-2-hydroxy-3,3-dimethylbutanoate;
(methylethoxycarbonyloxy)phenylmethyl(2R)-4-{[3-(acetylamino)propyl]sulfonyloxy}-2-hydroxy-3,3-dimethylbutanoate;
butoxycarbonyloxyphenylmethyl(2R)-4-{[3-(acetylamino)propyl]sulfonyloxy}-2-hydroxy-3,3-dimethylbutanoate;
(2-methylpropoxycarbonyloxy)phenylmethyl(2R)-4-{[3-(acetylamino)propyl]sulfonyloxy}-2-hydroxy-3,3-dimethylbutanoate;
cyclohexyloxycarbonyloxyphenylmethyl(2R)-4-{[3-(acetylamino)propyl]sulfonyloxy}-2-hydroxy-3,3-dimethylbutanoate;
phenylphenoxycarbonyloxymethyl(2R)-4-{[3-(acetylamino)propyl]sulfonyloxy}-2-hydroxy-3,3-dimethylbutanoate;
[2-(ethoxycarbonyl)phenoxycarbonyloxy]phenylmethyl (2R)-4-{[3-(acetylamino)propyl]sulfonyloxy}-2-hydroxy-3,3-dimethylbutanoate;
the (1S) diastereomer of any of the foregoing compounds;
the (1R) diastereomer of any of the foregoing compounds; and
a pharmaceutically acceptable salt of any of the foregoing.

In certain embodiments of a compound of Formula (I), the compound is chosen from:
(ethylethoxycarbonyloxy)methyl(2R)-4-{[3-(acetylamino)propyl]sulfonyloxy}-3,3-dimethyl-2-hydroxy-butanoate;
(2-phenylacetyloxy)methyl(2R)-4-{[3-(acetylamino)propyl]sulfonyloxy}-3,3-dimethyl-2-hydroxy-butanoate;
(2-methylpropanoyloxy)ethyl(2R)-4-{[3-(acetylamino)propyl]sulfonyloxy}-3,3-dimethyl-2-hydroxy-butanoate;
(1S)-(2-methylpropanoyloxy)ethyl(2R)-4-{[3-(acetylamino)propyl]sulfonyloxy}-3,3-dimethyl-2-hydroxy-butanoate;
(1R)-(2-methylpropanoyloxy)ethyl(2R)-4-{[3-(acetylamino)propyl]sulfonyloxy}-3,3-dimethyl-2-hydroxy-butanoate;
ethoxycarbonyloxyethyl(2R)-4-{[3-(acetylamino)propyl]sulfonyloxy}-3,3-dimethyl-2-hydroxy-butanoate;
(1R)-1-ethoxycarbonyloxyethyl(2R)-4-{[3-(acetylamino)propyl]sulfonyloxy}-3,3-dimethyl-2-hydroxy-butanoate;
(1S)-1-ethoxycarbonyloxyethyl(2R)-4-{[3-(acetylamino)propyl]sulfonyloxy}-3,3-dimethyl-2-hydroxy-butanoate;
ethoxycarbonyloxyethyl(2R)-4-{[3-(acetylamino)propyl]sulfonyloxy}-3,3-dimethyl-2-(2-methylpropanoyloxy)-butanoate;
ethoxycarbonyloxyethyl 4-{[3-(acetylamino)propyl]sulfonyloxy}-3,3-dimethyl-2-hydroxy-butanoate;
benzoyloxyethyl(2R)-4-{[3-(acetylamino)propyl]sulfonyloxy}-3,3-dimethyl-2-hydroxy-butanoate;
benzoyloxyethyl 4-{[3-(acetylamino)propyl]sulfonyloxy}-3,3-dimethyl-2-hydroxy-butanoate;
(methylethoxycarbonyloxy)ethyl(2R)-4-{[3-(acetylamino)propyl]sulfonyloxy}-2-hydroxy-3,3-dimethylbutanoate;
(1R)-(methylethoxycarbonyloxy)ethyl(2R)-4-{[3-(acetylamino)propyl]sulfonyloxy}-2-hydroxy-3,3-dimethylbutanoate;
(1S)-(methylethoxycarbonyloxy)ethyl(2R)-4-{[3-(acetylamino)propyl]sulfonyloxy}-2-hydroxy-3,3-dimethylbutanoate;
cyclohexyloxycarbonyloxyethyl(2R)-4-{[3-(acetylamino)propyl]sulfonyloxy}-2-hydroxy-3,3-dimethylbutanoate;
cyclohexylcarbonyloxyethyl(2R)-4-{[3-(acetylamino)propyl]sulfonyloxy}-2-hydroxy-3,3-dimethylbutanoate;
(2-hydroxyacetyloxy)ethyl(2R)-4-{[3-(acetylamino)propyl]sulfonyloxy}-2-hydroxy-3,3-dimethylbutanoate;
(3-hydroxy-2,2-dimethylpropanoyloxy)ethyl(2R)-4-{[3-(acetylamino)propyl]sulfonyloxy}-2-hydroxy-3,3-dimethylbutanoate;
2-methyl-1-(methylethoxycarbonyloxy)propyl(2R)-4-{[3-(acetylamino)propyl]sulfonyloxy}-3,3-dimethyl-2-hydroxy-butanoate;
(2-methylpropanoyloxy)ethyl(2R)-4-{[3-(acetylamino)propyl]sulfonyloxy}-3,3-dimethyl-2-(oxyphosphinyloxyphosphinyl)butanoate;
cyclohexylcarbonyloxyethyl(2R)-4-{[3-(acetylamino)propyl]sulfonyloxy}-3,3-dimethyl-2-(oxyphosphinyloxyphosphinyl)butanoate;
ethoxycarbonyloxyethyl(2R)-4-{[3-(acetylamino)propyl]sulfonyloxy}-3,3-dimethyl-2-(oxyphosphinyloxyphosphinyl)butanoate;
(methylethoxycarbonyloxy)ethyl(2R)-4-{[3-(acetylamino)propyl]sulfonyloxy}-3,3-dimethyl-2-(oxyphosphinylphosphinyl)butanoate;
[2-(oxyphosphinyloxyphosphinyl)acetyloxy]ethyl (2R)-4-{[3-(acetylamino)propyl]sulfonyloxy}-2-hydroxy-3,3-dimethylbutanoate; and
a pharmaceutically acceptable salt of any of the foregoing.
Certain embodiments provide a compound of Formula (II):

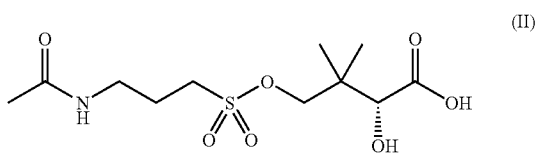

i.e., (2R)-4-{[3-(acetylamino)propyl]sulfonyloxy}-2-hydroxy-3,3-dimethylbutanoic acid, or a salt thereof.

In certain embodiments of compounds of Formula (I), a pharmaceutically acceptable salt is chosen from a hydrochloride salt, a sodium salt, a potassium salt, a lithium salt, an ammonium salt, a calcium salt, a zinc salt, and a magnesium salt. In certain embodiments, of compounds of Formula (I), a pharmaceutically acceptable salt is the hydrochloride salt, and in certain embodiments, the sodium salt.

In certain embodiments, the compounds of Formula (I) are free acids.

In certain embodiments of the compound of Formula (II), a salt is chosen from a hydrochloride salt, a sodium salt, a potassium salt, a lithium salt, an ammonium salt, a calcium salt, a zinc salt, and a magnesium salt. In certain embodiments of the compound of Formula (II), a salt is the hydrochloride salt, and in certain embodiments, the sodium salt.

In certain embodiments, the compound of Formula (II) is a free acid.

Synthesis

Compounds disclosed herein may be obtained via the synthetic methods illustrated in Schemes 1-24. Those of ordinary skill in the art will appreciate that a useful synthetic route to the disclosed compounds comprises bonding a substituted neopentyl alcohol or appropriate intermediate thereof bearing a suitable functional group at the neopentyl position of the promoiety to acamprosate, i.e. sulfonyl chloride, of acamprosate to form a substituted neopentyl sulfonyl ester moiety.

General synthetic methods useful in the synthesis of compounds described herein are available in the art. Starting materials useful for preparing compounds and intermediates thereof are commercially available or can be prepared by well-known synthetic methods. Other methods for the synthesis of compounds provided by the present disclosure are either described in the art or will be readily apparent to the skilled artisan in view of the references provided herein and may be used to synthesize the compounds provided by the present disclosure. Accordingly, the methods presented in the schemes are illustrative rather than comprehensive or limiting.

In certain embodiments, and referring to Scheme 1, commercially available homotaurine 1 can be converted to the corresponding 3-(N-acetyl) homotaurinate derivative 2 using methods or variations thereof disclosed in Durlach, et al., U.S. Pat. No. 4,355,043, DE 30 19 350 C2, or Berthelon, et al., U.S. Pat. No. 6,265,437 B1.

Scheme 1

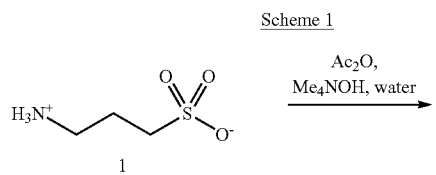

In certain embodiments, and referring to Scheme 2, commercially available potassium phthalimide 3 can be reacted with 3-propanesulton 4 in a solvent such as ethanol (EtOH) at a temperature from about 25° C. to about 80° C. to provide the corresponding potassium 3-(N-phthalimido) propylsulfonate 5, using methods or variations thereof described by Shue, et al., *Bioorg. Med. Chem. Lett.* 1996, 6, 1709.

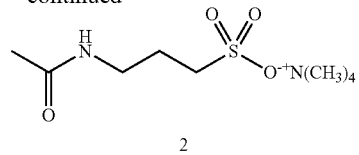

Scheme 2

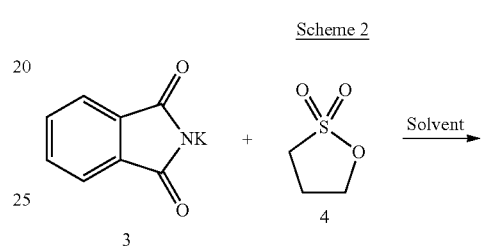

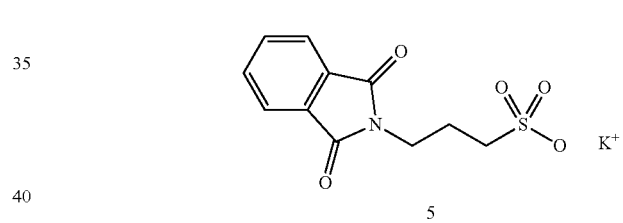

Referring to Scheme 3 (where Q is NHAc, phthalimido, or other useful amine precursor, M is a metal salt, and X is halogen), drugs or suitable precursors of drugs having at least one sulfonic acid group 6, a suitable sulfonic acid derivative thereof such as a tetraalkylammonium salt 7, or certain metal salts of sulfonic acids 8 can be reacted with activation agents to provide the corresponding activated sulfonic acid derivatives, i.e. sulfonyl chlorides. Useful methods are described in Shue, et al., *Bioorg. Med. Chem. Lett.* 1996, 6, 1709; and Korolev, et. al., *Synthesis* 2003, 3, 383-388. For example, activation of sulfonic acid 6, the corresponding tetraalkylammonium salt 7, such as the tetramethylammonium salt of a sulfonic acid derivative, or the corresponding alkali metal salt 8 (n is 1) can be accomplished by reaction with an appropriate chlorination agent such as phosphorous pentachloride ($PCl_5$), or, alternatively, thionyl chloride ($SOCl_2$), sulfuryl chloride ($SO_2Cl_2$), or cyanuric chloride (ClCN); in a solvent such as the chlorination agent itself, dichloromethane (DCM), and the like, optionally in the presence of a catalyst such as N,N-dimethylformamide (DMF); and at a temperature from about 0° C. to about 60° C.; to provide the corresponding sulfonic acid chlorides or sulfonyl chlorides 9 such as 3-(N-acetyl)propylsulfonyl chloride (acamprosate chloride) or 3-phthalimido propylsulfonyl chloride.

Scheme 3

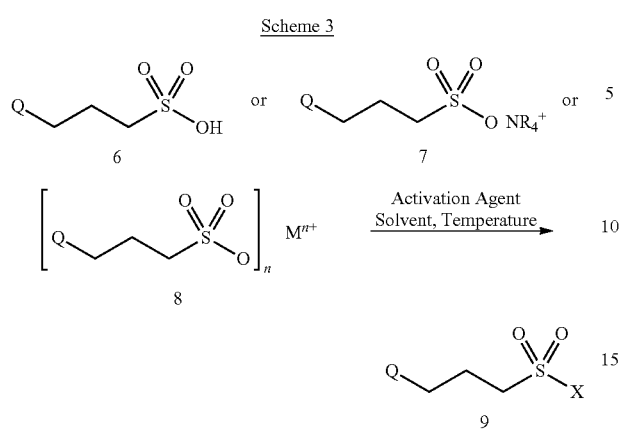

In certain embodiments, and referring to Scheme 3, certain activated precursors of drugs having at least one sulfonic acid group 6, for example, where Q is chlorine and X is chlorine, i.e. 3-chloropropylsulfonyl chloride, are commercially available and can be used directly as coupling partners for the synthesis of functionalized prodrug intermediates.

Masked carboxylate neopentyl sulfonic acid prodrugs, intermediates, and precursors of any of the foregoing can be prepared according to general synthetic Schemes 4-24. In general, activated sulfonic acid intermediates such as sulfonyl chlorides can be coupled with a functionalized neopentyl alcohol in the presence of a base and/or a catalyst at a temperature from about −78° C. to about 65° C. to provide neopentyl sulfonyl ester prodrugs, intermediates, or precursors. Depending on the nature of the functional groups of the sulfonyl moiety and/or the neopentyl alcohol, the intermediates or precursors may be further derivatized or interconverted to provide the desired prodrugs.

Examples for preparing functionalized neopentyl promoieties and appropriately functionalized neopentyl alcohols such as functionalized 2,2-bis-substituted 3-hydroxy propanoic acid derivatives, that are useful as coupling partners are shown in the following schemes.

Referring to Scheme 4, 2,2-bis-substituted 3-hydroxy propanoic acid derivative 11 (corresponding to n is 0 in Formula (I)) as a functionalized neopentyl promoiety is provided, where $R^1$, $R^2$, and $R^3$ are as defined herein. In certain embodiments, each of $R^2$ and $R^3$ is methyl, and $R^1$ is alkyl or substituted alkyl, and the starting material is 2,2-dimethyl 3-hydroxypropanoic acid (hydroxypivalic acid) 10. In certain embodiments, where $R^2$ and $R^3$ are independently chosen from methyl and hydroxymethyl, and $R^1$ is alkyl or substituted alkyl, the starting material is 2,2-(bis-hydroxymethyl) propionic acid.

Scheme 4

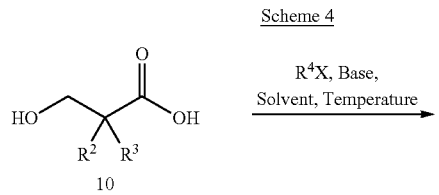

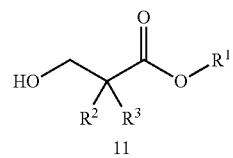

Using known synthetic methods, 2,2-bis-substituted 3-hydroxy propanoic acid derivatives such as 2,2-dimethyl 3-hydroxy propanoic acid (hydroxypivalic acid), 2,2-(bis-hydroxymethyl)propionic acid, and the like, can be converted to the corresponding ester derivative 11 in the presence of an inorganic base such as an alkali carbonate (e.g., $Cs_2CO_3$ or $K_2CO_3$), and an alkyl halide reagent such as alkyl or benzylic halides (e.g., ethyl iodide (EtI), isopropyl bromide (iPrBr), or benzyl bromide (BnBr)), in an inert solvent such as N,N-dimethylformamide (DMF), N-methylpyrrolidone (NMP), N,N-dimethylacetamide (DMA, DMAc), dimethylsulfoxide (DMSO), or tetrahydrofuran (THF), at a temperature from about 0° C. to about 100° C.

Methods for preparing acyloxyalkyl ester derivatives, and alkoxy- or aryloxycarbonyloxyoxy ester derivatives 14 of 2,2-bis-substituted 3-hydroxy propanoic acid derivatives 12 are shown in Scheme 5 where $R^2$, $R^3$, $R^5$, and $R^6$ are as defined herein, X is halogen, and Y is oxygen or a bond. In certain embodiments, where each of $R^2$ and $R^3$ is methyl, $R^5$ is ethyl, and $R^6$ is methyl; the starting materials are 2,2-dimethyl 3-hydroxy propanoic acid (hydroxypivalic acid) and rac-1-chloroethyl ethyl carbonate. Unsubstituted and substituted 1-halogenoalkyl carboxylates, or 1-halogenoalkyl alkyl- or aryl-carbonates are either commercially available or can be prepared from commercially available starting materials adapting procedures or variations thereof according to Harada, et al., *Synth. Commun.* 1994, 24, 767-772; Davidsen, et al., *J. Med. Chem.* 1994, 37, 4423-4429; Jasys, EP 0 061 274 B1; and Wheeler, et al., *J. Med. Chem.* 1979, 22, 657-661, or other methods known in the art. Acyloxyalkyl ester derivatives or alkoxy- and aryloxycarbonyloxyoxy ester derivative 14 can be obtained by reacting 2,2-bis-substituted 3-hydroxypropionic acid derivative 12 with a substituted 1-halogenoalkyl carboxylate or a 1-halogenoalkyl alkyl- or aryl-carbonate 13 in the presence of a tertiary organic base such as triethylamine ($Et_3N$, TEA), diethylisopropylamine (DIEA, Hünigs-base), or NMM (N-methylmorpholine); or an amidine base such as 1,8-diazabicyclo[5.4.0]undec-7-ene (DBU) or 1,5-diazabicyclo(4.3.0)non-5-ene (DBN); either in neat form or in an organic solvent such as 1,2-dichloroethane (DCE), at a temperature from about 0° C. to about 100° C.

Scheme 5

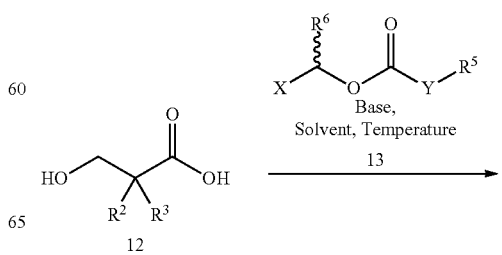

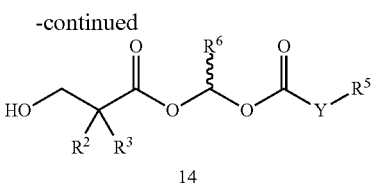

14

Alternatively, 2,2-bis-substituted 3-hydroxy propanoic acid derivatives can be prepared according to Scheme 6, where $R^1$, $R^2$, and $R^3$ are defined herein and Y is oxygen or a bond. In certain embodiments, each of $R^2$ and $R^3$ is methyl; $R^1$ is 3-pyridylmethyl (nicotinyl) or 2-(morpholin-4-yl)ethyl (mofetil); the starting material is 2,2-dimethyl 3-hydroxy propanoic acid (hydroxypivalic acid) 15; and Y is oxygen.

Scheme 6

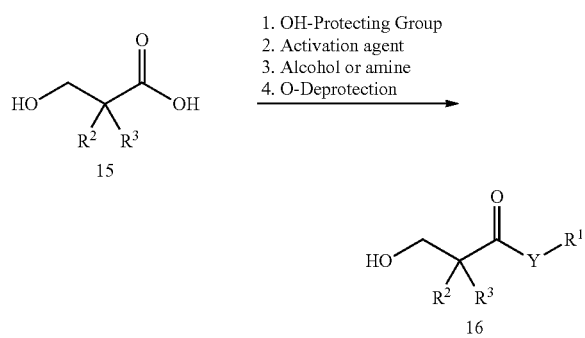

For example, referring to Scheme 6, protection of hydroxypivalic acid 15 with mixed trialkyl- or mixed trialkylarylchlorosilanes such as tert-butyl dimethylsilylchlorosilane (TBDMSCl), triisopropylchlorosilane (TIPSCl), tert-butyldiphenylsilyl chlorosilane (TBDPSCl), and the like, in an inert solvent such as dichloromethane (DCM), tetrahydrofuran (THF), or N,N-dimethylformamide (DMF), in the presence of an organic base such as imidazole or triethylamine ($Et_3N$, TEA), and optionally a catalytic amount of a nucleophilic catalyst such as 4-(N,N-dimethyl)aminopyridine (DMAP), at a temperature from about 0° C. to about 60° C., provides the corresponding 3-trialklyl- or mixed 3-alkylarylsiloxy 2,2-dimethyl propanoic acid intermediates. Other methods for the selective introduction and removal of protecting groups and alternative protection strategies are known in the art.

Functionalized carboxylic acid derivatives such as carboxylic acid esters or carboxamides of protected 3-trialklyl- or mixed 3-alkylarylsiloxy 2,2-bis-substituted propanoic acids can be obtained through an activation/coupling sequence. For example, 3-trialklyl- or mixed 3-alkylarylsiloxy 2,2-bis-substituted propanoic acids such as 2,2-dimethyl 3-(tert-butyldimethylsilyloxy) propanoic acid can be contacted with an activation agent such as a dehydration agent, e.g., N,N'-dicyclohexylcarbodiimide (DCC); in an inert solvent such as dichloromethane (DCM), acetonitrile (MeCN), and the like; in the presence of an additive such as a nucleophilic acylation catalyst, e.g. 4-(N,N-dimethyamino)pyridine (DMAP); at a temperature from about 0° C. to about 60° C. The activated intermediate of the 3-trialklyl- or mixed 3-alkylarylsiloxy 2,2-dimethyl propanoic acid, such as 2,2-dimethyl 3-(tert-butyldimethylsilyloxy) propanoic acid can then be reacted in the same solvent with a functionalized alcohol such as 2-(morpholin-4-yl)ethanol or 3-pyridylmethanol, to provide the corresponding alkyl-, aryl-, 3-trialklyl-, or mixed 3-alkylarylsiloxy 2,2-bis-substituted propanoate.

Reaction of alkyl or aryl 2,2-dialkyl 3-trialkylsilyoxy propanoates with reagents capable of selectively cleaving the 3-trialkyl or mixed alkylarylsilyl protecting group provide alkyl- or aryl-2,2-dialkyl 3-hydroxy propanoate 16 that is useful neopentyl alcohol promoieties and/or coupling partners. For example, trialkylsilyl or mixed alkylarylsilyl-protected derivatives can be selectively cleaved using fluoride-containing agents such as tetrabutylammonium fluoride (TBAF), potassium fluoride (KF), ammonium fluoride ($H_4NF$), and hydrogen fluoride (HF); or using hydrogen fluoride complexes with organic bases such as triethylamine trihydrofluoride ($Et_3N.3HF$) or pyridinium hydrofluoride; in an inert solvent such as tetrahydrofuran (THF); at a temperature from about 0° C. to about 100° C. to provide the corresponding desilylated alkyl 2,2-dialkyl 3-hydroxy propanoate 16.

As shown in Scheme 7, heteroatom-protected intermediate 18 can be synthesized from an appropriately functionalized 3-hydroxy propanoic acid derivative such as 2-amino-3-hydroxy-2-methylpropanoic acid 17. Standard esterification methods, e.g., anhydrous methanol (MeOH) in the presence of a catalytic amount of an acidic catalyst such as thionyl chloride ($SOCl_2$), sulfuryl chloride ($SO_2Cl_2$), concentrated sulfuric acid ($H_2SO_4$), or trimethylsilyl chloride (TMSCl); or a sulfonic acid derivative such as para-toluene sulfonic acid (TsOH) or camphor sulfonic acid (CSA); at a temperature from about 0° C. to about 100° C. can be used to provide the corresponding protected methyl ester. As shown in Scheme 7, Step 2, methyl 2-amino-3-hydroxy-2-methylpropanate can be reacted with di-tert-butylpyrocarbonate ($Boc_2O$) in the presence of a base to provide the corresponding N-Boc protected methyl 2-amino-3-hydroxy-2-methylpropanate 18. Examples of useful solvents for the reaction shown in Scheme 7, step 2, include a mixture of a 1N aqueous solution of sodium hydroxide (NaOH) and 1,4-dioxane, a saturated aqueous solution of sodium bicarbonate ($NaHCO_3$) with acetonitrile as a co-solvent, dichloromethane (DCM), and a tertiary organic base, optionally in the presence of a catalyst. Examples of useful tertiary organic bases include triethylamine (TEA) and a catalytic amount of 4-(N,N-dimethylamino)pyridine (DMAP).

Scheme 7

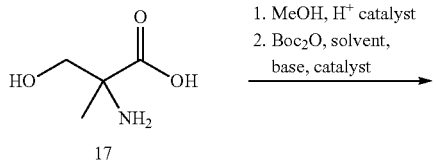

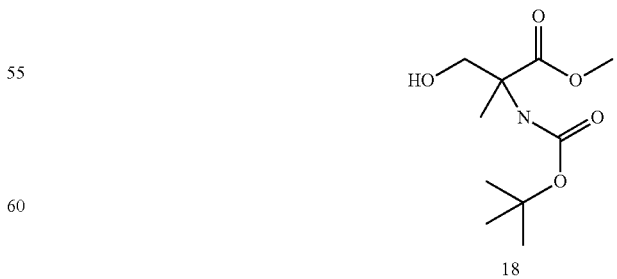

Scheme 8 shows the synthesis of alkyl- or aryl-2,2-alkoxy 3-hydroxy propanoate 20 as a functionalized neopentyl promoiety where $R^1$ is as defined herein and $R^c$ and $R^d$ are independently alkyl or $R^c$ and $R^d$ are linked by an alkyl to form a heteroalkyl ring. In certain embodiments where each of $R^c$ and $R^b$ is ethyl (Et), and $R^1$ is ethyl (Et) or benzyl (Bn), the starting material is the corresponding acrylic acid derivative 19. The carbon-carbon double bond of an acrylic acid ester such as an ethyl acrylate or benzyl acrylate can be dihydroxylated to obtain the corresponding alkyl glycerate using oxidation agents such as potassium permanganate ($KMnO_4$) in a solvent such as acetone and water, at a temperature from about −78° C. to about 60° C. Methods for the oxidative transformation of alkenes into vicinal diols are known in the art.

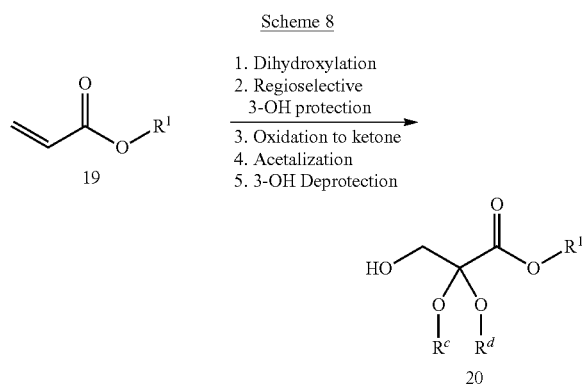

Scheme 8

1. Dihydroxylation
2. Regioselective 3-OH protection
3. Oxidation to ketone
4. Acetalization
5. 3-OH Deprotection The primary hydroxyl group of an alkyl glycerate can be selectively protected by reacting the alkyl glycerate with a bulky trialkyl chlorosilane such as tert-butyl dimethylsilylchlorosilane (TBDMSCl), triisopropylchlorosilane (TIPSCl), tert-butyl diphenylsilylchlorosilane (TBDPSCl), in an inert solvent such as dichloromethane (DCM), tetrahydrofuran (THF), or N,N-dimethylformamide (DMF), in the presence of an organic base such as imidazole or triethylamine ($Et_3N$, TEA), optionally in the presence of a catalytic amount of a nucleophilic catalyst such 4-(N,N-dimethyl)aminopyridine (DMAP) at a temperature from about 0° C. to about 60° C.

Methods for oxidizing secondary hydroxyl groups to oxo groups, i.e. ketones, are well known. For example, the 2-hydroxyl group of tris alkylsilyl- or mixed alkyl-arylsilyl-protected alkyl glycerate can be oxidized to provide the corresponding alkyl 2-oxo 3-silyoxy propanoate using 1,1,1-tris (acetyloxy)-1,1-dihydro-1,2-benziodoxol-3-(1H)-one (Dess-Martin periodinane) in a inert solvent such as dichloromethane (DCM) at a temperature from about −20° C. to about 25° C.

In certain embodiments of Scheme 8, alkyl 2,2-dialkoxy 3-trialkylsilyloxy propanoates are provided. Formation of ketals from oxo-compounds, i.e. ketones, is well known. For example, an alkyl 2-oxo 3-trialkylsilyoxy propanoate can be reacted with an excess of alcohol such as ethanol (EtOH) or an appropriately functionalized diol such as ethylene glycol; or with a suitable transacetalization reagent such as a trialkyl orthoformate, i.e. triethyl orthoformate, either in the neat form or in the presence of an inert solvent and a catalyst such as concentrated sulfuric acid ($H_2SO_4$), pyridinium para-toluene sulfonate (PPTS), para-toluene sulfonate (TsOH), or camphorsulfonic acid (CSA); at a temperature from about −20° C. to about 100° C. Alternatively, when alcohols are used, the reaction can be carried out by azeotropic removal of water generated during the reaction.

Reaction of an alkyl 2,2-dialkoxy 3-silyoxy propanoate with reagents capable of selectively cleaving the 3-silyl protecting group provide alkyl 2,2-dialkoxy 3-hydroxy propanoate 20 that is a useful neopentyl alcohol promoiety or coupling partner. For example, reacting an alkyl 2,2-dialkoxy 3-trialkylsilyoxy propanoate with an acid in a solvent at a temperature from about 0° C. to about 100° C. provides the corresponding desilylated alkyl 2,2-dialkoxy 3-hydroxy propanoate 20. Examples of useful acid and solvent mixtures for the reaction include mixtures of acetic acid (HOAc), water, and tetrahydrofuran (THF); and concentrated hydrochloric acid (HCl) in ethanol (EtOH). Alternatively, fluoride-containing agents can be used.

As shown in Scheme 9 (wherein n, $R^2$, $R^3$, and $R^4$ are as defined herein; X is halogen such as chloro; Y is hydrogen, alkoxy; and Q is a NHAc or a precursor to an amine), an activated sulfonic acid derivative such as a sulfonyl chloride of a drug having at least one sulfonic acid group 21, e.g., acamprosate chloride, or alternatively, a similarly activated sulfonic acid derivative of a precursor of a drug having at least one sulfonic acid group can be reacted with a functionalized and externally masked neopentyl alcohol 22 to provide externally masked neopentyl acamprosate prodrugs (neopentyl sulfonyl esters) or precursors or intermediates to such prodrugs 23. Examples of externally masked nucleophile 22 include functionalized 2,2-bis-substituted 3-hydroxy propanoic acid derivatives, such as esters.

Scheme 9

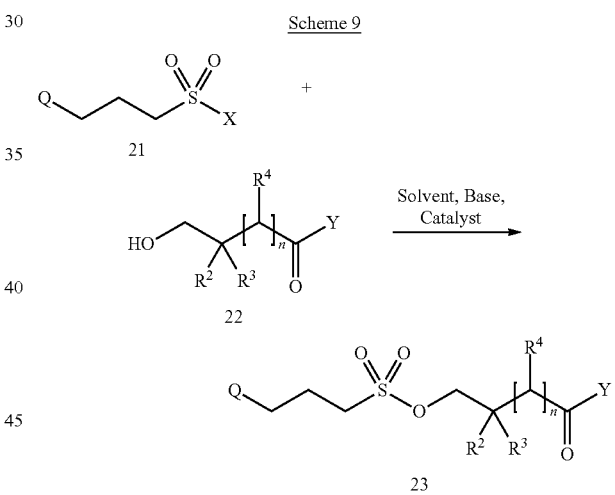

Referring to Scheme 9, when n is 0, a neopentyl promoiety 22 can be a functionalized 2,2-bis-substituted 3-hydroxy propanoic acid ester where Y is —$OR^1$, X is chlorine, Q is N-acetylamino (NHAc), and $R^2$, $R^3$, and $R^4$ are defined herein, and the activated sulfonic acid derivative is 3-(N-acetyl)propylsulfonyl chloride (acamprosate chloride) 21. Neopentyl alcohol 22 can be reacted with 3-(N-acetyl)propylsulfonyl chloride 21 in a solvent such as dichloromethane (DCM) in the presence of a base such as triethylamine ($Et_3N$, TEA), pyridine, or diisopropyl ethyl amine ($iPr_2EtN$, DIEA); and a nucleophilic catalyst such as 4-(N,N-dimethyl)pyridine (DMAP); at a temperature from about −20° C. to about 25° C. to provide the corresponding internally masked neopentyl sulfonyl ester 23.

When Q is N-acetylamino (NHAc), $R^2$ and $R^3$ are independently chosen from methyl and tert-butoxycarbonylamino (NHBoc), Y is methoxy, and n is 0 in Scheme 9, as shown in Scheme 10 the corresponding N-unprotected derivative of neopentyl sulfonylester acamprosate prodrug 25 can be prepared by reacting a N-Boc-protected neopentyl sulfonyl ester derivative 24 with a strong acid in an inert solvent such as trifluoroacetic acid in dichloromethane (DCM) or hydrogen chloride (HCl) in 1,4-dioxane. In the reaction the tert-butoxycarbonyl (Boc) protecting group can be cleaved to provide the corresponding unprotected species in either free amine or in N-protonated form, i.e. ammonium salt, where G is chosen from $NH_2$, $NH_3^+Cl^-$, and $NH_3^+F_3CCO_2^-$.

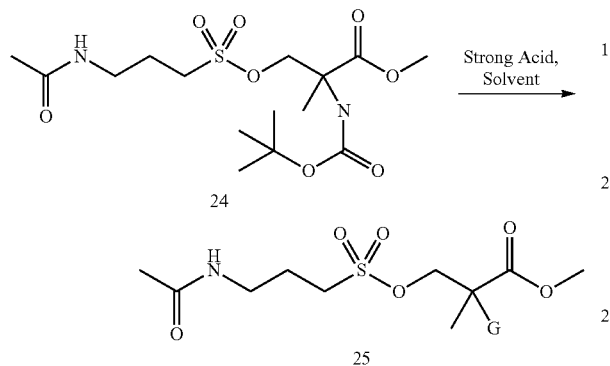

As shown in Scheme 11, and also referring to Scheme 9, when Q is N-acetylamino (NHAc), each of $R^2$ and $R^3$ is methyl, Y is benzoyloxy, i.e., phenylmethoxy, and n is 0; the free acid 27 of the corresponding benzyl hydroxypivalic acid conjugate 26 can be obtained by reacting the conjugate with hydrogen in the presence of a heterogeneous catalyst such as palladium on activated carbon, in a solvent such as methanol (MeOH), ethanol (EtOH), or ethyl acetate (EtOAc), at a temperature from about 0° C. to about 50° C. and under a pressure of about 15 psi to about 60 psi.

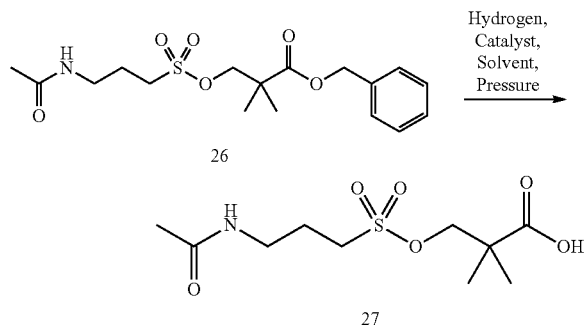

Examples of methods for synthesizing functionalized neopentyl promoieties, appropriately functionalized neopentyl alcohols, precursors, or derivatives thereof, such as suitably functionalized 2,2-bis-substituted ω-unsaturated alcohols that are useful as coupling partners are shown in the following schemes.

Scheme 12 (where $R^2$, $R^3$, and $R^4$ are as defined herein; $R^a$ is hydrogen; $R^b$ is hydrogen, alkyl, alkoxy, amide, substituted carbonyl or aryl; and A is hydrogen, hydroxyl, or alkoxy) shows the synthesis of 3,3-bis-substituted 4-hydroxy butanoic acid (corresponding to n is 1 in compound 20) and 4,4-bis-substituted 5-hydroxy pentanoic acid promoieties (corresponding to n is 2 in compound 20). The synthetic method illustrated in Scheme 12 is extendable to homologs such as 5,5-bis-substituted 6-hydroxy hexanoic acids. Conjugates based on 3,3-bis-substituted 4-hydroxy butanoic acid and 4,4-bis-substituted 5-hydroxy pentanoic acid precursor 29 can be derivatized after coupling to a sulfonyl group of a drug or a precursor of a drug having at least one sulfonic acid group to provide the corresponding neopentyl sulfonyl ester prodrug. In certain embodiments, where each of $R^2$ and $R^3$ is methyl, $R^4$ is hydrogen, and n is either 1 or 2, the starting material 28 can be chosen from 2,2-dimethyl-4-pentenoic acid, methyl 2,2-dimethyl-4-pentenoic acid, 2,2-dimethyl-4-pentenal, and 2,2-dimethyl-5-hexenoic acid.

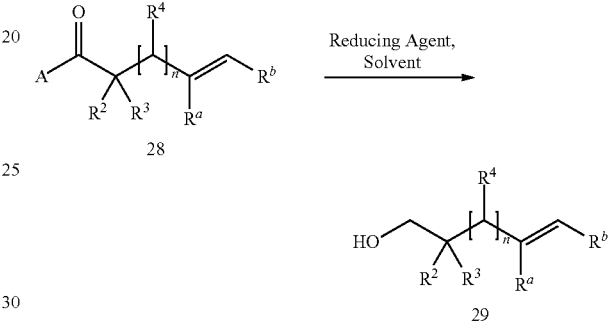

For example, referring to Scheme 12, in certain embodiments, A is lower alkoxy such as methoxy, hydroxyl, or hydrogen; each of $R^2$ and $R^3$ is methyl, $R^4$, each of $R^a$ and $R^b$ is hydrogen; and n is 1 or 2. Using standard synthetic methods, 2,2-dimethyl-4-pentenoic acid, its lower alkyl ester (A is OH or O-lower alkyl), or 2,2-dimethyl-5-hexenoic acid can be converted to the corresponding alcohol 29 by reaction with reducing agents such as lithium aluminum hydride (LiAlH$_4$, LAH); in an anhydrous inert solvent such as tetrahydrofuran (THF) or diethyl ether (Et$_2$O); at a temperature from about −78° C. to about 65° C. Alternatively, the reaction can be carried out using LiBH$_4$ in an inert solvent such as tetrahydrofuran, at a temperature from about 0° C. to about 25° C. Aldehydes 28, e.g., A is H, and n is 1, can be reduced to the corresponding alcohol 29 using boron hydride reagents such as alkali borohydrides, e.g., NaBH$_4$, in an alcohol solvent such as methanol (MeOH) or ethanol (EtOH).

Activated sulfonic acid derivatives such as a sulfonyl chloride of a drug or precursor of a drug having at least one sulfonic acid group 30, e.g. acamprosate chloride, can be reacted with a functionalized coupling partner to provide useful intermediates for preparing externally masked neopentyl sulfonyl ester prodrugs 32 as disclosed herein. Examples of coupling partners include functionalized 2,2-bis-substituted ω-unsaturated alcohols 31.

Referring to Scheme 13 (where n, $R^2$, $R^3$, and $R^4$ are as defined herein; $R^a$ is hydrogen, $R^b$ is hydroxy, alkyl, or an aromatic, X is halogen, and Q is an amine precursor), in certain embodiments where n is 1 or 2, and the corresponding neopentyl promoieties are functionalized 2,2-bis-substituted ω-unsaturated alcohols 31 wherein X is chlorine, and Q is N-acetylamino (NHAc), and the activated sulfonic acid derivative is 3-(N-acetyl)propylsulfonyl chloride (acamprosate chloride) 30. Functionalized 2,2-bis-substituted ω-unsaturated alcohol 31 can be reacted with 3-(N-acetyl)propylsulfonyl chloride (acamprosate chloride) 30 in a solvent such as dichloromethane (DCM) in the presence of a base such as triethylamine (Et$_3$N, TEA), pyridine, or diisopropyl ethyl amine (iPr$_2$EtN, DIEA) and a nucleophilic catalyst such as 4-(N,N-dimethyl)pyridine (DMAP) at a temperature from about −20° C. to about 25° C. to provide precursor or intermediate 32 to externally masked neopentyl sulfonyl esters.

Scheme 13

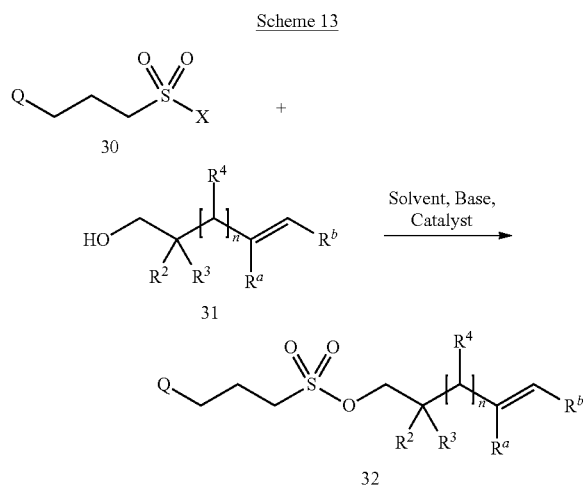

As shown in Scheme 14, terminally unsaturated sulfonyl ester coupling intermediates 33 can then be converted to carboxylic acid ester sulfonyl ester intermediates 35 such as ester or amide derivatives. Scheme 14 shows a method for converting the terminal carbon-carbon double bond to a one carbon shortened ester derivative. Other methods for the oxidative transformation of alkenes into aldehydes or carboxylic acid derivatives are described in the art.

Scheme 14

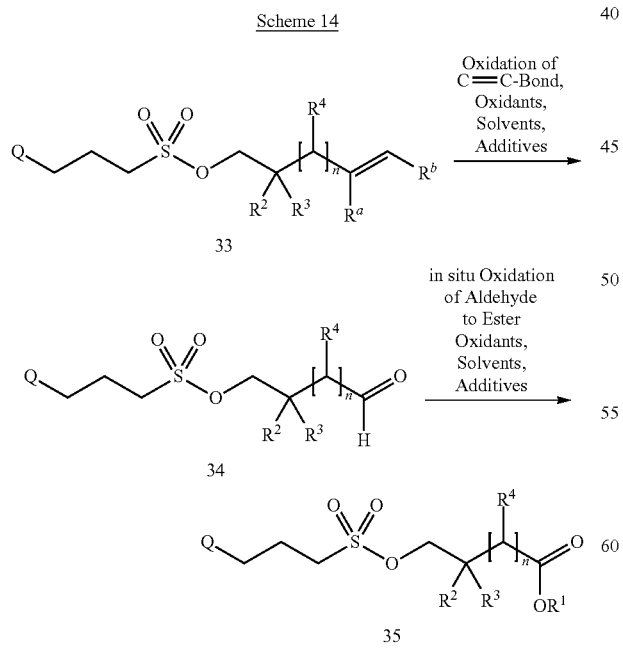

In certain embodiments of Scheme 14, Q is N-acetylamino (NHAc), each of R$^2$ and R$^3$ is methyl, R$^4$ is hydrogen, each of R$^a$ and R$^b$ is hydrogen, and n is 1 or 2. Oxidative cleavage of the terminal carbon-carbon double bond of alkene 33 by ozonolysis using a gaseous mixture of oxygen and ozone (O$_2$/O$_3$) in a solvent such as dichloromethane (DCM) or DCM/alcohol mixtures, i.e., DCM/MeOH=9:1-5:1, at a temperature of about −78° C. followed by reductive decomposition of the intermediate ozonide with a reducing agent such as dimethyl sulfide (Me$_2$S), triphenylphosphine (Ph$_3$P), or tributylphosphine (Bu$_3$P), provides intermediate one-carbon shortened aldehyde derivative 34. Alternatively, aldehyde derivative 34 can be prepared by oxidation methods using sodium meta-periodate (NaIO$_4$)/catalytic osmium tetroxide (OsO$_4$) (Lemineux-Johnson reagent) in a mixture of solvents such as tetrahydrofuran (THF) and water at a temperature from about 0° C. to about 40° C. Other oxidation methods such as the ruthenium-catalyzed oxidative cleavage of olefins to aldehydes can also be useful in preparing aldehyde precursors from unsaturated compounds 33 (Yang, et al., *J. Org. Chem.* 2001, 66, 4814).

Aldehyde 34 can be converted to the corresponding carboxylic acid ester under oxidative reaction conditions to provide externally masked neopentyl prodrugs that are based on functionalized (n-1),(n-1)-bis-substituted n-hydroxy alkanoic acids such as 3,3 bis-substituted 4-hydroxy butanoic acid or 4,4-bis-substituted 5-hydroxy pentanoic acid promoieties. For example, contacting aldehyde 34 with an oxidant such as N-iodosuccinimide (NIS); in the presence of an inorganic base such as alkali carbonate, e.g., K$_2$CO$_3$; in a solvent such as methanol or acetonitrile containing an excess of an alcohol; at a temperature from about 0° C. to about 40° C. and in the dark, provides the corresponding carboxylic acid ester as acamprosate prodrug 35 in a single step. Other oxidant systems that can be used in this transformation include Oxone® in an alcohol solvent, bromine or iodine (Br$_2$, I$_2$), N-bromosuccinimide (NBS)/2,2'-azobis(2-methylpropionitrile (AIBN), pyridinium dichromate (PDC), and manganese dioxide (MnO$_2$)/hydrogen cyanide (HCN).

When P is oxygen in Scheme 15 (where n, R$^1$, R$^2$, R$^3$, and R$^4$ are as defined herein, Q is NHAc or an amine precursor, R$^a$ is hydrogen (see Scheme 14), aldehyde derivative 36 can be oxidized to the corresponding free carboxylic acid derivative 37 using standard procedures. For example, Jones-oxidation of aldehyde 36 with excess chromic acid (H$_2$CrO$_4$) in a solvent such as acetone or a water/acetone mixture at a temperature from about −10° C. to about 40° C. provides the corresponding carboxylic acid 37. The oxidant Oxone® can also be used to oxidize aldehydes to carboxylic acids in solvents such as N,N-dimethylformamide (DMF) and at a temperature from about 0° C. to about 25° C. Other oxidation systems, for example transition metal-based systems comprising a co-oxidant and an oxidation catalyst can also be used and are well known in the art.

Scheme 15

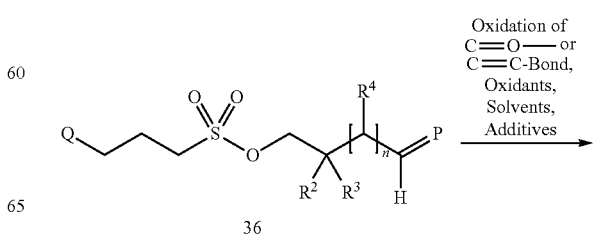

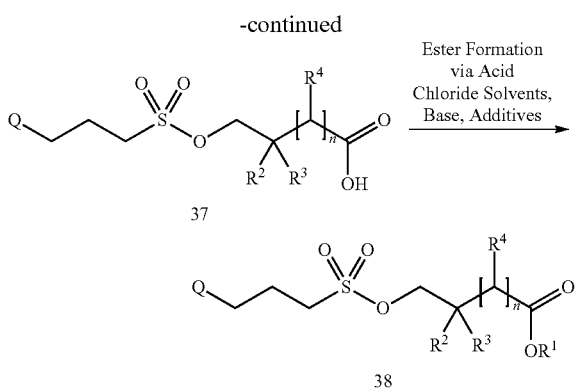

When P in Scheme 15 is =CHR$^b$ where R$^b$ is chosen from hydrogen; and n is 0, 1, or 2, using methods described by Henry, et al., *J. Org. Chem.* 1993, 58, 4745; and Travis, et al., *Org. Lett.* 2003, 5, 1031, the corresponding carboxylic acid intermediate 37 can be prepared by direct oxidation of unsaturated precursor 36 with oxidation mixtures such as chromic acid ($H_2CrO_4$, Jones-reagent) or Oxone® ($2HKSO_5 \cdot KHSO_4 \cdot K_2SO_4$) in the presence of a catalytic amount of osmiumtetroxide ($OsO_4$) in a solvent such acetone or N,N-dimethylformamide (DMF) at a temperature from about 0° C. to about 40° C. Other methods for effecting this transformation use systems comprising transition metal oxidation catalysts based on ruthenium, chromium, or tungsten in the presence of co-oxidants such as bleach (NaOCl) or sodium periodate ($NaIO_4$).

Carboxylic acids are useful precursors for preparing the corresponding carboxylic acid esters or amides of externally masked neopentyl prodrugs based on suitably functionalized 3,3-bis-substituted 4-hydroxy butanoic acid or 4,4-bis-substituted 5-hydroxy pentanoic acids. For example, referring to Scheme 15, carboxylic acids can be activated in situ to provide the corresponding acid chloride by reacting carboxylic acid 37 with an activating agent such as oxalyl chloride (($COCl)_2$) or thionyl chloride ($SOCl_2$) in a solvent such as the chlorination agent itself (neat) or an inert solvent such as dichloromethane (DCM); optionally in the presence of a catalyst such as a catalytic amount of N,N-dimethylformamide (DMF) at a temperature from about 0° C. to about 25° C. The acid chloride can then be quenched with an excess of a functionalized alcohol such as methanol (MeOH) or benzylic alcohol (BnOH) or other suitable alcohol or amine in the presence of a base such as pyridine, triethylamine ($Et_3N$, TEA), or diisopropylethylamine ($iPr_2EtN$, DIEA), in an inert solvent such as dichloromethane (DCM); at a temperature from about 0° C. to about 25° C. to provide the corresponding externally masked neopentyl prodrug 38, e.g., an acamprosate prodrug based on a functionalized 3,3-bis-substituted 4-hydroxy butanoic acid or 4,4-bis-substituted 5-hydroxy pentanoic acid.

Carboxylic acid derivatives may be activated using, for example, any of the activation agents described herein, and the activated intermediates can subsequently be coupled to an alcohol or other functionalized substrate.

Methods for preparing functionalized 2,2-bis-substituted ω-unsaturated alcohols (functionalized neopentyl alcohols), or derivatives thereof, useful as coupling partners with an activated sulfonic acid, such as sulfonyl chlorides of a drug or a precursor of a drug having at least one sulfonic acid group are provided in Scheme 16 (where n, R$^1$, R$^2$, and R$^3$ are as defined herein, R$^b$ is an aromatic, X is hydrogen or alkoxy, and B is hydroxyl and hydrogen or oxygen). For example, in certain embodiments of Scheme 16, wherein each of R$^1$ and R$^2$ is methyl; n is 0; R$^3$ is absent; B is hydroxyl and hydrogen, or oxygen; the starting materials are either pantolactone or dihydro-4,4-dimethyl-2,3-furandione; R$^b$ is hydrogen; and X is hydrogen or methoxy, 3-O-protected 2,2-dimethylpent-4-en-1-ol 43 can be prepared from the starting materials using protocols or variations thereof according to Blakemore, et al., *J. Org. Chem.* 2005, 70, 5449; Mandel, et al., *Org. Lett.* 2004, 6, 4801; Shiina, et al., *Bull. Chem. Soc. Jpn.* 2001, 74, 113; Lavallée, et al., *Tetrahedron Lett.* 1986, 27, 679; or Ito et al., *Synthesis* 1993, 137.

Scheme 16

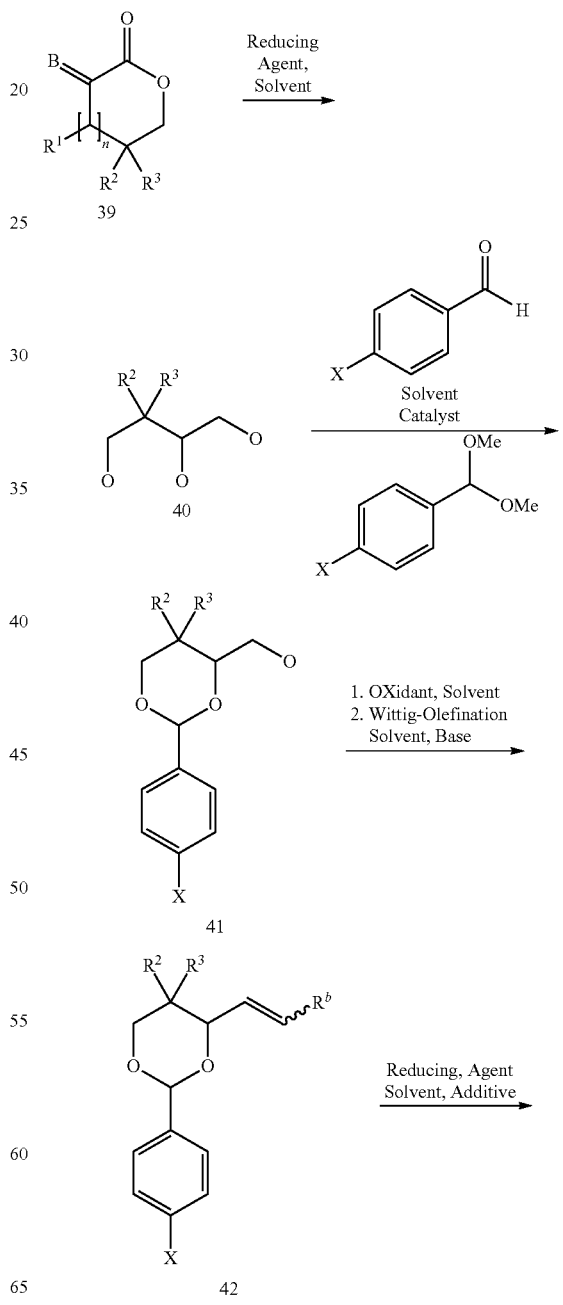

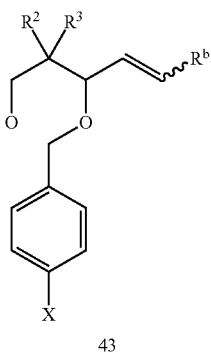

43

For example, pantolactone 39 where B is hydroxyl and hydrogen or dihydro-4,4-dimethyl-2,3-furandione 39 where B is oxygen can be converted to the corresponding 3,3-dimethylbutan-1,2,4-triol 40 by reaction with a reducing agent such as lithium aluminum hydride (LiAlH$_4$, LAH) in an anhydrous inert solvent such as tetrahydrofuran (THF) or diethyl ether (Et$_2$O), at a temperature from about −78° C. to about 65° C. Alternatively, excess borane dimethyl sulfide complex (BH$_3$.Me$_2$S) in the presence of a catalytic amount of sodium borohydride (NaBH$_4$) in an anhydrous inert solvent such as tetrahydrofuran (THF), at a temperature from about 0° C. to about 65° C. can be used for the reaction (Lavallée et al., *Tetrahedron Lett.* 1986, 27, 679-682; and Saito et al., *Chem. Lett.* 1984, 1389-1392). The reaction proceeds with conservation of stereochemical integrity (without racemization) when enantiomerically pure starting materials such as D-pantolactone are used.

Using methods described in the literature, triol 40 can be converted regioselectively to the corresponding 6-membered ring acetal (benzyliden-type acetal) under thermodynamic conditions using a suitable aldehyde derivative such as benzaldehyde (X is hydrogen), anisaldehyde (X is methoxy), benzaldehyde dimethyl acetal (X is hydrogen), or para-methoxybenzaldehyde dimethyl acetal (X is methoxy) in a solvent such as dichloromethane (DCM) or toluene; and in the presence of a catalyst such as phosphoryl chloride (POCl$_3$), camphorsulfonic acid (CSA), para-toluenesulfonic acid (TsOH), or pyridinium para-toluenesulfonate (PPTS), at a temperature from about 25° C. to about 110° C. The free hydroxyl group of the cyclic 1,3-acetal protected triol 41 can be oxidized to the corresponding aldehyde derivative using standard Swern-oxidation conditions such as dimethylsulfoxide (DMSO) in the presence of oxalyl chloride ((COCl)$_2$) and triethylamine (Et$_3$N, TEA) in dichloromethane (DCM) at a temperature of about −78° C. Alternatively, useful oxidants such a sulfur trioxide-pyridine complex (SO$_3$.Py) or pyridinium dichromate (PDC) (Cornforth reagent) in an inert solvent such as dichloromethane (DCM) at a temperature from about 0° C. to about 25° C. can be used. Another useful oxidant for this transformation is 1,1,1-tris(acetyloxy)-1,1-dihydro-1,2-benziodoxol-3-(1H)-one (Dess-Martin periodinane) in an inert solvent such as dichloromethane (DCM) at a temperature from about −20° C. to about 25° C.

Wittig-olefination or methylenation of the aldehyde derivative with an appropriately functionalized triphenylphosphoylide or methylenetriphenylphosphorane provides the corresponding alkene derivative 42. The functionalized phosphoylide or methylenetriphenylphosphorane can be generated in situ from the corresponding methyltriphenylphosphonium halide such as the bromide, in a solvent such as tetrahydrofuran (THF) using a base such n-butyllithium (n-BuLi) or potassium tert-butoxide (KOtBu) at a temperature from about −78° C. to about 25° C. Aldehydes and phosphoylides or phosphoranes are reacted in the same solvent at temperatures from about −78° C. to about 65° C. Mild and non-basic reaction conditions such as using alternative methylenation reagents in mixtures of solvents such as dichloromethane (DCM) and tetrahydrofuran (THF) at a temperature from about 0° C. to about 25° C. can also be used to convert aldehyde 41 to alkene 42. For example, methylenation reagents can be generated in situ from zinc dust (Zn), titanium(IV) halides such as titanium(IV) chloride (TiCl$_4$), and dihalomethanes such as dibromomethane (CH$_2$Br$_2$) in an inert organic solvents such tetrahydrofuran (THF) at temperatures from about −78° C. to about 0° C.

Using methods known to those skilled in the art, regioselective reductive ring opening of 1,3-benzylidene acetal 42 with dialkylaluminum hydride reagents such as diisobutylaluminum hydride (iBu$_2$AlH, DIBAL(H)) in an inert solvent such as dichloromethane (DCM) at temperatures from about −78° C. to about 25° C. provides the corresponding 3-O-protected 2,2-dimethylpent-4-en-1-ol derivative 43. Alternatively, regioselective reductive acetal ring opening can be accomplished using reducing agents generated from lithium aluminum hydride (LiAlH$_4$, LAH) and aluminum(III) chloride (AlCl$_3$) in an inert solvent such as diethyl ether (Et$_2$O), at temperature from about 0° C. to about 25° C.

Alternatively, as shown in Scheme 17 (where PG is a protecting group and R$^b$ is hydrogen, alkoxycarbonyl, or aryl) and using procedures or a variations thereof according to Mandel, et al., *Org. Lett.* 2004, 6, 4801; and Miyoka, et al., *Tetrahedron: Asymmetry* 1995, 6, 587, 3-O-benzylic-protected 2,2-dimethylpent-4-en-1-ol derivatives or 3-O-tert-butyldimethylsilyl protected 2,2-dimethylpent-4-en-1-ol derivatives can also be prepared from pantolactone 44 using a three step procedure. In certain embodiments of Scheme 17, PG is a protecting group such as benzyl, para-b methoxybenzyl, or tert-butyldimethylsilyl (TBDMS), and R$^b$ is hydrogen or methoxycarbonyl.

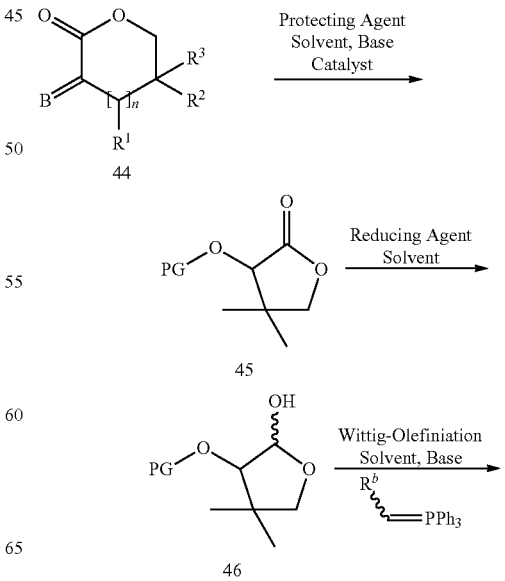

Scheme 17

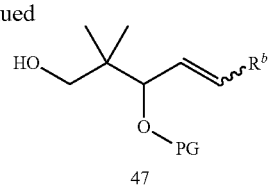

47

In certain embodiments, n is 0 and $R^1$ absent, each of $R^2$ and $R^3$ are methyl, B is hydroxyl and hydrogen and the starting material 44 is pantolactone. For example, under mildly basic conditions, the reaction of pantolactone 44 with benzyl bromide (BnBr) in the presence of silver(I) oxide ($Ag_2O$) in a solvent such as N,N-dimethylformamide (DMF) provides the corresponding O-benzyl-protected pantolactone 45. Other methods for introducing protecting groups into pantolactone are well known in the art and include basic conditions prone to partial racemization if the basicity of the reaction system is not controlled sufficiently. Examples include cesium carbonate promoted O-benzylation with benzyl chloride/cesium carbonate in dimethylformamide (DMF) at room temperature (Dueno et al., *Tetrahedron Lett.* 1999, 40, 1843); allylation with silver oxide/allyliodide in diethyl ether ($Et_2O$) (Aurich et al., *Liebigs Ann. Chem. Recueil* 1997, 2, 423); and alkali-metal hydrides, i.e., NaH or organic bases, i.e., diisopropyl-ethyl amine [$(iPr)_2EtN$, Hünigs-Base] with various alkylation agents (Pirrung et al., *Synthesis* 1995, 4, 458; Hart et al., *Heterocycles* 2000, 52(3), 1025; and Gimalova et al., *Russ. J. Org. Chem.* 2005, 41(8), 1183). The formation of the tetrahydropyranyl ether (Klar et al., *Synthesis* 2005, 2, 301) is acid catalyzed Using protocols or variations thereof according to O'Brien et al., *Tetrahedron Lett.* 2002, 43, 5491-5494; Weinges et al., *Chem. Ber.* 1994, 127, 1305-1309; Johnston et al., *J. Chem. Soc. Perkin Trans. I,* 2000, 5, 681-695; Iversen et al, *J. Chem. Soc. Chem. Commun.* 1981, 1240-1241; Wessel et al. *J. Chem. Soc. Perkin Trans. I,* 1985, 2247-2250; Enders et al., *Org. Syntheses* 2002, 78, 177-183; and Rai et al., *Tetrahedron Lett.* 2003, 44, 2267-2269, O-benzyl or O-para-methoxybenzyl protecting groups can be added to pantolactone 44 using functionalized acetimidates such as O-benzyl- or O-para-methoxybenzyl 2,2,2-trichloro acetimidates in the presence of a catalyst such triflic acid ($F_3CSO_3H$), a rare earth triflate such as scandium(III) triflate ($Sc(OTf)_3$), or others in solvent mixtures such as cyclohexane and dichloromethane (DCM), toluene, or acetonitrile (MeCN) at temperatures from about 0° C. to about 40° C. Other useful catalyst systems include Brønstedt-acids such as para-toluenesulfonic acid (TsOH), camphorsulphonic acid (CSA), trifluoroacetic acid (TFA), and Lewis-acids such as trifluoroborane diethyl ether complex ($BF_3.Et_2O$), trityl tetrafluoroborate ($TrBF_4$), trityl perchlorate ($TrClO_4$), trimethylsilyl trifluoromethanesulfonate (TMSOTf), or tin triflates ($Sn(OTf)_2$, under similar reaction conditions. When enantiopure starting material such as D-pantolactone is used, the reaction proceeds with conservation of stereochemical integrity (without racemization) of the stereogenic center.

Silicon-based protecting groups, such as mixed tris-alkyl or alkylaryl silyl-based protecting groups, i.e. tert-butyldimethyl silyl ($tBuMe_2Si$, TBDMS), or tert-butyldiphenyl silyl ($tBuPh_2Si$, TBDPS), also provide robust protection of the pantolactone hydroxyl group. For example, the free hydroxyl group of pantolactone 44 can be protected with tert-butyldimethyl chlorosilane ($tBuMe_2SiCl$, TBDMSCl) using an inert solvent such as dichloromethane (DCM) or N,N-dimethylformamide (DMF) and an organic base such as imidazole or triethylamine ($Et_3N$, TEA), optionally in the presence of additives such as catalytic amounts of nucleophilic alkylation catalysts such as 4-(N,N-dimethyl)aminopyridine (DMAP) at a temperature from about 0° C. to about 60° C. to provide the corresponding silyl protected pantolactone 45. When enantiopure starting material such as D-pantolactone is used, the reaction proceeds with conservation of stereochemical integrity (without racemization) of the stereogenic center.

Reduction of O-benzyl- or O-silyl-protected lactone 45 with dialkylaluminum hydride reducing reagents such as diisobutylaluminum hydride [$iBu_2AlH$, DIBAL(H)] in an inert solvent such as tetrahydrofuran (THF) at temperatures from about −78° C. to about 0° C. provides intermediate lactol or hemiacetal 46 as a mixture of diastereomers or anomers.

Wittig-olefination of lactol or hemiacetal diastereomer 46 with functionalized triphenylphosphoylides or methylenetriphenylphosphorane ($R^b$ is H) or methyl (triphenylphosphoraneylidene)acetate ($R^b$ is $CO_2Me$) provides the corresponding (substituted) alkene derivative 47. Functionalized phosphoylides can be generated in situ from the corresponding methyltriphenylphosphonium bromide or (carbomethoxymethyl)triphenylphosphonium bromide in a solvent such as tetrahydrofuran (THF) in the presence of a base such n-butyllithium (nBuLi) or potassium tert-butoxide (KOtBu) at temperatures from about −78° C. to about 25° C. Lactols 46, phosphoylides, or phosphoranes can then be reacted either in the same solvent or in a separate solvent such as 1,2-dichloroethane (DCE) at temperatures from about 0° C. to about 70° C. to provide the corresponding 3-O-benzyl or 3-O-tert-butyldimethylsilyl protected 2,2-dimethylpent-4-en-1-ol compound 47. Olefination or methylenation of the lactol 46 can also be accomplished under a variety of Horner-Wadsworth-Emmons (HWE)-conditions with trimethyl phosphonoacetate (i.e., Banwell et al., *J. Chem. Soc., Perkin Trans.* 1, 2002, 22) and an excess of Tebbe's reagent [$Cp_2TiCH_2ClAl(CH_3)_2$] (Martin et al., *Tetrahedron Lett.* 2001, 42, 8373.

Determination of enantiomeric excess (e.e.) of intermediate 47 can be accomplished by $^1H$ NMR spectroscopy in the presence of the diamagnetic enantiomerically pure chiral co-solvent (R)-(−)-2,2,2-trifluoro-1-(9-anthryl)ethanol (Pirkle-alcohol) and in comparison with $^1H$ NMR spectra of the corresponding racemic samples under similar conditions or using other analytical method such as HPLC using chiral stationary phases or enantiopure covalent derivatization agents such as Mosher's chloride.

Referring to Scheme 18 (where $R^1$, $R^2$, and $R^3$ are as defined herein, $R^b$ is hydrogen, alkyl, alkoxycarbonyl, or an aromatic, PG is a protecting group, and X is halogen), activated sulfonic acid derivatives such as a sulfonyl chlorides of a drug having at least one sulfonic acid group 48, e.g. 3-chloropropylsulfonyl chloride, can be reacted with a functionalized protected 2,2-disubstituted pent-4-en-ol derivative 49 to provide masked acamprosate neopentyl sulfonyl ester intermediates. The intermediates can be converted to the desired 2,4-dihydroxy 3,3-dimethyl butanoic acid- or pantoic acid-based prodrug. Examples of functionalized protected 2,2-disubstituted pent-4-en-ol derivative 49 include 3-O-protected 2,2-dimethylpent-4-en-1-ol or derivative thereof.

Scheme 18

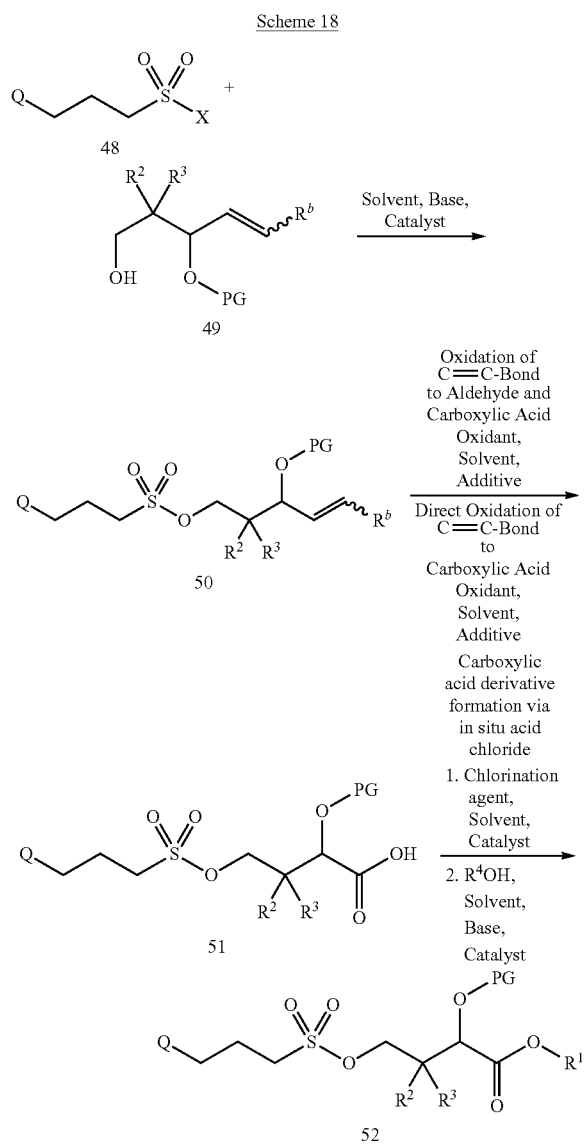

In certain embodiments of Scheme 18, the protected neopentyl alcohol 49 is a 3-O-protected 2,2-dimethylpent-4-en-1-ol or a derivative thereof, wherein each of $R^2$ and $R^3$ is methyl, $R^b$ is hydrogen or methoxycarbonyl, PG is benzyl, para-methoxybenzyl, or tert-butyl dimethylsilyl (TBDMS), X is chlorine, Q is NHAc, chlorine or 1,3-dioxobenzo[c]azolin-2-yl (phthalyl) and the activated sulfonic acid derivative 48 is either 3-chloropropylsulfonyl chloride, 2-[3-(chlorosulfonyl)propyl]benzo[c]azolin-1,3-dione, or N-[3-(chlorosulfonyl)propyl]acetamide. Functionalized 3-O-protected 2,2-dimethylpent-4-en-1-ol 49 or derivative thereof can be reacted with 3-chloropropylsulfonyl chloride or 2-[3-(chlorosulfonyl)propyl]benzo[c]azolin-1,3-dione in an inert solvent such as dichloromethane (DCM) in the presence of a base such as triethylamine ($Et_3N$, TEA), pyridine, or diisopropylethylamine ($iPr_2EtN$, DIEA) and a nucleophilic catalyst such as 4-(N,N-dimethyl)pyridine (DMAP) at a temperature from about −20° C. to about 25° C. to provide the corresponding neopentyl sulfonyl ester intermediate 50 as a precursor or intermediate to externally masked neopentyl sulfonyl ester prodrug 52.

The terminal alkene group of unsaturated neopentyl sulfonyl ester intermediate or coupling product 50 can be converted to a carboxylic acid derivative, such as an ester or amide derivative, to provide the corresponding functionalized externally masked neopentyl sulfonyl ester promoiety based on the pantoic acid scaffold. Methods for converting terminal carbon-carbon double bonds to ester derivatives are disclosed herein and shown in Scheme 18. Methods for the oxidative transformation of alkenes to aldehydes or carboxylic acid derivatives are also described in the art.

In certain embodiments of Scheme 18, each of $R^2$ and $R^3$ is methyl, $R^b$ is hydrogen or methoxycarbonyl, PG is benzyl, para-methoxybenzyl, or tert-butyl dimethylsilyl (TBDMD), X is chlorine, and Q is NHAc, chlorine, or 1,3-dioxobenzo[c]azolin-2-yl (phthalyl). Using synthetic methods and reaction conditions as previously described the terminal carbon-carbon double bond of alkene intermediate 50 can be oxidatively cleaved to provide the corresponding aldehyde. Using previously described methods and reaction conditions, aldehyde derivatives can be converted to the corresponding free carboxylic acid derivative 51 and subsequently converted to the corresponding carboxylic ester neopentyl intermediate 52.

Carboxylic acids are useful precursors for preparing the corresponding carboxylic acid esters of externally masked neopentyl sulfonyl ester intermediates or prodrugs based on functionalized (n-1),(n-1)-bis-substituted n-hydroxy alkanoic acids. Methods for preparing acyloxyalkyl ester derivatives, and alkoxy- or aryloxy-carbonyloxy ester derivatives 55 of (n-1),(n-1)-bis-substituted n-hydroxy alkanoic acid derivatives are shown in Scheme 19 where $R^2$, $R^3$, $R^4$, $R^5$, $R^6$, and PG are as defined herein, X is halogen such as chlorine or iodine, Y is oxygen or a bond, and Q is NHAc or an amine precursor. In certain embodiments each of $R^2$ and $R^3$ is methyl, $R^4$ is —OPG with PG is chosen from benzyl, para-methoxybenzyl, or tert-butyl dimethylsilyl (TBDMS), Y is oxygen, $R^5$ is isopropyl, ethyl, cyclohexyl, and $R^6$ is hydrogen, methyl or isopropyl.

Scheme 19

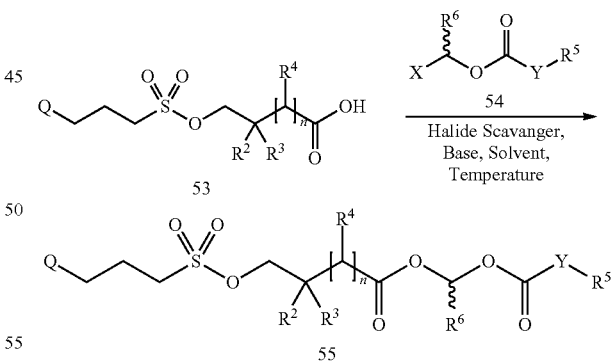

For example, chloromethyl carboxylates can be prepared from carboxylic acids using commercially available chloromethyl chlorosulfate in a biphasic mixture of dichloromethane (DCM) and aqueous sodium bicarbonate in the presence of a phase transfer catalyst such as tetra-n-butylammonium hydrogensulfate ($nBu_4NHSO_4$) at a temperature from about −20° C. to about 25° C. Alternative reaction conditions employ chloroiodomethane in the presence of a base such as triethylamine ($Et_3N$, TEA) in a suitable solvent such as N,N-dimethylformamide. Higher substituted 1-halogenoalkyl carboxylates can also be obtained from appropriately functionalized carboxylic acid chlorides and aldehydes in the presence of zinc(II) chloride either neat or in an inert solvent such as dichloromethane (DCM) at a temperature from about −20° C. to about 40° C. Furthermore, 1-halogenoalkyl alkyl- or aryl-carbonates 54 can be prepared from 1-halogenoalkyl chloroformates such as 1-chloroethyl chloroformate, and an alcohol in the presence of a base such as pyridine or triethylamine (Et$_3$N, TEA) in an inert solvent such as dichloromethane (DCM) at a temperature from about −20° C. to about 25° C.

Acyloxyalkyl ester derivatives or alkoxy- and aryloxycarbonyloxyoxy ester derivative 55 can be obtained by reacting carboxylic acid derivative 53 with a substituted 1-halogenoalkyl carboxylate, or a 1-halogenoalkyl alkyl- or aryl-carbonate 54 in the presence of a mild base and halide scavenger such silver(I) carbonate (Ag$_2$CO$_3$), silver(I) oxide (Ag$_2$O), mercury(II) oxide (HgO), or others, either in an inert organic solvent such as toluene, or optionally, neat at a temperature from about 0° C. to about 100° C.

Pantoic acid derived functionalized neopentyl sulfonyl ester intermediate 56 can be further modified to provide externally masked neopentyl sulfonyl ester prodrugs. Scheme 20 shows methods for converting the functional group Q of an acamprosate precursor to form a N-acetylamino (NHAc) functionality, where R$^1$ is as described herein, PG is a protecting group, and Q is an amine precursor. Depending on the nature of functional group Q, different synthetic methods can be used.

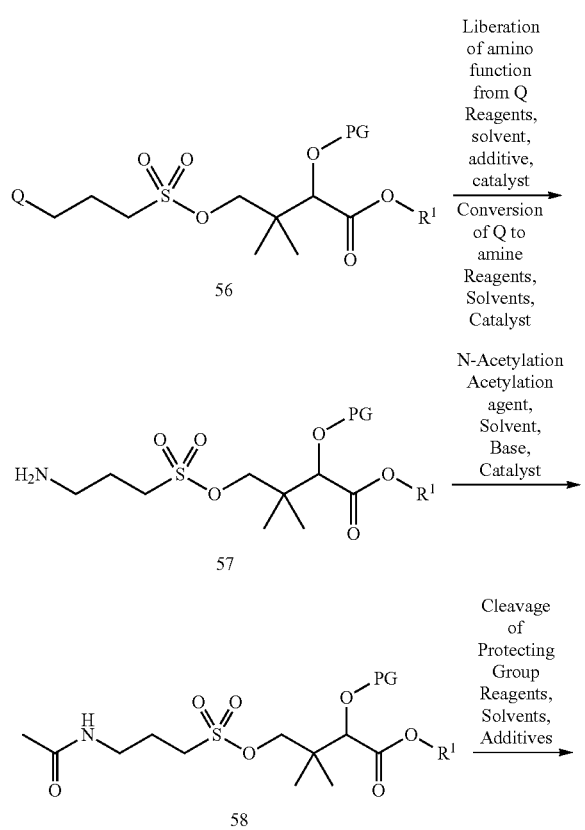

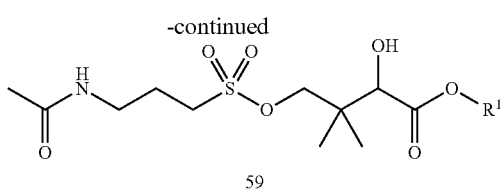

In certain embodiments of Scheme 20, R$^1$ is as defined herein, PG is benzyl or para-methoxybenzyl, and Q is chlorine or 1,3-dioxobenzo[c]azolin-2-yl (phthalyl). For example, when functional group Q of intermediate 56 is 1,3-dioxobenzo[c]azolin-2-yl (phthalyl), common synthetic protocols such as the Ing-Manske exchange procedure can be used to liberate the free amino group. When Q is 1,3-dioxobenzo[c]azolin-2-yl, externally masked neopentyl sulfonyl ester intermediate 56 can be reacted with an excess of hydrazine (H$_2$NNH$_2$) in a solvent such as ethyl acetate (EtOAc) and ethanol (EtOH) or mixtures thereof at temperatures from about 0° C. to about 60° C. to provide the corresponding free amine 57. Liberation of the free amine from phthalimide derivative 57 can also be accomplished by reacting with sodium sulfide (Na$_2$S) in aqueous tetrahydrofuran (THF) or acetone, sodium borohydride (NaBH$_4$)/acetic acid, or using acid or base catalyzed hydrolysis. Alternative useful and commonly used agents to deprotect phthalimide protecting groups include methylamine (MeNH$_2$) in ethanol (EtOH) or methanol (MeOH) at room temperature (Motawia et al., *Synthesis* 1989, 384; and Smith et al., *J. Am. Chem. Soc.* 1992, 114, 3134-3136), and n-butylamine (nBuNH$_2$) in methanol (MeOH) at reflux (Durette et al., *Tetrahedron Lett.* 1979, 42, 4013-4016).

Free amine 57 can be converted to the corresponding protected intermediate 58 by reaction with an acetylation agent such as acetic anhydride (Ac$_2$O) or acetyl chloride (AcCl) in a solvent such as dichloromethane (DCM), tetrahydrofuran (THF), or pyridine, optionally in the presence of a base such as pyridine, triethylamine (Et$_3$N, TEA), or diisopropylethylamine (iPr$_2$EtN, DIEA) and/or a nucleophilic acylation catalyst such 4-(N,N-dimethylaminopyridine (DMAP) at temperature from about −20° C. to about 40° C. to provide corresponding protected sulfonyl ester intermediate 58.

In certain embodiments of Scheme 20 where the functional group Q of intermediate 56 is chlorine, the chloro substituent can be converted to an N-acetyl functionality (Q is NHAc) using methods known in the art. For example, intermediate 56 can be reacted with a reagent capable of providing an azide-nucleophile such as sodium azide (NaN$_3$) or tetrabutylammonium azide (nBu$_4$NN$_3$), in a polar non-protic solvent such as anhydrous dimethyl sulfoxide (DMSO), anhydrous N,N-dimethylformamide (DMF), acetonitrile (H$_3$CCN), or mixtures thereof, at a temperature from about 0° C. to about 100° C., to provide the organic primary azide that can be isolated in pure form. Optionally, the azide can be used directly in the next step following aqueous work-up.

Primary azides (Q is N$_3$) can be converted to free amine intermediates that can be isolated in pure form as salts of mineral acids such as hydrogen chloride (HCl) or organic acids such as acetic acid (H$_3$CCO$_2$H) or trifluoroacetic acid (F$_3$CCO$_2$H), and the like. Appropriate reagents and reaction conditions for orthogonal and selective deprotection sequences and functional group interconversions can depend on the nature of the substituents and determined by those skilled in the art. In certain embodiments, where Q is azido, an azide-containing intermediate can be reacted with azide-reducing agents commonly used in similar chemical transformations. For example, azide reducing agents such as hydrogen (H$_2$) in the presence of a catalyst such a palladium on activated carbon, and a solvent such as methanol (MeOH), ethanol (EtOH), ethyl acetate (EtOAc), or mixtures of any of the foregoing under a pressure from about atmospheric pressure to about 100 psi at a temperature from about 0° C. to about 100° C. can be used.

Alternatively, the azide functionality can be reduced using metal salts such as stannous chloride (SnCl$_2$) in a protic solvent such as methanol (MeOH), at a temperature from about 0° C. to about 60° C., or, using aryl- or alkylphosphines such as triphenylphosphine (Ph$_3$P) or tributylphosphine (nBu$_3$P) in a solvent mixture such as tetrahydrofuran (THF) and water, at a temperature from about 0° C. to about 60° C. The corresponding amine intermediates 57 are provided in either free amine (Q is NH$_2$), or N-protonated, i.e. ammonium form (Q is NH$_3^+$), where the counter ion is Cl$^-$, H$_3$CCO$_2^-$, F$_3$CO$_2^-$, and the like.

Free amine 57 obtained from reduction of the azide may be directly converted to the corresponding N-acetyl derivative 58 by reacting with an acetylation agent such as acetic anhydride (Ac$_2$O) or acetyl chloride (AcCl) in a solvent such as dichloromethane (DCM), tetrahydrofuran (THF), or pyridine, optionally in the presence of a base such as pyridine, triethylamine (Et$_3$N, TEA), or diisopropylethylamine (iPr$_2$EtN, DIEA), and/or a nucleophilic acylation catalyst such 4-(N,N-dimethylaminopyridine (DMAP) at a temperature from about −20° C. to about 40° C. to provide the corresponding N-acetylated O-protected neopentyl sulfonyl ester prodrug 58 (Q is NHAc). In certain embodiments, acetylation agents, bases, and/or catalysts may be added during or immediately following the azide-reducing step.

In certain embodiments where PG is benzyl or para-methoxybenzyl and using hydrogenolysis conditions similar to those described herein, O-protecting groups can be cleaved simultaneously with the reduction of the azide-functionality to the corresponding amine to provide the free hydroxyl derivative. In embodiments where the O-deprotection is complete, selective N-acetylation with any of the aforementioned acetylation agents such as acetic anhydride (Ac$_2$O), acetyl chloride (AcCl) using similar reagents such as bases and/or catalysts as described herein may directly provide externally masked neopentyl sulfonyl ester acamprosate prodrugs 59 that incorporate the pantoic acid scaffold as a promoiety.

In certain embodiments of Scheme 20, where PG is benzyl or para-methoxybenzyl, O-protected externally masked neopentyl sulfonyl ester derivative 58 can be O-deprotected to generate the corresponding externally masked neopentyl sulfonyl ester acamprosate prodrug that incorporates the pantoic acid scaffold as a promoiety 59. The choice of reagents and reaction conditions will depend on the nature of the substituents. For example, in embodiments where PG is benzyl or para-methoxybenzyl, the reducing agent can be hydrogen (H$_2$), the catalyst can be palladium on activated carbon, and the solvent can be methanol (MeOH), ethanol (EtOH), or ethyl acetate (EtOAc), and reacted under a pressure from about atmospheric pressure to about 100 psi at a temperature from about 0° C. to about 100° C. In certain embodiments, the addition of a catalytic amount of an organic acid, i.e. acetic acid (HOAc), i.e mineral acids (HCl), or other acidic reagents may activate the catalyst system and facilitate the conversion rate for the transformation.

In certain embodiments of Scheme 20 where PG is para-methoxybenzyl, O-protected externally masked neopentyl sulfonyl ester derivative 58 may be O-deprotected using orthogonally applicable reagents and reaction conditions to provide the corresponding externally masked neopentyl sulfonyl ester prodrug 59. For example, reacting an O-protected externally masked neopentyl sulfonyl ester acamprosate prodrugs that incorporate the pantoic acid scaffold with an a excess of 2,3-dichloro-5,6-dicyano-1,4-benzoquinone (DDQ) in a mixture of solvents such as dichloromethane (DCM) at a temperature from about 0° C. to about 40° C. provides the corresponding externally masked neopentyl sulfonyl ester acamprosate prodrug containing the pantoic acid scaffold as a promoiety 58. Examples of additional reagents and reaction conditions for this transformation include ceric ammonium nitrate ((H$_4$N)$_2$Ce(NO$_3$)$_6$, CAN) and solvents such as water, dichloromethane, or acetonitrile.

Referring to Scheme 20, selective de-silylation of O-silyl-protected acamprosate prodrug 58 can be accomplished with methods well known in the art to provide acamprosate prodrug 59. For example, trialkylsilyl or mixed alkylarylsilyl-protected derivative 58 can be selectively deprotected using fluoride-containing agents such as tetrabutylammonium fluoride (TBAF), potassium fluoride (KF), ammonium fluoride (H$_4$NF), or hydrogen fluoride (HF); or using hydrogen fluoride complexes with organic bases such as triethylamine trihydrofluoride (Et$_3$N.3HF) or pyridinium hydrofluoride; in an inert solvent such as tetrahydrofuran (THF); at a temperature from about 0° C. to about 100° C. to provide the corresponding desilylated acamprosate prodrug 59

Alternative routes for preparing sulfonylester prodrugs, such as acamprosate prodrugs, from activated sulfonic acid intermediates are shown in Scheme 21. Functionalized 2,2-bis-substituted □-O-protected diol (functionalized neopentyl alcohols) 62, as functionalized coupling partners to activated sulfonic acid derivatives provide useful functionalized and protected neopentyl sulfonyl ester intermediates. The intermediates can be further modified to provide externally masked neopentyl sulfonyl ester prodrugs bearing functionalized (n-1),(n-1)-bis-substituted n-hydroxy alkanoic acid scaffolds in the promoiety and the parent alkananoic acid on which the prodrugs are based is either propanoic acid, butanoic acid, or pentanoic acid. R$^1$, R$^2$, R$^3$, R$^4$, Q, X, and PG are defined therein.

Scheme 21

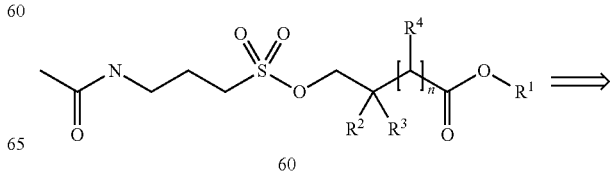

60

-continued

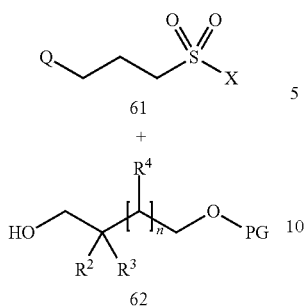

Referring to Scheme 22 (where n, $R^2$, $R^3$, $R^4$, Z, and PG are as defined herein), potentially useful starting materials and methods for preparing functionalized 2,2-bis-substituted ω-O-protected diol (functionalized neopentyl alcohol) 65 are useful as coupling partners with sulfonyl chlorides are either described in the art or will be readily apparent to those skilled in the art. Examples of useful protecting groups (PG) for functionalized 2,2-bis-substituted ω-O-protected diol 65 include benzyl or tris-alkylsilyls and mixed tris-alkyl-arylsilyls.

Scheme 22

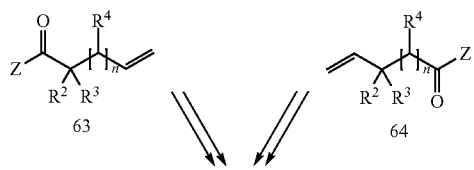

-continued

Activated sulfonic acid derivatives can be reacted with functionalized 2,2-bis-substituted ω-O-protected diol 65 to provide useful neopentyl sulfonyl ester intermediates. Referring to Scheme 23, in certain embodiments where each of $R^2$ and $R^3$ is methyl, $R^4$ is hydrogen, each of X and Q is chlorine, PG is benzyl, functionalized 2,2-bis-substituted ω-O-protected diol 68 is 2,2-dimethyl-5-benzylpentan-1-ol, and the activated sulfonic acid derivative 67 is 3-chloropropylsulfonyl chloride. Functionalized 2,2-bis-substituted ω-O-protected diol 68 can be reacted with 3-chloropropylsulfonyl chloride 67 using reaction conditions as described herein. The reaction can be carried out in an inert solvent such as dichloromethane (DCM) in the presence of a base such as triethylamine ($Et_3N$, TEA), pyridine, or diisopropylethylamine ($iPr_2EtN$, DIEA) and a nucleophilic catalyst such as 4-(N,N-dimethyl)pyridine (DMAP) at a temperature from about −20° C. to about 25° C. to provide the corresponding protected neopentyl sulfonyl ester intermediate 69.

Scheme 23

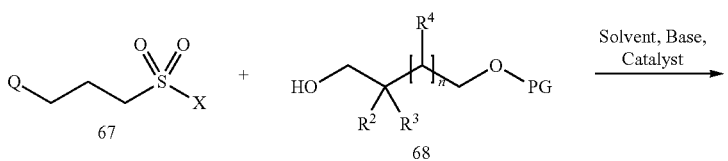

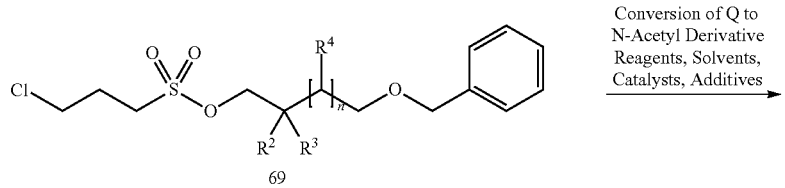

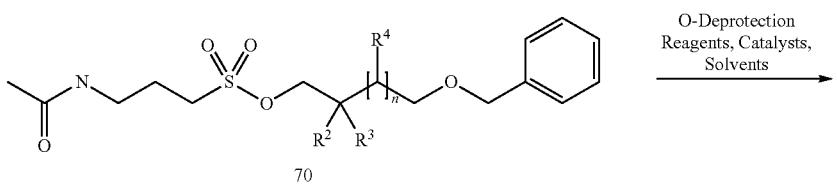

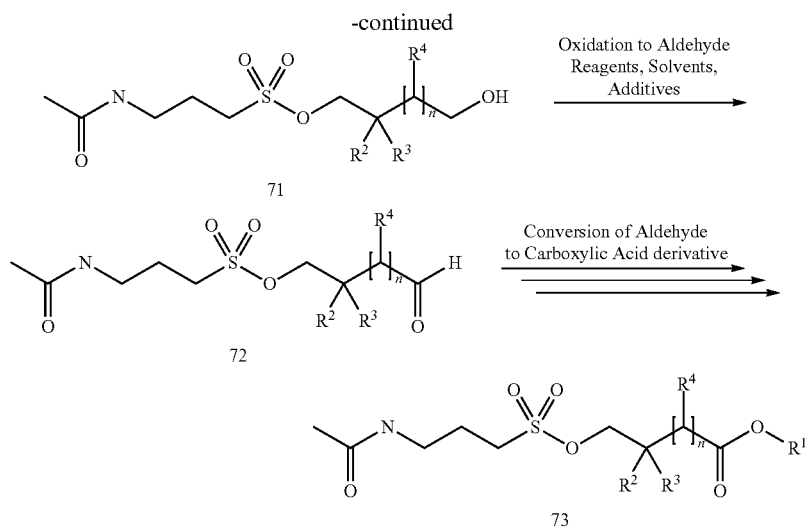

Protected neopentyl sulfonyl ester intermediate 69 can be derivatized after coupling to provide the externally masked neopentyl sulfonyl ester intermediate 70 or if a prodrug then 73. The chlorine group of intermediate 69 can be converted to the N-acetylamino (NHAc) using methods described herein followed by conversion of the protected hydroxyl group in the ω-position of the promoiety precursor to the corresponding carboxylic acid derivative 71 using methods described herein or known in the art.

In certain embodiments of Scheme 23, each of $R^2$ and $R^3$ is methyl, $R^4$ is hydrogen, m is 2, PG is benzyl, Q is chlorine, and neopentyl alcohol 68 can be derived from 2,2-dimethyl-glutaric anhydride. Briefly, neopentyl sulfonyl ester intermediate 69, where Q is chlorine, can be reacted with an azide-nucleophile such as sodium azide ($NaN_3$) or tetrabutylammonium azide ($nBu_4NN_3$), in a solvent such as dimethyl sulfoxide (DMSO), N,N-dimethylformamide (DMF), or acetonitrile ($H_3CCN$), at a temperature from about 0° C. to about 100° C., to provide the organic primary azide. Primary azides (Q is $N_3$) can be converted to the corresponding free amine intermediate that can be isolated in pure form as a salt of a mineral acid such as hydrogen chloride (HCl) or an organic acid such as acetic acid ($H_3CCO_2H$), trifluoroacetic acid ($F_3CCO_2H$), and the like. Reactants can include a reducing agent such as hydrogen ($H_2$), a catalyst such as palladium on activated carbon, and a solvent such as methanol (MeOH), ethanol (EtOH), or ethyl acetate (EtOAc) under a pressure from about atmospheric pressure to about 100 psi and at a temperature from about 0° C. to about 100° C. Other useful reducing agents and conditions include metal salts such as stannous chloride ($SnCl_2$) in a protic solvent such as methanol (MeOH), at a temperature from about 0° C. to about 60° C., or, alternatively, aryl- or alkyl-phosphines such as triphenylphosphine ($Ph_3P$) or tributylphosphine ($n-Bu_3P$) in a solvent mixture such as tetrahydrofuran (THF) and water, at a temperature from about 0° C. to about 60° C.

Free amines or salts thereof can be directly converted to the corresponding N-acetyl derivative 70 by reacting with an acetylation agent such as acetic anhydride ($Ac_2O$) or acetyl chloride (AcCl) in a solvent such as dichloromethane (DCM), tetrahydrofuran (THF), or pyridine, optionally in the presence of a base such as pyridine, triethylamine ($Et_3N$, TEA), or diisopropylethylamine ($iPr_2EtN$, DIEA), and/or a nucleophilic acylation catalyst such 4-(N,N-dimethylaminopyridine (DMAP) at a temperature from about −20° C. to about 40° C. to provide corresponding N-acetylated O-protected neopentyl sulfonyl ester intermediate 70 (Q is NHAc). In certain embodiments, acetylation agents, bases, and/or catalysts may be added directly during or immediately following the azido reducing step to provide corresponding N-acetylated O-protected neopentyl sulfonyl ester intermediate 70 (Q is NHAc).

In certain embodiments, where PG is benzyl or other benzylic protecting group, under hydrogenolysis conditions as described herein, O-protecting groups may be cleaved simultaneously with the reduction of the azide-functionality to provide the corresponding free hydroxyl derivative. In embodiments when O-deprotection is complete, selective N-acetylation with an acetylation agent provides the N-acetylated O-deprotected neopentyl sulfonyl ester intermediate 71 that can be further modified to provide neopentyl sulfonyl ester acamprosate prodrugs that incorporate the (n-1),(n-1)-bis-substituted n-hydroxy alkanoic acid scaffold as a promoiety.

In certain embodiments of Scheme 23, where PG is benzyl or other benzylic protecting group, N-acetylated O-deprotected neopentyl sulfonyl ester intermediate 71 can be prepared via hydrogenolysis of the protecting group using hydrogen ($H_2$) in the presence of a catalyst such a palladium on activated carbon in a solvent such as methanol (MeOH), ethanol (EtOH), or ethyl acetate (EtOAc) under a pressure from about atmospheric pressure to about 100 psi and at a temperature from about 0° C. to about 100° C. In certain embodiments, the addition of a catalytic amount of an organic acid such as acetic acid (HOAc), mineral acid such as hydrochloric acid (HCl), or other acid can be used to activate the catalyst system and facilitate the conversion rate for the transformation. In embodiments where PG is a tris-alkyl or mixed tris alkyl-arylsilyl protecting group, intermediate 70 can be contacted with a fluoride-containing desilylation agent such as tetrabutylammonium fluoride (TBAF), potassium fluoride (KF), ammonium fluoride ($H_4NF$), hydrogen fluoride (HF), or hydrogen fluoride complex in an organic base such as triethylamine trihydrofluoride ($Et_3N.3HF$) or pyridinium hydrofluoride, in an inert solvent such as tetrahydrofuran (THF) at a temperature from about 0° C. to about 100° C. to provide corresponding desilylated intermediate 71. Depending on the nature of PG, other reagents and reactions conditions can be used for the transformation.

Terminal hydroxyl groups of neopentyl sulfonyl ester intermediate 71 can be converted to aldehydes or carboxylic acids as functionalized building blocks for the preparation of externally masked neopentyl sulfonyl esters prodrugs based on (n-1),(n-1)-bis-substituted n-hydroxy alkanoic acid scaffolds. Methods for the oxidative transformation of primary alcohols into aldehydes or carboxylic acids are known to those skilled in the art.

In certain embodiments of Scheme 23, N-acetyl O-deprotected neopentyl sulfonyl ester intermediate 71 can be oxidized to the corresponding aldehyde 72 or directly to the corresponding carboxylic acid derivative 73. Methods for preparing aldehyde 72 include, for example, reaction with 1,1,1-tris(acetyloxy)-1,1-dihydro-1,2-benziodoxol-3-(1H)-one (Dess-Martin periodinane) in an inert solvent such as dichloromethane (DCM) at a temperature from about −20° C. to about 25° C. Standard Swern-oxidation conditions such as dimethylsulfoxide (DMSO) in the presence of oxalyl chloride ($(COCl)_2$) and triethylamine ($Et_3N$, TEA) in dichloromethane (DCM) at a temperature of about −78° C. can also be used. Alternatively, oxidants such a sulfur trioxide-pyridine complex ($SO_3.Py$) or pyridinium dichromate (PDC) (Cornforth reagent) in an inert solvent such as dichloromethane (DCM) at a temperature from about 0° C. to about 25° C. can be used. Methods for preparing free carboxylic acids include oxidation systems comprising transition metal oxidation catalysts based on ruthenium such as $RuCl_3$ in the presence of the co-oxidant sodium periodate ($NaIO_4$) in a mixture of acetonitrile/carbontetrachloride/water at a temperature from about 0° C. to about 40° C. Other useful ruthenium compounds include $RuO_2$ and $RuO_4$ under similar reaction conditions. In addition, high-valency chromium compounds such as chromium(VI), manganese(VII) compounds, or peroxytungsten compounds, optionally in the presence of a co-oxidant such as bleach (NaOCl) or others, can be used.

Phosphatases are important metabolic enzymes and are classified as phosphoric monoester hydrolases (phosphatases, E.C. 3.1.3., phosphoric diester hydrolases (phosphodiesterases, E.C. 3.1.4.), triphosphoric monoester hydrolases (E.C. 3.1.5.), diphosphoric monoester hydrolases (pyrophosphatases, E.C. 3.1.7.), and phosphoric ester trimester hydrolases (E.C. 3.1.8). Some of these enzymes are active in the de-phosphorylation reaction of xenobiotic organophosphorus compounds, including, for example, alkaline phosphatase, E.C. 3.1.3.1., and others. Phosphate conjugates of pharmaceutical interest are often monoesters. Enzymes believed to be able to dephosphorylate phosphate conjugates via hydrolysis or transphosphorylation include alkaline phosphatases and acid phosphatases. The de-phosphorylation reactions often proceed with high catalytic efficiency in vitro and also in vivo to provide the parent drug. Alkaline phosphatatase is a ubiquitous, extracellularly bound to membranes, and widely expressed non-specific esterase of phosphoric monoesters in mammals with an optimal pH for catalysis at about 8.0 and above. The enzyme is found particularly in the gastrointestinal tract, pancreas, liver, bile, placenta, and osteoplasts.

Incorporation of a phosphate group to has successfully overcome numerous drug delivery problems. Phosphate moieties can either be directly incorporated via a covalent bond to an alcoholic or phenolic hydroxyl group of a parent drug or prodrug (in form of a monoester) or via a chemical linker. Generally these phosphomonoester prodrugs are chemically very stable with long attractive shelf-lives. Introduction of a phosphate group into a xenobiotic often constructively influences a multitude of physiochemical and biological/pharmacokinetic parameters of a drug or prodrug including increasing the aqueous solubility, improving the parenteral dosing regime, and modulating specific pharmacokinetic parameters, i.e., half life ($t_{max}$), peak concentrations ($c_{max}$), or concentration time curves (AUCs).

Examples for phosphate ester prodrugs of alcohols and phenols include the gram-positive antibiotic clindamycin phosphate, the broad-spectrum antifungal fosfluconazole, the orally active human immunodeficiency virus (HIV) inhibitor fosamprenavir, the antineoplastic etoposide phosphate, and double prodrugs such as GPI 15715.

Methods for preparing phosphate conjugates of acamprosate prodrugs or derivatives thereof, with useful physiochemical, biological, or pharmacokinetic properties are provided in Scheme 24, where $R^1$, $R^2$ are defined herein, Y is oxygen or bond. For example and referring to Scheme 24, using methods well known in the art, the secondary hydroxyl group of acamprosate prodrugs 74, or any other hydroxyl group optionally incorporated in the $R^1$ and $R^2$ groups, can be phosphorylated with activated bis-O-protected phosphoric acid diester derivatives to provide the corresponding phosphorylated intermediate 75. The protecting groups of the phosphoric acid moiety are chosen in a way that the protecting groups in compound 75 can be removed orthogonally without affecting any of the additional functional groups to provide the free phosphate conjugate 76.

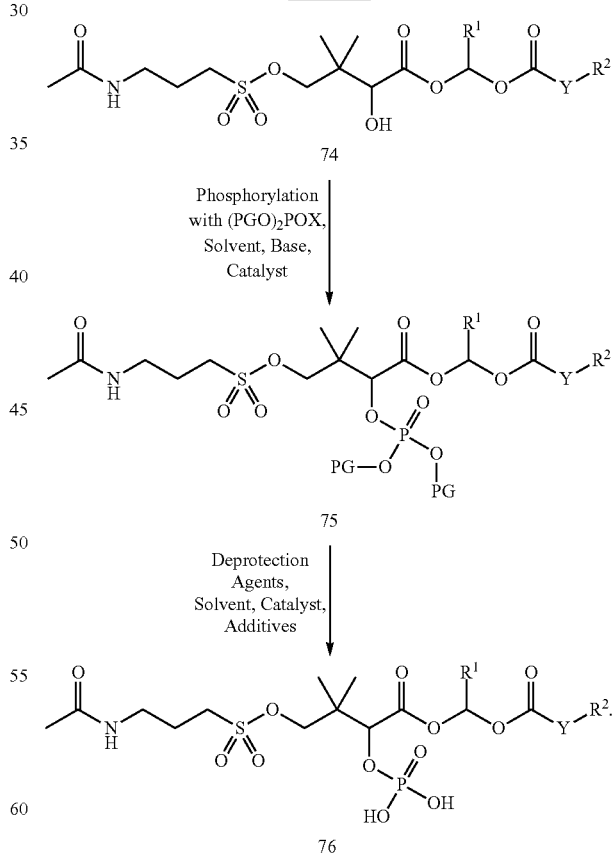

In certain embodiments of Scheme 24, where $R^1$ and $R^2$ are defined herein, Y is oxygen or bond, the free secondary hydroxyl group of acamprosate prodrug 74 can be reacted with protected and activated phosphorous acid derivatives such as commercially available diphenyl chlorophosphate (PhO)$_2$POCl, dibenzyl chlorophosphate (BnO)$_2$POCl, or di-tert-butyl chlorophosphate (tBuO)$_2$POCl) in a suitable solvent such as dichloromethane (DCM) and in the presence of suitable bases such as triethylamine (Et$_3$N, TEA), diisopropylethylamine [(iPr)$_2$EtN, DIEA, Hünigs-base], pyridine, and optionally in the presence of catalysts such 4-(N,N-dimethylamino)pyridine (DMAP) at a temperature from about 0° C. to about 40° C.

Referring to Scheme 24, intermediate 75 can be deprotected and converted the free phosphate monoesters of acamprosate prodrug 76 with methods known in the art where R$^1$ and R$^2$ are defined herein, Y is oxygen or bond. In certain embodiments, PG is phenyl and the phenyl groups are removed via hydrogenolysis under a hydrogen atmosphere format a pressure from about 1 atm to about 100 psi and at a temperature from about 0° C. to about 60° C. employing platinum(IV)-based heterogenous catalysts such as platinum (IV) oxide Pt(IV)O$_2$ or hydrates thereof, i.e. Pt(IV)O$_2$.H$_2$O, x~1) (Adam's catalysts) in suitable solvents such as methanol (MeOH), ethanol (EtOH), water, or mixtures thereof optionally in the presence of a trace amount of an acidic additive such as an organic acid, i.e. acetic acid (HOAc) or diluted mineral acid such as one molar (1.0 M) hydrochloric acid (HCl). If PG in compound 75 is chosen from Bn, then the heterogenous catalyst can also be palladium on activated carbon in a solvent such methanol (MeOH), ethyl acetate (EtOAc), mixtures thereof, or others (Scheme 24). If PG in compound 75 is optionally chosen from tBu then the protecting groups can be removed by contacting compounds 75 at temperatures from about 0° C. to about 40° C. with strong acids such as trifluoroacetic acid (TFA) in a suitable solvent such as dichloromethane (DCM) or, optionally, with hydrogen chloride (HCl) in 1,4-dioxane or diethyl ether (Et$_2$O).

Pharmaceutical Compositions

Pharmaceutical compositions provided by the present disclosure comprise a compound of Formula (I) together with a suitable amount of one or more pharmaceutically acceptable vehicles so as to provide a composition for proper administration to a patient. Examples of suitable pharmaceutical vehicles are known in the art.

Pharmaceutical compositions comprising a compound of Formula (I) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline form thereof and one or more pharmaceutically acceptable vehicles into formulations that can be used pharmaceutically. Proper formulation is dependent upon the route of administration chosen. In certain embodiments, a pharmaceutical composition comprising a compound of Formula (I) or crystalline form thereof may be formulated for oral administration, and in certain embodiments for sustained release oral administration. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of at least one compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage may be the same or different for each dose. One or more dosage forms may comprise a dose, which may be administered to a patient at a single point in time or during a time interval.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such oral compositions may be prepared in a manner known in the pharmaceutical art and comprise at least one compound of Formula (I) and at least one pharmaceutically acceptable vehicle. Oral pharmaceutical compositions may include a therapeutically effective amount of at least one compound of Formula (I) and a suitable amount of a pharmaceutically acceptable vehicle, so as to provide an appropriate form for administration to a patient.

Pharmaceutical compositions comprising at least one compound of Formula (I) may be formulated for immediate release for parenteral administration, oral administration, or for any other appropriate route of administration.

Controlled drug delivery systems may be designed to deliver a drug in such a way that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

In certain embodiments, an oral dosage form provided by the present disclosure may be a controlled release dosage form. Controlled delivery technologies can improve the absorption of a drug in a particular region or regions of the gastrointestinal tract.

The appropriate oral dosage form for a particular pharmaceutical composition provided by the present disclosure may depend, at least in part, on the gastrointestinal absorption properties of a compound of Formula (I), the stability of a compound of Formula (I) in the gastrointestinal tract, the pharmacokinetics of a compound of Formula (I), and the intended therapeutic profile. An appropriate controlled release oral dosage form may be selected for a particular compound of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

Gastric retention dosage forms, i.e., dosage forms that are designed to be retained in the stomach for a prolonged period of time, may increase the bioavailability of drugs that are most readily absorbed by the upper gastrointestinal tract. For example, certain compounds of Formula (I) may exhibit limited colonic absorption, and be absorbed primarily from the upper gastrointestinal tract. Thus, dosage forms that release a compound of Formula (I) in the upper gastrointestinal tract and/or retard transit of the dosage form through the upper gastrointestinal tract will tend to enhance the oral bioavailability of the compound of Formula (I). The residence time of a conventional dosage form in the stomach is about 1 to about 3 hours. After transiting the stomach, there is approximately a 3 to 5 hour window of bioavailability before the dosage form reaches the colon. However, if the dosage form is retained in the stomach, the drug may be released before it reaches the small intestine and will enter the intestine in solution in a state in which it can be more readily absorbed. Another use of gastric retention dosage forms is to improve the bioavailability of a drug that is unstable to the basic conditions of the intestine.

In certain embodiments, pharmaceutical compositions provided by the present disclosure may be practiced with dosage forms adapted to provide sustained release of a compound of Formula (I) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Sustained release oral dosage forms may be in any appropriate form for oral administration, such as, for example, in the form of tablets, pills, or granules. Granules can be filled into capsules, compressed into tablets, or included in a liquid suspension. Sustained release oral dosage forms may additionally include an exterior coating to provide, for example, acid protection, ease of swallowing, flavor, identification, and the like.

In certain embodiments, sustained release oral dosage forms may comprise a therapeutically effective amount of a compound of Formula (I) and at least one pharmaceutically acceptable vehicle. In certain embodiments, a sustained release oral dosage form may comprise less than a therapeutically effective amount of a compound of Formula (I) and a pharmaceutically effective vehicle. Multiple sustained release oral dosage forms, each dosage form comprising less than a therapeutically effective amount of a compound of Formula (I) may be administered at a single time or over a period of time to provide a therapeutically effective dose or regimen for treating a disease in a patient. In certain embodiments, a sustained release oral dosage form comprises more than one compound of Formula (I).

Sustained release oral dosage forms provided by the present disclosure can release a compound of Formula (I) from the dosage form to facilitate the ability of the compound of Formula (I) to be absorbed from an appropriate region of the gastrointestinal tract, for example, in the small intestine or in the colon. In certain embodiments, sustained release oral dosage forms may release a compound of Formula (I) from the dosage form over a period of at least about 4 hours, at least about 8 hours, at least about 12 hours, at least about 16 hours, at least about 20 hours, and in certain embodiments, at least about 24 hours. In certain embodiments, sustained release oral dosage forms may release a compound of Formula (I) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 24 hours; where wt % refers to the percent of the total weight of the compound in the dosage form. In certain embodiments, sustained release oral dosage forms may release a compound of Formula (I) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 20 hours. In certain embodiments, sustained release oral dosage forms may release a compound of Formula (I) from the dosage form in a delivery pattern corresponding to about 0 wt % to about 20 wt % in about 0 to about 2 hours; about 20 wt % to about 50 wt % in about 0 to about 4 hours; about 55 wt % to about 85 wt % in about 0 to about 7 hours; and about 80 wt % to about 100 wt % in about 0 to about 8 hours.

Sustained release oral dosage forms comprising a compound of Formula (I) may provide a concentration of the corresponding drug in the plasma, blood, cerebrospinal fluid, or tissue of a patient over time, following oral administration to the patient. The concentration profile of the drug may exhibit an AUC that is proportional to the dose of the corresponding compound of Formula (I).

Regardless of the specific type of controlled release oral dosage form used, a compound of Formula (I) may be released from an orally administered dosage form over a sufficient period of time to provide prolonged therapeutic concentrations of the compound of Formula (I) in the plasma and/or blood of a patient. Following oral administration, a dosage form comprising a compound of Formula (I) may provide a therapeutically effective concentration of the corresponding drug in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of the drug is maintained may be the same or different. The continuous period of time during which a therapeutically effective plasma concentration of the drug is maintained may begin shortly after oral administration or following a time interval.

An appropriate dosage of a compound of Formula (I) or pharmaceutical composition comprising a compound of Formula (I) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formula (I) are prodrugs of acamprosate. Thus, compounds of Formula (I) may be administered to a patient suffering from any disease including a disorder, condition, or symptom for which acamprosate is known or hereafter discovered to be therapeutically effective. Methods for treating a disease in a patient provided by the present disclosure comprise administering to a patient in need of such treatment a therapeutically effective amount of at least one compound of Formula (I).

Compounds of Formula (I) or pharmaceutical compositions thereof may provide therapeutic or prophylactic plasma and/or blood concentrations of the corresponding drug following oral administration to a patient. The promoiety(ies) of compounds of Formula (I) may be cleaved in vivo either chemically and/or enzymatically to release the parent drug. One or more enzymes present in the intestinal lumen, intestinal tissue, blood, liver, brain, or any other suitable tissue of a patient may enzymatically cleave the promoiety of the administered compounds. For example, a promoiety of a compound of Formula (I) may be cleaved following absorption of the compound from the gastrointestinal tract (e.g., in intestinal tissue, blood, liver, or other suitable tissue of a mammal). For compounds of Formula (I) the masking promoiety is first cleaved enzymatically, chemically, or by both mechanisms to provide a neopentyl promoiety terminated with a nitrogen or oxygen nucleophile. The structures of the oxygen nucleophile metabolic intermediates have the structures of Formula (II). The nucleophilic group can then internally cyclize to release acamprosate.

In certain embodiments, compounds of Formula (I) may be actively transported across the intestinal endothelium by transporters expressed in the gastrointestinal tract including the small intestine and colon. The drug, e.g., acamprosate, may remain conjugated to the promoiety during transit across the intestinal mucosal barrier to prevent or minimize presystemic metabolism. In certain embodiments, a compound of Formula (I) is essentially not metabolized to acamprosate within gastrointestinal enterocytes, but is metabolized to release acamprosate within the systemic circulation, for example in the intestinal tissue, blood/plasma, liver, or other suitable tissue of a mammal. In such embodiments, compounds of Formula (I) may be absorbed into the systemic circulation from the small and large intestines either by active transport, passive diffusion, or by both active and passive processes. For example, a promoiety may be cleaved after absorption from the gastrointestinal tract, for example, in intestinal tissue, blood, liver, or other suitable tissue of a mammal.

Compounds of Formula (I) may be administered in similar equivalent amounts of acamprosate and using a similar dosing schedule as described in the art for treatment of a particular disease. For example, in a human subject weighing about 70 kg, compounds of Formula (I) may be administered at a dose over time having an equivalent weight of acamprosate from about 10 mg to about 10 g per day, and in certain embodiments, an equivalent weight of acamprosate from about 1 mg to about 3 g per day. A dose of a compound of Formula (I) taken at any one time can have an equivalent weight of acamprosate from about 1 mg to about 3 g. An acamprosate dose may be determined based on several factors, including, for example, the body weight and/or condition of the patient being treated, the severity of the disease being treated, the incidence of side effects, the manner of administration, and the judgment of the prescribing physician. Dosage ranges may be determined by methods known to one skilled in the art. In certain embodiments, compounds of Formula (I) provide a higher oral bioavailability of acamprosate compared to the oral bioavailability of acamprosate itself when orally administered at an equivalent dose and in an equivalent dosage form. Consequently, a lesser equivalent amount of acamprosate derived from a compound of Formula (I) may be orally administered to achieve the same therapeutic effect as that achieved when acamprosate itself is orally administered.

Compounds of Formula (I) may be assayed in vitro and in vivo for the desired therapeutic or prophylactic activity prior to use in humans. For example, in vitro assays may be used to determine whether administration of a compound of Formula (I) is a substrate of a transporter protein, including transporters expressed in the gastrointestinal tract. Examples of certain assay methods applicable to analyzing the ability of compounds of Formula (I) to act as substrates for one or more transporter proteins are disclosed in Zerangue et al., US 2003/0158254. In vivo assays, for example using appropriate animal models, may also be used to determine whether administration of a compound of Formula (I) is therapeutically effective. Compounds of Formula (I) may also be demonstrated to be therapeutically effective and safe using animal model systems.

In certain embodiments, a therapeutically effective dose of a compound of Formula (I) may provide therapeutic benefit without causing substantial toxicity. Toxicity of compounds of Formula (I) prodrugs, and/or metabolites thereof may be determined using standard pharmaceutical procedures and may be ascertained by one skilled in the art. The dose ratio between toxic and therapeutic effect is the therapeutic index. A dose of a compound of Formula (I) may be within a range capable of establishing and maintaining a therapeutically effective circulating plasma and/or blood concentration of a compound of Formula (I) or acamprosate that exhibits little or no toxicity.

Compounds of Formula (I) may be used to treat diseases, disorders, conditions, and symptoms of any of the foregoing for which acamprosate is shown to provide therapeutic benefit. Hence, compounds of Formula (I) be used to treat neurodegenerative disorders, psychotic disorders, mood disorders, anxiety disorders, somatoform disorders, movement disorders, substance abuse disorders, binge eating disorder, cortical spreading depression related disorders, tinnitus, sleeping disorders, multiple sclerosis, and pain. The underlying etiology of any of the foregoing diseases being so treated may have a multiplicity of origins.

Further, in certain embodiments, a therapeutically effective amount of one or more compounds of Formula (I) may be administered to a patient, such as a human, as a preventative measure against various diseases or disorders. Thus, a therapeutically effective amount of one or more compounds of Formula (I) be administered as a preventative measure to a patient having a predisposition for a neurodegenerative disorder, a psychotic disorder, a mood disorder, an anxiety disorder, a somatoform disorder, a movement disorder, a substance abuse disorder, binge eating disorder, a cortical spreading depression related disorder, tinnitus, a sleeping disorder, multiple sclerosis, or pain.

Substance abuse disorders refer to disorders related to taking a drug of abuse, to the side effects of a medication, and to toxin exposure. Drugs of abuse include alcohol, amphetamines, caffeine, cannabis, cocaine, hallucinogens, inhalants, nicotine, opioids, phencyclidine, or similarly acting arylcyclohexylamines, sedatives, hypnotics, and anxiolytics.

Alcoholism or alcohol dependence is a chronic disorder with genetic, psychosocial, and environmental causes. Alcoholism refers to " . . . maladaptive alcohol use with clinically significant impairment as manifested by at least three of the following within any one-year period: tolerance; withdrawal; taken in greater amounts or over longer time course than intended; desire or unsuccessful attempts to cut down or control use; great deal of time spent obtaining, using, or recovering from use; social, occupational, or recreational activities given up or reduced; continued use despite knowledge of physical or psychological sequelae." (Diagnostic and Statistical Manual of Mental Disorders, Fourth Edition, Text Revision, Washington D.C., American Psychiatric Association, 2000 (DSM-IV)). Alcohol use disorders include alcohol dependence and alcohol abuse. Screening tests useful for identifying alcoholism include the Alcohol Dependence Data Questionnaire, the Michigan Alcohol Screening Test, the Alcohol Use Disorders Identification Test, and the Paddington Alcohol Test, and other generally recognized tests for diagnosing alcohol dependence.

Treatment for alcoholism generally includes psychological, social, and pharmacotherapeutic interventions aimed at reducing alcohol-associated problems and usually involves detoxification and rehabilitation phases. Medications useful in the pharmacologic treatment of alcohol dependence include disulfiram and naltrexone.

Studies suggest that modulation of mGluR5 receptors play a role in substance abuse disorders and that mGluR5 receptor antagonists such as MPEP may be useful in treating such conditions including drug abuse disorders.

Acamprosate has been shown to be effective for maintaining abstinence from alcohol in patients with alcohol dependence that are abstinent at the initiation of acamprosate treatment (Scott et al., *CNS Drugs* 2005, 19(5), 445-464; and Heilig and Egli, *Pharmacology & Therapeutics* 2006, 11, 855-876) and as such is marketed in the United States for the treatment of alcohol abstinence as Campral® (Forest Laboratories and Merck KGaA). Typical acamprosate doses range from about 1-2 gm per day to achieve a steady-state plasma concentration of about 370-640 ng/mL, which occurs at about 3-8 hours post-dose (Overman et al., *Annals Pharmacotherapy* 2003, 37, 1090-1099; Paille et al., *Alcohol.* 1995, 30, 239-47; and Pelc et al., *Br. Psychiatry* 1997, 171, 73-77) with a recommended dose of Campral® being two to three 333 mg tablets taken three times daily.

The efficacy of compounds of Formula (I) and compositions thereof for treating alcohol dependency may be assessed using animal models of alcoholism and using clinical studies. Animal models of alcoholism are known. Clinical protocols for assessing the efficacy of a compound of Formula (I) for treating alcoholism are known.

The effect of acamprosate on relapse in other substances of abuse has not been extensively studied; however administration of 100 mg/kg acamprosate for 3 days attenuated relapse-like behavior in cocaine conditioned mice (Mcgeehan and Olive, *Behav Pharmacol* 2006, 17(4), 363-7). Studies suggest that modulation of mGluR5 receptors play a role in substance abuse disorders and that mGluR5 receptor antagonists such as MPEP may be useful in treating such conditions including drug abuse disorders and nicotine abuse disorders. Therefore, acamprosate may have applicability in treating other substance abuse disorders, including narcotic abuse disorders and nicotine abuse disorders.

Binge eating disorder is characterized by recurrent episodes of distressing, uncontrollable eating of excessively large amounts of food without the inappropriate compensatory weight loss behaviors of bulimia nervosa or anorexia nervosa (DSM-IV, Fourth Ed., Text Revision, Washington D.C., American Psychiatric Assoc., 2000). The pathophysiology of binge eating disorders is unknown. Binge eating disorder is associated with psychopathology such as compulsive, impulsive, and affective disorders, medical comorbidity, especially obesity, impaired quality of life, and disability. Emotional cues such as anger, sadness, boredom, and anxiety can trigger binge eating. Impulsive behavior and certain other emotional problems can be more common in people with binge eating disorder. Antidepressant medications, including tricyclic antidepressants, selective serotonin re-uptake inhibitors, as well as some of certain antidepressants, have shown evidence of some therapeutic value in binge eating disorder (Bello and Jajnal, *Brain Res Bulletin* 2006, 70, 422-429; Buda-Levin et al., *Physiology & Behavior* 2005, 86, 176-184; and Han et al., *Drug Alcohol Dependence* 2007, prepublication no. DAD-3137, 5 pages).

The efficacy of compounds of acamprosate prodrugs and compositions for treating binge eating may be assessed using animal models of binge eating and using clinical studies. Animal models of binge eating are known. Clinical protocols useful for assessing the efficacy of an acamprosate prodrug for treating binge eating are also known.

In certain embodiments, compounds of Formula (I) can be used to treat tinnitus. Tinnitus is the perception of sound in the absence of acoustic stimulation and often involves sound sensations such as ringing, buzzing, roaring, whistling, or hissing that cannot be attributed to an external sound source. Tinnitus is a symptom associated with many forms of hearing loss and can also be a symptom of other health problems.

Tinnitus can be caused by hearing loss, loud noise, medicine, and other health problems such as allergies, head or neck tumors, cardiovascular disorders such as atherosclerosis, high blood pressure, turbulent blood flow, malformation of capillaries, trauma such as excessive exposure to loud noise, long-term use of certain medications such as salicylates, quinine, cisplatin and certain types of antibiotics, changes to ear bones such as otosclerosis, and jaw and neck injuries. In general, insults or damage to the auditory and somatosensory systems can create an imbalance between inhibitory and excitatory transmitter actions in the midbrain, auditory cortex, and brain stem. This imbalance can cause hyperexcitability of auditory neurons that can lead to the perception of phantom sounds. For acute tinnitus such as tinnitus induced by drugs or loud noises, increased spontaneous firing rates in the auditory nerve fibers have been attributed to reduced levels of central inhibition, presumably by GABA, in central auditory structures leading to neural hyperactivity in the inferior colliculus. Although chronic tinnitus may have a different cause than acute tinnitus, reduced GABA levels have also been implicated.

A recent clinical trial suggests that acamprosate may be effective in treating tinnitus (Azevedo and Figueiredo, *Rev Bras Otorrinolaringol* 2005, 71(5), 618-23).

Acamprosate prodrugs of Formula (I) can be used to treat tinnitus, including preventing, reducing, or eliminating tinnitus and/or the accompanying symptoms of tinnitus in a patient. Treating tinnitus refers to any indicia of success in prevention, reduction, elimination, or amelioration of tinnitus, including any objective or subjective parameter such as abatement, remission, diminishing of symptoms, prevention, or lessening of tinnitus symptoms or making the condition more tolerable to the patient, making the tinnitus less debilitating, or improving a patient's physical or mental well-being.

The efficacy of an acamprosate prodrug of Formula (I) for treating tinnitus can be assessed using animal models of tinnitus and in clinical results. Methods of evaluating tinnitus in animals and humans are known. The ability of a compound of Formula (I) to treat tinnitus in human patients may be assessed using objective and subjective tests such as those described in Bauer and Brozoski, *Laryngoscope* 2006, 116 (5), 675-681. An example of a test used in a clinical context to assess tinnitus treatment outcomes is the Tinnitus Handicap Inventory.

Neurodegenerative diseases are characterized by progressive dysfunction and neuronal death. Neurodegenerative diseases featuring cell death can be categorized as acute, i.e., stroke, traumatic brain injury, spinal cord injury, and chronic, i.e., amyotrophic lateral sclerosis, Huntington's disease, Parkinson's disease, and Alzheimer's disease. Although these diseases have different causes and affect different neuronal populations, they share similar impairment in intracellular energy metabolism NMDA receptor and non-NMDA receptor mediated excitotoxic injury results in neurodegeneration leading to necrotic or apoptotic cell death. Studies also suggest that mGluR5 receptor activity is involved in the etiology of neurodegenerative disorders and that mGluR5 modulators can be useful in treating movement and cognitive dysfunction associated with neurodegenerative disorders, as well as exhibit neuroprotective effects.

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to smooth muscle movements and coordinate changes in posture as normal, leading to tremor, incoordination, and slowed, reduced movement (bradykinesia).

Modulators of NMDA receptor activity have shown therapeutic potential in the management of Parkinson's disease, as well as have mGluR5 receptor antagonists. Accordingly, acamprosate may be useful in treating Parkinson's disease.

Studies suggest that agents that NMDA receptor antagonists or mGluR5 receptor antagonists are potentially useful for treating levodopa-induced dyskinesias such as levodopa-induced dyskinesias in Parkinson's disease Fabbrini et al., *Movement Disorders* 2007, 22(10), 1379-1389; and Mela et al., *J Neurochemistry* 2007, 101, 483-497). Accordingly, acamprosate prodrugs provided by the present disclosure may be useful in treating a movement disorder such as levodopa-induced dyskinesias in Parkinson's disease.

The efficacy of a compound of Formula (I) for treating Parkinson's disease may be assessed using animal models of Parkinson's disease and in clinical studies. Animal models of Parkinson's disease are known. The ability of acamprosate prodrugs to mitigate against L-dopa induced dyskinesias can be assessed using animal models and in clinical trials.

Alzheimer's disease is a progressive loss of mental function characterized by degeneration of brain tissue. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

Excitotoxic cell death is thought to contribute to neuronal cell injury and death in Alzheimer's diseases and other neurodegenerative disorders. Excitotoxicity is due, at least in part, to excessive acylation of NMDA-type glutamate receptors and the concomitant excessive $Ca^{2+}$ influx through the receptor's associated ion channel. NMDA receptor antagonists have shown neuroprotective effects in Alzheimer's disease (Lipton, *NeuroRx* 2004, 1(1), 101-110). As a modulator of the NMDA receptor, acamprosate may have similar effects.

The efficacy of administering a compound of Formula (I) for treating Alzheimer's disease may be assessed using animal models of Alzheimer's disease and in clinical studies. Useful animal models for assessing the efficacy of compounds for treating Alzheimer's disease are known.

Huntington's disease is an autosomal dominant neurodegenerative disorder in which specific cell death occurs in the neostriatum and cortex. Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

Neuroprotective effects of NMDA antagonists such as memantine and ketamine in Huntington's disease have been proposed (Murman et al., *Neurology* 1997, 49(1), 153-161; and Kozachuk, US 2004/0102525).

The efficacy of administering a compound of Formula (I) for treating Huntington's disease may be assessed using animal models of Huntington's disease and in clinical studies. Animal models of Huntington's disease are known.

Amyotrophic lateral sclerosis (ALS) is a progressive neurodegenerative disorder characterized by the progressive and specific loss of motor neurons in the brain, brain stem, and spinal cord. ALS begins with weakness, often in the hands and less frequently in the feet that generally progresses up an arm or leg. Over time, weakness increases and spasticity develops characterized by muscle twitching and tightening, followed by muscle spasms and possibly tremors.

A possible cause of ALS is constitutive opening of the calcium pore in glutamate responsive AMPA channels secondary to a failure of RNA editing. Recent work has shown that endogenous polyamines can block the vulnerability of motor neurons to cell death due to calcium influx through $Ca^{2+}$-permeable AMP receptors. Acamprosate is believed to have an action at AMPA receptors similar to that of endogenous polyamines. Accordingly, it has been proposed that acamprosate may be useful in treating ALS (Kast and Altschuler, *Med Hypotheses* 2007, 69(4), 836-837).

The efficacy of a compound of Formula (I) for treating ALS may be assessed using animal models of ALS and in clinical studies. Natural disease models of ALS include mouse models (motor neuron degeneration, progressive motor neuropathy, and wobbler) and the hereditary canine spinal muscular atrophy canine model. Experimentally produced and genetically engineered animal models of ALS can also useful in assessing therapeutic efficacy. Specifically, the SOD1-G93A mouse model is a recognized model for ALS. Examples of clinical trial protocols useful in assessing treatment of ALS are known.

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each patient exhibiting a particular pattern of motor, sensory, and sensory disturbances. MS is typified pathologically by multiple inflammatory foci, plaques of demyelination, gliosis, and axonal pathology within the brain and spinal cord, all of which contribute to the clinical manifestations of neurological disability. Although the causal events that precipitate MS are not fully understood, evidence implicates an autoimmune etiology together with environmental factors and specific genetic predispositions. Functional impairment, disability, and handicap are expressed as paralysis, sensory and octintive disturbances, spasticity, tremor, lack of coordination, and visual impairment. These symptoms significantly impact the quality of life of the individual.

Involvement of ionotropic glutamate receptor function including the NMDA receptor, AMPA receptor, and kainite receptor are implicated in the pathology of MS). Compounds that modulate the NMDA and AMPA/kainite family of glutamate receptors have shown neuroprotective effects in multiple sclerosis (Killestein et al., *J Neurol Sci* 2005, 233, 113-115). As a mediator of ionotropic glutamate receptors, acamprosate is potentially useful in treating MS.

Assessment of MS treatment efficacy in clinical trials can be accomplished using tools such as the Expanded Disability Status Scale and the MS Functional Composite as well as magnetic resonance imaging lesion load, biomarkers, and self-reported quality of life). Animal models of MS shown to be useful to identify and validate potential MS therapeutics include experimental autoimmune/allergic encephalomyelitis (EAE) rodent models that simulate the clinical and pathological manifestations of MS.

In certain embodiments, compounds of Formula (I) or pharmaceutical compositions thereof can be used to treat a psychotic disorder such as, for example, schizophrenia. Other psychotic disorders for which acamprosate prodrugs provided by the present disclosure may be useful include brief psychotic disorder, delusional disorder, schizoaffective disorder, and schizophreniform disorder.

Schizophrenia is a chronic, severe, and disabling brain disorder that affects about one percent of people worldwide, including 3.2 million Americans. Schizophrenia encompasses a group of psychotic disorders characterized by dysfunctions of the thinking process, such as delusions, hallucinations, and extensive withdrawal of the patient's interests form other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity, or the assumption of bizarre postures; undifferentiated schizophrenia characterized by a combination of symptoms characteristic of the other subtypes; and residual schizophrenia in which a person is not currently suffering from positive symptoms but manifests negative and/or cognitive symptoms of schizophrenia (DSM-IV-TR classifications 295.30 (Paranoid Type), 295.10 (Disorganized Type), 295.20 (Catatonic Type), 295.90 (Undifferentiated Type), and 295.60 (Residual Type) (Diagnostic and Statistical Manual of Mental Disorders, Fourth Edition, Text Revision, American Psychiatric Association, 2000). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders (DSM-IV-TR). Schizoaffective disorder is characterized by symptoms of schizophrenia as well as mood disorders such as major depression, bipolar mania, or mixed mania, is included as a subtype of schizophrenia.

Symptoms of schizophrenia can be classified as positive, negative, or cognitive. Positive symptoms of schizophrenia include delusion and hallucination, which can be measured using, for example, using the Positive and Negative Syndrome Scale (PANSS). Negative symptoms of schizophrenia include affect blunting, anergia, alogia and social withdrawal can be measured for example, using the Scales for the Assessment of Negative Symptoms (SANS) (Andreasen, 1983, *Scales for the Assessment of Negative Symptoms* (SANS), Iowa City, Iowa). Cognitive symptoms of schizophrenia include impairment in obtaining, organizing, and using intellectual knowledge, which can be measured using the Positive and Negative Syndrome Scale-cognitive subscale (PAN SS-cognitive subscale) or by assessing the ability to perform cognitive tasks such as, for example, using the Wisconsin Card Sorting Test.

The glutamatergic system has been implicated in the etiology and pathophysiology of schizophrenia and modulators of NMDA receptor activity and mGluR5 receptor activity such as acamprosate have been proposed as potential therapeutic agents for schizophrenia Paz et al., *Eur Neuropsychopharmacology* 2008, prepublication no. NEUPSY-10085, 14 pages). Accordingly, acamprosate and acamprosate prodrugs provided by the present disclosure may have efficacy in treating the positive, negative, and/or cognitive symptoms of schizophrenia (Kozachuk, US 2004/0102525; and Fogel, U.S. Pat. No. 6,689,816).

The efficacy of compounds of Formula (I) and pharmaceutical compositions of any of the foregoing for treating schizophrenia may be determined by methods known to those skilled in the art. For example, negative, positive, and/or cognitive symptom(s) of schizophrenia may be measured before, during, and/or after treating the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) and using Cognitive Deficits tests such as the Wisconsin Card Sorting Test (WCST).

The efficacy of a compound of Formula (I) and pharmaceutical compositions of any of the foregoing may be evaluated using animal models of schizophrenic disorders. For example, conditioned avoidance response behavior (CAR) and catalepsy tests in rats are shown to be useful in predicting antipsychotic activity and EPS effect liability.

In certain embodiments, compounds of Formula (I) or pharmaceutical compositions thereof can be used to treat a mood disorder such as, for example, a bipolar disorder and a depressive disorder.

Bipolar Disorder

Bipolar disorder is a psychiatric condition characterized by periods of extreme mood. The moods can occur on a spectrum ranging from depression (e.g., persistent feelings of sadness, anxiety, guilt, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability, chronic pain, lack of motivation, and morbid/suicidal ideation) to mania (e.g., elation, euphoria, irritation, and/or suspicious). Bipolar disorder is defined and classified in DSM-IV-TR. Bipolar disorder includes bipolar I disorder, bipolar II disorder, cyclothymia, and bipolar disorder not otherwise specified. Patients afflicted with this disorder typically alternate between episodes of depression (depressed mood, hopelessness, anhedonia, varying sleep disturbances, difficulty in concentration, psychomotor retardation and often, suicidal ideation) and episodes of mania (grandiosity, euphoria, racing thoughts, decreased need for sleep, increased energy, risk taking behavior).

Inhibitors of glutamate release such as lamotrigine and riluzole, and NMDA antagonists such as memantine and ketamine are being investigated for treating bipolar disorder (Zarate et al., *Am J Psychiatry* 2004, 161, 171-174; Zarate et al., *Biol Psychiatry* 2005, 57, 430-432; and Teng and Demetrio, *Rev Bras Psiquiatr* 2006, 28(3), 251-6).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score).

Depressive disorders include major depressive disorder, dysthymic disorder, premenstrual dysphoric disorder, minor depressive disorder, recurrent brief depressive disorder, and postpsychotic depressive disorder of schizophrenia (DSM IV).

Studies support the involvement of the glutamatergic system in the pathophysiology of depression. NMDA receptor antagonists have shown antidepressant effects in animal models and in clinical studies. Modulators of mGluR5 activity have also shown potential efficacy as antidepressants.

The efficacy of compounds provided by the present disclosure for treating depression can be evaluated in animal models of depression such as the forced swim test, the tail suspension test and others, and in clinical trials.

Anxiety is defined and classified in DSM-IV-TR. Anxiety disorders include panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, and anxiety disorder not otherwise specified.

Neurochemical investigations have linked anxiety to dysfunction in central GABAergic, serotonergic, and noradrenergic systems. Modulators of mGluR5 receptors such as the selective antagonist 2-methyl-6-(phenylethynyl)-pyridine have been shown to be effective in treating anxiety disorders (Lea and Faden, *CNS Drug Rev* 2006, 12(2), 149-66; and Molina-Hernandez et al., *Prog Neuro-Psychopharmacology Biolog Psychiatry* 2006, 30, 1129-1135). In particular, acamprosate has been proposed for the treatment of anxiety disorders (Fogel, U.S. Pat. No. 6,689,816).

Useful animal models for assessing treatment of anxiety include fear-potentiated startle, elevated plus-maze, X-maze test of anxiety, and the rat social interaction test. Genetic animal models of anxiety are also known as are other animal models sensitive to anti-anxiety agents.

In clinical trials, efficacy can be evaluated using psychological procedures for inducing experimental anxiety applied to healthy volunteers and patients with anxiety disorders or by selecting patients based on the Structured Clinical interview for DSM-IV Axis I Disorders. One or more scales can be used to evaluate anxiety and the efficacy of treatment including, for example, the Penn State Worry Questionnaire, the Hamilton Anxiety and Depression Scales, the Spielberger State-Trait Anxiety Inventory, and the Liebowitz Social Anxiety Scale.

In certain embodiments, acamprosate prodrugs provided by the present disclosure may be useful in treating somatoform disorders such as somatization disorder, conversion disorder, hypochondriasis, and body dysmorphic disorder.

In certain embodiments, movement disorders include myoclonus, tremor, tics, tardive dyskinesia, movement disorders associated with Parkinson's disease and Huntington's disease, progressive supranuclear palsy, Shy-Drager syndrome, tics, Tourette's syndrome, chorea and athetosis, spasmodic torticollis, ataxia, restless legs syndrome, and dystonias. Also included in movement disorders is spasticity.

Tardive dyskinesia is a neurological disorder caused by the long-term or high-dose use of dopamine antagonists such as antipsychotics. Tardive dyskinesia is characterized by repetitive, involuntary, purposeless movements such as grimacing, tongue protrusion, lip smacking, puckering and pursing of the lips, and rapid eye blinking, and can also involve rapid movements of the arms, legs, and trunk.

Studies suggest that NMDA receptors are involved in the dyskinesia observed in animal models of tardive dyskinesia and NMDA receptor modulators have to some extent been shown to reverse the effects of neuroleptic induced vacuous chewing movements, an animal model of tardive dyskinesia. Accordingly, acamprosate has been proposed for treating tardive dyskinesia and other movement disorders including tics, Tourette's syndrome, focal dystonias, blepharospasm, and Meige Syndrome (Fogel, U.S. Pat. No. 5,952,389, US 2002/0013366, and US 2006/1028802), and in studies on individual patients has been shown effective in treating tardive dyskinesia, dystonia, and tic at acamprosate doses from about 1,000 mg/day to about 2,000 mg/day.

Efficacy of tardive dyskinesia treatment can be assessed using animal models.

Spasticity

Spasticity is an involuntary, velocity-dependent, increased resistance to stretch. Spasticity is characterized by muscle hypertonia and displays increased resistance to externally imposed movement with increasing speed of stretch. Spasticity can be caused by lack of oxygen to the brain before, during, or after birth (cerebral palsy); physical trauma (brain or spinal cord injury); blockage of or bleeding from a blood vessel in the brain (stroke); certain metabolic diseases; adrenolekodystrophy; phenylketonuria; neurodegenerative diseases such as Parkinson's disease and amyotrophic lateral sclerosis; and neurological disorders such as multiple sclerosis. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient.

Symptoms of spasticity can include hypertonia (increased muscle tone), clonus (a series of rapid muscle contractions), exaggerated deep tendon reflexes, muscle spasms, scissoring (involuntary crossing of the legs), deformities with fixed joints, stiffness, and/or fatigue caused by trying to force the limbs to move normally. Other complications include urinary tract infections, chronic constipation, fever or other systemic illnesses, and/or pressure sores. The degree of spasticity varies from mild muscle stiffness to severe, painful, and uncontrollable muscle spasms. Spasticity may coexist with other conditions but is distinguished from rigidity (involuntary bidirectional non-velocity-dependent resistance to movement), clonus (self-sustaining oscillating movements secondary to hypertonicity), dystonia (involuntary sustained contractions resulting in twisting abnormal postures), athetoid movement (involuntary irregular confluent writhing movements), chorea (involuntary, abrupt, rapid, irregular, and unsustained movements), ballisms (involuntary flinging movements of the limbs or body), and tremor (involuntary rhythmic repetitive oscillations, not self-sustaining). Spasticity can lead to orthopedic deformity such as hip dislocation, contractures, or scoliosis; impairment of daily living activities such as dressing, bathing, and toileting; impairment of mobility such as inability to walk, roll, or sit; skin breakdown secondary to positioning difficulties and shearing pressure; pain or abnormal sensory feedback; poor weight gain secondary to high caloric expenditure; sleep disturbance; and/or depression secondary to lack of functional independence.

Treatment of spasticity includes physical and occupational therapy such as functional based therapies, rehabilitation, facilitation such as neurodevelopmental therapy, proprioceptive neuromuscular facilitation, and sensory integration; biofeedback: electrical stimulation; and orthoses. Oral medications useful in treating spasticity include baclofen, benzodiazepines such as diazepam, dantrolene sodium; imidazolines such as clonidine and tizanidine; and gabapentin. Intrathecal medications useful in treating spasticity include baclofen. Chemodenervation with local anesthetics such as lidocaine and xylocaine; type A botulinum toxin and type B botulinum toxin; phenol and alcohol injection can also be useful in treating spasticity. Surgical treatments useful in treating spasticity include neurosurgery such as selective dorsal rhizotomy; and orthopedic operations such as contracture release, tendon or muscle lengthening, tendon transfer, osteotomy, and arthrodesis.

Studies suggest that NMDA receptor may play a role in the activity of muscle relaxants and that NMDA receptor antagonists may have therapeutic potential in spasticity (Kornhuber and Quack, *Neurosci Lett* 1995, 195, 137-139).

The efficacy of a compound of Formula (I) for the treatment of spasticity can be assessed using animal models of spasticity and in clinically relevant studies of spasticity of different etiologies. The therapeutic activity may be determined without determining a specific mechanism of action. Animal models of spasticity are known. For example, animal models of spasticity include the mutant spastic mouse; the acute/chronic spinally transected rat and the acute decerebrate rat; primary observation Irwin Test in the rat; and Rotarod Test in the rat and mouse. Other animal models include spasticity induced in rats following transient spinal cord ischemia; spasticity in mouse models of multiple sclerosis; and spasticity in rat models of cerebral palsy.

The efficacy of compounds of Formula (I) may also be assessed in humans using double blind placebo-controlled clinical trials. Clinical trial outcome measures for spasticity include the Ashworth Scale, the modified Ashworth Scale, muscle stretch reflexes, presence of clonus and reflex response to noxious stimuli. Spasticity can be assessed using methods and procedures known in the art such as a combination of clinical examination, rating scales such as the Ashworth Scale, the modified Ashworth scale the spasm frequency scale and the reflex score, biomechanical studies such as the pendulum test, electrophysiologic studies including electromyography, and functional measurements such as the Fugl-Meyer Assessment of Sensorimotor Impairment scale. Other measures can be used to assess spasticity associated with a specific disorder such as the Multiple Sclerosis Spasticity Scale.

Cortical spreading depression (CSD) is a phenomena believed to be involved in the pathogenesis of migraine. During the early phase of CSD, a slow-propagating wave of hyper- then hypo-activity spreads through the cortex, resulting in hyper- then hypo-vascularization. This is followed by a prolonged period of neuronal depression, which is associated with disturbances in nerve cell metabolism and regional reductions in blood flow. CSD may also activate trigeminal nerve axons, which then release neuropeptides, such as substance P, neurokinin A, and CGRP from axon terminals near the meningeal and other blood vessels that produce an inflammatory response in the area around the innervated blood vessels. CSD is also implicated in progressive neuronal injury following stroke and head trauma; and cerebrovascular disease. Glutamate release and subsequent NMDA receptor activation have been implicated in the spread of CSD. NMDA antagonists such as ifenprodil have been shown effective in preventing CSD in the mouse entorhinal cortex and the NMDA receptor antagonist MK-801 was effective in blocking CSD caused by traumatic injury in rat neocortical brain slices. Accordingly, NMDA receptor antagonists that inhibit the release of glutamate in the neuron can potentially prevent CSD and its consequences. For example, (7-chloro-4-hydroxy-3-(3-phenoxy)phenyl-2-(1H)-quinolone, a high affinity antagonist at the glycine site of the NMDA receptor inhibits the initiation and propagation of spreading depression. Other selective NMDA antagonists and an uncompetitive NMDA receptor blocker have shown potential for treating cortical spreading depression migraine (Menniti et al., *Neuropharmacology* 2000, 39, 1147-1155; and Peeters et al., *J Pharmacology and Experimental Therapeutics* 2007, 321(2), 564-572). Accordingly, acamprosate prodrugs may be useful in treating cortical spreading depression related disorders such as migraine, cerebral injury, epilepsy, and cardiovascular disease.

Efficacy of acamprosate prodrugs provided by the present disclosure for treating cortical spreading depression can be assessed using animal models of cortical spreading depression.

Migraine is a neurological disorder that is characterized by recurrent attacks of headache, with pain most often occurring on one side of the head, accompanied by various combinations of symptoms such as nausea, vomiting, and sensitivity to light, sound, and odors. The exact mechanism of migraine initiation and progress is not known. Migraine can occur at any time of day or night, but occurs most frequently on arising in the morning. Migraine can be triggered by various factors, such as hormonal changes, stress, foods, lack of sleep, excessive sleep, or visual, auditory, olfactory, or somatosensory stimulation. In general, there are four phases to a migraine: the prodrome, auras, the attack phase, and postdrome. The prodrome phase is a group of vague symptoms that may precede a migraine attack by several hours, or even a few days before a migraine episode. Prodrome symptoms can include sensitivity to light and sound, changes in appetite, fatigue and yawning, malaise, mood changes, and food cravings. Auras are sensory disturbances that occur before the migraine attack in one in five patients. Positive auras include bright or shimmering light or shapes at the edge of the field of vision. Other positive aura experiences are zigzag lines or stars. Negative auras are dark holes, blind spots, or tunnel vision. Patients may have mixed positive and negative auras. Other neurologic symptoms that may occur at the same time as the aura include speech disturbances, tingling, numbness, or weakness in an arm or leg, perceptual disturbances such as space or size distortions, and confusion. A migraine attack usually lasts from 4 to 72 hours and typically produces throbbing pain on one side of the head, pain worsened by physical activity, nausea, visual symptoms, facial tingling or numbness, extreme sensitivity to light and noise, looking pale and feeling cold, and less commonly tearing and redness in one eye, swelling of the eyelid, and nasal congestion. During the attack the pain may migrate from one part of the head to another, and may radiate down the neck into the shoulder. Scalp tenderness occurs in the majority of patients during or after an attack. After a migraine attack, there is usually a postdrome phase, in which patients may feel exhausted, irritable, and/or be unable to concentrate. Other types of migraine include menstrual migraines, ophthalmologic migraine, retinal migraine, basilar migraine, familial hemiplegic migraine, and status migrainosus.

It is theorized that persons prone to migraine have a reduced threshold for neuronal excitability, possibly due to reduced activity of the inhibitory neurotransmitter γ-aminobutyric acid (GABA). GABA normally inhibits the activity of the neurotransmitters serotonin (5-HT) and glutamate, both of which appear to be involved in migraine attacks. The excitatory neurotransmitter glutamate is implicated in an electrical phenomenon called cortical spreading depression, which can initiate a migraine attack, while serotonin is implicated in vascular changes that occur as the migraine progresses.

Acamprosate prodrugs provided by the present disclosure or pharmaceutical composition thereof may be administered to a patient after initiation of the migraine. For example, a patient may be in the headache phase of the migraine or the postdrome phase before the prodrug or pharmaceutical composition is administered. Alternatively, acamprosate prodrugs provided by the present disclosure or pharmaceutical composition thereof may be administered to the patient before the migraine starts, such as once the patient senses that a migraine is developing or when the early symptoms of the migraine have begun. Acamprosate prodrugs provided by the present disclosure may also be administered to a patient on an ongoing or chronic basis to treat recurrent or frequent occurrences of migraine episodes.

Migraine may be diagnosed by determining whether some of a person's recurrent headaches meet migraine criteria as disclosed in, for example, see The International Classification of Headache Disorders, 2nd edition, Headache Classification Committee of the International Headache Society, *Cephalalgia* 2004, 24 (suppl 1), 8-160.

The efficacy of administering at least one compound of Formula (I) for treating migraine can be assessed using animal models of migraine and clinical studies. Animal models of migraine are known. For example, to delineate and assess the effectiveness of an acamprosate prodrug provided by the present disclosure, the frequency of migraine attacks, their severity and their accompanying symptoms may be recorded and measured at baseline, and at 3 months, and 6 months, etc., following initiation of treatment. Anti-migraine and cortical-spreading depression activity of compounds provided by the present disclosure may be determined using methods known in the art.

Therapeutic efficacy of a compound of Formula (I) or pharmaceutical composition of any of the foregoing for treating migraine may also be determined in various animal models of neuropathic pain or in clinically relevant studies of different types of neuropathic pain. The therapeutic activity may be determined without determining a specific mechanism of action. Animal models for neuropathic pain are known in the art and include, but are not limited to, animal models that determine analgesic activity or compounds that act on the CNS to reduce the phenomenon of central sensitization that results in pain from non-painful or non-noxious stimuli. Other animal models are known in the art, such as hot plate tests, model acute pain and are useful for determining analgesic properties of compounds that are effective when painful or noxious stimuli are present. The progression of migraine is believed to be similar to the progress of epilepsy because an episodic phenomenon underlies the initiation of the epileptic episode and, as such, it is believed that epilepsy animal models may be useful in determining a component of the therapeutic activity of the pharmaceutical composition.

Sleeping disorders include primary sleep disorders such as dysomnias characterized by abnormalities in the amount, quality, or timing of sleep and parasomnias characterized by abnormal behavioral or physiological events occurring in association with sleep, specific sleep stages, or sleep-wake transitions; sleep disorders related to another mental disorder, sleep disorders due to a general medical condition; and substance-induced sleep disorder (DSM-IV). Dysomnias include breathing-related sleep disorders such as obstructive sleep apnea syndrome characterized by repeated episodes of upper-airway obstruction during sleep; central sleep apnea syndrome characterized by episodic cessation of ventilation during sleep without airway obstruction; and central alveolar hypoventilation syndrome characterized by impairment in ventilatory control that results in abnormally low arterial oxygen levels further worsened by sleep.

Sleep apnea is a sleep disorder characterized by pauses in breathing during sleep. Clinically significant levels of sleep apnea are defined as five or more events of any type per hour of sleep time. Sleep apnea can be characterized as central, obstructive, and mixed. In central sleep apnea, breathing is interrupted by the lack of effort. In obstructive sleep apnea, a physical block to airflow despite effort results in interrupted breathing. In mixed sleep apnea, there is a transition from central to obstructive features during the events. Sleep apnea leads to interrupted, poor-quality sleep, nocturnal oxygen desaturation, and a reduction or absence of REM sleep. Sleep apnea may exacerbate or contribute to cardiovascular disease including coronary heart disease, hypertension, ventricular hypertrophy and dysfunction, cardiac arrhythmias, and stroke, by mechanisms such as endothelial damage and dysfunction, increases in inflammatory mediators, increases in prothromobitic factors, increased sympathetic activity, hypoxemia, impaired vagal activity and insulin resistance. Sleep apnea may also contribute to cognitive impairment.

Acamprosate has been shown to improve sleep in patients being treated for alcohol withdrawal (Staner et al., *Alcohol Clin Exp Res* 2006, 30(9), 1492-9) and preliminary studies suggest that acamprosate at doses of about 1,000 mg/day (333 mg three times per day) may be effective in treating central and obstructive sleep apnea (Hedner et al., WO 2007/032720).

Sleep apnea can be clinically evaluated using polysomnography or oximetry, and/or using tools such as the Epworth Sleepiness Scale and the Sleep Apnea Clinical Score and/or using polysomnographic recording. Animal models of sleep apnea are known and can be useful in assessing the efficacy of acamprosate prodrugs for treating sleep apnea.

Pain includes nociceptive pain caused by injury to bodily tissues and neuropathic pain caused by abnormalities in nerves, spinal cord, and/or brain. Pain includes mechanical allodynia, thermal allodnia, hyperplasia, central pain, peripheral neuropathic pain, diabetic neuropathy, breakthrough pain, cancer pain, deafferentation pain, dysesthesia, fibromyalgia syndrome, hyperpathia, incident pain, movement-related pain, myofacial pain, and paresthesia. Pain can be acute or chronic.

Studies demonstrate the involvement of mGluR5 receptors in nociceptive processes and that modulation of mGluR5 receptor activity can be useful in treating various pain states such as acute pain, persistent and chronic pain, inflammatory pain, visceral pain, neuropathic pain, nonioceptive pain, and post-operative pain. NMDA receptor antagonists have also been shown to attenuate central sensitization and hyperplasia in animals and humans.

Neuropathic pain involves an abnormal processing of sensory input usually occurring after direct injury or damage to nerve tissue. Neuropathic pain is a collection of disorders characterized by different etiologies including infection, inflammation, disease such as diabetes and multiple sclerosis, trauma or compression to major peripheral nerves, and chemical or irradiation-induced nerve damage. Neuropathic pain typically persists long after tissue injury has resolved.

An essential part of neuropathic pain is a loss (partial or complete) of afferent sensory function and the paradoxical presence of certain hyperphenomena in the painful area. The nerve tissue lesion may be found in the brain, spinal chord, or the peripheral nervous system. Symptoms vary depending on the condition but are usually the manifestations hyperalgesia (the lowering of pain threshold and an increased response to noxious stimuli), allodynia (the evocation of pain by non-noxious stimuli such as cold, warmth, or touch), hyperpathia (an explosive pain response that is suddenly evoked from cutaneous areas with increased sensory detection threshold when the stimulus intensity exceeds sensory threshold), paroxysms (a type of evoked pain characterized by shooting, electric, shock like or stabbing pain that occurs spontaneously, or following stimulation by an innocuous tactile stimulus or by a blunt pressure), paraesthesia (abnormal but non-painful sensations, which can be spontaneous or evoked, often described as pins and needles), dysesthesia (abnormal unpleasant but not necessarily painful sensation, which can be spontaneous or provoked by external stimuli), referred pain and abnormal pain radiation (abnormal spread of pain), and wind-up like pain and aftersensations (the persistence of pain long after termination of a painful stimulus). Patients with neuropathic pain typically describe burning, lancinating, stabbing, cramping, aching and sometimes vice-like pain. The pain can be paroxysmal or constant. Pathological changes to the peripheral nerve(s), spinal cord, and brain have been implicated in the induction and maintenance of chronic pain. Patients suffering from neuropathic pain typically endure chronic, debilitating episodes that are refractory to current pharmacotherapies and profoundly affect their quality of life. Currently available treatments for neuropathic pain, including tricyclic antidepressants and gabapentin, typically show limited efficacy in the majority of patients (Sindrup and Jensen, *Pain* 1999, 83, 389-400).

There are several types of neuropathic pain. A classification that relates to the type of damage or related pathophysiology causing a painful neuropathy includes neuropathies associated with mechanical nerve injury such as carpal tunnel syndrome, vertebral disk herniation, entrapment neuropathies, ulnar neuropathy, and neurogenetic thoracic outlet syndrome; metabolic disease associated neuropathies such as diabetic polyneuropathy; neuropathies associated with neurotropic viral disease such as herpes zoster and human immunodeficiency virus (HIV) disease; neuropathies associated with neurotoxicity such as chemotherapy of cancer or tuberculosis, radiation therapy, drug-induced neuropathy, and alcoholic neuropathy; neuropathies associated with inflammatory and/or immunologic mechanisms such as multiple sclerosis, anti-sulfatide antibody neuropathies, neuropathy associated with monoclonal gammopathy, Sjogren's disease, lupus, vasculitic neuropathy, polyclonal inflammatory neuropathies, Guillain-Barre syndrome, chronic inflammatory demyelinating neuropathy, multifocal motor neuropathy, paraneoplastic autonomic neuropathy, ganlinoic acetylcholine receptor antibody autonomic neuropathy, Lambert-Eaton myasthenic syndrome and myasthenia gravis; neuropathies associated with nervous system focal ischemia such as thalamic syndrome (anesthesia dolorosa); neuropathies associated with multiple neurotransmitter system dysfunction such as complex regional pain syndrome (CRPS); neuropathies associated with chronic/neuropathic pain such as osteoarthritis, lower back pain, fibromyalgia, cancer bone pain, chronic stump pain, phantom limb pain, and paraneoplastic neuropathies; neuropathies associated with neuropathic pain including peripheral neuropathies such as postherpetic neuralgia, toxic neuropathies (e.g., exposure to chemicals such as exposure to acrylamide, 3-chlorophene, carbamates, carbon disulfide, ethylene oxide, n-hexane, methyl n-butylketone, methyl bromide, organophosphates, polychlorinated biphenyls, pyriminil, trichlorethylene, or dichloroacetylene), focal traumatic neuropathies, phantom and stump pain, monoradiculopathy, and trigeminal neuralgia; and central neuropathies including ischemic cerebrovascular injury (stroke), multiple sclerosis, spinal cord injury, Parkinson's disease, amyotrophic lateral sclerosis, syringomyelia, neoplasms, arachnoiditis, and post-operative pain; mixed neuropathies such as diabetic neuropathies (including symmetric polyneuropathies such as sensory or sensorimotor polyneuropathy, selective small-fiber polyneuropathy, and autonomic neuropathy; focal and multifocal neuropathies such as cranial neuropathy, limb mononeuropathy, trunk mononeuro-pathy, mononeuropathy multiplex, and asymmetric lower limb motor neuropathy) and sympathetically maintained pain. Other neuropathies include focal neuropathy, glosopharyngeal neuralgia, ischemic pain, trigeminal neuralgia, atypical facial pain associated with Fabry's disease, Celiac disease, hereditary sensory neuropathy, or $B_{12}$-deficiency; mono-neuropathies, polyneuropathis, hereditary peripheral neuropathies such as Carcot-Marie-Tooth disease, Refsum's disease, Strumpell-Lorrain disease, and retinitis pigmentosa; acute polyradiculoneuropathy; and chronic polyradiculoneuropathy. Paraneoplastic neuropathies include paraneoplastic subacute sensory neuronopathy, paraneoplastic motor neuron disease, paraneoplastic neuromyotonia, paraneoplastic demyelinating neuropathies, paraneoplastic vasculitic neuropathy, and paraneoplastic autonomic insufficiency.

The important role of N-methyl-D-aspartate (NMDA) receptors in the development and maintenance of chronic pain associated with central and peripheral nerve injury is well documented. Consequently, NMDA antagonists have been proposed as potential therapeutics for neuropathic pain. NMDA antagonists of different classes have shown efficacy in preclinical models as well as in patients with chronic pain, including neuropathic pain. Several clinical studies have observed a long-lasting relief in some neuropathic pain patients treated with NMDA antagonists (Pud et al., *Pain* 1998, 75(2-3), 349-54; Eisenberg et al., *J Pain* 2007, 8(3), 223-9; Rabben et al., *J Pharmacol Exp Ther* 1999, 289(2), 1060-1066; Correll et al., *Pain Med* 2004, 5(3), 263-75; and Harbut et al., US 2005/0148673).

Other diseases or disorders for which NMDA antagonists and mGluR5 antagonists such as acamprosate may be therapeutically useful include neuroprotection in epilepsy (Chapman et al., *Neuropharmacol* 2000, 39, 1567-1574), cognitive dysfunction (Riedel et al., *Neuropharmacol* 2000, 39, 1943-1951), Down's syndrome, normal cognitive senescence, meningitis, sepsis and septic encephalopathy, CNS vasculities, leudodystrophies and X-ADL, childbirth and surgical anesthesia, spinal cord injury, hypoglycemia, encephalopathy, tumors and malignancies, cerebellar degenerations, ataxias, bowel syndromes, metabolic bone disease and osteoporosis, obesity, diabetes and pre-diabetic syndromes (Storto et al., *Molecular Pharmacology* 2006, 69(4), 1234-1241), and gastroesophageal reflux disease (Jensen et al., *Eur J Pharmacology* 2005, 519, 154-157).

Administration

Prodrugs of Formula (I), pharmaceutically acceptable salts of any of the foregoing, and/or pharmaceutical compositions thereof may be administered orally. Prodrugs of Formula (I) and/or pharmaceutical compositions thereof may also be administered by any other convenient route, for example, by infusion or bolus injection, by absorption through epithelial or mucocutaneous linings (e.g., oral mucosa, rectal, and intestinal mucosa, etc.). Administration may be systemic or local. Various delivery systems are known, (e.g., encapsulation in liposomes, microparticles, microcapsules, capsules, etc.) that may be used to administer a compound and/or pharmaceutical composition. Prodrugs of Formula (I) a pharmaceutically acceptable salt of any of the foregoing, or a pharmaceutical composition thereof may be administered by any appropriate route. Examples of suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

In certain embodiments, it may be desirable to introduce prodrugs of Formula (I) and/or pharmaceutical compositions thereof into the central nervous system, which may be by any suitable route, including intraventricular, intrathecal, and epidural injection. Intraventricular injection may be facilitated using an intraventricular catheter attached to a reservoir such as an Ommaya reservoir.

The amount of a prodrug of Formula (I) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of prodrug of Formula (I) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a compound of Formula (I) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, an acamprosate prodrug may exhibit a high therapeutic index. The data obtained from these cell culture assays and animal studies may be used in formulating a dosage range that is not toxic for use in humans. A dose of an acamprosate prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

In certain embodiments, prodrugs of Formula (I) or pharmaceutically acceptable salts of any of the foregoing can be used in combination therapy with at least one other therapeutic agent. Prodrugs of Formula (I) and the at least one other therapeutic agent(s) may act additively or, in certain embodiments, synergistically. In certain embodiments, prodrugs of Formula (I) be administered concurrently with the administration of another therapeutic agent. In certain embodiments, prodrugs of Formula (I) or pharmaceutically acceptable salts of any of the foregoing may be administered prior or subsequent to administration of another therapeutic agent. The at least one other therapeutic agent may be effective for treating the same or different disease or disorder.

When used to treat a disease or disorder a therapeutically effective amount of one or more compounds of Formula (I) may be administered singly, or in combination with other agents including pharmaceutically acceptable vehicles and/or pharmaceutically active agents for treating a disease or disorder, which may be the same or different disease or disorder as the disease or disorder being treated by the one or more compounds of Formula (I). A therapeutically effective amount of one or more compounds of Formula (I) may be delivered together with a compound disclosed herein or combination with another pharmaceutically active agent.

Methods of the present disclosure include administration of one or more compounds of Formula (I), or pharmaceutical compositions thereof and another therapeutic agent provided the other therapeutic agent does not inhibit the therapeutic efficacy of the one or more compounds of Formula (I) and/or does not produce adverse combination effects.

In certain embodiments, compositions provided by the present disclosure may be administered concurrently with the administration of another therapeutic agent, which can be part of the same pharmaceutical composition as, or in a different composition than that containing the compound provided by the present disclosure. In certain embodiments, a compound of Formula (I) may be administered prior or subsequent to administration of another therapeutic agent. In certain embodiments of combination therapy, the combination therapy comprises alternating between administering a composition of Formula (I) and a composition comprising another therapeutic agent, e.g., to minimize adverse side effects associated with a particular drug. When a compound of Formula (I) is administered concurrently with another therapeutic agent that may produce adverse side effects including, but not limited to, toxicity, the other therapeutic agent may be administered at a dose that falls below the threshold at which the adverse side effect is elicited.

In certain embodiments, a pharmaceutical composition may further comprise substances to enhance, modulate and/or control release, bioavailability, therapeutic efficacy, therapeutic potency, stability, and the like. For example, to enhance therapeutic efficacy a compound of Formula (I) may be co-administered with one or more active agents to increase the absorption or diffusion of the compound from the gastrointestinal tract or to inhibit degradation of the drug in the systemic circulation. In certain embodiments, a compound of Formula (I) may be co-administered with active agents having a pharmacological effect that enhance the therapeutic efficacy of the drug.

In certain embodiments, compounds of Formula (I) or pharmaceutical compositions thereof include, or may be administered to a patient together with, another compound for treating a neurodegenerative disorder, a psychotic disorder, a mood disorder, an anxiety disorder, a somatoform disorder, movement disorder, a substance abuse disorder, binge eating disorder, a cortical spreading depression related disorder, tinnitus, a sleeping disorder, multiple sclerosis, or pain.

In certain embodiments, acamprosate prodrugs provided by the present disclosure and pharmaceutical compositions thereof may be administered to a patient for treating a neurodegenerative disorder in combination with a therapy or another therapeutic agent known or believed to be effective in treating a neurodegenerative disorder. In certain embodiments, a neurodegenerative disorder is chosen from Alzheimer's disease, Parkinson's disease, Huntington's disease, and amyotrophic lateral sclerosis.

Therapeutic agents useful for treating Parkinson's disease include dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine; and β-blockers such as propranolol.

Useful drugs for treating Alzheimer's disease include rosiglitazone, roloxifene, vitamin E, donepezil, tacrine, rivastigmine, galantamine, and memantine.

Useful drugs for treating symptoms of Huntington's disease include antipsychotics such as haloperidol, chlorpromazine and olanzapine to control hallucinations, delusions and violent outbursts; antidepressants such as fluoxetine, sertraline, and nortryiptyline to control depression and obsessive-compulsive behavior; tranquilizers such as benzodiazepines, paroxetine, venflaxin and beta-blockers to control anxiety and chorea; mood stabilizers such as liethium, valproate, and carbamzepine to control mania and bipolar disorder; and botulinum toxin to control dystonia and jaw clenching. Useful drugs for treating symptoms of Huntington's disease further include selective serotonin reuptake inhibitors (SSRI) such as fluoxetine, paroxetine, sertraline, escitalopram, citalopram, fluvosamine; norepinephrine and serotonin reuptake inhibitors (NSRI) such as venlafaxine and duloxetine, benzodiazepines such as clonazepam, alprazolam, diazepam, and lorazepam, tricyclic antidepressants such as amitriptyline, nortriptyline, and imipramine; and atypical antidepressants such as busipirone, bupriopion, and mirtazepine for treating the symptoms of anxiety and depression; atomoxetine, dextroamphetamine, and modafinil for treating apathy symptoms; amantadine, memantine, and tetrabenazine for treating chorea symptoms; citalopram, atomoxetine, memantine, rivastigmine, and donepezil for treating cognitive symptoms; lorazepam and trazedone for treating insomnia; valproate, carbamazepine and lamotrigine for treating symptoms of irritability; SSRI antidepressants such as fluoxetine, paroxetine, sertaline, and fluvoxamine, NSRI antidepressants such as venlafaxine, and others such as mirtazepine, clomipramine, lomotrigine, gabapentin, valproate, carbamazepine, olanzapine, rispiridone, and quetiapine for treating symptoms of obsessive-compulsive disorder; haloperidol, quetiapine, clozapine, risperidone, olanzapine, ziprasidone, and aripiprazole for treating psychosis; and pramipexole, levodopa and amantadine for treating rigidity.

Useful drugs for treating ALS include riluzole. Other drugs of potential use in treating ALS include memantine, tamoxifen, thalidomide, ceftriaxone, sodium phenyl butyrate, celecoxib, glatiramer acetate, busipirone, creatine, minocycline, coenzyme Q10, oxandrolone, IGF-1, topiramate, xaliproden, and indinavir. Drugs such as baclofen and diazepam can be useful in treating spasticity associated with ALS.

In certain embodiments, acamprosate prodrugs provided by the present disclosure and pharmaceutical compositions thereof may be administered to a patient for treating a psychotic disorder in combination with a therapy or another therapeutic agent known or believed to be effective in treating a psychotic disorder. In certain embodiments a psychotic disorder is schizophrenia.

Examples of antipsychotic agents useful in treating positive symptoms of schizophrenia include, but are not limited to, acetophenazine, alseroxylon, amitriptyline, aripiprazole, astemizole, benzquinamide, carphenazine, chlormezanone, chlorpromazine, chlorprothixene, clozapine, desipramine, droperidol, aloperidol, fluphenazine, flupenthixol, glycine, oxapine, mesoridazine, molindone, olanzapine, ondansetron, perphenazine, pimozide, prochlorperazine, procyclidine, promazine, propiomazine, quetiapine, remoxipride, reserpine, risperidone, sertindole, sulpiride, terfenadine, thiethylperzaine, thioridazine, thiothixene, trifluoperazine, triflupromazine, trimeprazine, and ziprasidone. Examples of typical antipsychotic agents useful for treating positive symptoms of schizophrenia include acetophenazine, chlorpromazine, chlorprothixene, droperidol, fluphenazine, haloperidol, loxapine, mesoridazine, methotrimeprazine, molindone, perphenazine, pimozide, raclopride, remoxipride, thioridazine, thiothixene, and trifluoperazine. Examples of atypical antipsychotic agents useful for treating positive symptoms of schizophrenia include aripiprazole, clozapine, olanzapine, quetiapine, risperidone, sertindole, and ziprasidone.

Other antipsychotic agents useful for treating positive symptoms of schizophrenia include amisulpride, balaperidone, blonanserin, butaperazine, carphenazine, eplavanserin, iloperidone, lamictal, onsanetant, paliperidone, perospirone, piperacetazine, raclopride, remoxipride, sarizotan, sonepiprazole, sulpiride, ziprasidone, and zotepine; serotonin and dopamine (5HT/D2) agonists such as asenapine and bifeprunox; neurokinin 3 antagonists such as talnetant and osanetant; AMPAkines such as CX-516, galantamine, memantine, modafinil, ocaperidone, and tolcapone; and α-amino acids such as D-serine, D-alanine, D-cycloserine, and N-methylglycine. Thus, antipsychotic agents include typical antipsychotic agents, atypical antipsychotic agents, and other compounds useful for treating schizophrenia in a patient, and particularly useful for treating the positive symptoms of schizophrenia.

Examples of agents useful for treating cognitive and/or negative symptoms of schizophrenia include aripiprazole, clozapine, olanzapine, quetiapine, risperidone, sertindole, ziprasidone, asenapine, bifeprunox, iloperidone, lamictal, galantamine, memantine, modafininil, acaperidone, NK3 antagonists such as talnetant and osanetant, AMPAkines, tolcapone, amisulpride, mirtazapine, lamotrigine, idazoxan, neboglamine, sabcomeline, ispronicline, sarcosine, preclamol, L-carnosine, nicotine, raloxifene, pramipexol, escitalopram, estradiol, riluzole, creatine, entacapone, L-threonine, atomoxetine, divalproex sodium, pimozide, provastatin, duloxetine; and NMDA receptor modulators such as glycine, D-serine, and D-cycloserine.

In certain embodiments, pharmaceutical compositions provided by the present disclosure may be co-administered with another drug useful for treating a symptom of schizophrenia or a disease, disorder, or condition associated with schizophrenia and that is not an antipsychotic agent. For example, acamprosate prodrugs may be co-administered with an antidepressant, such as, but not limited to alprazolam, amitriptyline, amoxapine, bupropion, citalopram, clomipramine, desipramine, eoxepin, escitapopram, fluoxetine, fluvoxamine, imipramine, maprotiline, methylphenidate, mirtazapine, nefazodone, nortriptyline, paroxetine, phenelzine, protriptyline, sertraline, tranylcypromine, trazodone, trimipramine, venlafaxine, and combinations of any of the foregoing.

For example, in certain embodiments, an acamprosate prodrug provided by the present disclosure, or pharmaceutical compositions thereof may be administered to a patient for the treatment of schizophrenia in conjunction with a social therapy for treating schizophrenia such as rehabilitation, community support activities, cognitive behavioral therapy, training in illness management skills, participation in self-help groups, and/or psychotherapy. Examples of psychotherapies useful for treating schizophrenia include Alderian therapy, behavior therapy, existential therapy, Gestalt therapy, person-centered therapy, psychoanalytic therapy, rational-emotive and cognitive-behavioral therapy, reality therapy, and transactional analysis.

Other examples of drugs useful for treating psychotic disorders include aripiprazole, loxapine, mesoridazine, quetiapine, reserpine, thioridazine, trifluoperazine, and ziprasidone, chlorpromazine, clozapine, fluphenazine, haloperidol, olanzapine, perphenazine, prochlorperazine, risperidone, and thiothixene.

In certain embodiments, acamprosate prodrugs provided by the present disclosure and pharmaceutical compositions thereof may be administered to a patient for treating a mood disorder in combination with a therapy or another therapeutic agent known or believed to be effective in treating a mood disorder. In certain embodiments, a mood disorder is chosen from a bipolar disorder and a depressive disorder.

Examples of drugs useful for treating bipolar disorder include aripirprazole, verapamil, carbamazepine, clonidine, clonazepam, lamotrigine, olanzapine, quetiapine, fluoxetine, and ziprasidone.

In certain embodiments, acamprosate prodrugs provided by the present disclosure and pharmaceutical compositions thereof may be administered to a patient for treating depression in combination with a therapy or another therapeutic agent known or believed to be effective in treating depression.

Examples of drugs useful for treating depression include tricyclics such as amitriptyline, amoxapine, clomipramine, desipramine, doxepin, imipramine, maprotiline, nortryptyline, protryptyline, and trimipramine; tetracyclics such as maprotiline and mirtazapine; selective serotonin reuptake inhibitors (SSRI) such as citalopram, escitalopram, fluoxetine, fluvoxamine, paroxetine, and sertraline; serotonin and norepinephrine reuptake inhibitors (SNRI) such as venlafaxine and duloxetine; monoamine oxidase inhibitors such as isocarboxazid, phenelzine, selegiline, and tranylcypromine; psychostimulants such as dextroamphetamine and methylphenidate; and other drugs such as bupropion, mirtazapine, nefazodone, trazodone, lithium, and venlafaxine.

In certain embodiments, acamprosate prodrugs provided by the present disclosure and pharmaceutical compositions thereof may be administered to a patient for treating an anxiety disorder in combination with a therapy or another therapeutic agent known or believed to be effective in treating an anxiety disorder.

Examples of drugs for useful treating anxiety disorders include alprazolam, atenolol, busipirone, chlordiazepoxide, clonidine, clorazepate, diazepam, doxepin, escitalopram, halazepam, hydroxyzine, lorazepam, nadolol, oxazepam, paroxetine, prochlorperazine, trifluoperazine, venlafaxine, amitriptyline, sertraline, citalopram, clomipramine, fluoxetine, fluvoxamine, and paroxetine.

In certain embodiments, acamprosate prodrugs provided by the present disclosure and pharmaceutical compositions thereof may be administered to a patient for treating a somatoform disorder in combination with a therapy or another therapeutic agent known or believed to be effective in treating a somatoform disorder.

Examples of drugs useful for treating somatoform disorders include tricyclic antidepressants such as amitriptyline, and serotonin reuptake inhibitors.

In certain embodiments, acamprosate prodrugs provided by the present disclosure and pharmaceutical compositions thereof may be administered to a patient for treating a movement disorder in combination with a therapy or another therapeutic agent known or believed to be effective in treating a movement disorder. In certain embodiments, a movement disorder is selected from tardive dyskinesia and spasticity.

Examples of drugs useful for treating movement disorders include levodopa, mild sedatives such as benzodiazepines including alprazolam, chlordiazepoxide, clonazepam, clorazepate, diazepam, lorazepam, and oxazepam; muscle relaxants such as baclofen, anticholinergic drugs such as trihexyphenidyl and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline.

Examples of drugs useful for treating tardive dyskinesia include vitamin E, dizocilpine, memantine, clzapine, lorazepam, diazepam, clonazepam, glycine, D-cycloserine valproic acid, amantadine, ifenprodil, and tetrabenazine.

Examples of drugs useful for treating spasticity include baclofen, R-baclofen, diazepam, tizanidine, clonidine, dantrolene, 4-aminopyridine, cyclobenzaprine, ketazolam, tiagabine, and botulinum A toxin. Compounds having activity as $\alpha 2\delta$ subunit calcium channel modulators such as gabapentin and pregabalin are believed to be useful as antispasticity agents.

In certain embodiments, acamprosate prodrugs provided by the present disclosure and pharmaceutical compositions thereof may be administered to a patient for treating a substance abuse disorder in combination with a therapy or another therapeutic agent known or believed to be effective in treating a substance abuse disorder. In certain embodiments, a substance abuse disorder is chosen from an alcohol abuse disorder, a narcotic abuse disorder, and a nicotine abuse disorder.

Examples of drugs useful for treating alcohol dependency or alcohol abuse disorders include disulfiram, naltrexone, acamprosate, ondansetron, atenolol, chlordiazepoxide, clonidine, clorazepate, diazepam, oxazepam, methadone, topiramate, 1-alpha-acetylmethadol, buprenorphine, bupropion, and baclofen.

Examples of drugs useful for treating opioid abuse disorders include buprenorphine, naloxone, tramadol, methadone, and naltrexone.

Examples of drugs useful for treating cocaine abuse disorders include disulfiram, modafinil, propranolol, baclofen, vigabatrin, and topiramate.

Examples of drugs useful for treating nicotine abuse disorders include bupropion, clonidine, rimonabant, verenicline, and nicotine.

In certain embodiments, acamprosate prodrugs provided by the present disclosure and pharmaceutical compositions thereof may be administered to a patient for treating a cortical spreading depression related disorder in combination with a therapy or another therapeutic agent known or believed to be effective in treating a cortical spreading depression related disorder. In certain embodiments, a cortical spreading depression related disorder is selected from migraine, cerebral injury, epilepsy, and cardiovascular disease.

Drugs useful for treating migraine can prevent a migraine from occurring, abort a migraine that is beginning, or relieve pain during the migraine episode.

Prophylactic migraine treatments reduce the frequency of migraines and include non-steroidal anti-inflammatory agents (NSAIDs), adrenergic beta-blockers, calcium channel blockers, tricyclic antidepressants, selective serotonin reuptake inhibitors, anticonvulsants, NMDA receptor antagonists, angiotensin converting enzyme (ACE) inhibitors, angiotensin-receptor blockers (ARBs), leukotriene-antagonists, dopamine agonists, selective 5HT-1D agonists, selective 5HT-1F agonists, AMPA/KA antagonists, CGRP (calcitonin gene related peptide) antagonists, NOS (nitric oxide synthase) inhibitors, blockers of spreading cortical depression, and other therapy. Examples of NSAIDs useful for preventing migraine include aspirin, ibuprofen, fenoprofen, flurbiprofen, ketoprofen, mefenamic acid, and naproxen. Examples of adrenergic beta-blockers useful for preventing migraine include acebutolol, atenolol, imilol, metoprolol, nadolol, pindolol, propranolol, and timolol. Examples of calcium channel blockers useful for preventing migraine include amlodipine, diltiazem, dotarizine, felodipine, flunarizine, nicardipine, nifedipine, nimodipine, nisoldipine, and verapamil. Examples of tricyclic antidepressants useful for preventing migraine include amitriptyline, desipramine, doxepin, imipramine, nortriptyline, and protriptyline. Examples of selective serotonin reuptake inhibitors (SSRIs) useful for preventing migraine include fluoxetine, methysergide, nefazodone, paroxetine, sertraline, and venlafaxine. Examples of other antidepressants useful for preventing migraine include bupropion, nefazodone, norepinephrine, and trazodone.

Examples of anticonvulsants (antiepileptics) useful for preventing migraine include divalproex sodium, felbamate, gabapentin, lamotrigine, levetiracetam, oxcarbazepine, tiagabine, topiramate, valproate, and zonisamide. Examples of NMDA receptor antagonists useful for preventing migraine include dextromethorphan, magnesium, and ketamine. Examples of angiotensin converting enzyme (ACE) inhibitors useful for preventing migraine include lisinopril. Examples of angiotensin-receptor blockers (ARBs) useful for preventing migraine include candesartan. Examples of leukotriene-antagonists useful for preventing migraine include zileuton, zafirlukast, montelukast, and pranlukast. Examples of dopamine agonists useful for preventing migraine include α-dihydroergocryptine. Examples of other therapy useful for preventing migraine include botulinum toxin, magnesium, hormone therapies, riboflavin, methylergonovine, cyproheptadine, and phenelzine, and complementary therapies such as counseling/psychotherapy, relaxation training, progressive muscle relaxation, guided imagery, diaphragmatic breathing, biofeedback, acupuncture, and physical and massage therapy.

Acute migraine treatments intended to eliminate or reduce the severity of the headache and any associated symptoms after a migraine has begun include serotonin receptor agonists, such as triptans (5-hydroxytryptophan (5-HT) agonists) including almotriptan, eletriptan, frovatriptan, naratriptan, rizatriptan, sumatriptan, imotriptan, and zolmitriptan; ergotamine-based compounds such as dihydroergotamine and ergotamine; antiemetics such as metoclopramide and prochlorperazine; and compounds that provide analgesic effects.

Other examples of drugs used to treat migraine once started include, acetaminophen-aspirin, caffeine, cyproheptadine, methysergide, valproic acid, NSAIDs such as diclofenac, flurbiprofen, ketaprofen, ketorolac, ibuprofen, indomethacin, meclofenamate, and naproxen sodium, opioids such as codeine, meperidine, and oxycodone, and glucocorticoids including dexamethasone, prednisone and methylprednisolone.

GABA analog prodrugs provided by the present disclosure may also be administered in conjunction with drugs that are useful for treating symptoms associated with migraine such as nausea and vomiting, and depression. Examples of useful therapeutic agents for treating or preventing vomiting include, but are not limited to, $5-HT_3$ receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam. Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as fluoxetine, fluvoxamine, paroxetine, and setraline; monoamine oxidase inhibitors such as isocarboxazid, pargyline, phenizine, and tranylcypromine; and psychostimulants such as dextroamphetamine and methylphenidate.

Useful drugs for treating cerebral trauma include corticosteroids such as betamethasone, budesonide, cortisone, dexamethasone, hydrocortisone, methylprednisolone, predisolone, prednisone, and triamcinolone, and antithrombotics such as ticlopidine.

Useful drugs for treating epilepsy include acetazolamide, carbamazepine, gabapentin, mephobarbital, felbamate, fosphenyloin, phenyloin, pregabalin, and valproic acid.

In certain embodiments, acamprosate prodrugs provided by the present disclosure and pharmaceutical compositions thereof may be administered to a patient for treating tinnitus in combination with a therapy or another therapeutic agent known or believed to be effective in treating tinnitus.

A second therapeutic agent for treating or preventing tinnitus can have one or more of analgesic, anesthetic, sodium channel blocker, antiedemic, analgesic, and antipyretic properties. Analgesics include, for example, steroidal anti-inflammatory agents, non-steroidal anti-inflammatory agents, selective COX-2 inhibitors, and narcotics. Examples of analgesics include, for example, acetaminophen, amitriptyline, aspirin, buprenorphine, celecoxib, clonidine, codeine, diclofenac, diflunisal, etodolac, fenoprofen, fentanyl, flurbiprofen, hydromorphone, hydroxyzine, ibuprofen, imipramine, indomethacin, ketoprofen, ketorolac, levorphanol, meperidine, methadone, morphine, naproxen, oxycodone, piroxicam, propoxyphene, refecoxib, sulindac, tolmetin, tramadol, valdecoxib, and combinations of any of the foregoing.

In certain embodiments, a compound of the present disclosure or pharmaceutical composition thereof can be administered with a N-methyl-D-aspartate (NMDA) receptor antagonist that binds to the NMDA receptor at the competitive NMDA antagonist binding site, the non-competitive NMDA antagonist binding site within the ion channel, or to the glycine site. Examples of NMDA receptor antagonists include amantadine, D-2-amino-5-phosphonopentanoic acid (D-AP5), 3-((±)2-carboxypiperazin-4-yl)-propyl-1-phosphonic acid (CCP), conantokins, 7-chlorokynurenate (7-CK), dextromethorphan, ifenprodil, ketamine, memantine, dizocilpine, gacyclidine, licostinel, phencyclidine, riluzole, traxoprodil, and combinations of any of the foregoing (Sands, U.S. Pat. No. 5,716,961 and Guitton et al., US 2006/0063802). Other drugs that may be useful in treating tinnitus include baclofen, caroverine, piribedil, nimodipine, clonazepam, and trimetazidine.

An acamprosate prodrug of Formula (I) or pharmaceutical composition thereof can also be used in conjunction with non-pharmacological tinnitus therapies such as, for example, avoidance of ototoxic medications, reduced consumption of alcohol, caffeine and nicotine, reduced stress, the use of background noises or maskers, behavioral therapies such as hypnosis, cognitive therapy, biofeedback, tinnitus retraining therapy.

In certain embodiments, acamprosate prodrugs provided by the present disclosure and pharmaceutical compositions thereof may be administered to a patient for treating a sleeping disorder in combination with a therapy or another therapeutic agent known or believed to be effective in treating a sleeping disorder.

Examples of drugs useful for treating sleep apnea include mirtiazapine and modafinil.

In certain embodiments, acamprosate prodrugs provided by the present disclosure and pharmaceutical compositions thereof may be administered to a patient for treating multiple sclerosis in combination with a therapy or another therapeutic agent known or believed to be effective in treating multiple sclerosis.

Examples of drugs useful for treating MS include corticosteroids such as methylprednisolone; IFN-β such as IFN-β1a and IFN-β1b; glatiramer acetate; monoclonal antibodies that bind to the very late antigen-4 (VLA-4) integrin such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists.

In certain embodiments, acamprosate prodrugs provided by the present disclosure and pharmaceutical compositions thereof may be administered to a patient for treating pain in combination with a therapy or another therapeutic agent known or believed to be effective in treating pain. In certain embodiments, the pain is neuropathic pain.

Examples of drugs useful for treating pain include opioid analgesics such as morphine, codeine, fentanyl, meperidine, methadone, propoxyphene, levorphanol, hydromorphone, oxycodone, oxymorphone, and pentazocine; nonopioid analgesics such as aspirin, ibuprofen, ketoprofen, naproxen, and acetaminophen; nonsteroidal anti-inflammatory drugs such as aspirin, choline magnesium trisalicylate, diflunisal, salsalate, celecoxib, rofecoxib, valdecoxib, diclofenac, etodolac, fenoprofen, flubiprofen, ibuprofen, indomethacin, keto-profen, ketorolac, meclofanamate, mefenamic acid, meloxicam, nabumetone, naproxen, oxaprozin, piroxicam, sulindac, and tometin; and other drugs such as amitriptyline, desipramine, gabapentin, carbamazepine, phenyloin, clonazepam, divalproex, lamotrigine, topiramate, oxcarbazepine, divalproex, butorphanol, tramadol, valdecoxib, vicoprofen, pentazocine, propoxyhene, fenoprofen, piroxicam, indometnacin, hydroxyzine, buprenorphine, benzocaine, clonidine, flurbiprofen, and meperidine.

The weight ratio of compounds of Formula (I) to a second therapeutic agent may be varied and may depend upon the effective dose of each agent. A therapeutically effective dose of each compound will be used. Thus, for example, when a compound of Formula (I) is combined with another therapeutic agent, the weight ratio of the compound provided by the present disclosure to the second therapeutic agent can be from about 1000:1 to about 1:1000, and in certain embodiments, from about 200:1 to about 1:200.

Combinations of compounds of Formula (I) and a second therapeutic agent may also be within the aforementioned range, but in each case, an effective dose of each active compound can be used. In such combinations a compound of Formula (I) and second therapeutic agent may be administered separately or in conjunction. In addition, administration of one agent may be prior to, concurrent with, or subsequent to the administration of another therapeutic agent(s). Accordingly, compounds of Formula (I) may be used alone or in combination with other therapeutic agents that are known to be beneficial in treating the same disease being treated with the compound of Formula (I) or other therapeutic agents that affect receptors or enzymes that either increase the efficacy, safety, convenience, or reduce unwanted side effects or toxicity of the compound of Formula (I). Compounds of Formula (I) and the other therapeutic agent may be co-administered, either in concomitant therapy or in a fixed combination. The additional therapeutic agent may be administered by the same or different route than the route used to administer a compound of Formula (I) or pharmaceutical composition of any of the foregoing.

EXAMPLES

The following examples describe in detail synthesis of compounds of Formula (I), properties of compounds of Formula (I), and uses of compounds of Formula (I). It will be apparent to those skilled in the art that many modifications, both to materials and methods, may be practiced without departing from the scope of the disclosure.

Description 1

General Experimental Protocols

All reagents and solvents were purchased from commercial suppliers and used without further purification or manipulation.

Proton NMR spectra (400 MHz) were recorded on a Varian AS 400 NMR spectrometer equipped with an autosampler and data processing computation. CDCl$_3$ (99.8% D), DMSO-d$^6$ (99.9% D), or MeOH-d$^4$ (99.8+% D) were used as solvents unless otherwise noted. The CHCl$_3$, DMSO-d$^5$, or MeOH-d$^3$ solvent signals were used for calibration of the individual spectra. Determination of enantiomeric excess (e.e.) of intermediates was accomplished by $^1$H NMR spectroscopy in the presence of the diamagnetic enantiomerically pure chiral co-solvent (R)-(−)-2,2,2-trifluoro-1-(9-anthryl)ethanol (Pirkle-alcohol) and in comparison $^1$H NMR spectra of the corresponding racemic samples under similar conditions. Analytical thin layer chromatography (TLC) was performed using Whatman, Schleicher & Schuell TLC. MK6F silica gel plates (2.5×7.5 cm, 250 μm layer thickness). Dyeing or staining reagents for TLC detection and visualization were prepared according methods known in the art. Ozonolysis reactions were performed using a Welsbach Standard T-series ozone generator. Analytical LC/MS was performed on a Waters 2790 separation module equipped with a Waters Micromass QZ mass spectrometer, a Waters 996 photodiode detector, and a Merck Chromolith UM2072-027 or Phenomenex Luna C-18 analytical column. Mass-guided preparative HPLC purification of final compounds was performed on an instrument equipped with a Waters 600 controller, ZMD Micromass spectrometer, a Waters 2996 photodiode array detector, and a Waters 2700 Sample Manager. Acetonitrile/water gradients containing 0.05% formic acid were used as eluent in both analytical and preparative HPLC procedures. Compound isolation from aqueous solvent mixtures, e.g., acetonitrile/water/0.05% formic acid, was accomplished by primary lyophilization (freeze drying) of the frozen solutions under reduced pressure at room temperature using manifold freeze dryers such as Heto Drywinner DW 6-85-1, Heto FD4, or VIRTIS Freezemobile 25 ES equipped with a high vacuum pump. Optionally, and if the isolated compound had ionizable functional groups such as an amino group or a carboxylic acid, the lyophilization process was conducted in the presence of a slight excess of one molar (1.0 M) hydrochloric acid to yield the purified compound(s) as the corresponding hydrochloride salt (HCl-salt) or the corresponding protonated free carboxylic acid. Additionally, the separation of diastereomers was performed with a UV-guided preparative HPLC using a 250×21.2 mm chiral column Chiralpak IA (Daicel Chemical Industries, Ltd.) and a mixture of ethanol (EtOH) and hexanes (Hxn) (EtOH/Hxn=1:9) containing up to 0.1% formic acid or trifluoroacetic acid (TFA). The flow rate of the mobile phase was 20 mL/min at room temperature. The mixture of diastereomers was dissolved in a mixture of hexane (Hex) and isopropanol (iPrOH) (1:1). The injection volume was 20-60 mg/1,000 μL. Compounds were obtained following concentration under reduced pressure using a rotary evaporator.

Chemical names were generated with Chemistry 4-D Draw Pro Version 7.01c (Draw Chemical Structures Intelligently® 1993-2002) from ChemInnovation Software, Inc., San Diego, USA).

Description 2

General Procedures for the O-Protection of D- and D/L-Pantolactone

Introduction of an α-Hydroxyl Protecting Group via O-Benzylation of D- and D/L-Pantolactone Method A O-Benzyl 2,2,2-Trichloroacetimidate Method Adapting procedures or variations thereof according to O'Brien et al., *Tetrahedron Lett.* 2002, 43, 5491-5494; Weinges et al., *Chem. Ber.* 1994, 127, 1305-1309; Johnston et al., *J. Chem. Soc. Perkin Trans. I*, 2000, 5, 681-695; Iversen et al, *J. Chem. Soc. Chem. Commun.* 1981, 1240-1241; Wessel et al. *J. Chem. Soc. Perkin Trans. I*, 1985, 2247-2250; Enders et al., *Org. Syntheses* 2002, 78, 177-183; and Rai et al., *Tetrahedron Lett.* 2003, 44, 2267-2269, in a representative example, an oven-dried three necked 3,000 mL round bottomed flask equipped with a Tallboys 138 over-head mechanical stirrer was charged under a nitrogen atmosphere with 97.6-117.1 g (750-900 mmol, 1.25-1.5 mol-eq.) of D-pantolactone. The lactone was dissolved in a mixture of 700 mL of anhydrous cyclohexane (Chx) and 300 mL of anhydrous dichloromethane (DCM). One-hundred twelve (112) mL (151.5 g, 600 mmol) of commercially available O-benzyl 2,2,2-trichloroacetimidate or suitable derivative thereof such as O-(4-methoxybenzyl) 2,2,2-trichloroacetimidate was added and the solution cooled to ca. 0° C. (ice bath). Ca. 2.65 mL (ca. 4.50 g, ca. 30 mmol, ca. 5 mol-%) of anhydrous trifluoromethanesulfonic acid (triflic acid) was added dropwise to the stirred reaction mixture. (Caution: The O-benzylation reaction is exothermic!) Other useful catalyst systems include Brønstedt-acids such as para-toluenesulfonic acid (TsOH), camphorsulphonic acid (CSA), trifluoroacetic acid (TFA), and Lewis-acids such as trifluoroborane diethyl ether complex ($BF_3.Et_2O$), trityl tetrafluoroborate ($TrBF_4$), trityl perchlorate ($TrClO_4$), trimethylsilyl trifluoromethanesulfonate (TMSOTf), or tin- and lanthanide triflates ($Sn(OTf)_2$, $Ln(OTf)_3$ in similar or other suitable solvents such as toluene or acetonitrile. The reaction was stirred with gradual warming to room temperature for approximately 24 hours. The reaction was then quenched by addition of water and the reaction mixture was diluted with hexane (Hxn). The reaction mixture was stirred for an additional three hours to ensure hydrolysis of unreacted O-benzyl or (4-methoxybenzyl) 2,2,2-trichloroacetimidate. The reaction mixture was filtered to remove part of the precipitated 2,2,2-trichloroacetamide. After phase separation, the aqueous phase was extracted three more times with hexanes (Hxn), diethyl ether ($Et_2O$), or other suitable solvent. The combined organic extracts were washed with a saturated aqueous solution of sodium hydrogen carbonate ($NaHCO_3$), brine, and dried over anhydrous magnesium sulfate ($MgSO_4$). After filtration and evaporation of the solvents under reduced pressure using a rotary evaporator, the O-protected D- or D/L-pantolactone was obtained as a yellow-brown to colorless, clear oil, typically of high chemical purity as determined by TLC and/or $^1H$ NMR spectroscopy, that solidified upon refrigeration (4° C.). The material thus prepared was generally of sufficient purity to be used directly in the next step without further isolation or purification. Optionally, the isolated material was further purified by silica gel column chromatography using ethyl acetate (EtOAc) and hexane (Hxn) or n-heptane (Hptn) mixtures and/or gradients as eluent to provide O-protected D-pantolactone as a colorless, viscous oil or solid. O-protected D-pantolactone was also further purified by crystallization from pentane (Pnt), hexanes (Hxn), or n-heptane (Hptn) to provide colorless crystals.

Method B

Alkalimetal Hydride/Benzylic Halide Method

Adapting procedures or variations thereof for the synthesis of racemic O-alkylated D/L-pantolactone derivatives according to Aurich et al., *Synthesis* 1995, 9, 1171-1178; and Pirrung et al., *Synthesis* 1995, 4, 458-472, an oven dried 1,000 mL round-bottomed flask equipped with a magnetic stirring bar and an adapter connected to a nitrogen line or manifold was charged with 8.4 g of a 60 wt-% suspension of sodium hydride (NaH) in mineral oil (5.05 g, 210 mmol, 1.05 mol-eq.). The alkali metal hydride was washed twice with hexanes to remove the mineral oil. The solvent was decanted under nitrogen, and the residue dried under reduced pressure to yield a fine, colorless powder. Optionally, the activation procedure was repeated several times to ensure complete removal of the mineral oil additive. The activated hydride was suspended in 500 mL of anhydrous dimethylformamide (DMF), the mixture cooled to ca. 0° C. (ice bath), and 28.6 g (220 mmol, 1.1 mol-eq.) of commercially available D/L-pantolactone was added in divided portions. (Caution: The reaction is exothermic and highly flammable hydrogen gas is generated.) The reaction mixture was stirred for ca. two hours at ca. 0° C. (ice bath), followed by careful addition of 200 mmol (1.0 mol-eq.) of a suitably functionalized benzyl halide, i.e., 4-methoxybenzyl chloride (PMBCl) or benzyl bromide (BnBr), either in neat form or as a concentrated solution in DMF. The mixture was stirred overnight with gradual warming to room temperature. The reaction mixture was carefully quenched by the addition of water. (Caution: The quenching reaction is exothermic and some highly flammable hydrogen gas is generated.) The reaction mixture was further diluted with methyl tert-butyl ether (MTBE). The diluted solutions were washed with one molar (1.0) hydrochloric acid (HCl), water, a saturated aqueous solution of sodium hydrogen carbonate ($NaHCO_3$), brine, dried over anhydrous magnesium sulfate ($MgSO_4$), filtered, and the solvents were evaporated under reduced pressure using a rotary evaporator to provide the target compound as an oil, typically of high chemical purity as determined by TLC and/or $^1H$ NMR spectroscopy, that solidified at room temperature. The material thus prepared was generally of sufficient purity to be used directly in the next step without further isolation or purification. Optionally, the isolated material was further purified by silica gel column chromatography using ethyl acetate (EtOAc) and hexane (Hxn) or n-heptane (Hptn) mixtures and/or gradients as eluent to yield the O-protected D- or D/L-pantolactone as a colorless, viscous oil or solid. The target compound was also further purified by crystallization from pentane (Pnt), hexanes (Hxn), or n-heptane (Hptn) to yield colorless crystals.

Method C

Alkalimetal Carbonate/Benzylic Halide Method

Alternatively, adapting a procedure or a variation thereof according to Dueno et al., *Tetrahedron Lett.* 1999, 40, 1843-1846, an oven-dried 1,000 mL round-bottomed flask equipped with a magnetic stir bar and rubber septum was charged under a nitrogen atmosphere with 28.6 g (220 mmol, 1.1 mol-eq.) of commercially available D/L-pantolactone and 97.5 g (300 mmol, 1.5 mol-eq.) of freshly powdered cesium carbonate ($Cs_2CO_3$). The solids were suspended in 500 mL of anhydrous dimethylformamide (DMF) and 200 mmol (1.0 mol-eq.) of a suitably functionalized benzyl halide, i.e., 4-methoxybenzyl chloride (PMBCl) or benzyl bromide (BnBr), either in neat form or as a concentrated solution in DMF, was added. The reaction mixture was stirred for ca. 48 hours at room temperature. The reaction mixture was then diluted with methyl tert-butyl ether (MTBE) and solids were filtered off with a Büchner-funnel and O-protected D- or D/L-pantolactone was obtained using work-up procedures similar to those described in Method B.

Introduction of an α-Hydroxyl Protecting Group via O-Silylation of D- and D/L-Pantolactone Method D Adapting procedures or variations thereof according to Miyaoka et al., *Tetrahedron: Asymmetry* 1995, 6(2), 587-594; Hart et al., *Heterocycles* 2000, 52(3), 1025-1028; Martin et al., *Tetrahedron Lett.* 2001, 42, 8373-8377; Tokuzaki et al., *Tetrahedron Lett.* 2000, 41(31), 5923-5926; and Storer et al., *Chem. Eur. J.* 2004, 10(10), 2529-2547, an oven-dried 1,000 mL round-bottomed flask equipped with a magnetic stirring bar and a rubber septum was charged under a nitrogen atmosphere with 28.6 g (220 mmol, 1.1-mol-eq) of D-pantolactone, 27.2 g (400 mmol) of imidazole, and 400 mL of anhydrous dimethylformamide (DMF). To the solution was added portion-wise 200 mmol (1.0 mol-eq.) of a suitably substituted mixed-alkyl or aryl/alkyl chloro silane, i.e., tert-butyl dimethylsilyl chloride (TBDMSCl). The reaction mixture was stirred overnight at room temperature and then diluted with diethyl ether ($Et_2O$) or methyl tert-butyl ether (MTBE). The solution was washed successively several times with one molar (1.0 M) hydrochloric acid (HCl), water, a saturated aqueous solution of sodium hydrogen carbonate ($NaHCO_3$), brine, dried over anhydrous magnesium sulfate ($MgSO_4$), filtered, and the solvents evaporated under reduced pressure using a rotary evaporator to provide the target compound as an oil or solid, typically of high chemical purity as determined by TLC and/or $^1H$ NMR spectroscopy. The material thus prepared was generally of sufficient purity to be used directly in the next step without further isolation or purification. Optionally, the isolated material was further purified by silica gel column chromatography using diethyl ether ($Et_2O$) or methyl tert-butyl ether (MTBE) and hexane (Hxn) mixtures and/or gradients as eluent to provide O-protected D- or D/L-pantolactone as a colorless, viscous oil or solid. The target compounds were optionally further purified by crystallization from suitable solvents or mixtures thereof.

Description 3

General Procedure for the Reduction of O-Protected Pantolactone Derivatives to the Corresponding, Lactol Derivatives Adapting procedures or variations thereof according to O'Brien et al., *Tetrahedron Lett.* 2002, 43, 5491-5494; Weinges et al., *Chem. Ber.* 1994, 127, 1305-1309; Mandel et al., *Org. Lett.* 2004, 6(26), 4801-4803; Roy et al., *Can. J. Chem.* 1991, 69(1), 62-69; Aurich et al., *Synthesis* 1995, (9), 1171-1171; Aurich et al., *Chem. Ber.,* 1991, 124, 2329-2334; Hart et al., *J. Org. Chem.* 1992, 57, 5670-5680; Pirrung et al., *Synthesis* 1995, (4), 458-472; Gimalova et al., *Russ. J. Org. Chem.* 2005, 41(8), 1183-1186; Klar et al., *Synthesis* 2005, (2), 301-305; Miyaoka et al., *Tetrahedron: Asymmetry* 1995, 6(2), 587-594; Tokuzaki et al., *Tetrahedron Lett.* 2000, 41(31), 5923-5926; Hart et al., *Heterocycles* 2000, 52(3), 1025-1028; Martin et al., *Tetrahedron Lett.* 2001, 42, 8373-8377; and Storer et al., *Chem. Eur. J.* 2004, 10(10), 2529-2547, in a representative example, an oven-dried three-necked 2,000 mL round-bottomed flask equipped with a Tallboys 138 over-head mechanical stirrer, a pressure equilibrated addition funnel, and an internal thermometer was charged under a nitrogen atmosphere with 200 mmol (1.0 mol-eq) of the O-benzyl or O-silyl protected D- or D/L-pantolactone derivative and 300-600 mL of anhydrous dichloromethane (DCM) or other suitable solvents such as hexane, toluene, or others. The solution was cooled to ca. −78° C. (dry ice/acetone bath) and 240-300 mL (240-300 mmol, 1.2-1.5 mol-eq.) of a one molar (1 M) solution of diisobutylaluminum hydride [$(iBu)_2AlH$, DIBAL(H)] in heptane (or other suitable solvent) was slowly added such that the temperature in the flask did not rise above ca. −70° C. The reaction mixture was stirred for ca. two hours at this temperature. The progress of the reaction was monitored by TLC. The reaction mixture was carefully added to a 2,000-3,000 mL beaker containing a vigorously stirred pre-cooled (ca. 0° C.) mixture of a one to three molar (1-3 M) sulfuric acid ($H_2SO_4$) and methyl tert-butyl ether (MTBE) (400-800 mL total) in a ratio of v/v ~1:1. (Caution: Quenching of DIBAL(H) with protic solvents is very exothermic and may result in violent evolution of flammable hydrogen gas. The quenching process in this sequence proceeds normally rather smoothly). The quenched reaction mixture was further diluted with methyl tert-butyl ether (MTBE) (300-800 mL). After phase separation, the aqueous phase was extracted several times with methyl tert-butyl ether (MTBE). The combined organic extracts were successively washed with a one molar (1.0 M) hydrochloric acid (HCl), a saturated aqueous solution of sodium hydrogen carbonate ($NaHCO_3$), and brine. The solution was dried over anhydrous magnesium sulfate ($MgSO_4$), and filtered. Evaporation of the solvents under reduced pressure using a rotary evaporator yielded the target compound(s) as a viscous oil or solid, often of high chemical purity by TLC and/or $^1$H NMR spectroscopy. Oils often solidified upon refrigeration (4° C.). The lactols were obtained as inseparable mixtures of anomers (diastereomers) with variable anomeric ratios from different batches. The material thus prepared was generally of sufficient chemical purity to be used directly in the next step without further isolation or purification. Optionally, the isolated material was further purified by silica gel column chromatography using ethyl acetate (EtOAc) or methyl tert-butyl ether (MTBE) and hexane (Hxn) or n-heptane (Hptn) mixtures and/or gradients as eluent to provide the corresponding lactol derivative as a colorless, viscous oil or solid. The lactol derivatives were optionally further purified by crystallization from suitable solvents or mixtures thereof.

Description 4

General Procedure for Methylenation of Lactols via Wittig-Olefination

Method A

Wittig-Olefination Using Non-Stabilized Phosphoranes

Adapting procedures or variation thereof according to O'Brien et al., *Tetrahedron Lett.* 2002, 43, 5491-5494; Mandel et al., *Org. Lett.* 2004, 6(26), 4801-4803; Pirrung et al., *Synthesis* 1995, 4, 458-472; Martin et al., *Tetrahedron Lett.* 2001, 42, 8373-8377; and Klar et al., *Synthesis* 2005, 2, 301-305, in a representative example, an oven-dried three-necked 2,000 mL round bottomed flask equipped with a Tallboys 138 over-head mechanical stirrer, a pressure equilibrated addition funnel, and an internal thermometer was charged under a nitrogen atmosphere with 125.0 g (350 mmol, 3.0 mol-eq) of commercially available, optionally freshly powdered, methyltriphenylphosphonium bromide ($Ph_3PMeBr$). The salt was suspended in 300-500 mL of anhydrous tetrahydrofuran (THF). Three hundred thirty (330)-340 mL (330-340 mmol, 2.85-2.95 mol-eq.) of a one molar (1 M) solution of potassium tert-butoxide (KOtBu) in tetrahydrofuran (THF) was carefully added and vigorously stirred at a temperature between ca. 0° C. (ice bath) and room temperature. The reaction mixture turned from yellow to dark orange, and the reaction mixture was stirred overnight at room temperature to ensure that the alkoxide was completely consumed (Olmstead et al., *J. Org. Chem.* 1980, 45, 3295-3200; and Zhang et al., *J. Am. Chem. Soc.* 1994, 116, 968-972), thus preventing racemization of the stereogenic center by unreacted base. Alternatively, a commercially available solution of n-butyllithium (nBuLi) in a suitable inert solvent, i.e. 1.6 M in n-hexane, was also used as a base instead of potassium tert-butoxide (KOtBu). If n-BuLi was employed as a base, the formation of the corresponding triphenylphosphorane was always conducted at ca. 0° C. (ice bath). The reaction mixture was cooled to ca. −78° C. (dry ice/acetone bath). A solution of 115 mmol (1.0 mol-eq) of an appropriately protected lactol in ca. 100-200 mL of anhydrous tetrahydrofuran (THF) was slowly added at this temperature under a nitrogen atmosphere, and the reaction mixture stirred overnight with gradual warming to room temperature to ensure that the lactol component was completely consumed. The Wittig-olefination reaction was also run at higher temperatures (between ca. −78° C. and ca. 0° C.) with a slight compromise in the optical purity of the target compound. Olefination of racemic materials was conducted normally between ca. 0° C. (ice bath) and room temperature. Optionally, the reaction was quenched by adding water or one molar (1.0 M) hydrochloric acid (HCl). The solvent was partially removed under reduced pressure using a rotary evaporator. The dark orange residue was diluted with a mixture of methyl tert-butyl ether (MTBE) and n-heptane (Hptn) (v/v ~1:1), and the solids were finely suspended in the solvent mixture to yield a creamy, orange-brown suspension. After precipitation of the solids, the supernatant was filtered off using a short plug of Celite® in a Büchner-funnel. This procedure was repeated several times to obtain high recovery of the title compound. The clear orange combined filtrates were further diluted with water and methyl tert-butyl ether (MTBE) and the phases separated. The aqueous phase was extracted two additional times with methyl tert-butyl ether (MTBE) and the combined organic extracts were washed with a saturated aqueous solution of sodium hydrogen carbonate ($NaHCO_3$), water, and brine. The organic solution was dried over anhydrous magnesium sulfate ($MgSO_4$), filtered, and the solvents were removed under reduced pressure using a rotary evaporator. Additional side products, i.e., triphenyl phosphine oxide ($Ph_3PO$), usually precipitated during evaporation of the solvents that were removed by filtration from the partially evaporated solution. Optionally, residual side product was removed by crystallization from a solution of the crude isolated product in diethyl ether ($Et_2O$) or methyl tert-butyl ether (MTBE) and hexane (Hxn) or n-heptane (Hptn) mixtures at lowered temperatures, i.e. in a freezer at ca. −20° C. In some cases the desired alkenes were isolated in highly pure form and could be used in the next step without further isolation or purification. Optionally, the crude residue was further purified by silica gel column chromatography using mixtures of ethyl acetate (EtOAc), methyl tert-butyl ether (MTBE) and hexane (Hxn), or n-heptane (Hptn) as eluent. The desired alkene was isolated as pale-yellow to yellow, viscous liquids or oils after removing the solvents under reduced pressure.

Method B

Wittig-Olefination Using Stabilized Phosphoranes

Adapting a procedure or a variation thereof according to Miyaoka et al., *Tetrahedron: Asymmetry* 1995, 6(2), 587-594; Hart et al., *Heterocycles* 2000, 52(3), 1025-1028; and Tokuzaki et al., *Tetrahedron Lett.* 2000, 41(31), 5923-5926, in a typical example, an oven-dried three-necked 2,000 mL round bottomed flask equipped with a large magnetic stirring bar or a Tallboys 138 over-head mechanical stirrer and a reflux condenser was charged under a nitrogen atmosphere with 150 mmol (1.0 mol-eq) of an appropriately protected lactol. The lactol was dissolved in 150-800 mL of a suitable anhydrous solvent such as 1,2-dichloroethane (DCE), benzene ($C_6H_6$), or toluene ($C_6H_5CH_3$). Three-hundred (300) mmol-1.2 mol (2-6 mol-eq.) of a suitably functionalized alkyl triphenylphosphoranyl acetate, i.e., commercially available methyl triphenylphosphoranyl acetate, was added. The reaction mixture was heated to ca. 70-80° C. (oil bath) for six to 12 hours. The reaction was monitored by TLC. Upon completion and cooling, the solids were filtered off using a Büchner-funnel and the filter residue was washed with methyl tert-butyl ether (MTBE) or other suitable solvent. The solvents were removed under reduced pressure using a rotary evaporator, and the isolated material was further purified by silica gel column chromatography using methyl tert-butyl ether (MTBE) and hexane (Hxn) mixtures and/or gradients as eluent to provide the corresponding alkene as a colorless, viscous oil or solid.

Description 5

General Procedure for the Determination of Enantiomeric Excess (e.e.s) Using $^1$H NMR Shift and Diamagnetic Chiral Solvating Agents (CSAs) (Pirkle-Alcohol)

Ca. 10-12 µM of the corresponding racemic derivative was dissolved in 0.6-0.75 mL of deuterochloroform ($CDCl_3$, >99.9% d) in the presence of 3-15 mol-eq. of a diamagnetic chiral solvating agent (CSA), i.e. (R)-(−)-2,2,2-trifluoroethanol-1-(9-anthryl)ethanol (Pirkle-alcohol). The amount of the CSA was adjusted until an appropriate set of NMR signals showed a significant difference in chemical shift (typically about 10-12 mol-eq.). The enantiomerically enriched sample was treated in the same manner and $^1$H NMR spectroscopic shift analysis was performed using comparable conditions. The enantiomeric purity of the enantiomerically enriched material was then determined in comparison with the racemic sample.

Example 1

(3S)-2,2-Dimethyl-3-(phenylmethoxy)pent-4-en-1-ol (1)

Step A: (3R)-4,4-Dimethyl-3-(phenylmethoxy)-3,4,5-trihydrofuran-2-one (1a)

Following the general procedure for the introduction an α-hydroxyl protecting group via O-alkylation of D-pantolactone (Description 2, Method A) 65.1 g (500 mmol) of D-pantolactone was reacted with 62.2 mL (84.2 g, 333 mmol) of O-benzyl 2,2,2-trichloroacetimidate in a mixture of 500 mL of anhydrous cyclohexane (Chx) and 230-250 mL of anhydrous dichloromethane (DCM) in the presence of 1.47 mL (2.50 g, 16.7 mmol, 5 mol-%) of anhydrous trifluoromethanesulfonic acid (triflic acid). After work-up and isolation, the title compound (1a) was obtained as a yellow-brown to colorless oil of high chemical purity as determined by TLC and $^1$H NMR. The material was further purified by silica gel column chromatography using ethyl acetate (EtOAc) and n-heptane (Hptn) mixtures as eluent (EtOAc/Hptn=1:4 or 1:6) to provide 52.1 g (71% yield) of the title compound (1a) as a colorless, viscous oil that solidified at 4° C. to a colorless solid. M.p.: 42° C. (Lit: crystals from pentane, m.p. 48° C.). $R_f$=0.44 (EtOAc/Hptn=1:4). $^1$H NMR (400 MHz, $CDCl_3$): δ=1.12 (s, 3H), 1.15 (s, 3H), 3.75 (s, 1H), 3.88 (d, J=8.8 Hz, 1H), 4.01 (d, J=8.8 Hz, 1H), 4.76 (d, J=12.0 Hz, 1H), 5.05 (d, J=12.0 Hz, 1H), 7.30-7.40 (m, 5H) ppm. MS (ESI) m/z: 221.11 (M+H)$^+$. The analytical data was consistent with the proposed structure and with the data reported in the literature (Mandel et al., *Org. Lett.*, 2004, 6(26), 4801-4803; and Weinges et al., *Chem. Ber.*, 1994, 127, 1305-1309).

Alternatively, the α-hydroxyl group of D-pantolactone was O-benzylated in 86% yield with silver oxide/benzyl bromide ($Ag_2O$/BnBr) in dimethylformamide (DMF) at ambient temperature (Mandel et al., *Org. Lett.* 2004, 6(26), 4801-4803), albeit, in some cases, with partial racemization of the stereogenic center in the α-position to the carbonyl group if the basicity of the reaction medium was insufficiently controlled.

Step B: (2R/S)(3R)-4,4-Dimethyl-3-phenylmethoxy) oxolan-2-ol (1b)

Following the general procedure for the reduction of O-protected D-pantolactone derivatives to the corresponding lactol derivatives of Description 3, 95.7 g (435 mmol) of (3R)-4,4-dimethyl-3-(phenylmethoxy)-3,4,5-trihydrofuran-2-one (1a) was reduced at −78° C. in 1,000 mL of anhydrous dichloromethane (DCM) with 575 mL (575 mmol, ~1.3 mol-eq.) of a one molar (1 M) solution of diisobutylaluminum hydride [(iBu)$_2$AlH, DIBAL(H)] in n-heptane. After work-up and isolation, 84.6 g (87% yield) of the title compound (1b) was obtained as a viscous, yellow oil that eventually solidified to a colorless solid. The material consisted of an inseparable mixture of anomers (diastereomers) of variable ratio from several batches. The material was of sufficient chemical purity to be used directly in the next step without further purification. Alternatively, the material was purified by crystallization from n-pentane to yield colorless crystals. D.r.: ~3:2 (by $^1$H NMR spectroscopy, 400 MHz, $CDCl_3$); M.p.: 61.4-67.7° C. (Lit: crystals from n-pentane; m.p.=73° C.); $R_f$=0.18 (EtOAc/Hptn=1:4). $^1$H NMR (400 MHz, $CDCl_3$): Anomer 1: δ=1.09 (s, 3H), 1.14 (s, 3H), 3.44 (d, J=8.4 Hz, 1H), 3.46 (d, J=4.4 Hz, 1H), 3.73 (d, J=8.4 Hz, 1H), 4.01 (br. d, J=9.6 Hz, 1H), 4.60 (d, J=12.0 Hz, 1H), 4.72 (d, J=12.0 Hz, 1H), 5.48 (dd, J=9.6, 4.4 Hz, 1H), 7.27-7.41 (m, 5H) ppm. Anomer 2: δ=1.13 (s, 3H), 1.14 (s, 3H), 2.71-2.81 (br. m, 1H), 3.54 (d, J=2.8 Hz, 1H), 3.66 (d, J=8.4 Hz, 1H), 3.83 (d, J=8.4 Hz, 1H), 4.60 (d, J=11.6 Hz, 1H), 4.68 (d, J=10.8 Hz, 1H), 5.38 (dd, J=2.8 Hz, 1H), 7.27-7.41 (m, 5H) ppm. MS (ESI) m/z: 223.1 (M+H)$^+$, 245.1 (M+Na)$^+$. The analytical data was consistent with the proposed structure and with the data reported in the literature (Mandel et al., *Org. Lett.*, 2004, 6(26), 4801-4803; and Weinges et al., *Chem. Ber.*, 1994, 127, 1305-1309).

Step C: (3S)-2,2-Dimethyl-3-(phenylmethoxy)pent-4-en-1-ol (1)

Following the general procedure for the methylenation of lactols via Wittig-olefination (Description 4, Method A), 408 g (1.14 mmol) of freshly powdered methyltriphenylphosphonium bromide was reacted for six hours at room temperature with 1.1 L (1.1 mol) of a one molar (1 M) solution of potassium tert-butoxide (KOtBu) in 1 L of anhydrous tetrahydrofuran (THF). The phosphorane was subsequently reacted in situ at ca. −78° C. (dry ice/isopropanol bath) with 84.6 g (381 mmol) of (2R/S)(3R)-4,4-dimethyl-3-phenylmethoxy)oxolan-2-ol (1b) dissolved in 200 mL of anhydrous tetrahydrofuran (THF). After work-up and isolation, the crude product was purification in four portions by silica gel column chromatography using ethyl acetate (EtOAc) and n-heptane (Hptn) mixtures as eluent (EtOAc/Hptn=1:4) to provide 48.6 g (58% yield) of the title compound (1) as a colorless oil.

$R_f$=0.35 (EtOAc/Hxn=1:4); 0.19 (EtOAc/Hxn=1:6). $^1$H NMR (400 MHz, CDCl$_3$): δ=0.91 (s, 3H), 0.92 (s, 3H), 2.83 (t, J=6.0 Hz, 1H), 3.38 (dd, J=10.8, 6.0 Hz, 1H), 3.55 (dd, J=10.8, 6.4 Hz, 1H), 3.63 (d, J=8.4 Hz, 1H), 4.31 (d, J=12.0 Hz, 1H), 4.62 (d, J=11.6 Hz, 1H), 5.26 (ddd, J=17.0, 2.0, 0.8 Hz, 1H), 5.38 (ddd, J=10.6, 1.6, 0.8 Hz, 1H), 5.81 (ddd, J=17.2, 10.4, 8.4 Hz, 1H), 7.27-7.38 (m, 5H) ppm. MS (ESI) m/z: 221.1 (M+H)$^+$. The analytical data was consistent with the proposed structure and with the data reported in the literature (Mandel et al., Org. Lett. 2004, 6(26), 4801-4803; and Ito et al., Synthesis 1993, 137-140).

Following the general procedure for the determination of the enantiomeric excess using diamagnetic chiral cosolvents (CSAs) of Description 5, the enantiomeric excess (e.e.) was determined to be greater than 95% (by $^1$H NMR shift method (400 MHz, CDCl$_3$) using the commercially available diamagnetic chiral co-solvent (R)-(−)-2,2,2-trifluoro-1-(9-anthryl) ethanol (Pirkle-alcohol)) and in comparison with racemic (3R/S)-2,2-dimethyl-3-(phenylmethoxy)pent-4-en-1-ol (2).

Example 2

(3R/S)-2,2-Dimethyl-3-(phenylmethoxy)pent-4-en-1-ol (2)

Step A: (3R/S)-4,4-Dimethyl-3-(phenylmethoxy)-3,4,5-trihydrofuran-2-one (2a)

Following the general procedure for the O-alkyl protection of racemic pantolactones (Description 2, Method B), 2.86 g (22.0 mmol) of D/L-pantolactone (A) was reacted in 50 mL of anhydrous dimethylformamide (DMF) with 840 mg (21.0 mmol) of a 60 wt-% suspension of sodium hydride (NaH) and 2.38 mL (3.42 g, 20.0 mmol) of benzyl bromide (BnBr). After work-up and isolation, 3.47 g (79% yield) of the title compound (2a) was obtained as a pale-yellow oil. The material was of sufficient chemical purity to be used directly in the next step without further purification. $R_f$=0.37 (EtOAc/Hxn=1:6). MS (ESI) m/z: 221.10 (M+H)$^+$. The analytical data was consistent with the proposed structure, with the corresponding enantiopure compound (1a), and with the data reported in the literature (Mandel et al., Org. Lett. 2004, 6(26), 4801-4803; and Weinges et al., Chem. Ber. 1994, 127, 1305-1309).

Step B: (2R/S)(3R/S)-4,4-Dimethyl-3-phenyl-methoxy)oxolan-2-ol (2b)

Following the general procedure for the reduction of O-protected pantolactones of Description 3, 3.47 g (15.8 mmol) of (3R/S)-4,4-dimethyl-3-(phenylmethoxy)-3,4,5-trihydrofuran-2-one (2a) was reacted at −78° C. in 50 mL of anhydrous dichloromethane (DCM) with 19 mL (19 mmol) of a one molar solution of diisobutylaluminum hydride [(iBu)$_2$AlH, DIBAL(H)] in hexanes. After work-up and isolation, 3.22 g (92% yield) of the title compound (2b) was obtained as a pale-yellow, opaque oil as a mixture of diastereomers. The material was of sufficient chemical purity to be used directly in the next step without further purification. D.r. ~3:2 (by $^1$H NMR spectroscopy, 400 MHz, CDCl$_3$). $R_f$=0.45 (EtOAc/Hxn=1:2). MS (ESI) m/z: 223.14 (M+H)$^+$. The analytical data was consistent with the proposed structure, with the corresponding material (1b) obtained starting from enantiopure D-pantolactone, and with the data reported in the literature (Mandel et al., Org. Lett. 2004, 6(26), 4801-4803; and Weinges et al., Chem. Ber. 1994, 127, 1305-1309).

Step C: (3R/S)-2,2-Dimethyl-3-(phenylmethoxy) pent-4-en-1-ol (2)

Following the general procedure for the methylenation of lactols via Wittig-olefination (Description 4, Method A), 100 g (280 mmol) of methyltriphenylphosphonium bromide was reacted overnight at room temperature with 270 mL (270 mmol) of a one molar (1.0 M) solution of potassium tert-butoxide (KOtBu) in 350 mL of anhydrous tetrahydrofuran (THF). The phosphorane was subsequently reacted in situ at ca. 0° C. (ice bath) with 29.7 g (134 mmol) of (2R/S)(3R/S)-4,4-dimethyl-3-phenylmethoxy)oxolan-2-ol (2b) dissolved in 150 mL of anhydrous tetrahydrofuran (THF). After work-up and isolation, followed by repeated titruation of residual triphenylphosphine oxide (Ph$_3$PO) with methyl tert-butyl ether (MTBE) and hexane (Hxn) mixtures, i.e. MTBE/Hxn ~1:2 (v/v) at ca. −20° C. (freezer), the crude product was obtained. Purification by silica gel column chromatography using ethyl acetate (EtOAc) and hexane (Hxn) mixtures as eluent (EtOAc/Hxn=1:4→EtOAc/Hxn=1:3→EtOAc/Hxn=1:2) provided 18.0 g (61% yield) of the title compound (2) as a colorless liquid. $R_f$=0.63 (EtOAc/Hxn=1:3). MS (ESI) m/z: 221.1 (M+H)$^+$, 243.1 (M+Na)$^+$. The analytical data was consistent with the proposed structure, with the corresponding material (1) obtained starting from enantiopure D-pantolactone, and with the data reported in the literature (Mandel et al., Org. Lett. 2004, 6(26), 4801-4803; and Ito et al., Synthesis 1993, 137-140).

Example 3

(3R/S)-[(4-Methoxyphenyl)methoxy]-2,2-dimethyl-pent-4-en-1-ol (3)

Step A: (3R/S)-4,4-Dimethyl-3-[(4-methoxyphenyl) methoxy]-3,4,5-trihydrofuran-2-one (3a)

Following the general procedure for the O-alkyl protection of racemic pantolactones (Description 2. Method B), 28.6 g (220 mmol) of D/L-pantolactone was reacted in 500 mL of anhydrous dimethylformamide (DMF) with 8.4 g (210 mmol) of a 60 wt-% suspension of sodium hydride (NaH) and 27.1 mL (31.3 g, 200 mmol) of 4-methoxybenzyl chloride (PMBCl). After work-up and isolation, 46.0 g (92% yield) of the title compound (3a) was obtained as a clear oil that solidified to a pale-yellow solid. The material was of sufficient purity to be used directly in the next step without further purification. M.p.: 48.7-59.7° C.

Alternatively, following the general procedure for the O-alkyl protection of racemic pantolactones (Description 2, Method C), 28.6 g (220 mmol) of D/L-pantolactone was reacted in 500 mL of anhydrous dimethylformamide (DMF) with 97.8 g (300 mmol) of freshly powdered cesium carbonate (Cs$_2$CO$_3$) and 27.1 mL (31.3 g, 200 mmol) of 4-methoxy-benzyl chloride (PMBCl). After work-up and isolation, 39.6 g (79% yield) of the title compound (3a) was obtained as a turbid oil that solidified to a pale-yellow solid. The material was of sufficient purity to be used directly in the next step without further purification. M.p.: 48.7-59.4° C. $R_f$=0.61 (EtOAc/Hxn=1:2). $^1$H NMR (400 MHz, CDCl$_3$): δ=1.09 (s, 3H), 1.13 (s, 3H), 3.72 (s, 1H), 3.82 (s, 3H), 3.86 (d, J=8.8 Hz, 1H), 4.00 (d, J=8.8 Hz, 1H), 4.70 (d, J=11.6, 1H), 4.96 (d, J=11.6, 1H), 6.87-6.92 (m, 2H), 7.28-7.33 (m, 2H) ppm. MS (ESI) m/z: 250.08 (M+H)$^+$. The analytical data was consistent with the proposed structure.

Step B: (2R/S)(3R/S)-[(4-Methoxyphenyl)methoxy]-4,4-dimethyloxolan-2-ol (3b)

Following the general procedure for the reduction of O-protected pantolactones (Description 3), 47.1 g (188 mmol) of (3R/S)-4,4-dimethyl-3[(4-methoxyphenyl)methoxy]-3,4,5-trihydrofuran-2-one (3a) was reacted at −78° C. in 1,000 mL of anhydrous dichloromethane (DCM) with 230 mL (230 mmol) of a one molar solution (1.0 M) of diisobutylaluminum hydride [(iBu)$_2$AlH, DIBAL(H)] in hexanes. After work-up and isolation, 45.4 g (96% yield) of the title compound (3b) was obtained as an opaque oil as an inseparable mixture of anomers (diastereomers) of variable ratio from several batches. The material was of sufficient chemical purity to be used directly in the next step without further purification. D.r. ~2:1 (by $^1$H NMR spectroscopy, 400 MHz, CDCl$_3$). R$_f$=0.35 (EtOAc/Hxn=1:2). $^1$H NMR (400 MHz, CDCl$_3$): Major diastereomer: δ=1.10 (s, 3H), 1.11 (s, 3H), 3.08 (br. d, J=3.6 Hz, 1H), 3.51 (d, J=2.8 Hz, 1H), 3.64 (d, J=8.4 Hz, 1H), 3.81 (d, J=5.2 Hz, 1H), 3.814 (s, 3H), 4.52 (d, J=11.2 Hz, 1H), 4.64 (d, J=11.2 Hz, 1H), 5.36 (dd, J=3.6, 2.8 Hz, 1H), 6.86-6.90 (m, 2H), 7.26-7.30 (m, 2H) ppm. Minor diastereomer: δ=1.07 (s, 3H), 1.12 (s, 3H), 3.42 (d, J=7.6 Hz, 1H), 3.46 (d, J=2.8 Hz, 1H), 3.71 (d, J=8.4 Hz, 1H), 3.92 (s, 3H), 4.05, J=10.0 Hz, 1H), 4.56 (d, J=11.2 Hz, 1H), 4.60 (d, J=10.8 Hz, 1H), 5.45 (dd, J=9.6, 4.0 Hz, 1H), 6.88-6.92 (m, 2H), 7.26-7.30 (m, 2H) ppm. MS (ESI) m/z: 253.14 (M+H)$^+$. The analytical data was consistent with the proposed structure.

Step C: (3R/S)-[(4-Methoxyphenyl)methoxy]-2,2-dimethylpent-4-en-1-ol (3)

Following the general procedure for the methylenation of lactols by Wittig-olefination (Description 4, Method A), 81.1 g (227 mmol) of methyltriphenylphosphonium bromide was reacted for six hours at room temperature with 215 mL (215 mmol) of a one molar (1.0 M) solution of potassium tert-butoxide (KOtBu) in 500 mL of anhydrous tetrahydrofuran (THF). The phosphorane was subsequently reacted in situ at ca. 0° C. (ice bath) with 25.2 g (100 mmol) of (2R/S)(3R/S)-[(4-methoxyphenyl)methoxy]-4,4-dimethyloxolan-2-ol (3b) dissolved in 100 mL of anhydrous tetrahydrofuran (THF). Work-up and isolation, followed by repeated titration of residual triphenylphosphine oxide (Ph$_3$PO) with diethyl ether (Et$_2$O) and hexane (Hxn) mixtures, i.e. Et$_2$O/Hxn ca. 1:2 (v/v), yielded a crude product. Purification by silica gel column chromatography using methyl tert-butyl ether (MTBE) and hexane (Hxn) mixtures as eluent (MTBE/Hxn=1:6→MTBE/Hxn=1:4→MTBE/Hxn=1:3) provided the title compound (3) as a colorless, oily liquid. R$_f$=0.37 (EtOAc/Hxn=1:4). $^1$H NMR (400 MHz, CDCl$_3$): δ=0.89 (s, 3H), 0.90 (s, 3H), 2.88 (t, J=6.0 Hz, 1H), 3.35 (dd, J=10.8, 5.6 Hz, 1H), 3.52 (dd, J=10.8, 6.0 Hz, 1H), 3.82 (s, 3H), 4.23 (d, J=11.6 Hz, 1H), 4.55 (d, J=11.2 Hz, 1H), 5.24 (dd, J=17.2, 1.6 Hz, 1H), 5.37 (dd, J=10.0, 2.0 Hz, 1H), 5.80 (ddd, J=17.2, 10.2, 8.0 Hz, 1H), 6.86-6.90 (m, 2H), 7.21-7.24 (m, 2H) ppm. MS (ESI) m/z: 251.1 (M+H)$^+$. The analytical data was consistent with the proposed structure.

Example 4

Methyl (2E)(4S)-6-hydroxy-5,5-dimethyl-4-(1,1,2,2-tetramethyl-1-silapropoxy)hex-2-enoate (4)

Step A: (3R)-4,4-Dimethyl-3-(1,1,2,2-tetramethyl-1-silapropoxy)-3,4,5-trihydrofuran-2-one (4a)

Following the general procedure for the O-silyl protection of pantolactones (Description 2, Method D), 50.0 g (384.2 mmol) of D-pantolactone was reacted in 385 mL of anhydrous dimethylformamide (DMF) in the presence of 47.1 g (691.6 mmol) of imidazole with 52.1 g (345.8 mmol) of tert-butyldimethylsilyl chloride (TBDMSCl, tert-butyl(chloro)dimethylsilane). After work-up and isolation, 80 g (85% yield) of the title compound (4a) was obtained as a colorless solid. The material was of sufficient purity to be used directly in the next step without further purification. M.p.: 94.5-96.8° C. (Lit: m.p.: 96-97° C., 93-94° C.). R$_f$=0.51 (EtOAc/Hxn=1:6). $^1$H NMR (400 MHz, CDCl$_3$): δ=0.15 (s, 3H), 0.22 (s, 3H), 0.95 (s, 9H), 1.07 (s, 3H), 1.16 (s, 3H), 3.89 (d, J=9.2 Hz, 1H), 3.99 (s, 1H), 4.00 (d, superimposed, J=8.8 Hz, 1H) ppm. MS (ESI) m/z: 245.06 (M+H)$^+$. The analytical data was consistent with the proposed structure and with the data reported in the literature (Miyaoka et al., *Tetrahedron: Asymmetry* 1995, 6(2), 587-594; and Storer et al., *Chem. Eur. J.* 2004, 10, 2529-2547).

Step B: (2R/S)(3R)-4,4-Dimethyl-3-(1,1,2,2-tetramethyl-1-silapropoxy)oxolan-2-ol (4b)

Following the general procedure for the reduction of O-protected pantolactones (Description 3), 50.5 g (207 mmol) of (3R)-4,4-dimethyl-3-(1,1,2,2-tetramethyl-1-silapropoxy)-3,4,5-trihydrofuran-2-one (4a) was reacted at ca. −78° C. in 1,000 mL of anhydrous dichloromethane (DCM) with 250 mL (250 mmol) of a one molar (1.0 M) solution of diisobutylaluminum hydride [(iBu)$_2$AlH, DIBAL(H)] in heptane. After work-up and isolation, 48.6 g (96% yield) of the title compound (4b) was obtained as a colorless solid and as an inseparable mixture of anomers (diastereomers) of variable ratio from several batches. The material was of sufficient chemical purity to be used directly in the next step without further purification. D.r. ~5:1-2:1 (by $^1$H NMR spectroscopy, 400 MHz, CDCl$_3$). M.p. 44.1-45.3° C. (Lit: m.p. 50-52° C.). R$_f$=0.52 (Et$_2$O/Hxn=1:1). $^1$H NMR (400 MHz, CDCl$_3$): Anomer 1: δ=0.13 (s, 3H), 0.15 (s, 3H), 0.97 (s, 9H), 1.017 (s, 3H), 1.07 (s, 3H), 3.42 (d, J=8.0 Hz, 1H), 3.67 (d, superimposed, J=8.0 Hz, 1H), 3.72 (d, J=8.0 Hz, 1H), 3.85 (d, J=10.0 Hz, 1H), 5.38 (dd, J=9.6, 4.0 Hz, 1H) ppm. Anomer 2: δ=0.10 (s, 3H), 0.12 (s, 3H), 0.93 (s, 9H), 1.023 (s, 3H), 1.08 (s, 3H), 2.75 (d, J=4.0 Hz, 1H), 3.66 (d, J=8.4 Hz, 1H), 3.69 (d, J=2.8 Hz, 1H), 3.80 (d, J=10.4 Hz, 1H), 5.15 (dd, J=4.0, 2.8 Hz, 1H) ppm. MS (ESI) m/z: 247.17 (M+H)$^+$. The analytical data was consistent with the proposed structure and with the data reported in the literature (Miyaoka et al., *Tetrahedron: Asymmetry* 1995, 6(2), 587-594; and Storer et al., *Chem. Eur. J.* 2004, 10, 2529-2547).

Step C: Methyl (2E)(4S)-6-hydroxy-5,5-dimethyl-4-(1,1,2,2-tetramethyl-1-silapropoxy)hex-2-enoate (4)

Following the general procedure for the methylenation of lactols via Wittig-olefination (Description 4, Method B), 70 g (284 mmol) of (2R/S)(3R)-4,4-dimethyl-3-(1,1,2,2-tetramethyl-1-silapropoxy)oxolan-2-ol (4b) was reacted at ca. 70° C. (oil bath) with 475 g (1.33 mol) of commercially available methyl triphenylphosphoranyl acetate in 585 mL of 1,2-dichloroethane (DCE). After work-up and isolation, purification by silica gel column chromatography using a Biotage flash column and methyl tert-butyl ether (MTBE) and n-heptane (Hptn) mixtures as eluent (MTBE/Hptn=1:4) provided 40.0 g (46% yield) of the title compound (4) as a colorless, oily liquid. R$_f$=0.48 (Et$_2$O/Hxn=1:1). $^1$H NMR (400 MHz, CDCl$_3$): δ=0.02 (s, 3H), 0.10 (s, 3H), 0.85 (s, 3H), 0.94 (s, 9H), 1.01 (s, 3H), 2.36 (dd, J=6.4, 4.0 Hz, 1H), 3.30 (dd, J=10.8, 6.4 Hz, 1H), 3.59 (dd, J=11.2, 4.0 Hz, 1H), 3.77 (s, 3H), 4.15 (dd, J=6.0, 1.2 Hz, 1H), 5.98 (dd, J=15.6, 1.2 Hz, 1H), 7.00 (dd, J=16.0, 6.4 Hz, 1H) ppm. (ESI) m/z: 303.0 (M+H)⁺. The analytical data was consistent with the proposed structure and with the data reported in the literature (Miyoaki et al., *Tetrahedron: Asymmetry* 1995, 6(2), 587-594).

Following the general procedure for the determination of the enantiomeric excess using diamagnetic chiral cosolvents (CSAs) of Description 5, the enantiomeric excess (e.e.) was determined to be greater than 95% (by ¹H NMR shift method (400 MHz, CDCl₃) using the commercially available diamagnetic chiral co-solvent (R)-(−)-2,2,2-trifluoro-1-(9-anthryl) ethanol (Pirkle-alcohol) and in comparison with the corresponding methyl (2E)(4R/S)-6-hydroxy-5,5-dimethyl-4-(1,1,2,2-tetramethyl-1-silapropoxy)hex-2-enoate (5).

Example 5

Methyl (2E)(4R/S)-6-hydroxy-5,5-dimethyl-4-(1,1,2,2-tetramethyl-1-silapropoxy)hex-2-enoate (5)

Step A: (3R/S)-4,4-Dimethyl-3-(1,1,2,2-tetramethyl-1-silapropoxy)-3,4,5-trihydrofuran-2-one (5a)

Following the general procedure for the O-silyl protection of pantolactones (Description 2, Method D), 7.16 g (55.0 mmol) of D/L-pantolactone was reacted in 50 mL of anhydrous dimethylformamide (DMF) in the presence of 6.81 g (100.0 mmol) of imidazole with 7.54 g (50.0 mmol) of tert-butyldimethylsilyl chloride (TBDMSCl, tert-butyl(chloro)dimethylsilane). After work-up and isolation, 10.74 g (88% yield) of the title compound (5a) was obtained as a colorless solid. The material was of sufficient purity to be used directly in the next step without further purification. M.p.: 70.2-70.5° C. $R_f$=0.51 (EtOAc/Hxn=1:6). MS (ESI) m/z: 245.06 (M+H)⁺. The analytical data was consistent with the proposed structure, with the corresponding enantiopure compound (4a), and with the data reported in the literature (Miyaoka et al., *Tetrahedron: Asymmetry* 1995, 6(2), 587-594; and Storer et al., *Chem. Eur. J.* 2004, 10, 2529-2547).

Step B: (2R/S)(3R/S)-4,4-Dimethyl-3-(1,1,2,2-tetramethyl-1-silapropoxy)oxolan-2-ol (5b)

Following the general procedure for the reduction of O-protected pantolactones (Description 3), 10.7 g (43.9 mmol) of (3R/S)-4,4-dimethyl-3-(1,1,2,2-tetramethyl-1-silapropoxy)-3,4,5-trihydrofuran-2-one (5a) was reacted at ca. −78° C. (dry ice/acetone bath) in 300 mL of anhydrous dichloromethane (DCM) with 53 mL (53 mmol) of a one molar solution of diisobutylaluminum hydride [(iBu)₂AlH, DIBAL(H)] in hexanes. After work-up and isolation, 10.7 g (99% yield) of the title compound (5b) was obtained as a colorless oil as a mixture of diastereomers. The material was of sufficient chemical purity to be used directly in the next step without further purification. D.r. ~55:45 (by ¹H NMR spectroscopy, 400 MHz, CDCl₃; Lit: d.r.=5:1). $R_f$=0.52 (Et₂O/Hxn=1:1). MS (ESI) m/z: 247.08 (M+H)⁺. The analytical data was consistent with the proposed structure, with the corresponding material (4b) obtained starting from enantiopure D-pantolactone (A), and with the data reported in the literature (Miyoaki et al., *Tetrahedron: Asymmetry* 1995, 6(2), 587-594; and Storer et al., *Chem. Eur. J.* 2004, 10, 2529-2547).

Step C: Methyl (2E)(4R/S)-6-hydroxy-5,5-dimethyl-4-(1,1,2,2-tetramethyl-1-silapropoxy)hex-2-enoate (5)

Following the general procedure for the methylenation of lactols by Wittig-olefination (Description 4, Method B), 1.0 g (4.06 mmol) of (2R/S)(3R/S)-4,4-dimethyl-3-(1,1,2,2-tetramethyl-1-silapropoxy)oxolan-2-ol (5b) was reacted at 70° C. with 2.71 g (8.12 mmol) of methyl triphenylphosphoranyl acetate in 7 mL of 1,2-dichloroethane (DCE). After work-up and isolation, purification by silica gel column chromatography using diethyl ether (Et₂O) and hexane (Hxn) mixtures as eluent (Et₂O/Hxn=2:3) provided 497 mg (40% yield) of the title compound (5) as a colorless, oily liquid. $R_f$=0.41 (Et₂O/Hxn=1:1). MS (ESI) m/z: 303.1 (M+H)⁺. The analytical data was consistent with the proposed structure, with the corresponding material (4) obtained starting from enantiopure D-pantolactone, and with the data reported in the literature (Miyoaki et al., *Tetrahedron: Asymmetry* 1995, 6(2), 587-594).

Example 6

(2R)-3,3-Dimethylbutane-1,2,4-triol (6)

Adapting a procedure or a variation thereof according to Blakemore et al., *J. Org. Chem.* 2005, 70, 5449-5460; Mandel et al., *Org. Lett.* 2004, 6(26), 4801-4803; Lavallée et al., *Tetrahedron Lett.* 1986, 27, 679-682; Shiina et al., *Bull Chem. Soc. Jpn.* 2001, 74, 113-122; Ito et al., *Synthesis* 1993, 137-140; Callant et al., *Tetrahedron: Asymmetry* 1993, 4(2), 185-188; Dolle et al., *J. Am. Chem. Soc.* 1985, 107, 1691-1694; and Matsuo et al., *Tetrahedron Lett.* 1976, 17(23), 1979-1982, a dry 1,000 mL three-necked flask equipped with a magnetic stirring bar, addition funnel, and reflux condenser topped with rubber septa was charged under a nitrogen atmosphere with 7.8 g (60.0 mmol) of commercially available D-pantolactone. The material was dissolved in 100 mL of anhydrous tetrahydrofuran (THF) and the solution cooled to ca. 0° C. (ice bath). Sixty-five (65) mL (38.5 mmol) of a one molar (1.0 M) solution of lithium aluminum hydride (LAH) in THF was added dropwise and the reaction mixture stirred overnight with gradual warming to room temperature. (Note: To ensure complete global reduction of the lactone several authors recommend heating the reaction mixture to reflux for ca. two hours after the overnight reaction to complete the reduction.) The reaction mixture was again cooled to ca. 0° C. (ice bath) and 4.23 mL of water, 8.46 mL of an aqueous solution of sodium hydroxide (10 wt-%), and 4.23 mL of water were carefully added (Note: Initially, there is a vigorous evolution of hydrogen gas.) and the resulting colorless precipitate was filtered off. The filter residue was washed with dichloromethane (DCM) and the combined filtrates were dried over anhydrous magnesium sulfate (MgSO₄). After filtration and evaporation of the solvents under reduced pressure using a rotary evaporator, 6.6 g (82% yield) of the title compound (6) was obtained as a slightly yellow, viscous liquid that was of sufficient purity to be used in the next step without further purification. ¹H NMR (400 MHz, DMSO-d⁶): δ=0.768 (s, 3H), 0.777 (s, 3H), 3.15 (d, J=10.4 Hz, 1H), 3.21 (d, J=10.0 Hz, 1H), 3.22-32 (m, 2H), 3.44-3.52 (m, 1H), 4.20-4.40 (br. m, 3H) ppm. MS (ESI) m/z: 135.03 (M+H)⁺, 132.89 (M−H)⁻. The analytical data for the compound was consistent with the proposed structure and with the data given in the literature.

Description 6

General Procedure for the Formation of Benzylidene-Type Acetals from 1,3-Diols

Adapting procedures or a variations thereof according to Blakemore et al., *J. Org. Chem.* 2005, 70, 5449-5460; Mandel et al., *Org. Lett.* 2004, 6(26), 4801-4803; Lavallée et al., Tetrahedron Lett. 1986, 27, 679-682; Ito et al., *Synthesis* 1993, 137-140; Shiina et al., *Bull Chem. Soc. Jpn.* 2001, 74, 113-122; and Murrer et al., *Synthesis* 1979, 350-352, a dry 1,000 mL three-necked flask equipped with a magnetic stirring bar, and a reflux condenser topped with a rubber septum was charged under a nitrogen atmosphere with an appropriate 1,3-diol (50.0 mmol), i.e. (2R)-3,3-dimethylbutane-1,2,4-triol (6), and 150 mL of a suitable solvent such as anhydrous dichloromethane (DCM), methanol (MeOH), or benzene ($C_6H_6$). Seventy-five (75.0) mmol of an appropriately substituted benzaldehyde derivative, or optionally, its lower alkyl acetal such as a dimethyl acetal, and a catalytic amount of a suitable acidic catalyst such as pyridinium para-toluenesulfonate (PPTS), phosphorus(V) oxychloride (phosphoryl chloride) ($POCl_3$), camphorsulfonic acid (CSA), or para-toluenesulfonic acid (TsOH) (5.0-10.0 mmol, 10-20 mol-%), were added to the solution. Optionally and depending on the reaction system, activated 4 Å molecular sieves (MS) were added also. The reaction mixture was stirred either at room temperature or heated to reflux for ca. 18 hours, cooled to room temperature, and the reaction quenched with a saturated aqueous solution of sodium hydrogencarbonate ($NaHCO_3$). The aqueous layer was separated and extracted three times with diethyl ether ($Et_2O$) or methyl tert-butylether (MTBE). The combined organic extracts were washed with brine, dried over anhydrous magnesium sulfate ($MgSO_4$), filtered, and the solvent evaporated under reduced pressure using a rotary evaporator. The crude residue was purified by silica gel column chromatography using $Et_2O$ or MTBE and hexane (Hxn) mixtures as eluent to yield the corresponding benzylidene-type acetal as a colorless, viscous liquid or solid.

Description 7

General Procedure for the Oxidation of Alcohols to Carbaldehydes

Adapting procedures or a variations thereof according to Blakemore et al., *J. Org. Chem.,* 2005, 70, 5449-5460; Mandel et al., *Org. Lett.* 2004, 6(26), 4801-4803; Nicolaou et al., *Angew. Chem. Int. Ed. Engl.* 1997, 36, 1194-1196; and Parikh et al., *J. Am. Chem. Soc.* 1967, 89, 5505-5507, a dry 1,000 mL three-necked flask equipped with a magnetic stirring bar was charged under a nitrogen atmosphere with an appropriately protected alcohol (50.0 mmol) and 300 mL of anhydrous dichloromethane (DCM). Thirty-four point eight (34.8) mL (25.3 g, 250.0 mmol) of anhydrous triethylamine (TEA) and 28.4 mL (31.3 g, 400 mmol) of anhydrous dimethylsulfoxide (DMSO) were added to the solution. The solution was cooled to ca. 0° C. (ice bath) and 23.9 g (150.0 mmol) of sulfur trioxide pyridine complex ($SO_3$.pyridine) was added in three to five divided portions over a period of ca. one hour. The reaction was monitored by TLC. After the starting material was completely consumed, the solvents were partially removed under reduced pressure using a rotary evaporator and the residual solution was diluted with methyl tert-butyl ether (MTBE) or diethylether ($Et_2O$). The solution was washed three-times with water to remove the bulk of excess DMSO, TEA, and pyridine by-product. The solution was then washed with a diluted hydrochloric acid (HCl) (0.01-0.001 M), and brine. After drying over anhydrous magnesium sulfate ($MgSO_4$), the solution was filtered and the solvents were removed under reduced pressure using a rotary evaporator. The crude reaction product was purified by silica gel column chromatography using mixtures of methyl tert-butyl ether (MTBE) and hexane (Hxn) as eluent to yield the corresponding carbaldehyde, typically as a colorless or pale-yellow oil.

In some cases, the crude reaction product thus obtained was of sufficient purity to be used in the next step without further purification or isolation.

Description 8

General Procedure for Methylenation of Aldehydes via Wittig-Olefination

Adapting procedures or variation thereof according to Blakemore et al., *J. Org. Chem.* 2005, 70, 5449-5460; Mandel et al., *Org. Lett.* 2004, 6(26), 4801-4803; Shiina et al., *Bull. Chem. Soc. Jpn.* 2001, 74, 113-122, and Ito et al., *Synthesis* 1993, 137-140, an oven-dried 500 mL round-bottomed flask equipped with a magnetic stirring bar and a rubber septum was charged under an atmosphere of nitrogen with 17.86 g (50.0 mmol) of methyltriphenylphosphonium bromide ($Ph_3PMeBr$) and 125 mL of anhydrous tetrahydrofuran (THF). The suspension was cooled to ca. 0° C. (ice bath) and 31.0 mL (49.6 mmol) of a 1.6-molar solution of n-butyl-lithium (n-BuLi) in hexane was carefully added. Alternatively, an equimolar amount of a commercially available solution of potassium tert-butoxide (KOtBu) in tetrahydrofuran (THF), i.e. 1.0 M in THF, was also used as a base instead of n-butyllithium (n-BuLi). The reaction mixture was vigorously stirred for one to six hour(s) at this temperature to ensure that the alkoxide was completely consumed (Olmstead et al., *J. Org. Chem.* 1980, 45, 3295-3200; and Zhang et al., *J. Am. Chem. Soc.* 1994, 116, 968-972) thus preventing racemization of the stereogenic center by un-reacted base. A dark-yellow to orange suspension was obtained. A solution of 25.0 mmol of an appropriately functionalized aldehyde in 30 mL of anhydrous THF was added at this temperature or a lower temperature, i.e. between −78° C. (dry ice/acetone bath) and ca. 0° C. (ice bath) under a nitrogen atmosphere, and the reaction mixture was stirred overnight with gradual warming to room temperature to ensure that the aldehyde was completely consumed. Work-up and isolation procedures consistent with the general procedure for methylenation of lactols via Wittig-olefination (Description 4) were used.

Description 9

General Procedure for Regioselective Reductive Ring Opening of Benzylidene-Type Acetals of 1,3-Diols Adapting procedures or variation thereof according to Blakemore et al., *J. Org. Chem.* 2005, 70, 5449-5460; Ito et al., *Synthesis* 1993, 137-140; Shiina et al., *Bull. Chem. Soc. Jpn.* 2001, 74, 113-122; and Nakatsuka et al., *J. Am. Chem. Soc.* 1990, 112, 5583-5601, an oven-dried 500 mL round-bottomed flask equipped with a magnetic stirring bar and a rubber septum was charged under an atmosphere of nitrogen with 43.5 mmol of a benzylidene-type acetal of an appropriately functionalized 1,3-diol. The compound was dissolved in 150 mL of anhydrous dichloromethane (DCM) and the solution was cooled to ca. −78° C. (dry ice/acetone bath). At this temperature 25 mL (20.0 g, 140.3 mmol) of neat diisobutylaluminum hydride [$(iBu)_2AlH$, DIBAL(H)] was slowly added to control the temperature. The reaction mixture was stirred overnight with gradual warming to room temperature. The reaction was monitored by TLC. Upon completion of the reaction, the reaction mixture was very carefully added to a pre-cooled, e.g., ca. 0° C. (ice bath) and a vigorously stirred mixture of 400 mL of four molar (4.0 M) hydrochloric acid (HCl) and 400 mL of methyl tert-butyl ether (MTBE) in a 2 L glass beaker. (Caution: Quenching of DIBAL(H) with protic solvents is very exothermic and results in violent evolution of flammable hydrogen gas.) After the reaction mixture became clear, the two phases were separated, and the aqueous phase was extracted twice with MTBE. The combined organic extracts were washed with water and brine, dried over anhydrous magnesium sulfate ($MgSO_4$), filtered, and the solvents removed under reduced pressure using a rotary evaporator. The crude residue was purified by silica gel column chromatography using methyl tert-butyl ether (MTBE), ethyl acetate (EtOAc), and hexane (Hxn) mixtures as eluent to afford the corresponding target compound, typically as a colorless, clear, viscous oil or solid.

Example 7

(3S)-2,2-Dimethyl-3-(phenylmethoxy)pent-4-en-1-ol (7)

Step A: [(4R)-5,5-Dimethyl-2-phenyl-1,3-dioxan-4-yl]methan-1-ol (7a)

Following the general procedure for the transacetalization reaction of Description 6, 6.6 g (49.2 mmol) of (2R)-3,3-dimethylbutane-1,2,4-triol (6) was reacted in 120 mL of dichloromethane (DCM) in the presence of 2.51 g (10.0 mmol) of PPTS with 11.3 mL (11.4 g, 75.0 mmol) of benzaldehyde dimethyl acetal. Purification by silica gel column chromatography using diethylether ($Et_2O$) and hexane (Hxn) mixtures as eluent ($Et_2O$/Hxn=2:3→$Et_2O$/Hxn=1:1→$Et_2O$/Hxn=3:2) provided 4.9 g (45% yield) of the title compound (7a) as a colorless liquid. $R_f$=0.44 ($Et_2O$/Hxn=2:3). $^1$H NMR (400 MHz, $CHCl_3$): δ=0.86 (s, 3H), 1.16 (s, 3H), 2.02-2.06 (m, 1H), 3.60-3.64 (m, 1H), 3.68-3.72 (m, 4H), 5.52 (s, 1H), 7.33-7.41 (m, 3H), 7.49-7.53 (m, 2H) ppm. MS (ESI) m/z: 223.0 (M+H)$^+$, 245.0 (M+Na)$^+$. The analytical data for the compound was consistent with that given in the literature.

Step B: (4R)-5,5-Dimethyl-2-phenyl-1,3-dioxan-4-carbaldehyde (7b)

Following the general procedure for oxidation reactions of Description 7, 40.2 g (181.9 mmol) of [(4R)-5,5-dimethyl-2-phenyl-1,3-dioxan-4-yl]methan-1-ol (7a) in 1,100 mL of dichloromethane (DCM) in the presence of 126.8 mL (92.1 g, 0.910 mol) of triethylamine and 103.3 mL (113.8 g, 1.456 mol) of dimethylsulfoxide (DMSO) was reacted with 86.9 g (0.55 mol) of sulfur trioxide pyridine complex to afford 38.3 g (96% yield) of the crude title compound (7b). Purification by silica gel column chromatography using mixtures of methyl tert-butyl ether (MTBE) and hexane (Hxn) as eluent (MTBE/Hxn=1:9→MTBE/Hxn=1:6) provided 29.9 g (75% yield) of the title compound (7b) as a colorless liquid. $R_f$=0.58 (MTBE/Hxn=1:2). $^1$H NMR (400 MHz, $CHCl_3$): δ=1.04 (s, 3H), 1.27 (s, 3H), 3.69 (d, J=11.6 Hz, 1H), 3.75 (d, J=11.2 Hz, 1H), 3.97 (d, J=1.2 Hz, 1H), 5.56 (s, 1H), 7.35-7.44 (m, 3H), 7.54-7.58 (m, 2H), 9.66 (d, J=1.6 Hz, 1H) ppm. MS (ESI) m/z: 221.0 (M+H)$^+$, 242.9 (M+Na)$^+$. The analytical data for the compound was consistent with that given in the literature (Ito et al., *Synthesis*, 1993, 137-140).

Alternatively, adapting procedures or a variations thereof according to Blakemore et al., *J. Org. Chem* 2005, 70, 5449-5460; Mandel et al., *Org. Lett.* 2004, 6(26), 4801-4803; Shiina et al., *Bull. Chem. Soc. Jpn.* 2001, 74, 113-122; or Ito et al., *Synthesis* 1993, 137-140, the oxidation of the starting material [(4R)-5,5-dimethyl-2-phenyl-1,3-dioxan-4-yl]methan-1-ol (7a) to the title compound (7b) was accomplished with comparable results using classical Swern-oxidation conditions {oxalylchloride [$(COCl)_2$], dimethylsulfoxide (DMSO), triethylamine ($Et_3N$, TEA), dichloromethane (DCM), −78° C. (Mancusco et al., *J. Org. Chem.* 1978, 43, 2480-2482)}.

Step C: (4S)-5,5-Dimethyl-2-phenyl-4-vinyl-1,3-dioxane (7c)

Following the general procedure for methylenation via Wittig-olefination of Description 8, a phosphorous ylide generated from 17.86 g (50.0 mmol) of methyltriphenylphosphonium bromide and 31.0 mmol of n-BuLi in 125 mL of anhydrous tetrahydrofuran (THF), was reacted with 5.5 g (25.0 mmol) of (4R)-5,5-dimethyl-2-phenyl-1,3-dioxan-4-carbaldehyde (7b). Aqueous work-up followed by purification using column chromatography with mixtures of methyl tert-butyl ether (MTBE) and hexanes (Hxn) as eluent (MTBE/Hxn=9:1→MTBE/Hxn=6:1) provided 4.67 g (86% yield) of the title compound (7c) as a yellowish liquid. $R_f$=0.66 (MTBE/Hxn=1:6). $^1$H NMR (400 MHz, $CHCl_3$): δ=0.82 (s, 3H), 1.16 (s, 3H), 3.67 (d, J=10.8 Hz, 1H), 3.78 (d, J=10.8 Hz, 1H), 4.05 (d, J=6.0 Hz, 1H), 5.24-528 (m, 1H), 5.31-5.37 (m, 1H), 5.55 (s, 1H), 5.87 (ddd, J=17.6, 10.4, 6.0 Hz, 1H), 7.30-7.40 (m, 3H), 7.52-7.55 (m, 2H) ppm. MS (ESI) m/z: 219.1 (M+H)$^+$. The analytical data was consistent with that given in the literature (Ito, et al., *Synthesis* 1993, 137-140).

Optionally, an equimolar amount of a commercially available solution of potassium tert-butoxide (KOtBu) in tetrahydrofuran (THF), i.e. 1.0 M in THF, was used as a base instead of n-butyllithium (nBuLi). The material obtained using this procedure was of comparable quality and the yield after work-up and silica gel column chromatography was slightly higher (97% yield for the same scale).

Step D: (3S)-2,2-Dimethyl-3-(phenylmethoxy)pent-4-en-1-ol (7)

Following the general procedure for the reductive ring opening of benzylidene-type acetals of 1,3-diols of Description 9, 9.5 g (43.5 mmol) of (4S)-5,5-dimethyl-2-phenyl-4-vinyl-1,3-dioxane (7c) was reacted with 25.0 mL (19.9 g, 140.0 mmol) of diisobutylaluminum hydride [$(iBu)_2AlH$, DIBAL(H)] in 150 mL of anhydrous dichloromethane (DCM). After acidic aqueous work-up, the crude material was purified by silica gel column using mixtures of methyl tert-butyl ether (MTBE) and hexane (Hxn) as eluent (MTBE/Hxn=1:9→MTBE/Hxn=1:6→MTBE/Hxn=1:3) to provide 8.4 g (88% yield) of the title compound (7) as a colorless liquid. $R_f$=0.45 ($Et_2O$/Hxn=1:1). $^1$H NMR (400 MHz, $CHCl_3$): δ=0.91 (s, 3H), 0.92 (s, 3H), 2.82 (t, J=5.9 Hz, 1H), 3.38 (dd, J=10.8, 6.0 Hz, 1H), 3.55 (dd, J=10.8, 6.0 Hz, 1H), 3.64 (d, J=8.0 Hz, 1H), 4.31 (d, J=12.0 Hz, 1H), 4.62 (d, J=11.6 Hz, 1H), 5.22-5.28 (m, 1H), 5.36-5.40 (m, 1H), 5.81 (ddd, J=17.2, 10.4, 8.4 Hz, 1H), 7.27-7.38 (m, 5H) ppm. MS (ESI) m/z: 221.1 (M+H)$^+$, 243.1 (M+Na)$^+$. The analytical data for the compound was consistent with the proposed structure and with the data given in the literature (Ito et al., *Synthesis* 1993, 137-140; and Mandel et al., *Org. Lett.* 2004, 6(26), 4801-4803).

Following the general procedure for the determination of enantiomeric excess with diamagnetic chiral cosolvents (CSAs) of Description 5, the enantiomeric excess (e.e.) was determined to be greater than 95% (by $^1$H NMR shift method (400 MHz, $CDCl_3$) using the commercially available diamagnetic chiral co-solvent (R)-(−)-2,2,2-trifluoro-1-(9-anthryl)

ethanol (Pirkle-alcohol) and in comparison with rac-2,2-dimethyl-3-(phenylmethoxy)pent-4-en-1-ol.

Example 8

(3S)-3-[4-Methoxyphenyl)methoxy]-2,2-dimethylpent-4-en-1-ol (8)

Step A: [(4R)-5,5-Dimethyl-2-(4-methoxyphenyl)-1,3-dioxan-4-yl]methan-1-ol (8a)

Following the general procedure for the transacetalization reaction of Description 6, 21.4 g (160.0 mmol) of (2R)-3,3-dimethylbutane-1,2,4-triol (6) was reacted in 400 mL of dichloromethane (DCM) in the presence of 932 µL (1.53 g, 10.0 mmol) of phosphorus(V) oxychloride (POCl$_3$) with 45.6 g (250.0 mmol) of para-anisaldehyde dimethyl acetal. Twofold purification by silica gel column chromatography using tert-butyl methyl ether (MTBE) and hexane (Hxn) mixtures as eluent (MTBE/Hxn=3:7→MTBE/Hxn=2:3→MTBE/Hxn=1:1→MTBE/Hxn=2:1→MTBE/Hxn=3:1) provided 26.7 g (66% yield) of the title compound (8a) as a pale-yellow liquid. $R_f$=0.26 (MTBE/Hxn=2:3). $^1$H NMR (400 MHz, CHCl$_3$): δ=0.86 (s, 3H), 1.16 (s, 3H), 2.01-2.05 (m, 1H), 3.59-3.3.63 (m, 1H), 3.66-3.73 (m, 4H), 3.82 (s, 3H), 5.48 (s, 1H), 6.88-6.94 (m, 2H), 7.42-7.46 (m, 2H) ppm. MS (ESI) m/z: 253.1 (M+H)$^+$. The analytical data for the compound was consistent with that given in the literature (Blakemore et al., *J. Org. Chem.* 2005, 70, 5449-5460; and Shiina et al., *Bull. Chem. Soc. Jpn.* 2001, 74, 113-122). Similar yields were obtained using camphorsulfonic acid (CSA) as the acidic catalyst.

Step B: (4R)-2-(4-Methoxyphenyl)-5,5-dimethyl-1,3-dioxan-4-carbaldehyde (8b)

Following the general procedure for the oxidation reaction of Description 7, 23.0 g (91.2 mmol) of [(4R)-5,5-dimethyl-2-(4-methoxyphenyl)-1,3-dioxan-4-yl]methan-1-ol (8a) in 650 mL of dichloromethane (DCM) in the presence of 63.5 mL (46.1 g, 456 mmol) of triethylamine and 52.0 mL (57.3 g, 733 mmol) of dimethylsulfoxide (DMSO) was reacted with 43.5 g (274 mmol) of sulfur trioxide pyridine complex to afford 21.4 g (94% yield) of the crude title compound (8b) as a yellow oil. The crude material was of sufficient purity to be used in the next step without further isolation and purification. $R_f$=0.53 (MTBE/Hxn=1:2). $^1$H NMR (400 MHz, CHCl$_3$): δ=1.03 (s, 3H), 1.26 (s, 3H), 3.67 (d, J=11.6 Hz, 1H), 3.72 (d, J=11.6 Hz, 1H), 3.83 (s, 3H), 3.95 (d, J=1.2 Hz, 1H), 5.51 (s, 1H), 6.90-6.96 (m, 2H), 7.46-7.51 (m, 2H), 9.65 (d, J=1.6 Hz, 1H) ppm. MS (ESI) m/z: 251.1 (M+H)$^+$, 272.9 (M+Na)$^+$. The analytical data for the compound was consistent with the proposed structure and with the data given in the literature (Blakemore, et al., *J. Org. Chem.* 2005, 70, 5449-5460; and Shiina, et al., *Bull. Chem. Soc. Jpn.* 2001, 74, 113-122). Similar yields were obtained using classical Swern-oxidation conditions.

Step C: 1-((4S)-5,5-Dimethyl-4-vinyl(1,3-dioxan-2-yl))-4-methoxybenzene (8c)

Following the general procedure for the methylenation by Wittig-olefination of Description 8, a phosphorous ylide generated from 73.4 g (205.5 mmol) of methyltriphenylphosphonium bromide and 125.7 mL of 1.6 M n-BuLi in hexane (201.1 mmol) in 440 mL of anhydrous tetrahydrofuran (THF), was reacted with 25.0 g (100.0 mmol) of (4R)-2-(4-methoxyphenyl)-5,5-dimethyl-1,3-dioxan-4-carbaldehyde (8b). Aqueous work-up followed by purification using column chromatography with mixtures of diethyl ether (Et$_2$O), ethyl acetate (EtOAc), and hexanes (Hxn) as eluent (Et$_2$O/Hxn=1:25→EtOAc/Hxn=1:9) provided 20.0 g (81% yield) of the title compound (8c) as a yellow liquid. $R_f$=0.42 (MTBE/Hxn=1:9). $^1$H NMR (400 MHz, CHCl$_3$): δ=0.81 (s, 3H), 1.15 (s, 3H), 3.65 (d, J=10.8 Hz, 1H), 3.76 (d, J=11.2 Hz, 1H), 3.81 (s, 3H), 4.03 (d, J=6.4 Hz, 1H), 5.23-527 (m, 1H), 5.29-5.35 (m, 1H), 5.50 (s, 1H), 5.86 (ddd, J=17.2, 10.8, 6.4 Hz, 1H), 6.87-6.92 (m, 2H), 7.43-7.48 (m, 2H) ppm. MS (ESI) m/z: 249.1 (M+H)$^+$. The analytical data was consistent with the proposed structure and with the data given in the literature for the compound (Blakemore, et al., *J. Org. Chem.* 2005, 70, 5449-5460; and Shiina, et al., *Bull Chem. Soc. Jpn.* 2001, 74, 113-122).

Step D: (3S)-3-[4-Methoxyphenyl)methoxy]-2,2-dimethylpent-4-en-1-ol (8)

Following the general procedure for the reductive ring opening of benzylidene-type acetals of 1,3-diols of Description 9, 20.0 g (80.6 mmol) of 1-((4S)-5,5-dimethyl-4-vinyl(1,3-dioxan-2-yl))-4-methoxybenzene (8c) was reacted with 43.0 mL (34.4 g, 242.0 mmol) of diisobutylaluminum hydride ((iBu)$_2$AlH, DIBAL(H)) in 350 mL of anhydrous dichloromethane (DCM). After acidic aqueous work-up, the crude material was purified by silica gel column chromatography using mixtures of ethyl acetate (EtOAc) and hexane (Hxn) as eluent (EtOAc/Hxn=1:4) to provide 19.0 g (94% yield) of the title compound (8) as a colorless, opaque liquid. $R_f$=0.34 (EtOAc/Hxn=1:4). $^1$H NMR (400 MHz, CHCl$_3$): δ=0.89 (s, 3H), 0.90 (s, 3H), 2.88-2.92 (br. m, 1H), 3.36 (br. d, J=11.2 Hz, 1H), 3.52 (br. d, J=11.6 Hz, 1H), 3.61 (d, J=8.0 Hz, 1H), 4.24 (d, J=11.2 Hz, 1H), 4.46 (d, J=11.2 Hz, 1H), 5.21-5.27 (m, 1H), 3.35-3.39 (m, 1H), 5.79 (ddd, J=17.2, 10.4, 8.0 Hz, 1H), 6.80-6.90 (m, 2H), 7.22-7.7.25 (m, 2H) ppm. MS (ESI) m/z: 251.1 (M+H)$^+$. The analytical data was consistent with the proposed structure and with that given in the literature for the compound (Blakemore et al., *J. Org. Chem.*, 2005, 70, 5449-5460).

Following the general procedure for the determination of enantiomeric excess with diamagnetic chiral cosolvents (CSAs) of Description 5, the enantiomeric excess (e.e.) was determined to be greater than 95% (by $^1$H NMR shift method (400 MHz, CDCl$_3$) using commercially available diamagnetic chiral co-solvent (R)-(−)-2,2,2-trifluoro-1-(9-anthryl)ethanol (Pirkle-alcohol) and in comparison with rac-3-[4-methoxyphenyl)methoxy]-2,2-dimethylpent-4-en-1-ol).

Example 9

Synthesis of N-[3-(chlorosulfonyl)propyl]acetamide (9)

Step A: Tetramethylammonium N-acetylhomotaurate (9a)

Tetramethylammonium N-acetylhomotaurate (9a) was synthesized adapting procedures disclosed in Durlach, U.S. Pat. No. 4,355,043, DE 3019350, and U.S. Pat. No. 4,199,601. A 250 mL round bottomed flask equipped with a magnetic stir bar was charged with 3-amino-1-propanesulfonic acid (5.0 g, 36.0 mmol) and 20 mL of water. To the stirred solution, 13.0 g (36.0 mmol) of tetramethylammonium hydroxide (25 w-% in water) was added. The solution was stirred at room temperature for 1 hour and acetic anhydride (4.1 mL, 4.39 g, 43.0 mmol) was added. The mixture was stirred overnight at ca. 40° C. (oil bath) to ensure complete conversion. The resulting solution was extracted twice with 30 mL of diethyl ether or tert-butyl methyl ether (MTBE) and residual methanol in the aqueous phase was removed under reduced pressure using a rotary evaporator. The extract was isolated from the residual water in the solution by lyophilization to yield 9.1 g (quant.) of the title compound (9a) as a colorless powder and, after additional thorough drying under high vacuum, was used in the next step without further purification. $^1$H NMR (400 MHz, D$_2$O): δ=1.88-1.95 (m, 2H), 1.97 (s, 3H), 2.88-2.92 (m, 2H), 3.16 (s, 12H), 3.27 (m, 2H) ppm. MS (ESI) m/z 180.04 (M−H)$^−$. The analytical data was consistent the proposed structure.

Step B: N-[3-(Chlorosulfonyl)propyl]acetamide (9)

Adapting a procedure or a variation thereof according to Shue et al., *Bioorg. Med. Chem.* 1996, 6, 1709-1714, and Korolev et al., *Synthesis* 2003, 383-388, a 500 mL round bottomed flask equipped with a magnetic stir bar was charged with tetramethylammonium N-acetylhomotaurate (9a) (9.1 g, 36 mmol), phosphorus pentachloride (PCl$_5$) (7.9 g, 37 mmol), and 200 mL of anhydrous dichloromethane (DCM). The solution was heated to reflux overnight. The resulting mixture was washed twice with water (100 mL) and brine (100 mL). The organic layer was dried over anhydrous magnesium sulfate (MgSO$_4$), filtered, and the solvents removed by evaporation under reduced pressure using a rotary evaporator to provide 4.6 g (65% yield) of the title compound (9) as a slightly yellow, viscous liquid. The crude material was of sufficient purity to be used in the next step without further isolation. $^1$H NMR (400 MHz, CDCl$_3$): δ=2.07 (s, 3H), 2.23-2.32 (m, 2H), 3.46-3.51 (m, 2H), 3.76-3.80 (m, 2H) ppm. MS (ESI) m/z 200.01 (M+H)$^+$. The material thus obtained contained various amounts of the cyclization product 2-acetyl-1,1-dioxo-1,2-thiazolidine as determined by $^1$H NMR spectroscopy and mass spectroscopy. $^1$H NMR (400 MHz, CDCl$_3$): δ=2.37-2.44 (m, 5H), 3.41 (t, J=7.2 Hz, 2H), 3.84 (t, J=7.2 Hz, 2H) ppm. MS (ESI) m/z 164.01 (M+H)$^+$, 186.00 (M+Na)$^+$. The analytical data was consistent the proposed structure.

Example 10

2-[3-(Chlorosulfonyl)propyl]benzo[c]azolin-1,3-dione (10)

Step A: Potassium 3-(1,3-dioxobenzo[c]azolin-2-yl)propanesulfonate (10a)

Caution: 1,3-propansultone is considered harmful upon inhalation and in contact with skin, and may cause cancer.

Adapting a procedure or variation thereof according to Shue et al., *Bioorg. Med. Chem.* 1996, 6, 1709-1714, a 1,000 mL round-bottomed flask equipped with a magnetic stirring bar and a reflux condenser was charged under a nitrogen atmosphere with 18.5 g (100 mmol) of commercially available potassium phthalimide, 500 mL of ethanol (EtOH), and 12.2 g (100 mmol) of commercially available 1,3-propansultone. The reaction mixture was heated to reflux for two hours. The solvent was removed under reduced pressure using a rotary evaporator to yield 30.8 g (quant.) of the title compound (10a) as a white solid that was used in the next step without further purification or isolation. $^1$H NMR (400 MHz, DMSO-d$^6$): δ=1.84-1.92 (m, 2H), 2.42-2.46 (m, 2H), 3.62 (t, J=7.2 Hz, 2H), 7.80-7.86 (m, 4H) ppm. MS (ESI) m/z 270.00 (M+H)$^+$. The analytical data was consistent the proposed structure.

Step B: 2-[3-(Chlorosulfonyl)propyl]benzo[c]azolin-1,3-dione (10)

Adapting a procedure according to Shue et al., *Bioorg. Med. Chem.* 1996, 6, 1709-1714, a 250 mL round-bottomed flask equipped with a magnetic stirring bar and a reflux condenser was charged under an atmosphere of nitrogen with 5.4 g (20 mmol) of potassium 3-(1,3-dioxobenzo[c]azolin-2-yl)propanesulfonic acid (10a), 150 mL of anhydrous dichloromethane (DCM), and 4.6 g (22 mmol) of phosphorus pentachloride (PCl$_5$). The reaction mixture was heated to reflux. After reacting overnight, the reaction mixture was quenched with water and the phases were separated. The aqueous phase was extracted with dichloromethane (DCM). The combined organic extracts were washed with brine, dried over anhydrous magnesium sulfate (MgSO$_4$), filtered, and the solvents removed under reduced pressure using a rotary evaporator. After work-up, the crude material was purified by silica gel column chromatography using a mixture of ethyl acetate (EtOAc) and hexane (Hxn) (EtOAc/Hxn=1:2) as eluent to provide 2.0 g (35% yield) of the title compound (10) as an off-white to beige solid. $^1$H NMR (400 MHz, CDCl$_3$): δ=2.42-2.49 (m, 2H), 3.75-3.79 (m, 2H), 3.91 (t, J=6.4 Hz, 2H), 7.75-7.77 (m, 2H), 7.87-7.89 (m, 2H) ppm. MS (ESI) m/z 287.99 (M+H)$^+$. The analytical data was consistent the proposed structure.

Description 10

General Procedure for Synthesis of Neopentyl Sulfonylester Intermediates or Acamprosate Neopentyl Sulfonylester Prodrugs or Precursors A three-necked round-bottomed flask equipped with a magnetic stir bar or a mechanic overhead Talboys laboratory stirrer was charged, preferably under a nitrogen atmosphere, with 1.1-1.5 mol-eq. of an appropriately functionalized sulfonyl chloride of N-acetyl homotaurinate, i.e., N-[3-(chlorosulfonyl)propyl]acetamide (9), or a suitable precursor thereof, i.e., 3-chloropropylsulfonyl chloride, 2-[3-(chlorosulfonyl)propyl]benzo[c]azolin-1,3-dione (10), or others. The sulfonyl chloride was dissolved in anhydrous dichloromethane (DCM) (ca. 0.5-0.25 M). The solution was cooled to ca. −10° C. (dry ice/isopropanol bath) or 0° C. (ice bath), and 1.0 mol-eq. of an appropriately functionalized neopentylalcohol derivative was added, either in neat form or as a solution in anhydrous dichloromethane (DCM). To the cooled solution was added between 0.1 to 1.5 mol-eq. of 4-(N,N-dimethyl)aminopyridine (DMAP) followed by very slow addition of 1.1-1.5 mol-eq. of triethylamine (Et$_3$N, TEA), either neat or as a solution in dichloromethane (DCM). The solution was stirred with gradual warming to room temperature overnight during which time the reaction mixture turned dark brown yet remained homogenous. Upon completion of the reaction, the solvents were evaporated under reduced pressure using a rotary evaporator and the residue was diluted with ethyl acetate (EtOAc), diethyl ether (Et$_2$O), or methyl tert-butyl ether (MTBE). Dark solids (DMAP and TEA hydrochlorides, and others) precipitated and the supernatant was decanted. The procedure was repeated several times until the solvent remained almost colorless. Optionally, the residue obtained after initial evaporation was diluted with an appropriate organic solvent and quenched with one molar (1.0 M) hydrochloric acid (HCl). After vigorous mixing followed by phase separation, the aqueous layer was extracted twice more with the solvent. The combined organic extracts were successively washed with one molar (1.0 M) hydrochloric acid (HCl), a saturated aqueous sodium hydrogencarbonate ($NaHCO_3$) solution, brine, and dried over anhydrous magnesium sulfate ($MgSO_4$). After filtration, the solvent was evaporated under reduced pressure using a rotary evaporator. Neopentyl sulfonylester intermediates were generally purified by silica gel chromatography using ethyl acetate (EtOAc) or methyl tert-butyl ether (MTBE) and hexane (Hxn) or n-heptane (Hptn) mixtures and/or gradients as eluent followed by removal of the solvents under reduced pressure using a rotary evaporator to yield the target compound, generally as a pale-yellow oil.

When applicable, final acamprosate neopentyl sulfonylester prodrugs were either purified by silica gel chromatography using ethyl acetate (EtOAc) and hexane (Hxn) or ethyl acetate (EtOAc) and methanol (MeOH) mixtures and/or gradients as eluent followed by removal of the solvents under reduced pressure using a rotary evaporator, or were purified by mass-guided preparative HPLC. The residue was dissolved in a mixture of ca. 60% (v/v) acetonitrile/water and the solution was filtered through a 0.2-μm nylon syringe filter followed by mass-guided preparative HPLC. After lyophilization of the solvents, the corresponding acamprosate neopentyl sulfonylester prodrug was obtained as a colorless, viscous oil and/or solid.

Description 11

General Procedure for the Preparation of Aldehydes from Alkenes By Ozonolysis

In a representative synthesis, an oven-dried 250 mL round-bottomed flask equipped with a magnetic stirring bar and a 14 gauge stainless steel inlet needle connected via silicon tubing to a Welsbach Standard T-Series ozone generator was charged with 25 mmol (1.0 mol-eq.) of an appropriately functionalized olefin and ca. 100 mL of (anhydrous) dichloromethane (DCM) or mixtures of DCM with alcohols, i.e., methanol (MeOH), ethanol (EtOH), or isopropanol (iPrOH) in a ratio of 5:1 to 9:1 (v/v DCM/alcohol). At a temperature of ca. −78° C. (dry ice/acetone bath), the solution was purged for ca. 10 min with oxygen ($O_2$) followed by purging with a mixture of oxygen and ozone ($O_2/O_3$-mixture) at the same temperature until the solution turned slightly blue, indicating excess of ozone dissolved in the reaction mixture. For sensitive substrates, the reaction was monitored by TLC analysis to avoid overoxidation or unwanted side reactions. After the starting material was consumed, the solution was again purged with oxygen ($O_2$) and/or nitrogen ($N_2$) for an additional 10 min to remove any residual dissolved ozone from the reaction mixture. Excess (2-5 mol-eq.) of a suitable reducing agent, i.e., dimethylsulfide (DMS), triphenyl- or tributyl-phosphine ($Ph_3P$, $nBu_3P$), or others (Hon et al., Synth. Commun. 1993, 23(11), 1543-1553), was added to the reaction mixture and stirred overnight with gradual warming to room temperature. The solvents were removed under reduced pressure using a rotary evaporator. The residue was diluted with water and the aqueous layer extracted twice with diethyl ether ($Et_2O$), methyl tert-butyl ether (MTBE), or ethyl acetate (EtOAc). The combined organic extracts were washed with brine, dried over anhydrous magnesium sulfate ($MgSO_4$), filtered, and the solvents removed under reduced pressure using a rotary evaporator. The final target compounds were optionally further purified by silica gel column chromatography using methyl tert-butyl ether (MTBE), ethyl acetate (EtOAc) and hexane (Hxn), or n-heptane (Hptn) mixtures and/or gradients as eluent to remove any side products (Ewing et al., J. Am. Chem. Soc. 1989, 111, 5839-5844; and Angibeaud et al., Synthesis 1985, 1123-1125).

Alternatively, and adapting a procedure or a variation thereof according to Pappo et al., J. Org. Chem. 1956, 21, 478-479, an appropriately functionalized alkene starting material was converted to the corresponding aldehyde derivative by contacting a solutions of alkene dissolved in a mixture of water and tetrahydrofuran (THF) (1:1 v/v) with a catalytic amount (2-10 mol-%) of a 2.5 wt-% solution of osmium tetroxide ($OsO_4$) in tert-butanol and sodium metaperiodate ($NaIO_4$) as a co-oxidant. The reaction was quenched by adding a 10 wt-% aqueous solution of sodium hydrogensulfite ($NaHSO_3$) or sodium thiosulfate ($Na_2S_2O_3$). The reaction mixture was extracted twice with ethyl acetate (EtOAc) or methyl tert-butyl ether (MTBE). The combined organic extracts were subsequently washed with a 10 wt-% aqueous solution of sodium hydrogensulfite ($NaHSO_3$) or sodium thiosulfate ($Na_2S_2O_3$), brine, dried over anhydrous magnesium sulfate ($MgSO_4$), filtered, and the solvents removed under reduced pressure using a rotary evaporator to provide the target aldehyde, typically as a colorless oil and in almost quantitative yield. The resulting crude materials were generally of sufficient purity for use in the next step without further purification or isolation. The final target compounds were optionally further purified by silica gel column chromatography using methyl tert-butyl ether (MTBE) or ethyl acetate (EtOAc) and hexane (Hxn) or n-heptane (Hptn) mixtures and/or gradients as eluent.

Description 12

General procedure for the Preparation of Jones-Reagent (Chromic Acid)

Caution: Chromium(VI) oxide is a highly toxic cancer suspect agent. All chromium(VI) reagents must be handled with care. The mutagenicity of Cr(VI) compounds, i.e. chromic acid (Jones-Reagent), is well documented. Special care must always be exercised in adding $CrO_3$ to organic solvents. This reagent must be handled in a fume hood. Excess Jones-reagent can be destroyed by reaction with excess isopropanol (iPrOH).

Adapting a procedure or a variation thereof according to Fillmore et al., Encyclopedia of Reagents for Organic Synthesis, John Wiley & Sons, Ltd., 2001, Jones reagent (chromic acid) was freshly prepared prior to use. In a representative synthesis, 1.33 mL (2.45 g, 25.0 mmol, 1.25 mol-eq.) of concentrated sulfuric acid ($H_2SO_4$) was added to 2.00 g (20.0 mmol, 1 mol-eq.) of commercially available chromium trioxide ($CrO_3$). The chemicals were carefully mixed at ca. 0° C. (ice bath) and the resulting mixture was carefully diluted at the same temperature with water to a total volume of 10 mL. The resulting aqueous chromic acid preparation had an approximate two molar (2 M) concentration of chromic acid. The reagent was used without further purification or isolation in the next step.

Description 13

General Procedure for the Oxidation of Aldehydes to Carboxylic Acids with Jones-Reagent Adapting a procedure or variation thereof according to Petrini et al., Tetrahedron 1986, 42, 151-154, in a representative synthesis, a 100 mL round-bottomed flask equipped with a magnetic stirring bar was charged with 10.0 mmol (1 mol-eq.) of an appropriately functionalized aldehyde and 25-100 mL of acetone. The solution was cooled to ca. 0° C. (ice bath). At this temperature, between 5.0 and 6.5 mL (10.0-13.0 mmol, 1.0-1.3 mol-eq.) of the freshly prepared Jones-Reagent (2.0 M aqueous solution) was added to the stirred solution. The reaction mixture turned from brown to green in about 30 min. After the starting material was completely consumed (as determined by TLC or LC/MS analysis, typically between 0.5 and two hours), excess, i.e., 5 mL, isopropanol (iPrOH) was added to consume excess oxidant and the reaction mixture was stirred for an additional hour. The reaction mixture was diluted with water. Optionally, the aqueous solution was acidified with one molar (1.0 M) hydrochloric acid (HCl) (final pH ca. 1-4), and the aqueous solution was extracted with ethyl acetate (EtOAc). The combined organic extracts were washed with brine, dried over anhydrous magnesium sulfate ($MgSO_4$), filtered, and the solvents removed under reduced pressure using a rotary evaporator to yield the target compound, typically as a viscous oil. The carboxylic acids thus obtained were generally of sufficient purity to be used in the next step without further purification or isolation.

Description 14

General Procedure for the Direct Oxidation of Alkenes to Carboxylic Acids with Jones-Reagent/Osmium Tetroxide Adapting a method according to Henry et al., *J. Org. Chem.* 1993, 58, 4745, the targeted carboxylic acids could be prepared directly and under mild conditions starting from the unsaturated precursor compounds. In a representative synthesis, a solution of an appropriately functionalized alkene (1.0 mol-eq) in acetone (ca. 10 mL/mmol of alkene) at ca. 0° C. was reacted with a catalytic amount (ca. 10 mol-%) of a 2.0-4.0 wt-% solution of osmiumtetroxide ($OsO_4$) in tert-butanol (t-BuOH) or water and an excess (3-4 mol-eq) of freshly prepared Jones-reagent (ca. 2.0 M in water). The reaction mixture was stirred overnight with gradual warming to room temperature. Work-up and isolation procedures used were similar those described for the Jones-oxidation of aldehydes to carboxylic acids (Description 13). The carboxylic acids thus obtained were generally of sufficient purity to be used in the next step without further purification or isolation. The analytical data for the carboxylic acids thus obtained was consistent with the proposed structures and with the data obtained from materials prepared using the sequential route.

Example 11

(2R)-4-[(3-Chloropropyl)sulfonyloxy]-3,3-dimethyl-2-(phenylmethoxy)butanoic Acid (11)

Step A: (3S)-2,2-Dimethyl-3-(phenylmethoxy)pent-4-enyl(3-chloropropyl)sulfonate (11a)

Following the general procedure for the preparation of neopentyl sulfonylester intermediates of Description 10, 28.6 mL (41.6 g, 235 mmol) of 3-chloropropylsulfonyl chloride was reacted at ca. −10° C. to 0° C. in 500 mL of anhydrous dichloromethane (DCM) in the presence of 28.7 g (235 mmol) of 4-(N,N-dimethylamino)pyridine (DMAP) and 32.8 mL (23.8 g, 235 mmol) of triethylamine ($Et_3N$, TEA) with 34.0 g (154 mmol) of (3S)-[(4-methoxyphenyl)methoxy]-2,2-dimethylpent-4-en-1-ol (8). After work-up and isolation, 54.5 g (98% yield) of the crude title compound (11a) as a brown material was obtained. The material was of sufficient purity to be used without additional purification. Optionally, the product was purified by silica gel column chromatography using ethyl acetate (EtOAc) and hexane (Hxn) mixtures (EtOAc/Hxn=1:9→EtOAc/Hxn=1:6→EtOAc/Hxn=1:4) to yield the title compound (11a) as a colorless to pale-yellow oil in a comparable yield. $R_f$=0.44 (EtOAc/Hptn=1:4). $^1$H NMR (400 MHz, $CDCl_3$): δ=0.98 (s, 3H), 1.00 (s, 3H), 2.24-2.32 (m, 2H), 3.21-3.25 (m, 2H), 3.61-3.65 (m, 3H), 4.00 (d, J=9.2 Hz, 1H), 4.22 (d, J=9.2 Hz, 1H), 4.29 (d, J=12.0 Hz, 1H), 4.59 (d, J=11.6 Hz, 1H), 5.30 (ddd, J=17.0, 1.6, 0.8 Hz, 1H), 5.40 (ddd, J=10.4, 1.6, 0.4 Hz, 1H), 5.77 (ddd, J=17.2, 10.4, 8.4 Hz, 1H), 7.27-7.37 (m, 5H) ppm. MS (ESI) m/z 383.11 $(M+Na)^+$. The analytical data was consistent with the proposed structure.

Step B: (3R)-2,2-Dimethyl-4-oxo-3-(phenylmethoxy)butyl (3-chloropropyl)sulfonate (11b)

Following the general procedure for the preparation of aldehydes from alkenes of Description 11, (3S)-2,2-dimethyl-3-(phenylmethoxy)pent-4-enyl(3-chloropropyl)sulfonate (11a) (25.0 g, 69.3 mmol) dissolved in a mixture of 300 mL of dichloromethane (DCM) and 40 mL of ethanol was treated with a mixture of oxygen and ozone ($O_2/O_3$). Upon completion of the reaction, 10.6 mL (9.0 g, 138 mmol) of dimethyl sulfide (DMS) was added. After work-up, the crude material was purified by silica gel column chromatography using a mixture of ethyl acetate (EtOAc) and hexane (Hxn) (EtOAc/Hxn=1:6) as eluent to provide 15.0 g (60% yield) of the title compound (11b) as a colorless oil. $R_f$=0.22 (EtOAc/Hxn=1:6). $^1$H NMR (400 MHz, $CDCl_3$): δ=1.10 (s, 6H), 2.26-2.33 (m, 2H), 3.23-3.29 (m, 2H), 3.65 (d, J=2.8 Hz, 1H), 3.63-3.68 (m, 2H), 4.03 (d, J=9.6 Hz, 1H), 4.15 (d, J=8.8 Hz, 1H), 4.50 (d, J=11.2 Hz, 1H), 4.68 (d, J=11.2 Hz, 1H), 7.30-7.39 (m, 5H), 9.73 (d, J=2.8 Hz, 1H) ppm. MS (ESI) m/z 385.03 $(M+Na)^+$. The analytical data was consistent with the proposed structure.

Step C: (2R)-4-[(3-Chloropropyl)sulfonyloxy]-3,3-dimethyl-2-(phenylmethoxy)butanoic acid (11)

Following the general procedure for the oxidation of aldehydes to carboxylic acids of Description 13, (3R)-2,2-dimethyl-4-oxo-3-(phenylmethoxy)butyl (3-chloropropyl)sulfonate (11b) (10.0 g, 27.5 mmol) dissolved in 200 mL of acetone was reacted with 13.7 mL of Jones-reagent (2.0 M in water). After work-up, 10.0 g (96% yield) of the title compound (11) was obtained as a colorless oil. $^1$H NMR (400 MHz, $CDCl_3$): δ=1.11 (s, 3H), 1.13 (s, 3H), 2.27-2.34 (m, 2H), 3.26-3.29 (m, 2H), 3.65-3.68 (m, 2H), 3.91 (s, 1H), 4.04 (d, J=9.6 Hz, 1H), 4.21 (d, J=9.6 Hz, 1H), 4.50 (d, J=10.8 Hz, 1H), 4.69 (d, J=10.8 Hz, 1H), 7.33-7.38 (m, 5H) ppm. $^1$H NMR (400 MHz, DMSO-$d^6$): δ=0.97 (s, 3H), 1.01 (s, 3H), 2.07-2.16 (m, 2H), 3.41-3.46 (m, 2H), 3.69-3.73 (m, 2H), 3.76 (s, 1H), 3.99 (d, J=9.6 Hz, 1H), 4.14 (d, J=9.2 Hz, 1H), 4.35 (d, J=11.2 Hz, 1H), 4.53 (d, J=11.2 Hz, 1H), 7.27-7.37 (m, 5H), 12.05 (v. br., s, 1H) ppm. MS (ESI) m/z 379.12 $(M+H)^+$, 401.02 $(M+Na)^+$, 376.9 $(M-H)^-$. The analytical data was consistent with the proposed structure.

Example 12

(2R/S)-4-[(3-Chloropropyl)sulfonyloxy]-3,3-dimethyl-2-(phenylmethoxy)butanoic Acid (12)

Step A: (3R/S)-2,2-Dimethyl-3-(phenylmethoxy) pent-4-enyl(3-chloropropyl)sulfonate (12a)

Following the general procedure for the preparation of neopentyl sulfonylester intermediates of Description 10, 15.8 mL (23.1 g, 130 mmol) of 3-chloropropylsulfonyl chloride was reacted at ca. −10° C. to 0° C. in 500 mL of anhydrous dichloromethane (DCM) in the presence of 15.9 g (130 mmol) of 4-(N,N-dimethylamino)pyridine (DMAP) and 18.1 mL (13.1 g, 235 mmol) of triethylamine ($Et_3N$, TEA) with 17.9 g (81.5 mmol) of (3R/S)-[(4-methoxyphenyl)methoxy]-2,2-dimethylpent-4-en-1-ol (3). After work-up and isolation, 20 g (68% yield) of the crude title compound (12a) as a brown material was obtained. The material was of sufficient purity to be used without additional purification. Optionally, the product was purified by silica gel column chromatography using ethyl acetate (EtOAc) and hexane (Hxn) mixtures (EtOAc/Hxn=1:9→EtOAc/Hxn=1:6→EtOAc/Hxn=1:4) to yield the title compound (12a) as a colorless to pale-yellow oil in comparable yield. The analytical data was consistent with the proposed structure and with the data obtained for the enantiopure compound (11a).

Step B: (3R/S)-2,2-Dimethyl-4-oxo-3-(phenylmethoxy)butyl (3-chloropropyl)sulfonate (12b)

Following the general procedure for the preparation of aldehydes from alkenes of Description 11, (3R/S)-2,2-dimethyl-3-(phenylmethoxy)pent-4-enyl(3-chloropropyl]sulfonate (12a) (10.0 g, 27.7 mmol) dissolved in 150 mL of dichloromethane (DCM) was treated with a mixture of oxygen and ozone ($O_2/O_3$). Upon completion of the reaction, 4.0 mL (3.4 g, 55 mmol) of dimethyl sulfide (DMS) was added. After work-up, the crude material was purified by silica gel column chromatography using a mixture of ethyl acetate (EtOAc) and hexane (Hxn) (EtOAc/Hxn=1:2) as eluent to provide 7.6 g (76% yield) of the title compound (12b) as a colorless oil. The analytical data was consistent with the proposed structure and with the data obtained for the enantiopure compound (11b).

Step C: (2R/S)-4-[(3-Chloropropyl)sulfonyloxy]-3,3-dimethyl-2-(phenylmethoxy)butanoic acid (12)

Following the general procedure of the oxidation of aldehydes to carboxylic acids of Description 13, (3R/S)-2,2-dimethyl-4-oxo-3-(phenylmethoxy)butyl (3-chloropropyl)sulfonate (12b) (7.6 g, 21 mmol) dissolved in 100 mL of acetone was reacted with 10.5 mL of Jones-reagent (2.0 M in water). After work-up, 7.6 g (96% yield) of the title compound (12) was obtained as a colorless oil. The analytical data was consistent with the proposed structure and with the data obtained for the enantiopure compound (11).

Example 13

(2R)-4-[(3-Chloropropyl)sulfonyloxy]-2-[(4-methoxyphenyl)methoxy]-3,3-dimethylbutanoic Acid (13)

Step A: (3S)-3-[(4-Methoxyphenyl)methoxy]-2,2-dimethylpent-4-enyl(3-chloropropyl)sulfonate (13a)

Following the general procedure for the preparation of neopentyl sulfonylester intermediates of Description 10, 8.0 mL (11.7 g, 66.0 mmol) of 3-chloropropylsulfonyl chloride was in 300 mL of anhydrous dichloromethane (DCM) in the presence of 855 mg (7.0 mmol) of 4-(N,N-dimethylamino)pyridine (DMAP) and 9.2 mL (6.7 g, 66.0 mmol) of triethylamine ($Et_3N$, TEA) reacted at ca. 0° C. with 15.0 g (60.0 mmol) of (3S)-[(4-methoxyphenyl)methoxy]-2,2-dimethylpent-4-en-1-ol (8). After work-up and isolation, the crude material was purified by silica gel column chromatography using ethyl acetate (EtOAc) and hexane (Hxn) mixtures (EtOAc/Hxn=1:4) to provide 17.0 g (73% yield) of the title compound (13a) as a colorless to pale-yellow oil. $R_f$=0.48 (EtOAc/Hxn=1:4). $^1$H NMR (400 MHz, $CDCl_3$): δ=0.96 (s, 3H), 0.98 (s, 3H), 2.24-2.32 (m, 2H), 3.20-3.25 (m, 2H), 3.59 (d, J=8.0 Hz, 1H), 3.62-67 (m, 2H), 3.82 (s, 3H), 3.98 (d, J=8.8 Hz, 1H), 4.19 (d, J=8.8 Hz, 1H), 4.23 (d, J=10.4 Hz, 1H), 4.51 (d, J=11.2 Hz, 1H), 5.28 (ddd, J=17.2, 1.6, 0.8 Hz, 1H), 5.39 (dd, J=10.0, 1.6 Hz, 1H), 5.76 (ddd, J=17.2, 10.4, 8.0 Hz, 1H), 6.85-6.90 (m, 2H), 7.21-7.25 (m, 2H) ppm. MS (ESI) m/z 391.1 $(M+H)^+$. The analytical data was consistent with the proposed structure.

Step B: (3R)-3-[(4-Methoxyphenyl)methoxy]-2,2-dimethyl-4-oxobutyl (3-chloropropyl)sulfonate (13b)

Following the general procedure for the preparation of aldehydes from alkenes of Description 11, (3S)-3-[(4-methoxyphenyl)methoxy]-2,2-dimethylpent-4-enyl(3-chloropropyl)sulfonate (13a) (3.0 g, 7.7 mmol) dissolved in 100 mL of dichloromethane (DCM) was treated with a mixture of oxygen and ozone ($O_2/O_3$). Upon completion of the reaction, 2 mL (1.69 g, 27.2 mmol) of dimethyl sulfide (DMS) was added. After work-up, the crude material was purified by silica gel column chromatography using a mixture of ethyl acetate (EtOAc) and hexane (Hxn) (EtOAc/Hxn=1:2) as eluent to provide 2.0 g (66% yield) of the title compound (13b) as a colorless oil. $R_f$=0.49 (EtOAc/Hxn=1:2). $^1$H NMR (400 MHz, $CDCl_3$): δ=1.08 (s, 6H), 2.27-2.33 (m, 2H), 3.24-3.28 (m, 2H), 3.53 (d, J=2.4 Hz, 1H), 3.65-3.68 (m, 2H), 3.82 (s, 3H), 4.00 (d, J=9.2 Hz, 1H), 4.13 (d, J=9.2 Hz, 1H), 4.44 (d, J=11.2 Hz, 1H), 4.60 (d, J=11.2 Hz, 1H), 6.88 (d, J=8.4 Hz, 2H), 7.26 (d, J=8.4 Hz, 2H), 9.69 (d, J=2.4 Hz, 1H) ppm. MS (ESI) m/z 415.11 $(M+Na)^+$. The analytical data was consistent with the proposed structure.

Step C: (2R)-4-[(3-Chloropropyl)sulfonyloxy]-2-[(4-methoxyphenyl)methoxy]-3,3-dimethylbutanoic acid (13)

Following the general procedure for the oxidation of aldehydes to carboxylic acids of Description 13, (3R)-3-[(4-methoxyphenyl)methoxy]-2,2-dimethyl-4-oxobutyl (3-chloropropyl)sulfonate (13b) (2.0 g, 5.1 mmol) dissolved in 30 mL of acetone was reacted with 2.6 mL of Jones-reagent (2.0 M in water). After work-up, 2.0 g (96% yield) of the title compound (13) was obtained as a colorless oil. $^1$H NMR (400 MHz, $CDCl_3$): δ=1.09 (s, 3H), 1.10 (s, 3H), 2.28-2.35 (m, 2H), 3.27-3.31 (m, 2H), 3.66-3.69 (m, 2H), 3.82 (s, 3H), 3.88 (s, 1H), 4.02 (d, J=9.2 Hz, 1H), 4.19 (d, J=9.2 Hz, 1H), 4.45 (d, J=10.8 Hz, 1H), 4.60 (d, J=10.8 Hz, 1H), 6.90 (d, J=8.8 Hz, 2H), 7.28 (d, J=8.8 Hz, 2H) ppm. MS (ESI) m/z 430.90 $(M+Na)^+$. The analytical data was consistent with the proposed structure.

Example 14

(2R/S)-4-[(3-Chloropropyl)sulfonyloxy]-2-[(4-methoxyphenyl)methoxy]-3,3-dimethylbutanoic Acid (14)

Step A: (3R/S)-3-[(4-Methoxyphenyl)methoxy]-2,2-dimethylpent-4-enyl(3-chloropropyl)sulfonate (14a)

Following the general procedure for the preparation of neopentyl sulfonylester intermediates of Description 10, 1.52 mL (2.21 g, 12.5 mmol) of 3-chloropropylsulfonyl chloride in 50 mL of anhydrous dichloromethane (DCM) in the presence of 1.53 g (12.5 mmol) of 4-(N,N-dimethylamino)pyridine (DMAP) and 1.74 mL (1.26 g, 12.5 mmol) of triethylamine (Et$_3$N, TEA) was reacted at ca. 0° C. with 2.00 g (8.0 mmol) of (3R/S)-[(4-methoxyphenyl)methoxy]-2,2-dimethylpent-4-en-1-ol (3). After work-up and isolation, the crude material was purified by silica gel column chromatography using ethyl acetate (EtOAc) and hexane (Hxn) mixtures (EtOAc/Hxn=1:6→EtOAc/Hxn=1:5) to provide 2.48 g (79% yield) of the title compound (14a) as a colorless to pale-yellow oil. $R_f$=0.48 (EtOAc/Hxn=1:4). MS (ESI) m/z 391.1 (M+H)$^+$. The analytical data was consistent with the proposed structure and with the data obtained for the enantiopure compound (13a).

Step B: (3R/S)-3-[(4-Methoxyphenyl)methoxy]-2,2-dimethyl-4-oxobutyl (3-chloropropyl)sulfonate (14b)

Following the general procedure for the preparation of aldehydes from alkenes of Description 11, (3R/S)-3-[(4-methoxyphenyl)methoxy]-2,2-dimethylpent-4-enyl(3-chloropropyl)sulfonate (14a) (4.0 g, 10.2 mmol) dissolved in 100 mL of dichloromethane (DCM) was treated with a mixture of oxygen and ozone (O$_2$/O$_3$). Upon completion of the reaction, 2 mL (1.69 g, 27.2 mmol) of dimethyl sulfide (DMS) was added. After work-up, the crude material was purified by silica gel column chromatography using a mixture of ethyl acetate (EtOAc) and hexane (Hxn) (EtOAc/Hxn=1:2) as eluent to provide 3.1 g (77% yield) of the title compound (14b) as a colorless oil. The analytical data was consistent with the proposed structure and with the data obtained for the enantiopure compound (13b).

Step C: (2R/S)-4-[(3-Chloropropyl)sulfonyloxy]-2-[(4-methoxyphenyl)methoxy]-3,3-dimethylbutanoic Acid (14)

Following the general procedure of the oxidation of aldehydes to carboxylic acids of Description 13, (3R/S)-3-[(4-methoxyphenyl)methoxy]-2,2-dimethyl-4-oxobutyl (3-chloropropyl)sulfonate (14b) (3.1 g, 7.9 mmol) dissolved in 40 mL of acetone was reacted with 3.9 mL of Jones-reagent (2.0 M in water). After work-up, 2.8 g (87% yield) of the title compound (14) was obtained as a colorless oil. The analytical data was consistent with the proposed structure and with the data obtained for the enantiopure compound (13).

Example 15

(2R)-4-[(3-Chloropropyl)sulfonyloxy]-3,3-dimethyl-2-(1,1,2,2-tetramethyl-1-silapropoxy)butanoic Acid (15)

Step A: Methyl (2E)(4S)-6-[(3-chloropropyl)sulfonyloxy]-5,5-dimethyl-4-(1,1,2,2-tetramethyl-1-silapropoxy)hex-2-enoate (15a)

Following the general procedure for the preparation of neopentyl sulfonylester intermediates of Description 10, 25.7 mL (37.4 g, 211.4 mmol) of 3-chloropropylsulfonyl chloride in 500 mL of anhydrous dichloromethane (DCM) in the presence of 25.8 g (211.4 mmol) of 4-(N,N-dimethylamino)pyridine (DMAP) and 29.5 mL (21.4 g, 211.4 mmol) of triethylamine (Et$_3$N, TEA) was reacted at ca. 0° C. with 40.5 g (133.9 mmol) of methyl (2E)(4S)-6-hydroxy-5,5-dimethyl-4-(1,1,2,2-tetramethyl-1-silapropoxy)hex-2-enoate (4). After work-up and isolation, the crude material was purified by silica gel column chromatography using methyl tert-butyl ether (MTBE) and hexane (Hxn) mixtures (MTBE/Hxn=1:6 MTBE/Hxn=1:5→MTBE/Hxn=1:4) as eluent to provide 50.0 g (84% yield) of the title compound (15a) as a pale-yellow oil. $R_f$=0.46 (MTBE/Hxn=1:4). $^1$H NMR (400 MHz, CDCl$_3$): δ=0.01 (s, 3H), 0.09 (s, 3H), 0.93 (s, 9H), 0.97 (s, 3H), 0.98 (s, 3H), 2.30-2.38 (m, 2H), 3.27-3.33 (m, 2H), 3.68-3.73 (m, 2H), 3.77 (s, 3H), 3.98 (d, J=9.6 Hz, 1H), 4.10 (d, J=9.2 Hz, 1H), 4.11 (dd, superimposed, J=6.4, 1.6 Hz, 1H), 5.97 (dd, J=15.6, 1.2 Hz, 1H), 6.90 (dd, J=15.6, 6.8 Hz, 1H) ppm. MS (ESI) m/z 442.9 (M+H)$^+$, 464.9 (M+Na)$^+$. The analytical data was consistent the proposed structure.

Step B: (3R)-2,2-Dimethyl-4-oxo-3-(1,1,2,2-tetramethyl-1-silapropoxy)butyl (3-chloropropyl)sulfonate (15b)

Following the general procedure for the preparation of aldehydes from alkenes of Description 11, methyl (2E)(4S)-6-[(3-chloropropyl)sulfonyloxy]-5,5-dimethyl-4-(1,1,2,2-tetramethyl-1-silapropoxy)hex-2-enoate (15a) (2.4 g, 5.4 mmol) dissolved in 25 mL of dichloromethane (DCM) was treated with a mixture of oxygen and ozone (O$_2$/O$_3$). Upon completion of the reaction, 2 mL (1.59 g, 27.2 mmol) of dimethyl sulfide (DMS) was added. After work-up, the crude material was purified by silica gel column chromatography using a mixture of ethyl acetate (EtOAc) and hexane (Hxn) (EtOAc/Hxn=1:3) as eluent to provide 1.1 g (52% yield) of the title compound (15b) as a colorless oil. $R_f$=0.75 (EtOAc/Hxn=1:2). $^1$H NMR (400 MHz, CDCl$_3$): δ=0.07 (s, 3H), 0.10 (s, 3H), 0.96 (s, 9H), 1.06 (s, 3H), 1.09 (s, 3H), 2.30-2.37 (m, 2H), 3.28-3.32 (m, 2H), 3.69-3.73 (m, 3H), 4.01 (d, J=9.6 Hz, 1H), 4.12 (d, J=9.6 Hz, 1H), 9.62 (d, J=2.4 Hz, 1H) ppm. MS (ESI) m/z 409.13 (M+Na)$^+$. The analytical data was consistent with the proposed structure.

Step C: (2R)-4-[(3-Chloropropyl)sulfonyloxy]-3,3-dimethyl-2-(1,1,2,2-tetramethyl-1-silapropoxy)butanoic acid (15)

Following the general procedure of the oxidation of aldehydes to carboxylic acids of Description 13, (3R)-2,2-dimethyl-4-oxo-3-(1,1,2,2-tetramethyl-1-silapropoxy)butyl (3-chloropropyl)sulfonate (15b) (1.1 g, 2.8 mmol) dissolved in 20 mL of acetone was reacted with 1.4 mL of Jones-reagent (2.0 M in water). After work-up, 0.9 g (79% yield) of the title compound (15) was obtained as a colorless oil. $^1$H NMR (400 MHz, CDCl$_3$): δ=0.13 (s, 3H), 0.16 (s, 3H), 0.98 (s, 9H), 1.05 (s, 3H), 1.11 (s, 3H), 2.32-2.39 (m, 2H), 3.33-3.36 (m, 2H), 3.69-3.72 (m, 2H), 4.04 (d, J=9.6 Hz, 1H), 4.09 (s, 1H), 4.12 (d, J=9.6 Hz, 1H) ppm. MS (ESI) m/z 403.00 (M+H)$^+$; 401.05 (M−H)$^-$. The analytical data was consistent with the proposed structure.

Example 16

(2R)-4-[(3-Chloropropyl)sulfonyloxy]-2-acetyloxy-3,3-dimethylbutanoic Acid (16)

Step A: (3S)-3-Hydroxy-2,2-dimethylpent-4-enyl(3-chloropropyl)sulfonate (16a)

Following the general procedure for the oxidative cleavage of (4-methoxy)benzyl ethers of Description 19, (3S)-3-[(4-methoxyphenyl)methoxy]-2,2-dimethylpent-4-enyl(3-chloropropyl)sulfonate (13a) (0.50 g, 1.3 mmol) dissolved in a mixture of dichloromethane (DCM) and water (10:1) (10 mL) was treated with 2,3-dichloro-5,6-dicyano-1,4-benzoquinone (DDQ) (0.35 g, 1.5 mmol). After work-up, the crude material was purified by silica gel column chromatography using a mixture of ethyl acetate (EtOAc) and hexane (Hxn) to provide 0.32 g (91% yield) of the title compound (16a) as a colorless oil. $R_f$=0.48 (EtOAc/Hxn=1:2). $^1$H NMR (400 MHz, CDCl$_3$): δ=0.95 (s, 3H), 1.00 (s, 3H), 1.75 (d, J=3.6 Hz, 1H), 2.32-2.39 (m, 2H), 3.31-3.35 (m, 2H), 3.70-3.73 (m, 2H), 3.97 (d, J=9.2 Hz, 1H), 4.02-4.04 (m, 1H), 4.26 (d, J=9.2 Hz, 1H), 5.25-5.33 (m, 2H), 5.87-5.96 (m, 1H) ppm. MS (ESI) m/z: 271.08 (M+H)$^+$. The analytical data was consistent with the proposed structure.

Step B: (1S)-1-{2-[3-(Chloropropyl)sulfonyloxy]-tert-butyl}prop-2-enyl acetate (16b)

(3S)-3-Hydroxy-2,2-dimethylpent-4-enyl(3-chloropropyl)sulfonate (16a) (0.32 g, 1.2 mmol) was reacted with 0.17 mL (0.19 g, 2.4 mmol) acetyl chloride in 10 mL of anhydrous dichloromethane (DCM) in the presence of 0.26 mL (0.19 g, 2.4 mmol) of pyridine. After work-up and isolation, the crude material was purified by silica gel column chromatography using ethyl acetate (EtOAc) and hexane (Hxn) mixtures (EtOAc/Hxn=1:2) as eluent to provide 0.32 g (85% yield) of the title compound (16b) as colorless oil. $R_f$=0.61 (EtOAc/Hxn=1:2). $^1$H NMR (400 MHz, CDCl$_3$): δ=1.02 (s, 3H), 1.03 (s, 3H), 2.11 (s, 3H), 2.31-2.38 (m, 2H), 3.29-3.33 (m, 2H), 3.79-3.72 (m, 2H), 3.94 (d, J=9.6 Hz, 1H), 4.10 (d, J=9.2 Hz, 1H), 5.18 (d, J=7.2 Hz, 1H), 5.29 (d, J=7.6 Hz, 1H), 5.32 (d, J=0.8 Hz, 1H), 5.73-5.82 (m, 1H) ppm. The analytical data was consistent with the proposed structure.

Step C: (1R)-1-{2-[3-(Chloropropyl)sulfonyloxy]-tert-butyl}-2-oxoethyl acetate (16c)

Following the general procedure for the preparation of aldehydes from alkenes of Description 11, (1S)-1-{2-[3-(chloropropyl)sulfonyloxy]-tert-butyl}prop-2-enyl acetate (16a) (0.32 g, 1.02 mmol) dissolved in 10 mL of dichloromethane (DCM) was treated with a mixture of oxygen and ozone (O$_2$/O$_3$). Upon completion of the reaction, 0.5 mL (0.42 g, 6.81 mmol) of dimethyl sulfide (DMS) was added. After work-up, 0.32 g (quant. yield) of the title compound (16c) was obtained as a colorless oil. $R_f$=0.30 (EtOAc/Hxn=1:2). $^1$H NMR (400 MHz, CDCl$_3$): δ=1.14 (s, 3H), 1.18 (s, 3H), 2.21 (s, 3H), 2.28-2.34 (m, 2H), 3.28-3.32 (m, 2H), 3.67-3.70 (m, 2H), 4.00 (d, J=9.6 Hz, 1H), 4.12 (d, J=9.6 Hz, 1H), 4.84 (d, J=1.2 Hz, 1H), 9.56 (d, J=1.2 Hz, 1H) ppm. MS (ESI) m/z 314.99 (M+H)$^+$. The analytical data was consistent with the proposed structure.

Step D: (2R)-4-[(3-Chloropropyl)sulfonyloxy]-2-acetyloxy-3,3-dimethylbutanoic acid (16)

Following the general procedure of the oxidation of aldehydes to carboxylic acids of Description 13, (1R)-1-{2-[3-(chloropropyl)sulfonyloxy]-tert-butyl}-2-oxoethyl acetate (16b) (0.32 g, 1.0 mmol) dissolved in 5 mL of acetone was reacted with 0.53 mL of Jones-reagent (2.0 M in water). After work-up, 0.31 g (92% yield) of the title compound (16) was obtained as a colorless oil. $^1$H NMR (400 MHz, CDCl$_3$): δ=1.15 (s, 3H), 1.19 (s, 3H), 2.19 (s, 3H), 2.31-2.37 (m, 2H), 3.31-3.35 (m, 2H), 3.69-3.72 (m, 2H), 4.03 (d, J=10.0 Hz, 1H), 4.21 (d, J=10.0 Hz, 1H), 4.85 (s, 1H). MS (ESI) m/z 352.96 (M+Na)$^+$, 328.91 (M−H). The analytical data was consistent with the proposed structure.

Example 17

(2R)-4-{[3-(Acetylamino)propyl]sulfonyloxy}-3,3-dimethyl-2-(phenylmethoxy)butanoic Acid (17)

Method 1

Step A: (3S)-2,2-Dimethyl-3-(phenylmethoxy)pent-4-enyl[3-aminopropyl]sulfonate (17a)

Adapting procedures or variations thereof according to Duncan et al., *J. Org. Chem.*, 2001, 66, 5237-5240; Shue et al., *Bioorg. Med. Chem. Lett.* 1996, 6, 1709-1714; and Khan, *J. Org. Chem.* 1995, 60, 4536-4541, a 250 mL round-bottomed flask equipped with a magnetic stirring bar and a rubber septum was charged with 4.47 g (9.48 mmol) of (3S)-2,2-dimethyl-3-(phenylmethoxy)pent-4-enyl[3-(1,3-dioxobenzo[c]azolin-2-yl)propyl]sulfonate (20a) and 40 mL of ethanol (EtOH). Hydrazine (H$_2$N—NH$_2$) (893 µL, 912 mg, 28.4 mmol) was added at room temperature and the reaction was stirred overnight. The reaction was monitored by LC/MS and TLC. Upon completion of the reaction, precipitates were filtered off and the filter residue washed with solvent. The solvents were evaporated under reduced pressure using a rotary evaporator and the residue was dissolved in dichloromethane (DCM). Additional solids were filtered off and the solvent was removed under reduced pressure to provide the title compound (17a), which was used directly in the next step without further isolation. MS (ESI) m/z 342.0 (M+H)$^+$.

Step B: (3S)-2,2-Dimethyl-3-(phenylmethoxy)pent-4-enyl[3-(acetylamino)propyl]sulfonate (17b)

Acetic anhydride (Ac$_2$O) (1.54 mL, 1.66 g, 16.3 mmol), 4-(N,N-dimethyamino)pyridine (DMAP) (249 mg, 2.03 mmol), followed by triethylamine (Et$_3$N, TEA) (2.44 mL, 1.77 g, 17.5 mmol) were added to a solution of (3S)-2,2-dimethyl-3-(phenylmethoxy)pent-4-enyl[3-aminopropyl] sulfonate (17a) in 50 mL of anhydrous dichloromethane (DCM) at ca. 0° C. The reaction mixture was stirred overnight with gradual warming to room temperature. The solvents were then evaporated under reduced pressure using a rotary evaporator. The residue was diluted with ethyl acetate (EtOAc) and washed with one molar (1.0 M) hydrochloric acid (HCl), a saturated aqueous solution of sodium hydrogencarbonate (NaHCO$_3$), brine, dried over anhydrous magnesium sulfate (MgSO$_4$), filtered, and the solvents removed under reduced pressure using a rotary evaporator. The crude product was purified by silica gel column chromatography using a mixture of ethyl acetate (EtOAc) and n-heptane (Hptn) (EtOAc/Hptn=4:1→EtOAc/Hptn=6:1→EtOAc/Hptn=9:1) as eluent to provide 2.20 g (61% yield, two steps) of the title compound (17b) as a pale-yellow, viscous oil. $R_f$=0.28 (EtOAc/Hptn=4:1). $^1$H NMR (400 MHz, CDCl$_3$): δ=0.98 (s, 3H), 0.99 (s, 3H), 1.97 (s, 3H), 1.97-2.06 (m, 2H), 3.06-3.11 (m, 2H), 3.32-3.39 (m, 2H), 3.62 (d, J=8.4 Hz, 1H), 3.97 (d, J=9.2 Hz, 1H), 4.19 (d, J=9.2 Hz, 2H), 4.28 (d, J=12.0 Hz, 1H), 4.59 (d, J=12.0 Hz, 1H), 5.30 (ddd, J=16.8, 2.0, 1.2 Hz, 1H), 5.40 (ddd, J=10.0, 1.2, 0.8 Hz, 1H), 5.62 (br. m, 1H), 5.71-5.81 (m, 1H), 7.27-7.38 (m, 5H), ppm. MS (ESI) m/z 384.0 (M+H)$^+$, 405.9 (M+Na)$^+$. The analytical data was consistent the proposed structure.

Step C: (3R)-2,2-Dimethyl-4-oxo-3-(phenylmethoxy)butyl[3-(acetylamino)propyl]sulfonate (17c)

Following the general procedure for the preparation of aldehydes from alkenes of Description 11, (3S)-2,2-dimethyl-3-(phenylmethoxy)pent-4-enyl[3-(acetylamino)propyl]sulfonate (17b) (2.20 g, 5.75 mmol) dissolved in 30 mL of a mixture of dichloromethane (DCM) and ethanol (EtOH) (v/v=9:1) was reacted with ozone. Upon completion of reaction, 1.0 mL (846 mg, 13.62 mmol) of dimethyl sulfide (DMS) was added. After work-up, the crude material was purified by silica gel column chromatography using ethyl acetate (EtOAc) as eluent to provide 1.45 g (65% yield) of the title compound (17c) as a colorless oil. $R_f$=0.40 (EtOAc). $^1$H NMR (400 MHz, CDCl$_3$): δ=1.09 (s, 3H), 1.11 (s, 3H), 1.99 (s, 3H), 2.00-2.07 (m, 2H), 3.09-3.14 (m, 2H), 3.35-3.39 (m, 2H), 3.46 (br. d, J=2.8 Hz, 1H), 4.02 (d, J=9.6 Hz, 1H), 4.10 (d, J=9.2 Hz, 1H), 4.49 (d, J=11.2 Hz, 1H), 4.67 (d, J=11.2 Hz, 1H), 5.72-78 (br. t, 1H), 7.30-7.40 (m, 5H), 7.73-7.75 (m, 2H), 9.74 (br. d, 1H) ppm. MS (ESI) m/z 386.1 (M+H)$^+$, 408.0 (M+Na)$^+$. The analytical data was consistent the proposed structure.

Step D: (2R)-4-{[3-(Acetylamino)propyl]sulfonyloxy}-3,3-dimethyl-2-(phenylmethoxy)butanoic acid (17)

Following the general procedure for the oxidation of aldehydes to carboxylic acids of Description 13, (3R)-2,2-dimethyl-4-oxo-3-(phenylmethoxy)butyl[3-(acetylamino)propyl]sulfonate (17c) (1.45 g, 3.75 mmol) dissolved in 15 mL of acetone was reacted with 2.0 mL (4.0 mmol) of Jones-reagent (2.0 M aqueous solution). After work-up, 1.26 g (83% yield) of the title compound (17) was obtained as a slightly green, viscous oil. $^1$H NMR (400 MHz, DMSO-d$^6$): δ=0.97 (s, 3H), 1.00 (s, 3H), 1.72-1.85 (m, 5H), 3.08-3.14 (m, 2H), 3.28-3.33 (m, 2H, superimposed with residual water), 3.75 (s, 1H), 3.97 (d, J=9.6 Hz, 1H), 4.11 (d, J=9.2 Hz, 1H), 4.35 (d, J=11.2 Hz, 1H), 4.52 (d, J=12.0 Hz, 1H), 7.24-7.38 (m, 5H), 7.89 (br. t, J=5.2 Hz, 1H) ppm. MS (ESI) m/402.2 (M+H)$^+$, 424.0 (M+Na)$^+$, 400.1 (M−H)$^−$. The analytical data was consistent the proposed structure.

Alternative Synthesis of (3S)-2,2-Dimethyl-3-(phenylmethoxy)pent-4-enyl[3-(acetylamino)propyl]sulfonate (17)

Method 2

Step A: (3S)-2,2-Dimethyl-3-(phenylmethoxy)pent-4-enyl[3-azidopropyl]sulfonate (17A)

Following the general procedure for the preparation of azides of Description 16, (3S)-2,2-dimethyl-3-(phenylmethoxy)pent-4-enyl(3-chloropropyl)sulfonate (11a) (750 mg, 2.08 mmol) dissolved in 10 mL of anhydrous dimethyl sulfoxide (DMSO) was reacted with 402 g (6.18 mmol) of sodium azide (NaN$_3$). After work-up, 847 mg (~quant. yield) of the crude title compound (17A) was obtained that was of sufficient purity to be used in the next step without further purification. $R_f$=0.59 (Et$_2$O/Hxn=1:1). $^1$H NMR (400 MHz, CDCl$_3$): δ=0.98 (s, 3H), 1.00 (s, 3H), 2.02-2.10 (m, 2H), 3.10-3.15 (m, 2H), 3.42-3.46 (m, 2H), 3.62 (d, J=8.0 Hz, 1H), 3.98 (d, J=8.8 Hz, 1H), 4.21 (d, J=8.8 Hz, 1H), 4.29 (d, J=11.6, 1H), 4.58 (d, J=12.0 Hz, 1H), 5.30 (dd, J=16.8, 1.6 Hz, 1H), 5.40 (dd, J=10.4, 2.0 Hz, 1H), 5.77 (ddd, J=17.2, 10.0, 8.0 Hz, 1H), 7.27-7.37 (m, 5H), ppm MS (ESI) m/z 365.5 (M+Na)$^+$. The analytical data was consistent the proposed structure.

Step B: (3S)-2,2-Dimethyl-3-(phenylmethoxy)pent-4-enyl[3-aminopropyl]sulfonate (17a)

Following the general procedure for the reduction of azides by triphenylphosphine/water of Description 17, a mixture of (3S)-2,2-dimethyl-3-(phenylmethoxy)pent-4-enyl[3-azidopropyl]sulfonate (17A) (764 mg, 2.08 mmol) and triphenylphosphine (Ph$_3$P) (551 mg, 2.1 mmol) in ca. 15 mL of tetrahydrofuran (THF) containing water (45 μL, 45 mg, 2.5 mmol) was stirred under a nitrogen atmosphere. After aqueous work up and extraction, the crude title compound (17a) was obtained and used in the next step without further purification. MS (ESI) m/z 342.0 (M+H)$^+$, 364.0 (M+Na)$^+$. The analytical data was consistent with the data for the compound prepared using Method 1.

Step C: (3S)-2,2-Dimethyl-3-(phenylmethoxy)pent-4-enyl[3-(acetylamino)propyl]sulfonate (17b)

Acetic anhydride (Ac$_2$O) (236 μL, 255 mg, 2.35 mmol), 4-(N,N-dimethyamino)pyridine (DMAP) (30.5 mg, 0.25 mmol) followed by triethylamine (Et$_3$N, TEA) (349 μL, 235 mg, 2.5 mmol) were added to a solution of (3S)-2,2-dimethyl-3-(phenylmethoxy)pent-4-enyl[3-aminopropyl]sulfonate (17a) in 10 mL of anhydrous dichloromethane (DCM) at ca. 0° C. The reaction mixture was stirred overnight with gradual warming to room temperature and the solvents evaporated under reduced pressure using a rotary evaporator. The residue was diluted with ethyl acetate and washed with one molar (1.0 M) hydrochloric acid (HCl), a saturated aqueous solution of sodium hydrogencarbonate (NaHCO$_3$), brine, dried over anhydrous magnesium sulfate (MgSO$_4$), filtered, and the solvents removed under reduced pressure using a rotary evaporator. The crude product was purified by silica gel column chromatography using a mixture of ethyl acetate (EtOAc) and n-heptane (Hptn) (EtOAc/Hptn=4:1→EtOAc/Hptn=9:1) as eluent to provide 520 mg (65% yield, two steps) of the title compound (17b) as a pale-yellow, viscous oil. $R_f$=0.28 (EtOAc/Hptn=4:1). The analytical data was consistent with the data for the title compound (17b) prepared using Method 1 and Method 3.

Method 3

Step A: (3S)-2,2-Dimethyl-3-(phenylmethoxy)pent-4-enyl[3-(acetylamino)propyl]sulfonate (17b)

Following the general procedure for the preparation of neopentyl sulfonylester intermediates of Description 10, ca. 1.13 g (ca. 5.7 mmol) of N-[3-(chlorosulfonyl)propyl]acetamide (9) was reacted at ca. 0° C. in 25 mL of anhydrous dichloromethane (DCM) in the presence of 73 mg (0.6 mmol) of 4-(N,N-dimethylamino)pyridine (DMAP) and 800 μL (570 mg, 5.7 mmol) of triethylamine (Et$_3$N, TEA) with 600 mg (2.75 mmol) of (3S)-2,2-dimethyl-3-(phenylmethoxy)pent-4-en-1-ol (1). After work-up and isolation, the crude material was purified by silica gel column chromatography using an ethyl acetate (EtOAc) and methanol (MeOH) mixture (EtOAc/MeOH=95:5) as eluent to provide 400 mg (40% yield) of the title compound (17b) as a pale-yellow oil. $R_f$=0.36 (EtOAc). The analytical data was consistent with the data for the title compound (17b) prepared using Method I and Method 2.

Example 18

(2R/S)-4-{[3-(Acetylamino)propyl]sulfonyloxy}-3,3-dimethyl-2-(phenylmethoxy)butanoic Acid (18)

Step A: (3R/S)-2,2-Dimethyl-3-(phenylmethoxy)pent-4-enyl[3-(acetylamino)propyl]sulfonate (18a)

Following the general procedure for the preparation of neopentyl sulfonylester intermediates of Description 10, N-[3-(chlorosulfonyl)propyl]acetamide (9) (1.1 g, 5.7 mmol) in dichloromethane (DCM) in the presence of 73 mg (0.6 mmol) of 4-(N,N-dimethylamino)pyridine (DMAP) and 0.8 mL (0.57 g, 5.7 mmol) of triethylamine ($Et_3N$, TEA) was reacted at ca. −10° C. to 0° C. with 0.63 g (2.9 mmol) of (3R/S-2,2-dimethyl-3-(phenylmethoxy)pent-4-en-1-ol (2). After work-up and isolation, the crude material was purified by silica gel column chromatography using ethyl acetate (EtOAc) and methanol (MeOH) mixtures (EtOAc/MeOH=95:5) as eluent to provide 0.53 g (48% yield) the title compound (18a) as a pale-yellow oil. The analytical data was consistent with the proposed structure and with the data obtained for the enantiopure compound (17b).

Step B: (3R/S)-2,2-Dimethyl-4-oxo-3-(phenylmethoxy)butyl[3-(acetylamino)propyl]sulfonate (18b)

Following the general procedure for the preparation of aldehydes from alkenes of Description 11, (3R/S)-2,2-dimethyl-3-(phenylmethoxy)pent-4-enyl[3-(acetylamino)propyl]sulfonate (18a) (0.50 g, 1.3 mmol) dissolved in dichloromethane (DCM) was treated with a mixture of oxygen and ozone ($O_2/O_3$). Upon completion of the reaction, 0.29 mL (0.24 g, 3.9 mmol) of dimethyl sulfide (DMS) was added. After work-up, the crude material was purified by silica gel column chromatography using a mixture of ethyl acetate (EtOAc) and methanol (MeOH) (EtOAc/MeOH=9:1) as eluent to provide the title compound (18b). The analytical data was consistent with the proposed structure and with the data obtained for the enantiopure compound (17c).

Step C: (2R/S)-4-{[3-(Acetylamino) propyl]sulfonyloxy}-3,3-dimethyl-2-(phenylmethoxy)butanoic acid (18)

Following the general procedure of the oxidation of aldehydes to carboxylic acids of Description 13, (3R/S)-2,2-dimethyl-4-oxo-3-(phenylmethoxy)butyl[3-(acetylamino)propyl]sulfonate (18b) (60 mg, 0.17 mmol) dissolved in 1.5 mL of acetone was reacted with 93 μL (0.186 mmol) of Jones-reagent (2.0 M in water). After work-up, 60 mg (96% yield) of the title compound (18) was obtained. The analytical data was consistent with the proposed structure and with the data obtained for the enantiopure compound (17).

Example 19

(2R)-4-{[3-(Acetylamino)propyl]sulfonyloxy}-3,3-dimethyl-2-(1,1,2,2-tetramethyl-1-silapropoxy)butanoic Acid (19)

Step A: Methyl (2E)(4S)-6-{[3-(acetylamino)propyl]sulfonyloxy}-5,5-dimethyl-4-(1,1,2,2-tetramethyl-1-silapropoxy)hex-2-enoate (19a)

Following the general procedure for the preparation of neopentyl sulfonylester intermediates of Description 10, N-[3-(chlorosulfonyl)propyl]acetamide (9) (4.0 g, 19.8 mmol) in 40 mL of dichloromethane (DCM) in the presence of 1.2 g (9.8 mmol) of 4-(N,N-dimethylamino)pyridine (DMAP) and 2.8 mL (2.0 g, 19.8 mmol) of triethylamine ($Et_3N$, TEA) was reacted at ca. 0° C. with 3.0 g (9.9 mmol) of methyl (2E)(4S)-6-hydroxy-5,5-dimethyl-4-(1,1,2,2-tetramethyl-1-silapropoxy)hex-2-enoate (4). After work-up and isolation, the crude material was purified by silica gel column chromatography using ethyl acetate (EtOAc) and methanol (MeOH) mixtures (EtOAc/MeOH=9:1) as eluent to provide 2.5 g (55% yield) the title compound (19a) as a colorless oil. $R_f$=0.46 (EtOAc). $^1$H NMR (400 MHz, $CDCl_3$): δ=0.01 (s, 3H), 0.08 (s, 3H), 0.93 (s, 9H), 0.97 (s, 6H), 2.06 (s, 3H) 2.07-2.11 (m, 2H), 3.14-3.18 (m, 2H), 3.40-3.45 (m, 2H), 3.77 (s, 3H), 3.98 (d, J=9.6 Hz, 1H), 4.06 (d, J=9.2 Hz, 1H), 4.09 (dd, superimposed, J=6.4, 1.6 Hz, 1H), 5.93 (br., 1H), 5.96 (dd, J=15.6, 1H), 6.90 (dd, J=15.6, 6.4 Hz, 1H) ppm. MS (ESI) m/z 466.10 $(M+H)^+$. The analytical data was consistent with the proposed structure.

Step B: (3R)-2,2-Dimethyl-4-oxo-3-(1,1,2,2-tetramethyl-1-silapropoxy)butyl 13-(acetylamino)propyl)sulfonate (19b)

Following the general procedure for the preparation of aldehydes from alkenes of Description 11, methyl (2E)(4S)-6-{[3-(acetylamino)propyl]sulfonyloxy}-5,5-dimethyl-4-(1,1,2,2-tetramethyl-1-silapropoxy)hex-2-enoate (19a) (2.5 g, 5.4 mmol) dissolved in 50 mL of dichloromethane (DCM) was treated with a mixture of oxygen and ozone ($O_2/O_3$). Upon completion of the reaction, 0.78 mL (0.66 g, 10.7 mmol) of dimethyl sulfide (DMS) was added. After work-up, the crude material was purified by silica gel column chromatography using a mixture of ethyl acetate (EtOAc) and methanol (MeOH) (EtOAc/MeOH=9:1) as eluent to provide 2.0 g (91% yield) of the title compound (19b) as a colorless oil. $R_f$=0.51 (EtOAc). $^1$H NMR (400 MHz, $CDCl_3$): δ=0.07 (s, 3H), 0.10 (s, 3H), 0.96 (s, 9H), 1.05 (s, 3H), 1.10 (s, 3H), 2.06 (s, 3H), 2.04-2.11 (m, 2H), 3.14-3.19 (m, 2H), 3.40-3.44 (m, 2H), 3.72 (d, J=2.8 Hz, 1H), 3.97 (d, J=9.2 Hz, 1H), 4.11 (d, J=9.2 Hz, 1H), 5.84 (br., 1H), 9.62 (d, J=2.0 Hz, 1H) ppm. MS (ESI) m/z 410.10 $(M+H)^+$, 432.07 $(M+Na)^+$. The analytical data was consistent with the proposed structure.

Step C: (2R)-4-{[3-(Acetylamino)propyl]sulfonyloxy}-3,3-dimethyl-2-(1,1,2,2-tetramethyl-1-silapropoxy)butanoic acid (19)

Following the general procedure of the oxidation of aldehydes to carboxylic acids of Description 13, (3R)-2,2-dimethyl-4-oxo-3-(1,1,2,2-tetramethyl-1-silapropoxy)butyl[3-(acetylamino)propyl]sulfonate (19b) (2.0 g, 4.9 mmol) dissolved in 20 mL of acetone was reacted with 2.3 mL of Jones-reagent (2.0 M in water). After work-up, 1.5 g (72% yield) of the title compound (19) was obtained as a green oil. $^1$H NMR (400 MHz, $CDCl_3$): δ=0.12 (s, 3H), 0.13 (s, 3H), 0.96 (s, 9H), 1.03 (s, 3H), 1.15 (s, 3H), 2.04 (s, 3H), 2.07-2.12 (m, 2H), 3.12-3.18 (m, 2H), 3.38-3.45 (m, 2H), 3.96 (d, J=9.2 Hz, 1H), 4.00 (s, 1H), 4.21 (d, J=9.6 Hz, 1H), 6.12 (br. M, 1H) ppm. MS (ESI) m/z 426.11 $(M+H)^+$; 424.15 $(M-H)^-$. The analytical data was consistent with the proposed structure.

Example 20

(2R)-4-{[3-(1,3-Dioxobenzo[c]azolin-2-yl)propyl]sulfonyloxy}-3,3-dimethyl-2-(phenylmethoxy)butanoic Acid (20)

Step A: (3S)-2,2-Dimethyl-3-(phenylmethoxy)pent-4-enyl[3-(1,3-dioxobenzo[c]azolin-2-yl)propyl]sulfonate (20a)

Following the general procedure for the preparation of neopentyl sulfonylester intermediates of Description 10, 1.8 g, (6.0 mmol) of 2-[3-(chlorosulfonyl)propyl]benzo[c]azolin-1,3-dione (10) in 50 mL of anhydrous dichloromethane (DCM) in the presence of 150 mg (1.2 mmol) of 4-(N,N-dimethylamino)pyridine (DMAP) and 830 μL (23.8 g, 6.0 mmol) of triethylamine ($Et_3N$, TEA) was reacted at ca. 0° C. with 1.17 g (5.3 mmol) of (3S)-2,2-dimethyl-3-(phenylmethoxy)pent-4-en-1-ol (1). After work-up, the crude material was purified by silica gel column chromatography using a mixture of ethyl acetate (EtOAc) and hexane (Hxn) (EtOAc/Hxn=1:1) as eluent to provide 2.1 g (84% yield) of the title compound (20a) as a white solid. $R_f$=0.45 (EtOAc/Hxn=1:2). $^1$H NMR (400 MHz, $CDCl_3$): δ=0.96 (s, 3H), 0.98 (s, 3H), 2.18-2.26 (m, 2H), 3.11-3.15 (m, 2H), 3.61 (d, J=8.0 Hz, 1H), 3.78 (t, J=6.4 Hz, 2H), 3.97 (d, J=8.8 Hz, 1H), 4.20 (d, J=9.2 Hz, 1H), 4.28 (d, J=11.6 Hz, 1H), 4.57 (d, J=12.0 Hz, 1H), 5.26-5.40 (m, 2H), 5.71-5.80 (m, 1H), 7.30-7.32 (m, 5H), 7.73-7.77 (m, 2H), 7.84-7.88 (m, 2H) ppm. MS (ESI) m/z 494.17 $(M+Na)^+$. The analytical data was consistent with the proposed structure.

Step B: (3R)-2,2-Dimethyl-4-oxo-3-(phenylmethoxy)butyl[3-(1,3-dioxobenzo[c]azolin-2-yl)propyl]sulfonate (20b)

Following the general procedure for the preparation of aldehydes from alkenes of Description 11, (3S)-2,2-dimethyl-3-(phenylmethoxy)pent-4-enyl[3-(1,3-dioxobenzo[c]azolin-2-yl)propyl]sulfonate (20a) (2.1 g, 4.4 mmol) dissolved in 40 mL of dichloromethane (DCM) was reacted with ozone. Upon completion of the reaction, 1.0 mL (846 mg, 13.62 mmol) of dimethyl sulfide (DMS) was added. After work-up, the crude material was purified by silica gel column chromatography using a mixture of ethyl acetate (EtOAc) and hexane (Hxn) (EtOAc/Hxn=1:2) as eluent to provide 1.8 g (85% yield) of the title compound (20b) as a colorless oil. $R_f$=0.30 (EtOAc/Hxn=1:2). $^1$H NMR (400 MHz, $CDCl_3$): δ=1.07 (s, 3H), 1.08 (s, 3H), 2.18-2.26 (m, 2H), 3.14-3.18 (m, 2H), 3.56 (d, J=2.8 Hz, 1H), 3.81 (t, J=6.8 Hz, 2H), 4.00 (d, J=9.2 Hz, 1H), 4.15 (d, J=9.2 Hz, 1H), 4.49 (d, J=11.2 Hz, 1H), 4.66 (d, J=11.6 Hz, 1H), 7.32-7.34 (m, 5H), 7.73-7.75 (m, 2H), 7.84-7.87 (m, 2H) ppm. MS (ESI) m/z 496.14 $(M+Na)^+$. The analytical data was consistent with the proposed structure.

Step C: (2R)-4-{[3-(1,3-Dioxobenzo[c]azolin-2-yl)propyl]sulfonyloxy}-3,3-dimethyl-2-(phenylmethoxy)butanoic Acid (20)

Following the general procedure for the oxidation of aldehydes to carboxylic acids of Description 13, (3R)-2,2-dimethyl-4-oxo-3-(phenylmethoxy)butyl[3-(1,3-dioxobenzo[c]azolin-2-yl)propyl]sulfonate (20b) (1.7 g, 3.6 mmol) dissolved in 20 mL of acetone was reacted with 1.9 mL (3.8 mmol) of Jones-reagent (2.0 M aqueous solution). After work-up, 1.6 g (91% yield) of the title compound (20) was obtained as a colorless oil. $^1$H NMR (400 MHz, $CDCl_3$): δ=1.10 (s, 6H), 2.19-2.26 (m, 2H), 3.14-3.22 (m, 2H), 3.81 (t, J=7.2 Hz, 2H), 3.88 (s, 1H), 4.05 (d, J=9.2 Hz, 1H), 4.17 (d, J=9.2 Hz, 1H), 4.46 (d, J=11.2 Hz, 1H), 4.69 (d, J=11.2 Hz, 1H), 7.30-7.35 (m, 5H), 7.72-7.74 (m, 2H), 7.84-7.86 (m, 2H) ppm. MS (ESI) m/z 490.13 $(M+H)^+$, 512.13 $(M+Na)^+$, 488.16 $(M-H)^-$. The analytical data was consistent with the proposed structure.

Example 21

(2R/S)-4-{[3-(1,3-Dioxobenzo[c]azolin-2-yl)propyl]sulfonyloxy}-2-[(4-methoxyphenyl)methoxy]-3,3-dimethylbutanoic Acid (21)

Step A: (3R/S)-3-[(4-Methoxyphenyl)methoxy]-2,2-dimethylpent-4-enyl[3-(1,3-dioxobenzo[c]azolin-2-yl)propyl]sulfonate (21a)

Following the general procedure for the preparation of neopentyl sulfonylester intermediates of Description 10, 0.41 g, (1.4 mmol) of 2-[3-(chlorosulfonyl)propyl]benzo[c]azolin-1,3-dione (10) in 10 mL of tetrahydrofuran (THF) in the presence of 34 mg (0.28 mmol) of 4-(N,N-dimethylamino)pyridine (DMAP) and 0.19 mL (0.14 g, 1.4 mmol) of triethylamine ($Et_3N$, TEA) was reacted at ca. 0° C. with 0.3 g (1.2 mmol) of (3R/S)-[(4-methoxyphenyl)methoxy]-2,2-dimethylpent-4-en-1-ol (3). After work-up and isolation, the crude material was purified by silica gel column chromatography using ethyl acetate (EtOAc) and hexane (Hxn) mixtures (EtOAc/Hxn=1:1) as eluent to provide 0.6 g (quant. yield) of the title compound (21a) as a white solid. $R_f$=0.73 (EtOAc/Hxn=1:1). $^1$H NMR (400 MHz, $CDCl_3$): δ=0.94 (s, 3H), 0.96 (s, 3H), 2.22-2.25 (m, 2H), 3.11-3.15 (m, 2H), 3.59 (d, J=8.0 Hz, 1H), 3.78-3.81 (m, 5H), 3.95 (d, J=9.2 Hz, 1H), 4.18 (d, J=8.8 Hz, 1H), 4.21 (d, J=10.8 Hz, 1H), 4.50 (d, J=10.8 Hz, 1H), 5.25-5.39 (m, 2H), 5.69-5.78 (m, 1H), 6.85 (d, J=8.4 Hz, 2H), 7.22 (d, J=8.4 Hz, 2H), 7.73-7.75 (m, 2H), 7.84-7.86 (m, 2H) ppm. MS (ESI) m/z 524.17 $(M+Na)^+$. The analytical data was consistent with the proposed structure.

Step B: (3R/S)-3-[(4-Methoxyphenyl)methoxy]-2,2-dimethyl-4-oxobutyl[3-(1,3-dioxobenzo[c]azolin-2-yl)propyl]sulfonate (21b)

Following the general procedure for the preparation of aldehydes from alkenes of Description 11, (3R/S)-3-[(4-methoxyphenyl)methoxy]-2,2-dimethylpent-4-enyl[3-(1,3-dioxobenzo[c]azolin-2-yl)propyl]sulfonate (21a) (0.6 g, 1.2 mmol) dissolved in dichloromethane (DCM) was treated with a mixture of oxygen and ozone ($O_2/O_3$). Upon completion of the reaction, 2 mL (1.69 g, 27.2 mmol) of dimethyl sulfide (DMS) was added. After work-up, the crude material was purified by silica gel column chromatography using a mixture of ethyl acetate (EtOAc) and hexane (Hxn) (EtOAc/Hxn=1:1) as eluent to provide 330 mg (55% yield) of the title compound (21b) as a colorless oil. $R_f$=0.54 (EtOAc/Hxn=1:1). $^1$H NMR (400 MHz, $CDCl_3$): δ=1.04 (s, 6H), 2.17-2.24 (m, 2H), 3.14-3.18 (m, 2H), 3.52 (d, J=3.2 Hz, 1H), 3.78-3.82 (m, 5H), 3.97 (d, J=8.8 Hz, 1H), 4.11 (d, J=9.6 Hz, 1H), 4.42 (d, J=10.8 Hz, 1H), 4.56 (d, J=11.2 Hz, 1H), 6.84 (d, J=8.0 Hz, 2H), 7.24 (d, J=8.0 Hz, 2H), 7.71-7.73 (m, 2H), 7.82-7.84 (m, 2H), 9.66 (d, J=2.8 Hz, 1H) ppm. MS (ESI) m/z 526.13 (M+Na)⁺. The analytical data was consistent with the proposed structure.

Step C: (2R/S)-4-{[3-(1,3-Dioxobenzo[c]azolin-2-yl)propyl]sulfonyloxy}-2-[(4-methoxyphenyl)methoxy]-3,3-dimethylbutanoic acid (21)

Following the general procedure of the oxidation of aldehydes to carboxylic acids of Description 13, (3R/S)-3-[(4-methoxyphenyl)methoxy]-2,2-dimethyl-4-oxobutyl[3-(1,3-dioxobenzo[c]azolin-2-yl)propyl]sulfonate (21b) (0.33 g, 0.66 mmol) dissolved in acetone was reacted with 0.33 mL (0.66 mmol) of Jones-reagent (2.0 M in water). After work-up, 0.31 g (90% yield) of the title compound (21) was obtained as a colorless oil. $^1$H NMR (400 MHz, CDCl$_3$): δ=1.07 (s, 6H), 2.18-2.25 (m, 2H), 3.14-3.22 (m, 2H), 3.79-3.85 (m, 6H), 4.02 (d, J=9.2 Hz, 1H), 4.09-4.11 (m, 1H), 4.39 (d, J=11.2 Hz, 1H), 4.60 (d, J=11.2 Hz, 1H), 6.85 (d, J=7.6 Hz, 2H), 7.27 (d, J=7.6 Hz, 2H), 7.71-7.74 (m, 2H), 7.83-7.85 (m, 2H) ppm. MS (ESI) m/z 542.10 (M+Na)⁺, 518.18 (M−H)⁻. The analytical data was consistent the proposed structure.

Description 15

General Procedure for the Preparation of Carboxylic Esters from Carboxylic Acids In a representative synthesis, an oven-dried suitably sized round-bottomed flask equipped with a magnetic stirring bar was charged with 10.0 mmol (1.0 mol-eq.) of a carboxylic acid derivative and 25-100 mL of anhydrous dichloromethane (DCM). At ca. 0° C. (ice bath), 6.0-10.0 mL (12.0-20.0 mmol, 1.2-2.0 mol-eq.) of oxalyl chloride (ClOCCOCl) (2.0 M in DCM) was added to the stirred solution, followed by the addition of a few drops (1-3) of anhydrous dimethylformamide (DMF) to catalyze the reaction. The reaction mixture was stirred for approximately one hour at this temperature. The solvents were removed under reduced pressure using a rotary evaporator. The residue was dissolved in 25-100 mL of anhydrous dichloromethane (DCM) and the solution was optionally cooled to ca. 0° C. (ice bath). A solution of 20.0-30.0 mmol (2.0-3.0 mol-eq.) of an appropriate anhydrous alcohol and 0.81-1.62 mL (0.79-1.58 g, 10.0-20.0 mmol, 1.0-2.0 mol-eq.) of anhydrous pyridine in about 25-100 mL of anhydrous dichloromethane (DCM) was added to the carboxylic acid chloride. The reaction mixture was stirred overnight with gradual warming to room temperature. The solvents were removed under reduced pressure using a rotary evaporator. The residue was diluted with ethyl acetate (EtOAc) and one molar (1 M) hydrochloric acid (HCl) or a saturated aqueous solution of sodium hydrogen carbonate (NaHCO$_3$). After phase separation, the aqueous solution was extracted with ethyl acetate (EtOAc). The combined organic extracts were washed with brine, dried over anhydrous magnesium sulfate (MgSO$_4$), filtered, and the solvents removed under reduced pressure using a rotary evaporator. The crude material was further purified by silica gel column chromatography using ethyl acetate (EtOAc) and hexane (Hxn) mixtures and/or gradients as eluent to yield the desired products generally as pale-yellow to colorless oils or solids.

Description 16

General Procedure for the Preparation of Azides from Alkylchlorides

Caution: (Organic) azides can be explosive. The use of appropriate safety measures for experimental work and proper waste disposal are strongly recommended.

Adapting procedures or variations thereof according to de la Mora et al., *Tetrahedron Lett.* 2001, 42, 5351-5353; Wagner et al., *J. Am. Chem. Soc.* 1979, 101, 378-383; De Kimpe et al., *Tetrahedron* 1997, 53, 3693-3706; Singh et al., *Tetrahedron Lett.* 2003, 44, 9169-9171; and Singh et al., *Tetrahedron Lett.* 2005, 46, 4213-4217, in a representative synthesis, an oven-dried 250 mL round-bottomed flask equipped with a magnetic stirring bar was charged with 10.0 mmol (1.0 mol-eq.) of an appropriately functionalized organic alkyl halide, i.e. alkyl chloride, and 25-50 mL of anhydrous dimethylsulfoxide (DMSO). To the stirred solution was added 1.3-3.9 g (20.0-60.0 mmol, 2.0-6.0 mol-eq.) of sodium azide (NaN$_3$). The reaction mixture was heated to ca. 50-60° C. (oil bath) and stirred overnight at this temperature. The reaction was monitored by TLC and/or LC/MS. Upon completion of the reaction, the mixture was diluted with a saturated aqueous solution of sodium hydrogen carbonate (NaHCO$_3$) or water and the aqueous layer extracted several times with methyl tert-butyl ether (MTBE) or ethyl acetate (EtOAc) or mixtures thereof. The combined organic extracts were successively washed with water, brine, dried over anhydrous magnesium sulfate (MgSO$_4$), filtered, and the solvents removed under reduced pressure using a rotary evaporator. The target compounds were generally obtained in high purity, and were used in the next step without further purification or isolation. Optionally, after extraction the solvents were only partially removed under reduced pressure using a rotary evaporator and the resulting solutions containing the azides were used directly in the next step without further purification or isolation.

Description 17

General Procedure for the Reduction of Azides to Amines and In Situ Conversion to N-Acetyl Derivatives Method A Reduction of Azides via Hydrogenation and In Situ Conversion to N-Acetyl Derivatives Caution: Hydrogen is a highly flammable gas. The use of appropriate safety precautions and equipment is highly advised.

In a representative synthesis, a round-bottomed flask equipped with a magnetic stirring bar and a three-way adapter connected to a hydrogen-filled balloon (ca. 15 psi) was charged with 10.0 mmol (1.0 mol-eq.) of an appropriately functionalized organic azide, 25-100 mL of methanol (MeOH) or ethyl acetate (EtOAc) or mixtures thereof, i.e. v/v=1:1, and 10-100 mass-% of 5-10 wt-% of palladium on activated carbon. Acetic anhydride (Ac$_2$O) 1.89-3.78 mL (2.04-4.08 g, 20.0-40.0 mmol, 2-4 mol-eq.) was added to the mixture. Alternatively, acetic anhydride was also added after the reduction of the azide was complete without significantly altering the reaction outcome. Alternatively, a Parr-hydrogenation vessel and Parr-hydrogenation apparatus were used for reactions requiring a higher pressure or larger scale. The atmosphere in the reaction vessel was exchanged to hydrogen (H$_2$) using three evacuation and refill cycles and the reaction mixture was stirred or shaken overnight at room temperature at a pressure of approximately 15 psi or higher (up to 60 psi) or until the reduction/N-acetylation procedure was complete (as determined by TLC; typically over night). Upon completion of the reaction, the solids (heterogeneous catalyst) were filtered off using a short plug of Celite® and the solvents were removed under reduced pressure using a rotary evaporator. Alternatively, the residue was diluted with a saturated aqueous solution of sodium hydrogencarbonate (NaHCO$_3$) and the solution was extracted twice with ethyl acetate (EtOAc). The combined organic extracts were washed with brine, dried over anhydrous magnesium sulfate (MgSO$_4$), filtered, and the solvents removed under reduced pressure using a rotary evaporator. The crude material was purified by silica gel column chromatography using ethyl acetate (EtOAc)/methanol (MeOH) mixtures and/or gradients as eluent or by mass-guided preparative HPLC to yield the desired product, typically as a colorless oil or solid.

Method B

Reduction of Azides by Tin(II) Dichloride and In Situ Conversion to N-Acetyl Derivatives In a representative synthesis and adapting a procedure or a variation thereof according to Samarendra et al., *Tetrahedron Letters* 1986, 27, 1423-1424, a round-bottomed flask equipped with a magnetic stirring bar was charged with 10.0 mmol (1.0 mol-eq.) of an appropriately functionalized organic azide, 50-100 mL of methanol (MeOH) and 2.84 g (15.0 mmol, 1.5 mol-eq.) of tin(II) dichloride (stannous chloride, SnCl$_2$). The reaction mixture was stirred overnight at room temperature. The reaction was monitored by LC/MS. Upon completion of the reaction, the solvent was removed under reduced pressure using a rotary evaporator. The residue was then dissolved in 50-100 mL of ethyl acetate (EtOAc). Acetic anhydride (Ac$_2$O) 2.84 mL (3.06 g, 30.0 mmol, 3 mol-eq.) and pyridine 2.43 mL (2.37 g, 30.0 mmol, 3.0 mol-eq.) were added to the solution. The mixture was stirred at room temperature until the N-acetylation reaction was complete, e.g., about two hours. The reaction mixture was diluted with a saturated aqueous solution of sodium hydrogencarbonate (NaHCO$_3$) and then extracted with ethyl acetate (EtOAc). The combined organic extracts were washed with brine, dried over anhydrous magnesium sulfate (MgSO$_4$), filtered, and the solvents removed under reduced pressure using a rotary evaporator. The crude material was purified by silica gel column chromatography using ethyl acetate (EtOAc) and methanol (MeOH) mixtures as eluent to yield the desired product, generally as a colorless oil.

Method C

Reduction of Azides by Triphenylphosphine/Water and In Situ Conversion to N-Acetyl Derivatives (Staudinger-Reaction)

Adapting procedures or variations thereof according to Nagarajan et al., *J. Org. Chem.*, 1987, 52, 5044-5046; and Pillard et al., *Tetrahedron Lett.* 1984, 25, 1555-1556, in a representative synthesis, a suitably sized round-bottomed flask equipped with a magnetic stirring bar was charged with 10.0 mmol of an appropriately functionalized azide and 25-50 mL of tetrahydrofuran (THF). 0.18-0.2 mL (180-198 mg, 10.0-11.0 mmol, 1.0-0.1 mol-eq.) of water and 2.62-2.89 g (10.0-11.0 mmol, 1.0-1.1 mol-eq.) of triphenylphosphine (Ph$_3$P) were added to the solution. The reaction mixture was stirred overnight at room temperature and the reaction monitored by LC/MS or TLC. The solvents were then removed under reduced pressure using a rotary evaporator and the residue was either used directly without further isolation or purification, or, alternatively, was purified by silica gel column chromatography using dichloromethane (DCM) and methanol (MeOH) mixtures optionally containing one to two vol-% of triethylamine as eluent. The corresponding free amine derivatives were typically obtained as colorless, viscous oils. The crude or purified material was then dissolved in 25-50 mL of ethyl acetate (EtOAc) or dichloromethane (DCM). Acetic anhydride (Ac$_2$O) (1.13 mL, (2.04-4.08 g, 20.0-40.0 mmol, 2.0-4.0 mol-eq.) and pyridine 0.81-1.62 mL (0.79-1.58 g, 10.0-20.0 mmol, 1.0-2.0 mol-eq.) were added to the solution. The mixture was stirred at room temperature until the N-acetylation reaction was complete, e.g., about two hours. The reaction mixture was diluted with a saturated aqueous solution of sodium hydrogencarbonate (NaHCO$_3$) and extracted twice with ethyl acetate. The combined organic extracts were washed with brine, dried over anhydrous magnesium sulfate (MgSO$_4$), filtered, and the solvents removed under reduced pressure using a rotary evaporator. The crude material was purified by silica gel column chromatography using ethyl acetate (EtOAc) and methanol (MeOH) mixtures as eluent to yield the desired N-acetyl derivative, generally as a colorless oil.

Description 18

General Procedure of the Removal of Benzyl Protecting Groups via Catalytic Hydrogenolysis Caution: Hydrogen is a highly flammable gas. The use of appropriate safety precautions and equipment is highly advised.

In a representative synthesis, a round-bottomed flask equipped with a magnetic stirring bar and a three-way adapter connected to a hydrogen-filled balloon (ca. 15 psi) was charged with 10.0 mmol (1.0 mol-eq.) of an appropriately functionalized O-benzyl ether protected derivative, 25-100 mL of methanol (MeOH), ethanol (EtOH), water, or mixtures thereof, and 50-100 mass-% of 5-10 wt-% of palladium on activated carbon. Optionally, 50-100 mass-% of 5-10 wt-% of a safer heterogenous catalyst, i.e., palladium on wet carbon (~50% water) (Degussa-type), was employed with comparable results. Also optionally, a catalytic amount of one molar (1.0 M) hydrochloric acid (HCl) or acetic acid (HOAc) was added to activate the catalyst system and facilitate the reaction. Alternatively, a Parr-hydrogenation vessel and Parr-hydrogenation apparatus were used for reactions requiring a higher pressure or larger scale. The atmosphere in the reaction vessel was exchanged to hydrogen (H$_2$) using three evacuation and refill cycles and the reaction mixture was stirred or shaken overnight at room temperature under the established hydrogen atmosphere at a pressure of approximately 15 psi or higher (up to 60 psi) or until the catalytic reductive O-debenzylation was complete (as determined by TLC; typically overnight). Upon completion of the reaction, the solids (heterogeneous catalyst) were filtered off using a short plug of Celite®, the filter cake was washed with the same or other suitable solvent, and the solvents were removed under reduced pressure using a rotary evaporator. The residue was optionally further purified by silica gel column chromatography using methyl tert-butyl ether (MTBE), ethyl acetate (EtOAc), methanol (MeOH), and hexanes (Hxn) or mixtures and/or gradients as eluent. If the hydrogenolytic deprotection of the benzyl ether protecting group was the final step in the preparation of neopentyl acamprosate sulfonylester prodrug, the residue was dissolved in a mixture of ca. 40-60% (v/v) acetonitrile/water, the solution filtered through a 0.2-μm nylon syringe filter, and purified by mass-guided preparative HPLC. After lyophilization of the solvents, optionally in the presence of one molar (1.0 M) hydrochloric acid (HCl), the corresponding acamprosate neopentyl sulfonylester prodrug or appropriately functionalized precursor was obtained usually as a colorless oil or solid.

Description 19

General Procedure for the Oxidative Cleavage of (4-Methoxy)benzyl Ethers

Adapting procedures or variations thereof according to Tanaka et al., *Tetrahedron Lett*. 1986, 27, 3651-3654; Oikawa et al., *Tetrahedron Lett*. 1984, 25, 5397-5400; Oikawa et al., *Tetrahedron Lett*. 1982, 23, 885-888; and Horita et al., *Tetrahedron* 1986, 42, 3021-3028, in a representative synthesis, 2,3-dichloro-5,6-dicyano-1,4-benzoquinone (DDQ) 2.72 g (12.0 mmol, 1.2 mol-eq.) was added to a stirred solution of an appropriately functionalized (4-methoxy)benzyl ether 10.0 mmol (1.0 mol-eq.) dissolved in a mixture of dichloromethane (DCM) and water (10:1 v/v) (50-100 mL). The solution turned from dark green to crimson red as the reaction progressed and a crimson red precipitate was generated. The reaction was monitored by LC/MS and/or TLC. Upon completion of the reaction, the precipitate was filtered through a short plug of Celite®, and the plug washed with a suitable solvent such as dichloromethane (DCM) or ethyl acetate (EtOAc). The solvents were removed under reduced pressure using a rotary evaporator. The residue was optionally further purified by silica gel column chromatography using methyl tert-butyl ether (MTBE), ethyl acetate (EtOAc), methanol (MeOH), and hexanes (Hxn) or mixtures and/or gradients thereof. If the oxidative deprotection of the 4-methoxy benzyl ether protecting group was the final step in the preparation of the neopentyl acamprosate sulfonylester prodrug the residue was dissolved in a mixture of ca. 40-60% (v/v) acetonitrile/water, the solution filtered through a 0.2-μm nylon syringe filter, and purified by mass-guided preparative HPLC. After lyophilization of the solvents, optionally in the presence of one molar (1.0 M) hydrochloric acid (HCl), the corresponding acamprosate neopentyl sulfonylester prodrug or appropriately functionalized precursor was obtained, usually as a colorless oil or solid.

Description 20

General Procedure for the Cleavage of Silyl Ethers with Triethylamine Trihydrofluoride Adapting a procedure or a variation thereof according to Pirrung et al., *Bioorg. Med. Chem. Lett*. 1994, 4, 1345-1346; and McClinton, *Aldrichimica Acta* 1995, 28(2), 31-34, in a representative synthesis, a flask equipped with a magnetic stirring bar and a rubber septum was charged with 10.0 mmol (1.0 mol-eq.) of an appropriately functionalized silyl ether, i.e. tert-butyl dimethylsilyl ether (TBDMS-ether). Commercially available triethylamine trihydrofluoride ($Et_3N \cdot 3HF$) 4.84 g (30.0 mmol, 3.0 mol-eq.) was added to a stirred solution of in 50-100 mL of anhydrous tetrahydrofuran (THF). The reaction mixture was stirred overnight at ca. 50-60° C. After the starting material was completely consumed (as determined by TLC), the solvent was removed under reduced pressure using a rotary evaporator. The residue was optionally further purified by silica gel column chromatography using methyl tert-butyl ether (MTBE), ethyl acetate (EtOAc), methanol (MeOH), and hexanes (Hxn) or mixtures and/or gradients as eluent. If the desilylation was the final step in the preparation of neopentyl acamprosate sulfonylester prodrug, the residue was dissolved in a mixture of ca. 40-60% (v/v) acetonitrile/water, the solution filtered through a 0.2-μm nylon syringe filter, and purified by mass-guided preparative HPLC. After lyophilization of the solvents, optionally in the presence of one molar (1.0 M) hydrochloric acid (HCl), the corresponding acamprosate neopentyl sulfonylester prodrug or appropriately functionalized precursor was obtained, typically as a colorless oil or solid.

Description 21

General Procedure for the Synthesis of 1-Chloroalkyl Carboxylic Esters

Adapting procedures or variations thereof according to Ulich et al., *J. Am. Chem. Soc.*, 1921, 43, 660-667; and Sarri et al., *J. Med. Chem* 1978, 21(8), 746-753, in a representative synthesis, a 500 mL round bottomed flask equipped with a magnetic stirring bar was charged with 100 mmol (1.0 mol-eq.) of an acyl chloride, a catalytic amount of anhydrous zinc chloride ($ZnCl_2$) (1.36-2.73 g, 10-20 mol-%) and 250 mL of anhydrous dichloromethane (DCM). The reaction mixture was cooled to ca. 0° C. (ice/water bath) and 1.2-1.5 mol-eq. of an appropriate aldehyde, optionally dissolved a small volume of anhydrous dichloromethane (DCM), was slowly added. Alternatively, the sequence of addition of the reactants was reversed without compromising the result. The reaction mixture was stirred for 2-10 hours with gradual warming to room temperature. Optionally, the reaction mixture was heated. The dichloromethane (DCM) was removed under reduced pressure. The crude material was further diluted with water and methyl tert-butyl ether (MTBE) and the phases separated. The aqueous phase was extracted two additional times with methyl tert-butyl ether (MTBE) and the combined organic extracts were washed with a saturated aqueous solution of sodium hydrogen carbonate ($NaHCO_3$), water, and brine. The organic solution was dried over anhydrous magnesium sulfate ($MgSO_4$), filtered, and the solvents were removed under reduced pressure using a rotary evaporator. The residue was further purified by silica gel column chromatography using a mixture of hexane (Hxn) and diethyl ether ($Et_2O$) or ethyl acetate (EtOAc) as eluent to provide the target product. Optionally, the product was further purified by fractional distillation under reduced pressure.

Example 22

1-Chloroethyl 2-methylpropanoate (22)

Following the general procedure for the synthesis of 1-chloroalkyl carboxylic esters of Description 21, 10 mL (10.5 g, 98.0 mmol) of isobutyryl chloride (iPrCOCl) was reacted with 8.2 mL (6.5 g, 147 mmol) of acetaldehyde in 250 mL of anhydrous dichloromethane (DCM) in the presence of 1.6 g (9.8 mmol) of zinc chloride ($ZnCl_2$). After work-up and isolation, the product was purified by silica gel column chromatography using diethyl ether ($Et_2O$) and hexane (Hxn) mixtures as eluent ($Et_2O$/Hxn=1:19) to provide 7.3 g (49% yield) of the title compound (22) as a colorless liquid. $^1H$ NMR (400 MHz, $CDCl_3$): δ=1.17-1.20 (m, 6H), 1.79 (d, J=6.0 Hz, 3H), 2.51-2.61 (m, 1H), 6.54 (q, J=6.0 Hz, 1H) ppm. The analytical data was consistent with the proposed structure.

Example 23

1-Chloroethyl Benzoate (23)

Following the general procedure for the synthesis of 1-chloroalkyl carboxylic esters of Description 21, 2.9 mL (3.5 g, 25.0 mmol) of benzoyl chloride (PhCOCl) was reacted with 1.7 mL (1.3 g, 30.0 mmol) of acetaldehyde in 30 mL of anhydrous dichloromethane (DCM) in the presence of 0.1 g (0.75 mmol) of zinc chloride ($ZnCl_2$). The reaction mixture was heated to ca. 50° C. (oilbath) for two to three hours. After work-up and isolation, the material was purified by silica gel column chromatography using ethyl acetate (EtOAc) and hexane (Hxn) mixtures as eluent (EtOAc/Hxn=1:10) to provide 1.2 g (30% yield) of the title compound (23) as a colorless liquid. $^1$H NMR (400 MHz, $CDCl_3$): δ=1.95 (d, J=6.0 Hz, 3H), 6.80 (q, J=5.6 Hz, 1H), 7.45-7.49 (m, 2H), 7.59-7.63 (m, 1H), 8.07-8.09 (m, 2H) ppm. The analytical data was consistent with the proposed structure.

Example 24

1-Chloroethyl Cyclohexanecarboxylate (24)

Following the general procedure for the synthesis of 1-chloroalkyl carboxylic esters of Description 21, 10.0 g (68.2 mmol) of cyclohexanecarbonyl chloride was reacted with 7.65 mL (6.0 g, 136.4 mmol) of acetaldehyde in 300 mL of anhydrous dichloromethane (DCM) in the presence of 0.68 g (5.0 mmol) of zinc chloride ($ZnCl_2$). After work-up and isolation, the material was purified by silica gel column chromatography using methyl tert-butyl ether (MTBE) and n-heptane (Hptn) mixtures as eluent (MTBE/Hptn=1:14→MTBE/Hptn=1:9) to provide 5.6 g (43% yield) of the title compound (24) as a colorless liquid. $R_f$=0.73 (MTBE/Hptn=1:14). $^1$H NMR (400 MHz, $CDCl_3$): δ=1.21-1.31 (br. m, 3H), 1.41-1.51 (br. m, 2H), 1.62-1.66 (br. m, 1H), 1.75-1.78 (br. m, 2H), 1.78 (d, J=6.0 Hz, 3H), 1.88-1.95 (br. m, 2H), 2.27-2.42 (m, 1H), 6.55 (q, J=5.6 Hz, 1H) ppm. The analytical data was consistent with the proposed structure.

Example 25

1-Chloroethyl 2-(Phenylmethoxy)acetate (25)

Following the general procedure for the synthesis of 1-chloroalkyl carboxylic esters of Description 21, 5.0 mL (11.8 g, 63.8 mmol) of 2-phenylmethoxy acetyl chloride was reacted with 3.6 mL (5.6 g, 128.0 mmol) of acetaldehyde in 130 mL of anhydrous dichloromethane (DCM) in the presence of 0.436 g (3.2 mmol) of zinc chloride ($ZnCl_2$). After work-up and isolation, the material was further purified by silica gel column chromatography using ethyl ether ($Et_2O$) and n-heptane (Hptn) mixtures as eluent ($Et_2O$/Hptn=1:9) to provide 2.8 g (39% yield) of the title compound (25) as a colorless liquid. $R_f$=0.25 (EtOAc/Hptn=1:9). $^1$H NMR (400 MHz, $CDCl_3$): δ=1.81 (d, J=5.6 Hz, 3H), 4.15 (s, 2H), 4.66 (s, 2H), 6.62 (q, J=6.0 Hz, 1H), 7.31-7.38 (m, 5H) ppm. The analytical data was consistent with the proposed structure.

Example 26

Chloroethyl 2,2-dimethyl-3-(phenylmethoxy)propanoate (26)

Step A: Methyl 2,2-dimethyl-3-(phenylmethoxy)propanoate (26a)

Adapting procedures or variations thereof according to Eliel et al., *J. Org. Chem.*, 1985, 50(15), 2707-2711; Roth et al., *J. Agri. & Food. Chem.* 1991, 39(3), 612-616; and Rega et al., *Eur. J. Org. Chem.* 2007, 6, 934-942, in an oven dried 500 mL round bottomed flask equipped with a magnetic stir bar and rubber septum, was added under a nitrogen atmosphere, 2.4 g of a 60 mass-% suspension of sodium hydride (NaH) in mineral oil (1.44 g of NaH, 60.0 mmol). The mineral oil was removed by washing with hexanes (Hxn) and the residue was dried under reduced pressure to yield a colorless solid (activated sodium hydride). Seven point nine (7.9) g (60 mmol) of methyl 3-hydroxy-2,2-dimethylpropanoate was added to a suspension of the activated sodium hydride in 200 mL of anhydrous N,N-dimethylformamide (DMF). The suspension was stirred until the hydrogen evolution ceased. Five-point-nine (5.9) mL (8.5 g, 50.0 mmol) of benzyl bromide (BnBr) was added and the mixture was stirred at ca. 60° C. for more than 10 hours. Upon completion and cooling, the reaction mixture was further diluted with one molar (1.0 M) hydrochloric acid (HCl) and methyl tert-butyl ether (MTBE) and the phases were separated. The aqueous phase was extracted two additional times with methyl tert-butyl ether (MTBE) and the combined organic extracts were washed with a saturated aqueous solution of sodium hydrogen carbonate ($NaHCO_3$), water, and brine. The organic solution was dried over anhydrous magnesium sulfate ($MgSO_4$), filtered, and the solvents were removed under reduced pressure using a rotary evaporator. The residue was further purified by silica gel column chromatography using a mixture of n-heptane (Hptn) and ethyl acetate (EtOAc) as eluent (EtOAc/Hptn=1:9) to provide 3.7 g (33% yield) of the title compound (26a) as a yellow oil. $R_f$=0.45 (EtOAc/Hptn=1:9). $^1$H NMR (400 MHz, $CDCl_3$): δ=1.22 (s, 6H), 3.46 (s, 2H), 3.69 (s, 3H), 4.53 (s, 2H), 7.26-7.36 (m, 5H) ppm. The analytical data was consistent with the proposed structure.

Step B: 2,2-Dimethyl-3-(phenylmethoxy)propanoic acid (26b)

Adapting procedures or variations thereof according to Rega et al., *Eur. J. Org. Chem.* 2007, 6, 934-942; Woo et al., *J. Org. Chem.* 2004, 69(25), 8984-8986; and Abiko et al., *Tetrahedron Lett* 1986, 27(38), 4537-40, 3.4 mL of an ten molar (10 M) aqueous solution of sodium hydroxide (NaOH) (34.0 mmol) was added to a solution of 3.7 g (16.9 mmol) of methyl-2,2-dimethyl-3-(phenylmethoxy)propanoate (26a) in a mixture of 15 mL of tetrahydrofuran (THF) and 5 mL of methanol (MeOH). The solution was vigorously stirred overnight at room temperature. Upon completion of the reaction, the reaction mixture was further diluted with one molar (1.0 M) hydrochloric acid (HCl) and ethyl acetate (EtOAc) and the phases were separated. The aqueous phase was extracted two additional times with ethyl acetate (EtOAc) and the combined organic extracts were washed with brine. The organic solution was dried over anhydrous magnesium sulfate ($MgSO_4$), filtered, and the solvents and benzyl alcohol were removed under reduced pressure using a rotary evaporator. The crude material was used in the next step without further purification. Three-point-three (3.3) g (93% yield) of the title compound (26b) was obtained as a colorless solid. $^1$H NMR (400 MHz, $CDCl_3$): δ=1.10 (s, 6H), 3.40 (s, 2H), 4.47 (s, 2H), 7.26-7.35 (m, 5H) ppm. The analytical data was consistent with the proposed structure.

Step C: 2,2-Dimethyl-3-(phenylmethoxy)propanoyl chloride (26c)

Adapting procedures or variations thereof according to Lopez et al., *Bioorg. & Med. Lett.* 2003, 13(11), 1873-1878, a 500 mL round-bottomed flask equipped with a magnetic stirring bar was charged with 5.7 g (27.6 mmol) of 2,2-dimethyl-3-(phenylmethoxy)propanoic acid (26b), 20 mL of anhydrous dichloromethane (DCM), and 3 drops of N,N-dimethylformamide (DMF). Four-point-eight (4.8) mL (7.1 g, 55.2 mmol) of neat oxalyl chloride was slowly added to the solution. The reaction mixture was stirred at ca. 0° C. (ice-bath) for 5 hours. The solvents were removed under reduced pressure to provide the crude title compound (26c), which was used in the next step without further purification. $^1$H NMR (400 MHz, CDCl$_3$): δ=1.34 (s, 6H), 3.54 (s, 2H), 4.56 (s, 2H), 7.29-7.37 (m, 5H) ppm. The analytical data was consistent with the proposed structure.

Step D: 1-Chloroethyl-2,2-dimethyl-3-(phenyl-methoxy)propanoate (26)

Following the general procedure for the synthesis of 1-chloroalkyl carboxylic esters of Description 21, 3.7 g (16.5 mmol) of 2,2-dimethyl-3-(phenylmethoxy)propanoyl chloride (26c) was reacted with 1.4 mL (1.1 g, 25 mmol) of acetaldehyde in 70 mL of anhydrous dichloromethane (DCM) in the presence of 0.25 g (1.8 mmol) of zinc chloride (ZnCl$_2$). After work-up and isolation, the product was further purified by silica gel column chromatography using methyl tert-butyl ether (MTBE) and n-heptane (Hptn) mixtures as eluent (MTBE/Hptn=1:9) to provide 0.21 g (5% yield) of the title compound (26) as a yellow oil. R$_f$=0.24 (MTBE/Hptn=1:9). $^1$H NMR (400 MHz, CDCl$_3$): δ=1.17 (s, 6H), 1.44 (d, J=5.6 Hz, 3H), 3.54 (s, 2H), 4.50 (s, 2H), 6.87 (q, J=5.6 Hz, 1H), 7.26-7.33 (m, 5H) ppm. The analytical data was consistent with the proposed structure.

Description 22

General Procedure for the Preparation of Acyloxyalkyl/Alkoxycarbonyloxyalkyl Carboxylic Esters In a representative synthesis, a three-necked round bottomed flask equipped with a Tallboys 138 over-head mechanical stirrer or a magnetic stir bar was charged with 1.0 mol-eq of an appropriately Functionalized carboxylic acid, i.e., (2R)-4-[(3-chloropropyl)sulfonyloxy]-3,3-dimethyl-2-(phenylmethoxy)butanoic acid (11), (2R)-4-{[3-(acetylamino)propyl]sulfonyloxy}-3,3-dimethyl-2-(phenylmethoxy)butanoic acid (17), or others. The carboxylic acid was dissolved in anhydrous toluene (ca. 0.3-0.5 M). One (1)-3 mol-eq. of an appropriately functionalized 1-haloalkyl carboxylate or 1-haloalkyl carbonate (1-acyloxyalkyalkyl halide or alkoxy-/aryloxycarbonyloxyalkyl halide, i.e., 1-acyloxyethyl chloride or alkoxy-/aryloxycarbonyloxyethyl chloride) and 1-3 mol-eq. of silver carbonate (Ag$_2$CO$_3$) or other silver or mercury salt were added to the stirred solution. The reaction mixture was stirred at ca. 45-50° C. (oil bath) for over 12 hours. The precipitate and residual solids were filtered off using a short plug of Celite® in a Büchner-funnel. The solvents were removed under reduced pressure. The crude material was further purified by silica gel column chromatography using ethyl acetate (EtOAc) and hexane (Hxn) or n-heptane (Hptn) mixtures and/or gradients as eluent to yield the target compound, typically as a colorless, viscous oil.

Example 27

(Methylethoxycarbonyloxy)methyl (2R)-4-{[3-(acetylamino)propyl]sulfonyloxy}-2-hydroxy-3,3-dimethylbutanoate (27)

Step A: (Methylethoxycarbonyloxy)methyl (2R)-4-[(3-chloropropyl)sulfonyloxy]-3,3-dimethyl-2-(phenylmethoxy)butanoate (27a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (0.3 g, 0.79 mmol) dissolved in 5 mL of anhydrous toluene was reacted with 0.58 g (2.4 mmol) of methylethyl (iodomethoxy)formate in the presence of 0.27 g (1.0 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 0.14 g (36% yield) of the title compound (27a) as a colorless oil. R$_f$=0.59 (EtOAc/Hxn=1:2). $^1$H NMR (400 MHz, CDCl$_3$): δ=1.07 (s, 3H), 1.08 (s, 3H), 1.31-1.34 (m, 6H), 2.25-2.32 (m, 2H), 3.32-3.36 (m, 2H), 3.63-3.65 (m, 2H), 3.90 (s, 1H), 3.96 (d, J=9.2 Hz, 1H), 4.21 (d, J=9.6 Hz, 1H), 4.37 (d, J=11.2 Hz, 1H), 4.64 (d, J=11.2 Hz, 1H), 4.89-4.95 (m, 1H), 5.78 (d, J=5.6 Hz, 1H), 5.87 (d, J=5.6 Hz, 1H), 7.30-7.37 (m, 5H) ppm. MS (ESI) m/z 495.02 (M+H)$^+$, 516.98 (M+Na)$^+$. The analytical data was consistent with the proposed structure.

Step B: (Methylethoxycarbonyloxy)methyl (2R)-4-[(3-azidopropyl)sulfonyloxy]-3,3-dimethyl-2-(phenylmethoxy)butanoate (27b)

Following the general procedure for the preparation of azides of Description 16, (methylethoxycarbonyloxy)methyl (2R)-4-[(3-chloropropyl)sulfonyloxy]-3,3-dimethyl-2-(phenylmethoxy)butanoate (27a) (0.14 g, 0.28 mmol) dissolved in 3 mL of anhydrous dimethyl sulfoxide (DMSO) was reacted with 45 mg (0.7 mmol) of sodium azide (NaN$_3$). After work-up, the crude title compound (27) was used in the next step without further purification. MS (ESI) m/z 524.06 (M+Na)$^+$.

Step C: (Methylethoxycarbonyloxy)methyl (2R)-4-{[(3-acetylamino)propyl]sulfonyloxy}-3,3-dimethyl-2-(phenylmethoxy)butanoate (27c)

Following the general procedure for the reduction of azides by hydrogenation of Description 17, a mixture of (methylethoxycarbonyloxy)methyl (2R)-4-[(3-azidopropyl)sulfonyloxy]-3,3-dimethyl-2-(phenylmethoxy)butanoate (27b) (0.14 g, 0.28 mmol), 0.2 mL of acetic anhydride (Ac$_2$O) and 50 mg of 10 wt-% palladium on activated carbon in a mixture of methanol (MeOH) and ethyl acetate (EtOAc) was stirred overnight under a hydrogen atmosphere. After work-up, the crude material was purified by silica gel column chromatography using a mixture of ethyl acetate (EtOAc) and methanol (MeOH) (EtOAc/MeOH=9:1) as eluent to provide 16 mg (15% yield) of the title compound (27c) as a colorless oil. R$_f$=0.65 (EtOAc/MeOH=19:1). $^1$H NMR (400 MHz, CDCl$_3$): δ=1.07 (s, 6H), 1.31-1.34 (m, 6H), 1.98 (s, 3H), 2.01-2.05 (m, 2H), 3.09-3.13 (m, 2H), 3.33-3.39 (m, 2H), 3.89 (s, 1H), 3.95 (d, J=9.2 Hz, 1H), 4.17 (d, J=9.2 Hz, 1H), 4.37 (d, J=11.2 Hz, 1H), 4.63 (d, J=11.2 Hz, 1H), 4.92 (sept., J=6.4 Hz, 1H), 5.77 (d, J=5.6 Hz, 1H), 5.81-5.83 (br. m, 1H), 5.87 (d, J=5.2 Hz, 1H), 7.32-7.35 (m, 5H) ppm. MS (ESI) m/z 518.10 (M+H)$^+$, 540.09 (M+Na)$^+$. The analytical data was consistent with the proposed structure.

Step D: (Methylethoxycarbonyloxy)methyl (2R)-4-{[3-(acetylamino)propyl]sulfonyloxy}-2-hydroxy-3,3-dimethylbutanoate (27)

Following the general procedure of hydrogenolysis of benzyl ethers of Description 18, a mixture of (methylethoxycarbonyloxy)methyl (2R)-4-{[3-(acetylamino)propyl]sulfonyloxy}-3,3-dimethyl-2-(phenylmethoxy)butanoate (27c) (16 mg, 0.03 mmol) and 20 mg of 10 wt.-% palladium on activated carbon in 2 mL of ethanol (EtOH) was stirred overnight under a hydrogen atmosphere. After purification by mass-guided preparative HPLC, 11 mg (83% yield) of the title compound (27) was obtained as a colorless, viscous oil. $^1$H NMR (400 MHz, CDCl$_3$): δ=1.01 (s, 3H), 1.13 (s, 3H), 1.33-1.35 (m, 6H), 2.00 (s, 3H), 2.07-2.11 (m, 2H), 3.13-3.26 (m, 2H), 3.35-3.45 (m, 2H), 3.97 (d, J=9.2 Hz, 1H), 4.12 (s, 1H), 4.16 (d, J=9.6 Hz, 1H), 4.94 (sept., J=6.4 Hz, 1H), 5.79 (d, J=5.6 Hz, 1H), 5.81-5.89 (br. m, 1H), 5.91 (d, J=5.6 Hz, 1H), ppm. MS (ESI) m/z: 428.04 (M+H)$^+$, 450.02 (M+Na)$^+$. The analytical data was consistent with the proposed structure.

Example 28

(2-Phenylacetyloxy)methyl (2R)-4-{[3-(acetylamino)propyl]sulfonyloxy}-2-hydroxy-3,3-dimethylbutanoate (28)

Step A: (2-Phenylacetyloxy)methyl (2R)-4-[(3-chloropropyl)sulfonyloxy]-3,3-dimethyl-2-(phenylmethoxy)butanoate (28a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (0.5 g, 1.3 mmol) dissolved in 10 mL of anhydrous toluene was reacted with 1.1 g (4.0 mmol) of chloromethyl 2-phenylacetate in the presence of 0.44 g (1.6 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 0.44 g (64% yield) of the title compound (28a) as a colorless oil. R$_f$=0.47 (EtOAc/Hxn=1:2). $^1$H NMR (400 MHz, CDCl$_3$): δ=0.97 (s, 3H), 0.99 (s, 3H), 2.24-2.30 (m, 2H), 3.20-3.24 (m, 2H), 3.62-3.65 (m, 2H), 3.68 (s, 2H), 3.84 (s, 1H), 3.91 (d, J=9.2 Hz, 1H), 4.15 (d, J=9.6 Hz, 1H), 4.28 (d, J=10.8 Hz, 1H), 4.53 (d, J=11.2 Hz, 1H), 5.78 (d, J=5.6 Hz, 1H), 5.87 (d, J=5.6 Hz, 1H), 7.25-7.38 (m, 10H) ppm. MS (ESI) m/z 548.99 (M+Na)$^+$. The analytical data was consistent with the proposed structure.

Step B: (2-Phenylacetyloxy)methyl (2R)-4-[(3-azidopropyl)sulfonyloxy]-3,3-dimethyl-2-(phenylmethoxy)butanoate (28b)

Following the general procedure for the preparation of azides of Description 16, (2-phenylacetyloxy)methyl (2R)-4-[(3-chloropropyl)sulfonyloxy]-3,3-dimethyl-2-(phenylmethoxy)butanoate (28a) (0.44 g, 0.84 mmol) dissolved in 5 mL of anhydrous dimethyl sulfoxide (DMSO) was reacted with 140 mg (2.1 mmol) of sodium azide (NaN$_3$). After work-up, the crude title compound (28b) was used in the next step without further purification. MS (ESI) m/z 556.12 (M+Na)$^+$.

Step C: (2-Phenylacetyloxy)methyl (2R)-4-{[(3-acetylamino)propyl]sulfonyloxy}-3,3-dimethyl-2-(phenylmethoxy)butanoate (28c)

Following the general procedure for the reduction of azides by hydrogenation of Description 17, a mixture of (2-phenylacetyloxy)methyl (2R)-4-[(3-azidopropyl)sulfonyloxy]-3,3-dimethyl-2-(phenylmethoxy)butanoate (28b) (0.44 g, 0.84 mmol), 0.2 mL (0.21 g, 2.1 mmol) of acetic anhydride (Ac$_2$O), and 100 mg of 10 wt-% palladium on activated carbon in 5 mL of a mixture of methanol (MeOH) and ethyl acetate (EtOAc) was stirred overnight under a hydrogen atmosphere. After work-up, the crude material was purified by silica gel column chromatography using a mixture of ethyl acetate (EtOAc) and methanol (MeOH) (EtOAc/MeOH=9:1) as eluent to provide 60 mg (13% yield) of the title compound (28c) as a colorless oil. $^1$H NMR (400 MHz, CDCl$_3$): δ=0.96 (s, 3H), 0.99 (s, 3H), 1.93 (s, 3H), 1.95-2.01 (m, 2H), 3.05-3.08 (m, 2H), 3.28-3.33 (m, 2H), 3.68 (s, 2H), 3.82 (s, 1H), 3.88 (d, J=9.2 Hz, 1H), 4.10 (d, J=9.2 Hz, 1H), 4.29 (d, J=11.2 Hz, 1H), 4.53 (d, J=11.6 Hz, 1H), 5.77 (d, J=5.6 Hz, 1H), 5.87 (d, J=5.2 Hz, 1H), 6.07 (br. m, 1H), 7.22-7.34 (m, 10H) ppm. MS (ESI) m/z 550.14 (M+H)$^+$, 572.14 (M+Na)$^+$. The analytical data was consistent with the proposed structure.

Step D: (2-Phenylacetyloxy)methyl (2R)-4-{[3-(acetylamino)propyl]sulfonyloxy}-2-hydroxy-3,3-dimethylbutanoate (28)

Following the general procedure of hydrogenolysis of benzyl ethers of Description 18, a mixture of (2-phenylacetyloxy)methyl (2R)-4-{[3-(acetylamino)propyl]sulfonyloxy}-3,3-dimethyl-2-(phenylmethoxy)butanoate (28c) (60 mg, 0.11 mmol) and 60 mg of 10 wt.-% of palladium on activated carbon in 2 mL of ethanol (EtOH) was stirred overnight under a hydrogen atmosphere. After purification by mass-guided preparative HPLC, 10 mg (20% yield) of the title compound (28) was obtained as a colorless, viscous oil. $^1$H NMR (400 MHz, CDCl$_3$): δ=0.91 (s, 3H), 1.00 (s, 3H), 1.98 (s, 3H), 2.03-2.10 (m, 2H), 3.10-3.23 (m, 2H), 3.26 (br., 1H), 3.32-3.45 (m, 2H), 3.70 (s, 2H), 3.90 (d, J=9.6 Hz, 1H), 4.07 (s, 1H), 4.10 (d, J=9.2 Hz, 1H), 5.79 (d, J=5.6 Hz, 1H), 5.85 (br. m, 1H), 5.93 (d, J=5.6 Hz, 1H) 7.26-7.35 (m, 5H) ppm. MS (ESI) m/z: 460.05 (M+H)$^+$, 481.99 (M+Na)$^+$. The analytical data was consistent with the proposed structure.

Example 29

(2-Methylpropanoyloxy)ethyl (2R)-4-{[3-(acetylamino)propyl]sulfonyloxy}-2-hydroxy-3,3-dimethylbutanoate (29)

Step A: (2-Methylpropanoyloxy)ethyl (2R)-4-[(3-chloropropyl)sulfonyloxy]-3,3-dimethyl-2-(phenylmethoxy)butanoate (29a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (13.0 g, 34.3 mmol) dissolved in 300 mL of anhydrous toluene was reacted with 15.4 g (103 mmol) of 1-chloroethyl 2-methylpropanoate (22) in the presence of 23 g (86 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 11 g (65% yield) of the title compound (29a) as a colorless oil. R$_f$=0.63 (EtOAc/Hxn=1:2). $^1$H NMR (400 MHz, CDCl$_3$, both diastereomers): δ=1.06-1.23 (m, 12H), 1.53 (d, J=5.6 Hz, 3H), 2.24-2.32 (m, 2H), 2.51-2.65 (m, 1H), 3.21-3.26 (m, 2H), 3.63-3.66 (m, 2H), 3.83-3.85 (2s, 1H), 3.96 (d, J=9.6 Hz, 1H), 4.20-4.24 (2d, J=8.8, 9.2 Hz, 1H), 4.33-4.37 (2d, J=11.2, 11.6 Hz, 1H), 4.60-4.66 (2d, J=11.6, 11.6 Hz, 1H), 6.91-6.95 (m, 1H), 7.30-7.37 (m, 5H) ppm. MS (ESI) m/z 514.90 (M+Na)$^+$.

Step B: (2-Methylpropanoyloxy)ethyl (2R)-4-[(3-azidopropyl)sulfonyloxy]-3,3-dimethyl-2-(phenylmethoxy)butanoate (29b)

Following the general procedure for the preparation of azides of Description 16, (2-methylpropanoyloxy)ethyl (2R)-4-[(3-chloropropyl)sulfonyloxy]-3,3-dimethyl-2-(phenylmethoxy)butanoate (29a) (11 g, 22 mmol) dissolved in 120 mL of anhydrous dimethyl sulfoxide (DMSO) was reacted with 3.9 g (60 mmol) of sodium azide (NaN$_3$). After work-up, the crude material (29b) was used in the next step without further purification. MS (ESI) m/z 522.08 (M+Na)$^+$.

Step C: (2-Methylpropanoyloxy)ethyl (2R)-4-{[(3-acetylamino)propyl]sulfonyloxy}-3,3-dimethyl-2-(phenylmethoxy)butanoate (29c)

Following the general procedure for the reduction of azides by hydrogenation of Description 17, a mixture of (2-methylpropanoyloxy)ethyl (2R)-4-[(3-azidopropyl)sulfonyloxy]-3,3-dimethyl-2-(phenylmethoxy)butanoate (29b) (11.0 g, 22 mmol), 6.0 mL of acetic anhydride (Ac$_2$O), and 1.5 g of 10 wt-% palladium on activated carbon in 100 mL of a mixture of methanol (MeOH) and ethyl acetate (EtOAc) was stirred overnight under a hydrogen atmosphere. After work-up, the crude material was purified by silica gel column chromatography using a mixture of ethyl acetate (EtOAc) and methanol (MeOH) (EtOAc/MeOH=19:1) as eluent to provide 8.0 g (70% yield) of the title compound (29c) as a colorless oil. R$_f$=0.48 (EtOAc). $^1$H NMR (400 MHz, CDCl$_3$, both diastereomers): δ=0.98-1.14 (m, 12H), 1.46 (d, J=5.6 Hz, 3H), 1.90 (s, 3H), 1.92-1.98 (m, 2H), 2.44-2.55 (m, 1H), 3.01-3.06 (m, 2H), 3.25-3.30 (m, 2H), 3.74-3.76 (2s, 1H), 3.86-3.88 (2d, J=9.2, 9.2 Hz, 1H), 4.08-4.13 (2d, J=9.6, 8.8 Hz, 1H), 4.26-4.30 (2d, J=11.2, 11.6 Hz, 1H), 4.51-4.57 (2d, J=11.6, 11.6 Hz, 1H), 6.06-6.12 (br. m, 1H), 6.84-6.87 (m, 1H), 7.20-7.30 (m, 5H) ppm. MS (ESI) m/z 516.13 (M+H)$^+$, 538.14 (M+Na)$^+$.

Step D: (2-Methylpropanoyloxy)ethyl (2R)-4-{[3-(acetylamino)propyl]sulfonyloxy}-2-hydroxy-3,3-dimethylbutanoate (29)

Following the general procedure of hydrogenolysis of benzyl ethers of Description 18, a mixture of (2-methylpropanoyloxy)ethyl (2R)-4-{[3-(acetylamino)propyl]sulfonyloxy}-3,3-dimethyl-2-(phenylmethoxy)butanoate (29c) (4.0 g, 9.4 mmol), 1.0 g of 10 wt.-% of palladium on activated carbon in 20 mL of methanol (MeOH) and 0.15 mL of one molar (1.0 M) hydrochloric acid (HCl) was stirred overnight under a hydrogen atmosphere. Upon completion of reaction and following aqueous work-up, 3.4 g (85% yield) of the title compound (29) was obtained as a colorless, viscous oil. R$_T$=13.59 min and 18.45 min (by LC/UV). $^1$H NMR (400 MHz, CDCl$_3$, both diastereomers): δ=0.95-0.99 (2s, 3H), 1.12-1.14 (2s, 3H), 1.17-1.20 (m, 6H), 1.55-1.57 (2d, J=5.6, 5.6 Hz, 3H), 1.99-2.00 (2s, 3H), 2.04-2.12 (m, 2H), 2.53-2.62 (m, 1H), 3.13-3.23 (m, 2H), 3.26-3.29 (br. m, 1H), 3.34-3.45 (m, 2H), 3.91-3.97 (2d, J=9.6, 9.2 Hz, 1H), 4.03-4.06 (m, 1H), 4.14-4.19 (2d, J=9.2, 9.2 Hz, 1H), 5.96-6.01 (br. m, 1H), 6.91-6.97 (m, 1H) ppm. MS (ESI) m/z: 426.04 (M+H)$^+$, 447.99 (M+Na)$^+$. The analytical data was consistent with the proposed structure.

Example 30

(1S)-(2-Methylpropanoyloxy)ethyl (2R)-4-{[3-(acetylamino)propyl]sulfonyloxy}-2-hydroxy-3,3-dimethylbutanoate (30) and (1S)-1-[(methylethyl)oxycarbonyl]ethyl (2R)-4-{[3-(acetylamino)propyl]sulfonyloxy}-2-hydroxy-3,3-dimethylbutanoate (30R)

Step A: (1S)-1,3-Dimethyl-2-oxobutyl (2R)-4-[(3-chloropropyl)sulfonyloxy]-3,3-dimethyl-2-(1,1,2,2-tetramethyl-1-silapropoxy)butanoate (30a)

Following the general procedure for the preparation of carboxylic esters from carboxylic acids of Description 15, (2R)-4-[(3-chloropropyl)sulfonyloxy]-3,3-dimethyl-2-(1,1,2,2-tetramethyl-1-silapropoxy)butanoic acid (15) (2.0 g, 5.0 mmol) dissolved in 25 mL of anhydrous dichloromethane (DCM) was reacted with 0.90 mL (1.31 g, 10 mmol) of oxalyl chloride. Upon completion of the reaction, a solution of 2 mL (1.2 g, 10.0 mmol) of (2S)-2-hydroxy-4-methylpentan-3-one (synthesized following procedures according to Gallop et al., U.S. Pat. No. 6,927,036) and 0.85 mL of pyridine (0.79 g, 10.0 mmol) in 20 mL of anhydrous dichloromethane (DCM) was added to the acid chloride. After work-up, the crude material was purified by silica gel column chromatography using a mixture of ethyl acetate (EtOAc) and hexane (Hxn) (EtOAc/Hxn=1:9) as eluent to provide 0.9 g (36% yield) of the title compound (30a) as a colorless oil. R$_f$=0.39 (EtOAc/Hxn=1:4). $^1$H NMR (400 MHz, CDCl$_3$): δ=0.05 (s, 3H), 0.10 (s, 3H), 0.94 (s, 9H), 1.09 (s, 6H), 1.12 (d, J=7.2 Hz, 3H), 1.19 (d, J=7.2 Hz, 3H), 1.46 (d, J=7.2 Hz, 3H), 2.32-2.39 (m, 2H), 2.83 (sept., J=7.2 Hz, 1H), 3.31-3.35 (m, 2H), 3.69-3.72 (m, 2H), 4.10-4.13 (m, 3H), 5.24 (q, J=7.2 Hz, 1H) ppm. MS (ESI) m/z 501.09 (M+H)$^+$, 523.03 (M+Na)$^+$. The analytical data was consistent with the proposed structure.

Step B: (1S)-(2-Methylpropanoyloxy)ethyl (2R)-4-[(3-chloropropyl)sulfonyloxy]-3,3-dimethyl-2-(1,1,2,2-tetramethyl-1-silapropoxy)butanoate (30b) and (1S)-1-[(methylethyl)oxycarbonyl]ethyl (2R)-4-[(3-chloropropyl)sulfonyloxy]-3,3-dimethyl-2-(1,1,2,2-tetramethyl-1-silapropoxy)butanoate (30B)

Adapting procedures or variations thereof according to Gallop et al., U.S. Pat. No. 6,927,036), at ca. 0° C. (ice-bath), urea hydrogen peroxide (3.2 g, 34 mmol) and trifluoroacetic anhydride (2.43 mL, 3.6 g, 17.2 mmol) were added to a solution of (1S)-1,3-dimethyl-2-oxobutyl (2R)-4-[(3-chloropropyl)sulfonyloxy]-3,3-dimethyl-2-(1,1,2,2-tetramethyl-1-silapropoxy)butanoate (30a) (0.86 g, 1.7 mmol) in 30 mL dichloromethane (DCM). The mixture was stirred for over 20 hours. The reaction mixture was diluted with water and diethyl ether (Et$_2$O) and the phases were separated. The aqueous phase was extracted two additional times with diethyl ether (Et$_2$O) and the combined organic extracts were washed with a saturated aqueous solution of sodium hydrogen carbonate (NaHCO$_3$), water, and brine. The organic solution was dried over anhydrous magnesium sulfate (MgSO$_4$), filtered, and the solvents were removed under reduced pressure using a rotary evaporator. The crude material was further purified by mass-guided preparative HPLC to give 0.12 g of a mixture of the title compound (30b) and the regioisomer (30B). MS (ESI) m/z 538.99 (M+Na)$^+$.

Step C: (1S)-(2-Methylpropanoyloxy)ethyl (2R)-4-[(3-azidopropyl)sulfonyloxy]-3,3-dimethyl-2-(1,1,2,2-tetramethyl-1-silapropoxy)butanoate (30c) and (1S)-1-[(methylethyl)oxycarbonyl]ethyl (2R)-4-[(3-azidopropyl)sulfonyloxy]-3,3-dimethyl-2-(1,1,2,2-tetramethyl-1-silapropoxy)butanoate (30C)

Following the general procedure for the preparation of azides of Description 16, a mixture of (1S)-(2-methylpropanoyloxy)ethyl (2R)-4-[(3-chloropropyl)sulfonyloxy]-3,3-dimethyl-2-(1,1,2,2-tetramethyl-1-silapropoxy)butanoate (30b) and (1S)-1-[(methylethyl)oxycarbonyl]ethyl (2R)-4-[(3-chloropropyl)sulfonyloxy]-3,3-dimethyl-2-(1,1,2,2-tetramethyl-1-silapropoxy)butanoate (30B) (0.12 g) dissolved in 3 mL of anhydrous dimethyl sulfoxide (DMSO) was reacted with 30 mg (0.46 mmol) of sodium azide ($NaN_3$). After work-up, the mixture of the crude title compounds, 30c and 30C, was obtained and used in the next step without further purification or isolation. MS (ESI) m/z 524.12 $(M+H)^+$, 546.13 $(M+Na)^+$.

Step D: (1S)-(2-Methylpropanoyloxy)ethyl (2R)-4-{[(3-acetylamino)propyl]sulfonyloxy}-3,3-dimethyl-2-(1,1,2,2-tetramethyl-1-silapropoxy)butanoate (30d) and (1S)-1-[(methylethyl)oxycarbonyl]ethyl (2R)-4-{[(3-acetylamino)propyl]sulfonyloxy}-3,3-dimethyl-2-(1,1,2,2-tetramethyl-1-silapropoxy)butanoate (30D)

Following the general procedure for the reduction of azides by hydrogenation of Description 17, a mixture of (1S)-(2-methylpropanoyloxy)ethyl (2R)-4-[(3-azidopropyl)sulfonyloxy]-3,3-dimethyl-2-(1,1,2,2-tetramethyl-1-silapropoxy)butanoate (30c) and (1S)-1-[(methylethyl)oxycarbonyl]ethyl (2R)-4-[(3-azidopropyl)sulfonyloxy]-3,3-dimethyl-2-(1,1,2,2-tetramethyl-1-silapropoxy)butanoate (30C) (0.12 g max.), 0.15 mL (162 mg, 1.59 mmol) of acetic anhydride ($Ac_2O$), and 70 mg of 10 wt-% palladium on activated carbon in 5 mL of a mixture of methanol (MeOH) and ethyl acetate (EtOAc) was stirred overnight under a hydrogen atmosphere. After work-up, the mixture of the crude title compounds, 30d and 30D, was obtained and used in the next step without further purification or isolation. MS (ESI) m/z 540.18 $(M+H)^+$, 562.19 $(M+Na)^+$.

Step E: (1S)-(2-Methylpropanoyloxy)ethyl (2R)-4-{[3-(acetylamino)propyl]sulfonyloxy}-2-hydroxy-3,3-dimethylbutanoate (30) and (1S)-1-[(methylethyl)oxycarbonyl]ethyl (2R)-4-{[3-(acetylamino)propyl]sulfonyloxy}-2-hydroxy-3,3-dimethylbutanoate (30R)

Following the general procedure for the cleavage of silyl ethers with triethylamine trihydrofluoride of Description 20, a mixture of (1S)-(2-methylpropanoyloxy)ethyl (2R)-4-{[(3-acetylamino)propyl]sulfonyloxy}-3,3-dimethyl-2-(1,1,2,2-tetramethyl-1-silapropoxy)butanoate (30d) (0.12 g max.) and triethylamine trihydrofluoride ($Et_3N.3HF$) (180 mg, 1.1 mmol) in 3 mL tetrahydrofuran (THF) was stirred overnight at ca. 50-60° C. After work-up and further purification by mass-guided preparative HPLC, 4 mg of the title compound (30) was obtained as colorless oil after lyophilization of the solvents. $R_T$=18.45 min (by LC/UV). $^1$H NMR (400 MHz, $CDCl_3$): δ=1.00 (s, 3H), 1.14 (s, 3H), 1.19 (d, J=7.2 Hz, 6H), 1.56 (d, J=5.6 Hz, 3H), 2.02 (s, 3H), 2.05-2.12 (m, 2H), 2.58 (sept., J=6.8 Hz, 1H), 3.12-3.25 (m, 2H), 3.33-3.48 (m, 2H), 3.96 (d, J=8.8 Hz, 1H), 4.05 (s, 1H), 4.15 (d, J=9.2 Hz, 1H), 5.98-6.03 (br. m, 1H), 6.94 (q, J=5.6 Hz, 1H) ppm. MS (ESI) m/z: 426.03 $(M+H)^+$, 447.99 $(M+Na)^+$. The analytical data was consistent with the proposed structure.

After purification by mass-guided preparative HPLC, 40 mg of the title compound (30R) was also obtained as colorless oil after lyophilization of the solvents. $R_T$=32.19 min (by LC/UV). $^1$H NMR (400 MHz, $CDCl_3$): δ=1.03 (s, 3H), 1.15 (s, 3H), 1.26 (d, J=6.0 Hz, 3H), 1.29 (d, J=6.4 Hz, 3H), 1.55 (d, J=7.2 Hz, 3H), 2.00 (s, 3H), 2.05-2.12 (m, 2H), 3.13-3.25 (m, 2H), 3.32-3.45 (m, 2H), 3.98 (d, J=9.6 Hz, 1H), 4.16 (s, 1H), 4.19 (d, J=9.2 Hz, 1H), 5.03-5.15 (m, 2H), 5.88-6.00 (br. m, 1H) ppm. MS (ESI) m/z: 426.10 $(M+H)^+$, 448.06 $(M+Na)^+$. The analytical data was consistent with the proposed structure.

Example 31

(1R)-(2-Methylpropanoyloxy)ethyl (2R)-4-{[3-(acetylamino)propyl]sulfonyloxy}-2-hydroxy-3,3-dimethylbutanoate (31)

(1R)-(2-Methylpropanoyloxy)ethyl (2R)-4-{[3-(acetylamino)propyl]sulfonyloxy}-2-hydroxy-3,3-dimethylbutanoate was isolated from a mixture of diastereomers of Example 29 by preparative HPLC with a chiral column (Chiralpak IA). The title compound (31) was obtained as a colorless, viscous oil. $R_T$=13.59 min (by LC/UV). D.e. >98% (by $^1$H NMR spectroscopy, 400 MHz, $CDCl_3$ and analytical LC/UV). $^1$H NMR (400 MHz, $CDCl_3$): δ=0.92 (s, 3H), 1.08 (s, 3H), 1.15 (d, J=7.2 Hz, 6H), 1.52 (d, J=5.6 Hz, 3H), 1.96 (s, 3H), 2.01-2.08 (m, 2H), 2.54 (sept., J=6.8 Hz, 1H), 3.12-3.22 (m, 2H), 3.28-3.42 (m, 2H), 3.88 (d, J=9.2 Hz, 1H), 4.03 (s, 1H), 4.16 (d, J=9.2 Hz, 1H), 6.37-6.39 (br. m, 1H), 6.91 (q, J=5.6 Hz, 1H) ppm. MS (ESI) m/z: 426.03 $(M+H)^+$, 447.99 $(M+Na)^+$. The analytical data was consistent with the proposed structure.

Isomer (1S)-(2-methylpropanoyloxy)ethyl (2R)-4-{[3-(acetylamino)propyl]sulfonyloxy}-2-hydroxy-3,3-dimethylbutanoate (30) was also was isolated from a mixture of diastereomers of Example 29 by preparative HPLC with a chiral column (Chiralpak IA). $R_T$=18.45 min (by LC/UV). D.e. >98% (by $^1$H NMR spectroscopy, 400 MHz, $CDCl_3$ and analytical LC/UV).

Example 32

(Ethoxycarbonyloxy)ethyl (2R)-4-{[3-(acetylamino)propyl]sulfonyloxy}-2-hydroxy-3,3-dimethylbutanoate (32)

Step A: (Ethoxycarbonyloxy)ethyl (2R)-4-[(3-chloropropyl)sulfonyloxy]-3,3-dimethyl-2-(phenylmethoxy)butanoate (32a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (11.0 g, 29.0 mmol) dissolved in 150 mL of anhydrous toluene was reacted with 13.3 g (87.0 mmol) of commercially available 1-chloroethyl ethoxyformate in the presence of 20.0 g (72.0 mmol) of silver carbonate ($Ag_2CO_3$). After work-up, the crude material was purified by silica gel column chromatography using a mixture of ethyl acetate (EtOAc) and hexane (Hxn) (EtOAc/Hxn=1:2) as eluent to provide 11.0 g of a mixture of the title compound (32a) and (3R)-4,4-dimethyl- 3-(phenylmethoxy)-3,4,5-trihydrofuran-2-one (1a). $R_f$=0.41 (EtOAc/Hxn=1:2). MS (ESI) m/z 517.01 (M+Na)$^+$.

Step B: (Ethoxycarbonyloxy)ethyl (2R)-4-[(3-azidopropyl)sulfonyloxy]-3,3-dimethyl-2-(phenylmethoxy)butanoate (32b)

Following the general procedure for the preparation of azides of Description 16, 11.0 g of a mixture of (ethoxycarbonyloxy)ethyl (2R)-4-[(3-chloropropyl)sulfonyloxy]-3,3-dimethyl-2-(phenylmethoxy)butanoate (32a) and (3R)-4,4-dimethyl-3-(phenylmethoxy)-3,4,5-trihydrofuran-2-one (1) dissolved in 100 mL of anhydrous dimethyl sulfoxide (DMSO) was reacted with 2.4 g (37 mmol) of sodium azide (NaN$_3$). After work-up, the crude title compound (32b) was obtained and used in the next step without further purification. MS (ESI) m/z 524.07 (M+Na)$^+$.

Step C: (Ethoxycarbonyloxy)ethyl (2R)-4-{[(3-acetylamino)propyl]sulfonyloxy}-3,3-dimethyl-2-(phenylmethoxy)butanoate (32c)

Following the general procedure for the reduction of azides by hydrogenation of Description 17, a mixture of (ethoxycarbonyloxy)ethyl (2R)-4-[(3-azidopropyl)sulfonyloxy]-3,3-dimethyl-2-(phenylmethoxy)butanoate (32b) (11.0 g max.), 4.5 mL of acetic anhydride (Ac$_2$O), and 0.3 g of 10 wt-% palladium on activated carbon in 100 mL of a mixture of methanol (MeOH) and ethyl acetate (EtOAc) was stirred overnight under a hydrogen atmosphere. After work-up, the crude material was purified by silica gel column chromatography using ethyl acetate (EtOAc) as eluent to provide 5.8 g (39% yield over three steps) of the title compound (32c) as a colorless oil. $R_f$=0.33 (EtOAc). $^1$H NMR (400 MHz, CDCl$_3$, both diastereomers): δ=1.07 (m, 6H), 1.26-1.31 (m, 3H), 1.57 (d, J=5.6 Hz, 3H), 1.99 (s, 3H), 1.99-2.06 (m, 2H), 3.08-3.13 (m, 2H), 3.34-3.39 (m, 2H), 3.83-3.85 (2s, 1H), 3.94-3.97 (2d, J=9.2, 9.6 Hz, 1H), 4.10-4.22 (m, 3H), 4.34-4.39 (2d, J=11.2, 11.2 Hz, 1H), 4.61-4.66 (m, 1H), 5.73-5.79 (br. m, 1H), 6.81-6.86 (m, 1H), 7.31-7.35 (m, 5H) ppm. MS (ESI) m/z 518.15 (M+H)$^+$, 540.11 (M+Na)$^+$. The analytical data was consistent with the proposed structure.

Step D: (Ethoxycarbonyloxy)ethyl (2R)-4-{[3-(acetylamino)propyl]sulfonyloxy}-2-hydroxy-3,3-dimethylbutanoate (32)

Following the general procedure of hydrogenolysis of benzyl ethers of Description 18, a mixture of (ethoxycarbonyloxy)ethyl (2R)-4-{[3-(acetylamino)propyl]sulfonyloxy}-3,3-dimethyl-2-(phenylmethoxy)butanoate (32c) (5.2 g, 10 mmol), 1.3 g of 10 wt.-% of palladium on activated carbon in 20 mL of methanol (MeOH), and 1.0 mL (1.05 g, 17.5 mmol) of glacial acetic acid was stirred overnight under a hydrogen atmosphere. Upon the completion of reaction and following aqueous work-up, 3.6 g (84% yield) of the title compound (32) was obtained as a colorless, viscous oil. $R_T$=21.95 min and 30.99 min (by LC/UV). $^1$H NMR (400 MHz, CDCl$_3$, both diastereomers): δ=0.99-1.01 (2s, 3H), 1.13-1.15 (2s, 3H), 1.32-1.37 (m, 3H), 1.59-1.62 (m, 3H), 2.00-2.01 (2s, 3H), 2.04-2.12 (m, 2H), 3.12-3.26 (m, 3H), 3.33-3.47 (m, 2H), 3.94-3.98 (m, 1H), 4.06-4.08 (2d, J=6.8, 6.0 Hz, 1H), 4.14-4.19 (2d, J=8.8, 8.8 Hz, 1H), 4.23-4.28 (m, 2H), 5.85-5.88 (br. m, 1H), 6.85 (m, 1H) ppm. MS (ESI) m/z: 428.14 (M+H)$^+$, 450.14 (M+Na)$^+$. The analytical data was consistent with the proposed structure.

Example 33

(Ethoxycarbonyloxy)ethyl (2R)-4-{[3-(acetylamino) propyl]sulfonyloxy}-2-hydroxy-3,3-dimethylbutanoate (33)

A single isomer of (ethoxycarbonyloxy)ethyl (2R)-4-{[3-(acetylamino)propyl]sulfonyloxy}-2-hydroxy-3,3-dimethylbutanoate was isolated from a mixture of diastereomers of Example 32 by preparative HPLC with a chiral column (Chiralpak IA). The title compound (33) was obtained as colorless, viscous oil. $R_T$=21.95 min (by LC/UV). D.e. >98% (by $^1$H NMR spectroscopy, 400 MHz, CDCl$_3$ and analytical LC/UV). $^1$H NMR (400 MHz, CDCl$_3$): δ=0.99 (s, 3H), 1.13 (s, 3H), 1.34 (t, J=7.6 Hz, 3H), 1.59 (d, J=5.2 Hz, 3H), 2.01 (s, 3H), 2.06-2.13 (m, 2H), 3.14-3.27 (m, 2H), 3.35-3.48 (m, 2H), 3.95 (d, J=9.6 Hz, 1H), 4.07 (s, 1H), 4.19 (d, J=9.2 Hz, 1H), 4.25 (q, J=7.2 Hz, 2H), 5.86-5.98 (br. m, 1H), 6.85 (q, J=5.6 Hz, 1H) ppm. MS (ESI) m/z: 428.14 (M+H)$^+$, 450.14 (M+Na)$^+$. The analytical data was consistent with the proposed structure.

Example 34

(Ethoxycarbonyloxy)ethyl (2R)-4-{[3-(acetylamino) propyl]sulfonyloxy}-2-hydroxy-3,3-dimethylbutanoate (34)

A single isomer of (ethoxycarbonyloxy)ethyl (2R)-4-{[3-(acetylamino)propyl]sulfonyloxy}-2-hydroxy-3,3-dimethylbutanoate was isolated from a mixture of diastereomers of Example 32 by preparative HPLC with a chiral column (Chiralpak IA). The title compound (34) was obtained as a colorless, viscous oil. $R_T$=30.99 min (by LC/UV). D.e. >98% (by $^1$H NMR spectroscopy, 400 MHz, CDCl$_3$ and analytical LC/UV). $^1$H NMR (400 MHz, CDCl$_3$): δ=1.01 (s, 3H), 1.14 (s, 3H), 1.35 (t, J=7.6 Hz, 3H), 1.60 (d, J=5.6 Hz, 3H), 2.01 (s, 3H), 2.05-2.12 (m, 2H), 3.12-3.25 (m, 2H), 3.33-3.46 (m, 2H), 3.97 (d, J=9.2 Hz, 1H), 4.07 (s, 1H), 4.15 (d, J=9.2 Hz, 1H), 4.25 (q, J=7.2 Hz, 2H), 5.92-5.98 (br. m, 1H), 6.84 (q, J=5.6 Hz, 1H) ppm. MS (ESI) m/z: 428.13 (M+H)$^+$, 450.14 (M+Na)$^+$. The analytical data was consistent with the proposed structure.

Example 35

2-[(2R/S, 4R)-2-Methyl-5-oxo(1,3-dioxolan-4-yl)]-2-methylpropyl[3-(acetylamino)propyl]sulfonate (35)

(Ethoxycarbonyloxy)ethyl (2R)-4-{[3-(acetylamino)propyl]sulfonyloxy}-2-hydroxy-3,3-dimethylbutanoate (32) (100 mg, 0.23 mmol) in a 20 mL vial equipped with a magnetic stir bar was heated to ca. 100° C. for one hour. The crude material was then diluted with 10 mL of water and acetonitrile (1:1). Zero-point-two (0.2) mL of a one molar (1.0 M) aqueous solution of sodium hydroxide (NaOH) was added to the mixture. The clear solution was sonicated for 10 min at room temperature and then neutralized with 0.2 mL of a one molar (1.0 M) of hydrochloric acid (HCl). The solvents were removed by lyophilization. The residue was further purified by mass-guided preparative HPLC to give 27 mg (34% yield) of the title compound (35) as a colorless, viscous oil after lyophilization of the solvents. $^1$H NMR (400 MHz, CDCl$_3$, both diastereomers): δ=1.14-1.15 (2s, 3H), 1.16-1.17 (2s, 3H), 1.55-1.59 (2d, J=5.2, 5.2 Hz, 3H), 2.00 (2s, 3H), 2.03-2.12 (m, 2H), 3.13-3.26 (m, 2H), 3.31-3.49 (m, 2H), 4.01-

4.07 (2d, J=9.2, 9.2 Hz, 1H), 4.14-4.25 (m, 2H), 5.63-5.87 (m, 1H), 5.97-6.04 (br. m, 1H) ppm. MS (ESI) m/z: 338.03 (M+H)$^+$, 359.90 (M+Na)$^+$. The analytical data was consistent with the proposed structure.

Example 36

(Ethoxycarbonyloxy)ethyl (2R)-4-{[3-(acetylamino) propyl]sulfonyloxy}-3,3-dimethyl-2-(2-methylpropanoyloxy)butanoate (36)

Step A: (Ethoxycarbonyloxy)ethyl (2R)-4-[(3-chloropropyl)sulfonyloxy]-2-[(4-methoxyphenyl)methoxy]-3,3-dimethylbutanoate (36a)

Following the general procedure for the preparation of acyloxyalkyl/alkoxycarbonyloxyalkyl carboxylic esters from carboxylic acids of Description 22, (2R)-4-[(3-chloropropyl) sulfonyloxy]-2-[(4-methoxyphenyl)methoxy]-3,3-dimethylbutanoic acid (11) (1.0 g, 2.4 mmol) dissolved in 15 mL of anhydrous toluene was reacted with 1.1 g (7.3 mmol) of commercially available 1-chloroethyl ethoxyformate in the presence of 0.81 g (2.9 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 0.77 g of a mixture of the title compound (36a) and (3R)-4,4-dimethyl-3-[(4-methoxyphenyl)methoxy]-3,4,5-trihydrofuran-2-one. MS (ESI) m/z 546.99 (M+Na)$^+$.

Step B: (Ethoxycarbonyloxy)ethyl (2R)-4-[(3-chloropropyl)sulfonyloxy]-2-hydroxy-3,3-dimethylbutanoate (36b)

Following the general procedure for the oxidative cleavage of (4-methoxy)benzyl ethers of Description 19, (ethoxycarbonyloxy)ethyl (2R)-4-[(3-chloropropyl)sulfonyloxy]-2-[(4-methoxyphenyl)methoxy]-3,3-dimethylbutanoate (36a) (0.77 g max.) dissolved in a mixture of dichloromethane (DCM) and water (10:1) (10 mL) was treated with 2,3-dichloro-5,6-dicyano-1,4-benzoquinone (DDQ) (0.68 g, 3.0 mmol). After work-up, the crude material was purified by silica gel column chromatography using a mixture of ethyl acetate (EtOAc) and hexane (Hxn) (EtOAc/Hxn=1:2) as eluent to provide 0.2 g (19% yield over two steps) of the title compound (36b) as a colorless oil. R$_f$=0.57 (EtOAc/Hxn=1: 2). $^1$H NMR (400 MHz, CDCl$_3$, both diastereomers): δ=0.99-1.01 (2s, 3H), 1.12-1.14 (2s, 3H), 1.32-1.37 (m, 3H), 1.59-1.62 (m, 3H), 2.31-2.38 (m, 2H), 2.89-2.94 (2d, J=6.0, 6.8 Hz, 1H), 3.31-3.35 (m, 2H), 3.69-3.72 (m, 2H), 3.97-4.02 (m, 1H), 4.06-4.08 (m, 1H), 4.10-4.22 (m, 1H), 4.21-4.28 (m, 2H), 6.83-6.89 (m, 1H) ppm. MS (ESI) m/z: 426.94 (M+H)$^+$. The analytical data was consistent with the proposed structure.

Step C: (Ethoxycarbonyloxy)ethyl (2R)-4-[(3-chloropropyl)sulfonyloxy]-3,3-dimethyl-2-(2-methylpropanoyloxy)butanoate (36c)

(Ethoxycarbonyloxy)ethyl (2R)-4-[(3-chloropropyl)sulfonyloxy]-2-hydroxy-3,3-dimethylbutanoate (36b) (0.2 g, 0.49 mmol) was reacted with 0.16 mL (0.16 g, 1.5 mmol) of 2-methylpropanoyl chloride in 5 mL of anhydrous dichloromethane (DCM) in the presence of 0.11 mL (0.11 g, 1.3 mmol) of pyridine. After work-up and isolation, the crude material was purified by silica gel column chromatography using ethyl acetate (EtOAc) and hexane (Hxn) mixtures (EtOAc/Hxn=1:2) as eluent to provide 0.23 g (99% yield) of the title compound (36c) as a colorless oil. R$_f$=0.55 (EtOAc/ Hxn=1:2). $^1$H NMR (400 MHz, CDCl$_3$, both diastereomers): δ=1.12-1.15 (2s, 3H), 1.21-1.26 (m, 12H), 1.50-1.58 (2d, J=5.2, 5.6 Hz, 3H), 2.30-2.36 (m, 2H), 2.64-2.71 (m, 1H), 3.31-3.36 (m, 2H), 3.69-3.72 (m, 2H), 3.99-4.02 (2d, J=9.2, 9.6 Hz, 1H), 4.16 (d, J=9.6 Hz, 1H), 4.21-4.28 (m, 2H), 4.75-4.79 (2s, 1H), 6.77-6.82 (m, 1H) ppm. MS (ESI) m/z: 496.99 (M+Na)$^+$. The analytical data was consistent with the proposed structure.

Step D: (Ethoxycarbonyloxy)ethyl (2R)-4-[(3-azidopropyl)sulfonyloxy]-3,3-dimethyl-2-(2-methylpropanoyloxy)butanoate (36d)

Following the general procedure for the preparation of azides of Description 16, (ethoxycarbonyloxy)ethyl (2R)-4-[(3-chloropropyl)sulfonyloxy]-3,3-dimethyl-2-(2-methylpropanoyloxy)butanoate (36c) (0.23 g, 0.49 mmol) dissolved in 3 mL of anhydrous dimethyl sulfoxide (DMSO) was reacted with 64 mg (0.98 mmol) of sodium azide (NaN$_3$). After work-up, the crude material (36d) was obtained and used in the next step without further purification. MS (ESI) m/z 504.01 (M+Na)$^+$.

Step E: (Ethoxycarbonyloxy)ethyl (2R)-4-{[(3-acetylamino)propyl]sulfonyloxy}-3,3-dimethyl-2-(2-methylpropanoyloxy)butanoate (36)

Following the general procedure for the reduction of azides by hydrogenation of Description 17, a mixture of (ethoxycarbonyloxy)ethyl (2R)-4-[(3-azidopropyl)sulfonyloxy]-3,3-dimethyl-2-(2-methylpropanoyloxy)butanoate (36d) (0.23 g, 0.49 mmol), 0.23 mL of acetic anhydride (Ac$_2$O), and 80 mg of 10 wt-% palladium on activated carbon in 5 mL of a mixture of methanol (MeOH) and ethyl acetate (EtOAc) was stirred overnight under a hydrogen atmosphere. After purification by mass-guided preparative HPLC, 89 mg (36% yield) of the title compound (36) was obtained as a colorless, viscous oil after lyophilization of the solvents. $^1$H NMR (400 MHz, CDCl$_3$, both diastereomers): δ=1.11 (m, 3H), 1.12 (m, 3H), 1.19-1.23 (m, 6H), 1.327 (t, J=7.2 Hz, 3H), 1.49-1.57 (2d, J=5.6, 5.6 Hz, 3H), 1.99 (s, 3H), 2.03-2.10 (m, 2H), 2.68-2.70 (m, 1H), 3.16-3.22 (m, 2H), 3.37-3.43 (m, 2H), 3.96-3.99 (2d, J=9.6, 9.6 Hz, 1H), 4.11-4.14 (2d, J=10.0, 10.0 Hz, 1H), 4.20-4.24 (m, 2H), 4.74-4.77 (2s, 1H), 6.02-6.08 (br. m, 1H), 6.76-6.82 (m, 1H) ppm. MS (ESI) m/z 498.17 (M+H)$^+$, 520.19 (M+Na)$^+$. The analytical data was consistent with the proposed structure.

Example 37

(Ethoxycarbonyloxy)ethyl (2R/S)-4-{[3-(acetylamino)propyl]sulfonyloxy}-2-hydroxy-3,3-dimethylbutanoate (37)

Step A: (Ethoxycarbonyloxy)ethyl (2R/S)-4-[(3-chloropropyl)sulfonyloxy]-3,3-dimethyl-2-(phenylmethoxy)butanoate (37a)

Following the general procedure for the preparation of acyloxyalkyl/alkoxycarbonyloxyalkyl carboxylic esters from carboxylic acids of Description 22, (2R/S)-4-[(3-chloropropyl)sulfonyloxy]-3,3-dimethyl-2-(phenylmethoxy)butanoic acid (12) (5.0 g, 13.2 mmol) dissolved in 60 mL of anhydrous toluene was reacted with 6.0 g (40 mmol) of commercially available 1-chloroethyl ethoxyformate in the presence of 3.9 g (14 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 4.5 g of a mixture of the title compound (37a) and (3R/S)-4,4-dimethyl-3-(phenylmethoxy)-3,4,5-trihydrofuran-2-one (2). The analytical data was consistent with the proposed structure and with the data obtained for (ethoxycarbonyloxy)ethyl (2R)-4-[(3-chloropropyl)sulfonyloxy]-3,3-dimethyl-2-(phenylmethoxy)butanoate (32a).

Step B: (Ethoxycarbonyloxy)ethyl (2R/S)-4-[(3-azidopropyl)sulfonyloxy]-3,3-dimethyl-2-(phenylmethoxy)butanoate (37b)

Following the general procedure for the preparation of azides of Description 16, (ethoxycarbonyloxy)ethyl (2R/S)-4-[(3-chloropropyl)sulfonyloxy]-3,3-dimethyl-2-(phenylmethoxy)butanoate (37a) (4.5 g max.) dissolved in 50 mL of anhydrous dimethyl sulfoxide (DMSO) was reacted with 0.88 g (13.5 mmol) of sodium azide (NaN$_3$). After work-up, the crude title compound (37b) was obtained and used in the next step without further purification. The analytical data was consistent with the data obtained for (ethoxycarbonyloxy) ethyl (2R)-4-[(3-azidopropyl)sulfonyloxy]-3,3-dimethyl-2-(phenylmethoxy)butanoate (32b).

Step C: (Ethoxycarbonyloxy)ethyl (2R/S)-4-{[(3-acetylamino)propyl]sulfonyloxy}-3,3-dimethyl-2-(phenylmethoxy)butanoate (37c)

Following the general procedure for the reduction of azides by hydrogenation of Description 17, a mixture of (ethoxycarbonyloxy)ethyl (2R/S)-4-[(3-azidopropyl)sulfonyloxy]-3,3-dimethyl-2-(phenylmethoxy)butanoate (37b) (4.5 g maximum), 1.0 mL (1.08 g, 10.6 mmol) of acetic anhydride (Ac$_2$O), and 0.3 g of 10 wt-% palladium on activated carbon in 30 mL of a mixture of methanol (MeOH) and ethyl acetate (EtOAc), was stirred overnight under a hydrogen atmosphere. After work-up, the crude material was purified by silica gel column chromatography using a mixture of ethyl acetate (EtOAc) and methanol (MeOH) (EtOAc/MeOH=19:1) as eluent to provide 1.7 g (25% yield over three steps) of the title compound (37c) as a colorless oil. The analytical data was consistent with the data obtained for (ethoxycarbonyloxy) ethyl (2R)-4-{[(3-acetylamino)propyl]sulfonyloxy}-3,3-dimethyl-2-(phenylmethoxy)butanoate (32c).

Step D: (Ethoxycarbonyloxy)ethyl (2R/S)-4-{[3-(acetylamino)propyl]sulfonyloxy}-2-hydroxy-3,3-dimethylbutanoate (37)

Following the general procedure for the hydrogenolysis of benzyl ethers of Description 18, a mixture of (ethoxycarbonyloxy)ethyl (2R/S)-4-{[3-(acetylamino)propyl]sulfonyloxy}-3,3-dimethyl-2-(phenylmethoxy)butanoate (37c) (1.7 g, 3.3 mmol) and 1.4 g of 10 wt.-% of palladium on activated carbon in 30 mL of methanol (MeOH) was stirred overnight under a hydrogen atmosphere. After purification by mass-guided preparative HPLC, 500 mg (35% yield) of the title compound (37) was obtained as a yellow viscous oil after lyophilization of the solvents. The analytical data was consistent with the data obtained for (ethoxycarbonyloxy)ethyl (2R)-4-{[3-(acetylamino)propyl]sulfonyloxy}-2-hydroxy-3,3-dimethylbutanoate (32).

Example 38

Benzoyloxyethyl (2R)-4-{[3-(acetylamino)propyl] sulfonyloxy}-2-hydroxy-3,3-dimethylbutanoate (38)

Step A: Benzoyloxyethyl (2R)-4-[(3-chloropropyl) sulfonyloxy]-3,3-dimethyl-2-(1,1,2,2-tetramethyl-1-silapropoxy)butanoate (38a)

Following the general procedure for the preparation of acyloxyalkyl/alkoxycarbonyloxyalkyl carboxylic esters from carboxylic acids of Description 22, (2R)-4-[(3-chloropropyl) sulfonyloxy]-3,3-dimethyl-2-(1,1,2,2-tetramethyl-1-silapropoxy)butanoic acid (15) (0.4 g, 0.99 mmol) dissolved in 5 mL of anhydrous toluene was reacted with 0.55 g (3.0 mmol) of 1-chloroethyl benzoate (23) in the presence of 0.33 g (1.1 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 0.6 g of a mixture of the title compound (38a) and (3R)-4,4-dimethyl-3-(1,1,2,2-tetramethyl-1-silapropoxy)-3,4,5-trihydrofuran-2-one (4a). MS (ESI) m/z 573.01 (M+Na)$^+$.

Step B: Benzoyloxyethyl (2R)-4-[(3-azidopropyl) sulfonyloxy]-3,3-dimethyl-2-(1,1,2,22-tetramethyl-1-silapropoxy)butanoate (38b)

Following the general procedure for the preparation of azides of Description 16, benzoyloxyethyl (2R)-4-[(3-chloropropyl)sulfonyloxy]-3,3-dimethyl-2-(1,1,2,2-tetramethyl-1-silapropoxy)butanoate (38a) (0.6 g max.) dissolved in 5 mL of anhydrous dimethyl sulfoxide (DMSO) was reacted with 0.11 g (1.6 mmol) of sodium azide (NaN$_3$). After work-up, the crude title compound (38b) was used in the next step without further purification. MS (ESI) m/z 580.17 (M+Na)$^+$.

Step C: Benzoyloxyethyl (2R)-4-{[(3-acetylamino) propyl]sulfonyloxy}-3,3-dimethyl-2-(1,1,2,2-tetramethyl-1-silapropoxy)butanoate (38c)

Following the general procedure for the reduction of azides by hydrogenation of Description 17, a mixture of benzoyloxyethyl (2R)-4-[(3-azidopropyl)sulfonyloxy]-3,3-dimethyl-2-(1,1,2,2-tetramethyl-1-silapropoxy)butanoate (38b) (0.6 g maximum), 0.3 mL (0.324 g, 3.2 mmol) of acetic anhydride (Ac$_2$O), and 100 mg of 10 wt-% palladium on activated carbon in 10 mL of a mixture of methanol (MeOH) and ethyl acetate (EtOAc) was stirred overnight under a hydrogen atmosphere. After work-up, the crude material was purified by silica gel column chromatography using ethyl acetate (EtOAc) as eluent to provide 100 mg (18% yield over three steps) of the title compound (38c) as a colorless oil. $^1$H NMR (400 MHz, CDCl$_3$, both diastereomers): δ=0.05-0.07 (m, 6H), 0.91 (s, 9H), 1.03-1.06 (m, 6H), 1.65 (d, J=5.6 Hz, 3H), 1.99 (s, 3H), 2.02-2.10 (m, 2H), 3.11-3.17 (m, 2H), 3.33-3.43 (m, 2H), 4.00-4.08 (m, 3H), 6.02-6.06 (br. m, 1H), 7.12-7.18 (m, 1H), 7.43-7.47 (m, 2H), 7.57-7.61 (m, 1H), 8.00-8.03 (m, 2H) ppm. MS (ESI) m/z 574.19 (M+H)$^+$, 596.21 (M+Na)$^+$. The analytical data was consistent with the proposed structure.

Step D: Benzoyloxyethyl (2R)-4-{[3-(acetylamino) propyl]sulfonyloxy}-2-hydroxy-3,3-dimethylbutanoate (38)

Following the general procedure for the cleavage of silyl ethers with triethylamine trihydrofluoride of Description 20, a mixture of benzoyloxyethyl (2R)-4-{[(3-acetylamino)propyl]sulfonyloxy}-3,3-dimethyl-2-(1,1,2,2-tetramethyl-1-silapropoxy)butanoate (38c) (0.1 g, 0.17 mmol) and triethylamine trihydrofluoride (Et$_3$N.3HF) (0.23 mL, 0.22 g, 1.4 mmol) in 3 mL tetrahydrofuran (THF) was stirred overnight at 50-60° C. After work-up and isolation, the crude material was purified by silica gel column chromatography using ethyl acetate (EtOAc) and methanol (MeOH) mixtures (EtOAc/MeOH=19:1) as eluent to provide 70 mg (90% yield) of the title compound (38) as a colorless oil. $^1$H NMR (400 MHz, CDCl$_3$, both diastereomers): δ=0.95-1.01 (2s, 3H), 1.11-1.14 (2s, 3H), 1.68-1.70 (2d, J=5.6, 5.6 Hz, 3H), 1.97-1.99 (2s, 3H), 2.00-2.08 (m, 2H), 3.11-3.21 (m, 2H), 3.30-3.41 (m, 2H), 3.45-3.55 (2d, J=6.4, 6.8 Hz, 1H), 3.90-3.97 (2d, J=9.2, 8.8 Hz, 1H), 4.06-4.12 (m, 1H), 4.16-4.19 (m, 1H), 6.10-6.18 (br. m, 1H), 7.17-7.22 (m, 1H), 7.43-7.47 (m, 2H), 7.57-7.62 (m, 1H), 8.00-8.05 (m, 2H) ppm. MS (ESI) m/z 460.05 (M+H)$^+$, 481.99 (M+Na)$^+$. The analytical data was consistent with proposed structure.

Example 39

Benzoyloxyethyl (2R/S)-4-{[3-(acetylamino)propyl]sulfonyloxy}-2-hydroxy-3,3-dimethylbutanoate (39)

Step A: Benzoyloxyethyl (2R/S)-4-[(3-chloropropyl)sulfonyloxy]-3,3-dimethyl-2-(phenylmethoxy)butanoate (39a)

Following the general procedure for the preparation of acyloxyalkyl/alkoxycarbonyloxyalkyl carboxylic esters from carboxylic acids of Description 22, (2R/S)-4-[(3-chloropropyl)sulfonyloxy]-3,3-dimethyl-2-(phenylmethoxy)butanoic acid (12) (3.0 g, 7.9 mmol) dissolved in 30 mL of anhydrous toluene was reacted with 4.4 g (23.7 mmol) of 1-chloroethyl benzoate (23) in the presence of 2.6 g (9.5 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 3.2 g of a mixture of the title compound (39a) and (3R/S)-4,4-dimethyl-3-(phenylmethoxy)-3,4,5-trihydrofuran-2-one (2a). MS (ESI) m/z 548.97 (M+Na)$^+$.

Step B: Benzoyloxyethyl (2R/S)-4-[(3-azidopropyl)sulfonyloxy]-3,3-dimethyl-2-(phenylmethoxy)butanoate (39b)

Following the general procedure for the preparation of azides of Description 16, benzoyloxyethyl (2R/S)-4-[(3-chloropropyl)sulfonyloxy]-3,3-dimethyl-2-(phenylmethoxy)butanoate (39a) (3.2 g max.) dissolved in 30 mL of anhydrous dimethyl sulfoxide (DMSO) was reacted with 0.51 g (8.0 mmol) of sodium azide (NaN$_3$). After work-up, the crude title compound (39b) was obtained and used in the next step without further purification. MS (ESI) m/z 555.83 (M+Na)$^+$.

Step C: Benzoyloxyethyl (2R/S)-4-{[(3-acetylamino)propyl]sulfonyloxy}-3,3-dimethyl-2-(phenylmethoxy)butanoate (39c)

Following the general procedure for the reduction of azides by hydrogenation of Description 17, a mixture of benzoyloxyethyl (2R/S)-4-[(3-azidopropyl)sulfonyloxy]-3,3-dimethyl-2-(phenylmethoxy)butanoate (39b) (3.2 g maximum), 0.7 mL (0.76 g, 7.4 mmol) of acetic anhydride (Ac$_2$O), and 0.2 g of 10 wt-% palladium on activated carbon in 20 mL of a mixture of methanol (MeOH) and ethyl acetate (EtOAc), was stirred overnight under a hydrogen atmosphere. After work-up, the crude material was purified by silica gel column chromatography using a mixture of ethyl acetate (EtOAc) and methanol (MeOH) (EtOAc/MeOH=19:1) as eluent to provide 1.7 g (39% yield over three steps) of the title compound (39c) as a colorless oil. $^1$H NMR (400 MHz, CDCl$_3$, both diastereomers): δ=1.07-1.09 (m, 6H), 1.67 (d, J=5.6 Hz, 3H), 1.96-1.97 (2s, 3H), 1.97-2.03 (m, 2H), 3.06-3.10 (m, 2H), 3.32-3.36 (m, 2H), 3.83-3.86 (2s, 1H), 3.94-3.97 (2d, J=9.2, 9.2 Hz, 1H), 4.15-4.19 (m, 1H), 4.37 (d, J=11.2 Hz, 1H), 4.59-4.68 (2d, J=11.2, 11.6 Hz, 1H), 5.75-5.80 (br. m, 1H), 7.17-7.21 (m, 1H), 7.28-7.34 (m, 5H), 7.45-7.49 (m, 2H), 7.57-7.63 (m, 1H), 8.00-8.07 (m, 2H) ppm. MS (ESI) m/z 549.87 (M+H)$^+$, 571.92 (M+Na)$^+$. The analytical data was consistent with the proposed structure.

Step D: Benzoyloxyethyl (2R/S)-4-{[3-(acetylamino)propyl]sulfonyloxy}-2-hydroxy-3,3-dimethylbutanoate (39)

Following the general procedure for the hydrogenolysis of benzyl ethers of Description 18, a mixture of benzoyloxyethyl (2R/S)-4-{[3-(acetylamino)propyl]sulfonyloxy}-3,3-dimethyl-2-(phenylmethoxy)butanoate (39c) (1.7 g, 3.1 mmol) and 1.0 g of 10 wt.-% of palladium on activated carbon in 20 mL of ethanol (EtOH) was stirred overnight under a hydrogen atmosphere. After work-up, the crude material was purified by silica gel column chromatography using a mixture of ethyl acetate (EtOAc) and methanol (MeOH) (EtOAc/MeOH=9:1) as eluent to provide 0.67 g (47% yield) of the title compound (39) as a colorless oil. The analytical data was consistent with the data obtained for benzoyloxyethyl (2R)-4-{[(3-acetylamino)propyl]sulfonyloxy}-3,3-dimethyl-2-(phenylmethoxy)butanoate (38).

Example 40

(Methylethoxycarbonyloxy)ethyl (2R)-4-{[3-(acetylamino)propyl]sulfonyloxy}-2-hydroxy-3,3-dimethylbutanoate (40)

Step A: (Methylethoxycarbonyloxy)ethyl (2R)-4-[(3-chloropropyl)sulfonyloxy]-3,3-dimethyl-2-(phenylmethoxy)butanoate (40a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (34.0 g, 89.7 mmol) dissolved in 300 mL of anhydrous toluene was reacted with 30 g (179.5 mmol) of commercially available 1-chloroethyl methylethoxyformate in the presence of 47 g (179.5 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 23.0 g (50% yield) of the title compound (40a). R$_f$=0.32 (EtOAc/Hxn=1:4). $^1$H NMR (400 MHz, CDCl$_3$, both diastereomers): δ=1.06-1.08 (m, 6H), 1.24-1.35 (m, 6H), 1.57 (d, J=5.2 Hz, 3H), 2.24-2.31 (m, 2H), 3.20-3.26 (m, 2H), 3.63-3.66 (m, 2H), 3.85-3.86 (2s, 1H), 3.94-3.97 (2d, J=9.6, 9.6 Hz, 1H), 4.19-4.23 (2d, J=9.2, 9.6 Hz, 1H), 4.33-4.38 (2d, J=11.2, 11.6 Hz, 1H), 4.64 (t, J=11.2 Hz, 1H), 4.81-4.97 (m, 1H), 6.81-6.87 (m, 1H), 7.30-7.37 (m, 5H) ppm. MS (ESI) m/z 531.02 (M+Na)$^+$. The analytical data was consistent with the proposed structure.

Step B: (Methylethoxycarbonyloxy)ethyl (2R)-4-[(3-azidopropyl)sulfonyloxy]-3,3-dimethyl-2-(phenylmethoxy)butanoate (40b)

Following the general procedure for the preparation of azides of Description 16, 23.0 g (45.3 mmol) of (methylethoxycarbonyloxy)ethyl (2R)-4-[(3-chloropropyl)sulfonyloxy]-3,3-dimethyl-2-(phenylmethoxy)butanoate (40a) dissolved in 210 mL of anhydrous dimethyl sulfoxide (DMSO) was reacted with 5.9 g (93.6 mmol) of sodium azide (NaN$_3$). After work-up, the crude title compound (40b) was obtained and used in the next step without further purification. R$_f$=0.29 (EtOAc/Hxn=1:4). $^1$H NMR (400 MHz, CDCl$_3$, both diastereomers): δ=1.06-1.08 (m, 6H), 1.24-1.35 (m, 6H), 1.57 (d, J=5.2 Hz, 3H), 2.03-2.10 (m, 2H), 3.10-3.16 (m, 2H), 3.44-3.48 (m, 2H), 3.84-3.85 (2s, 1H), 3.94-3.96 (2d, J=8.8, 9.2 Hz, 1H), 4.18-4.22 (2d, J=9.2, 9.6 Hz, 1H), 4.33-4.38 (2d, J=11.2, 11.2 Hz, 1H), 4.64 (t, J=11.2 Hz, 1H), 4.78-4.97 (m, 1H), 6.82-6.87 (m, 1H), 7.32-7.37 (m, 5H) ppm. MS (ESI) m/z 538.07 (M+Na)$^+$. The analytical data was consistent with the proposed structure.

Step C: (Methylethoxycarbonyloxy)ethyl (2R)-4-{[(3-acetylamino)propyl]sulfonyloxy}-3,3-dimethyl-2-(phenylmethoxy)butanoate (40c)

Following the general procedure for the reduction of azides by hydrogenation of Description 17, (methylethoxycarbonyloxy)ethyl (2R)-4-[(3-azidopropyl)sulfonyloxy]-3,3-dimethyl-2-(phenylmethoxy)butanoate (40b) (23 g, 45 mmol), 6.8 mL (7.34 g, 71.9 mmol) of acetic anhydride (Ac$_2$O), and 2.4 g of 10 wt-% palladium on activated carbon in 100 mL of a mixture of methanol (MeOH) and ethyl acetate (EtOAc), was stirred overnight under a hydrogen atmosphere. After work-up, the crude material was purified by silica gel column chromatography using ethyl acetate (EtOAc) as eluent to provide 18.0 g (75% yield) of the title compound (40c) as a colorless oil. R$_f$=0.44 (EtOAc/MeOH=3:1). $^1$H NMR (400 MHz, CDCl$_3$, both diastereomers): δ=1.07-1.08 (m, 6H), 1.27-1.35 (m, 6H), 1.57 (d, J=5.2 Hz, 3H), 1.98 (s, 3H), 1.99-2.05 (m, 2H), 3.07-3.12 (m, 2H), 3.34-3.39 (m, 2H), 3.83-3.84 (2s, 1H), 3.94-3.97 (2d, J=9.2, 9.6 Hz, 1H), 4.15-4.19 (m, 1H), 4.33-4.38 (2d, J=11.2, 11.6 Hz, 1H), 4.64 (t, J=11.2 Hz, 1H), 4.81-4.95 (m, 1H), 5.74-5.80 (br. m, 1H), 6.81-6.86 (m, 1H), 7.32-7.35 (m, 5H) ppm. MS (ESI) m/z 532.17 (M+H)$^+$, 554.11 (M+Na)$^+$. The analytical data was consistent with the proposed structure.

Step D: (Methylethoxycarbonyloxy)ethyl (2R)-4-{[3-(acetylamino)propyl]sulfonyloxy}-2-hydroxy-3,3-dimethylbutanoate (40)

Following the general procedure of hydrogenolysis of benzyl ethers of Description 18, a mixture of (methylethoxycarbonyloxy)ethyl (2R)-4-{[3-(acetylamino)propyl]sulfonyloxy}-3,3-dimethyl-2-(phenylmethoxy)butanoate (40c) (13.0 g, 24.4 mmol), 3.2 g of 10 wt.-% of palladium on activated carbon in 40 mL of methanol (MeOH), and 0.2 mL of one molar (1.0 M) hydrochloric acid (HCl) was stirred overnight under a hydrogen atmosphere. Upon the completion of reaction and following aqueous work-up, 10.0 g (93% yield) of the title compound (40) was obtained as a colorless, viscous oil. R$_T$=12.46 min and 14.22 min. $^1$H NMR (400 MHz, DMSO-d$^6$, both diastereomers): δ=0.89-0.91 (2s, 3H), 0.93-0.95 (2s, 3H), 1.21-1.24 (m, 6H), 1.45-1.47 (2d, J=5.2, 5.2 Hz, 3H), 1.78-1.83 (m, 5H), 3.10-3.15 (m, 2H), 3.30-3.33 (m, 2H), 3.89-3.93 (m, 2H), 4.05-4.08 (2d, J=9.2, 9.6 Hz, 1H), 4.73-4.82 (m, 1H), 5.78-5.85 (2d, J=6.0, 6.0 Hz, 1H), 6.65-6.71 (m, 1H), 7.89-7.92 (br. m, 1H) ppm. MS (ESI) m/z: 442.08 (M+H)$^+$, 464.02 (M+Na)$^+$. The analytical data was consistent with the proposed structure.

Example 41

(Methylethoxycarbonyloxy)ethyl (2R)-4-{[3-(acetylamino)propyl]sulfonyloxy}-2-hydroxy-3,3-dimethylbutanoate (41)

A single isomer of (methylethoxycarbonyloxy)ethyl (2R)-4-{[3-(acetylamino)propyl]sulfonyloxy}-2-hydroxy-3,3-dimethylbutanoate was isolated from a mixture of diastereomers of Example 40 by preparative HPLC with a chiral column (Chiralpak IA). The title compound (41) was obtained as a colorless, viscous oil. R$_T$=12.46 min (by LC/UV). D.e. >98% (by $^1$H NMR spectroscopy, 400 MHz, CDCl$_3$ and LC/UV). $^1$H NMR (400 MHz, CDCl$_3$): δ=0.96 (s, 3H), 1.11 (s, 3H), 1.31 (t, J=6.0 Hz, 6H), 1.57 (d, J=5.2 Hz, 3H), 1.99 (s, 3H), 2.04-2.11 (m, 2H), 3.13-3.26 (m, 2H), 3.32-3.46 (m, 2H), 3.91 (d, J=9.2 Hz, 1H), 4.06 (s, 1H), 4.17 (d, J=9.2 Hz, 1H), 4.84-4.92 (m, 1H), 6.13-6.17 (br. m, 1H), 6.83 (q, J=5.2 Hz, 1H) ppm. MS (ESI) m/z: 442.08 (M+H)$^+$, 464.02 (M+Na)$^+$. The analytical data was consistent with the proposed structure.

Example 42

Methylethoxycarbonyloxy)ethyl (2R)-4-{[3-(acetylamino)propyl]sulfonyloxy}-2-hydroxy-3,3-dimethylbutanoate (42)

A single isomer of (methylethoxycarbonyloxy)ethyl (2R)-4-{[3-(acetylamino)propyl]sulfonyloxy}-2-hydroxy-3,3-dimethylbutanoate was isolated from a mixture of diastereomers of Example 40 by preparative HPLC with a chiral column (Chiralpak IA). The title compound (42) was obtained as a colorless, viscous oil. R$_T$=14.22 min (by LC/UV). D.e. >98% (by $^1$H NMR spectroscopy, 400 MHz, CDCl$_3$ and LC/UV). $^1$H NMR (400 MHz, CDCl$_3$): δ=1.00 (s, 3H), 1.14 (s, 3H), 1.32-1.34 (dd, J=6.4 Hz, 6.4 Hz, 6H), 1.59 (d, J=4.8 Hz, 3H), 2.01 (s, 3H), 2.04-2.11 (m, 2H), 3.13-3.25 (m, 2H), 3.33-3.46 (m, 2H), 3.95 (d, J=9.6 Hz, 1H), 4.06 (s, 1H), 4.15 (d, J=9.2 Hz, 1H), 4.90 (sept, J=6.0 Hz, 1H), 6.18-6.25 (br. m, 1H), 6.83 (q, J=5.2 Hz, 1H) ppm. MS (ESI) m/z: 442.08 (M+H)$^+$, 464.02 (M+Na)$^+$. The analytical data was consistent with the proposed structure.

Example 43

(Cyclohexyloxycarbonyloxy)ethyl (2R)-4-{[3-(acetylamino)propyl]sulfonyloxy}-2-hydroxy-3,3-dimethylbutanoate (43)

Step A: (Cyclohexyloxycarbonyloxy)ethyl (2R)-4-[(3-chloropropyl)sulfonyloxy]-3,3-dimethyl-2-(phenylmethoxy)butanoate (43a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (0.4 g, 1.0 mmol) dissolved in 5 mL of anhydrous toluene was reacted with 0.67 g (4.0 mmol) of 1-chloroethyl cyclohexyloxyformate in the presence of 0.55 g (2.0 mmol) of silver carbonate (Ag$_2$CO$_3$). After work-up, the crude product was purified by silica gel column chromatography using a mixture of ethyl acetate (EtOAc) and hexane (Hxn) (EtOAc/Hxn=1:4) as eluent to provide 0.41 g (71% yield) of the title compound (43a). $R_f$=0.40 (EtOAc/Hxn=1:4). $^1$H NMR (400 MHz, CDCl$_3$, both diastereomers): δ=1.06-1.08 (m, 6H), 1.25-1.58 (br. m, 9H), 1.73-1.78 (br. m, 2H), 1.88-1.95 (br. m, 2H), 2.24-2.31 (m, 2H), 3.20-3.25 (m, 2H), 3.63-3.66 (m, 2H), 3.84-3.85 (2s, 1H), 3.94-3.97 (2d, J=9.2, 8.8 Hz, 1H), 4.19-4.23 (2d, J=9.2, 8.8 Hz, 1H), 4.33-4.38 (2d, J=11.2, 11.6 Hz, 1H), 4.55-4.70 (m, 2H), 6.81-6.87 (m, 1H), 7.31-7.37 (m, 5H) ppm. MS (ESI) m/z 571.05 (M+Na)$^+$. The analytical data was consistent with the proposed structure.

Step B: (Cyclohexyloxycarbonyloxy)ethyl (2R)-4-[(3-azidopropyl)sulfonyloxy]-3,3-dimethyl-2-(phenylmethoxy)butanoate (43b)

Following the general procedure for the preparation of azides of Description 16, 0.4 g (0.73 mmol) of (cyclohexyloxycarbonyloxy)ethyl (2R)-4-[(3-chloropropyl)sulfonyloxy]-3,3-dimethyl-2-(phenylmethoxy)butanoate (43a) dissolved in 4 mL of anhydrous dimethyl sulfoxide (DMSO) was reacted with 0.16 g (2.5 mmol) of sodium azide (NaN$_3$). After work-up, 0.35 g (85% yield) of the title compound (43b) was obtained as a colorless oil. $R_f$=0.35 (EtOAc/Hxn=1:4). $^1$H NMR (400 MHz, CDCl$_3$, both diastereomers): δ=1.06-1.08 (m, 6H), 1.25-1.58 (br. m, 9H), 1.72-1.78 (br. m, 2H), 1.88-1.96 (br. m, 2H), 2.03-2.10 (m, 2H), 3.10-3.16 (m, 2H), 3.44-3.48 (m, 2H), 3.84-3.85 (2s, 1H), 3.94-3.96 (2d, J=9.2, 8.8 Hz, 1H), 4.18-4.23 (2d, J=9.2, 9.2 Hz, 1H), 4.33-4.38 (2d, J=11.2 Hz, 11.6 Hz, 1H), 4.54-4.72 (m, 2H), 6.81-6.87 (m, 1H), 7.30-7.38 (m, 5H) ppm. MS (ESI) m/z 577.89 (M+Na)$^+$. The analytical data was consistent with the proposed structure.

Step C: (Cyclohexyloxycarbonyloxy)ethyl (2R)-4-{[(3-acetylamino)propyl]sulfonyloxy}-3,3-dimethyl-2-(phenylmethoxy)butanoate (43c)

Following the general procedure for the reduction of azides by hydrogenation of Description 17, (cyclohexyloxycarbonyloxy)ethyl (2R)-4-[(3-azidopropyl)sulfonyloxy]-3,3-dimethyl-2-(phenylmethoxy)butanoate (43b) (0.35 g, 0.63 mmol), 0.12 mL (0.13 g, 1.3 mmol) of acetic anhydride (Ac$_2$O), and 0.17 g of 10 wt-% palladium on activated carbon in 20 mL of a mixture of methanol (MeOH) and ethanol (EtOH), was stirred overnight under a hydrogen atmosphere. After work-up, 0.19 g (54% yield) of the title compound (43c) was obtained as a colorless oil. $R_f$=0.44 (EtOAc/MeOH=3:1). MS (ESI) m/z 572.03 (M+H)$^+$, 594.00 (M+Na)$^+$.

Step D: (Cyclohexyloxycarbonyloxy)ethyl (2R)-4-{[3-(acetylamino)propyl]sulfonyloxy}-2-hydroxy-3,3-dimethylbutanoate (43)

Following the general procedure of hydrogenolysis of benzyl ethers of Description 18, a mixture of (cyclohexyloxycarbonyloxy)ethyl (2R)-4-{[3-(acetylamino)propyl]sulfonyloxy}-3,3-dimethyl-2-(phenylmethoxy)butanoate (43c) (0.19 g, 0.34 mmol) and 0.13 g of 10 wt.-% of palladium on activated carbon in 10 mL of methanol (MeOH) was stirred overnight under a hydrogen atmosphere. After purification by mass-guided preparative HPLC, 0.13 g (80% yield) of the title compound (43) was obtained as a colorless, viscous oil. $^1$H NMR (400 MHz, DMSO-d$^6$, both diastereomers): δ=0.89-0.90 (2s, 3H), 0.93-0.94 (2s, 3H), 1.31-1.47 (br. m, 9H), 1.60-1.68 (br. m, 2H), 1.78-1.83 (br. m, 7H), 3.10-3.15 (m, 2H), 3.28-3.35 (m, 2H), 3.89-3.92 (m, 2H), 4.05-4.08 (2d, J=9.2, 9.6 Hz, 1H), 4.52-4.58 (m, 1H), 5.78-5.85 (2d, J=5.6, 5.6 Hz, 1H), 6.66-6.72 (m, 1H), 7.89-7.92 (br. m, 1H) ppm. MS (ESI) m/z: 482.07 (M+H)$^+$, 503.83 (M+Na)$^+$. The analytical data was consistent with the proposed structure.

Example 44

(Cyclohexylcarbonyloxy)ethyl (2R)-4-{[3-(acetylamino)propyl]sulfonyloxy}-2-hydroxy-3,3-dimethylbutanoate (44)

Step A: (Cyclohexylcarbonyloxy)ethyl (2R)-4-[(3-chloropropyl)sulfonyloxy]-3,3-dimethyl-2-(phenylmethoxy)butanoate (44a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (1.2 g, 3.3 mmol) dissolved in 10 mL of anhydrous toluene was reacted with 1.9 g (10.0 mmol) of chloroethyl cyclohexanecarboxylate (24) in the presence of 1.4 g (5.0 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:9→EtOAc/Hxn=1:5) as eluent to provide 0.69 g (39% yield) of the title compound (44a) as a colorless oil. $R_f$=0.11 (EtOAc/Hxn=1:9). $^1$H NMR (400 MHz, CDCl$_3$, both diastereomers): δ=1.06-1.08 (m, 6H), 1.23-1.36 (br. m, 3H), 1.44-1.50 (br. m, 2H), 1.53 (d, J=5.6 Hz, 3H), 1.58-1.68 (br. m, 1H), 1.74-1.80 (br. m, 2H), 1.86-1.97 (br. m, 2H), 2.25-2.39 (m, 3H), 3.21-3.26 (m, 2H), 3.63-3.66 (m, 2H), 3.82-3.84 (2s, 1H), 3.96 (d, J=9.2 Hz, 1H), 4.20-4.24 (m, 1H), 4.33-4.37 (2d, J=11.6, 11.6 Hz, 1H), 4.59-4.66 (2d, J=10.8, 11.2 Hz, 1H), 6.91-6.95 (m, 1H), 7.30-7.37 (m, 5H) ppm. MS (ESI) m/z 554.92 (M+Na)$^+$. The analytical data was consistent with the proposed structure.

Step B: (Cyclohexylcarbonyloxy)ethyl (2R)-4-[(3-azidopropyl)sulfonyloxy]-3,3-dimethyl-2-(phenylmethoxy)butanoate (44b)

Following the general procedure for the preparation of azides of Description 16, (cyclohexylcarbonyloxy)ethyl (2R)-4-[(3-chloropropyl)sulfonyloxy]-3,3-dimethyl-2-(phenylmethoxy)butanoate (44a) (1.6 g, 3.0 mmol) dissolved in 15 mL of anhydrous dimethyl sulfoxide (DMSO) was reacted with 0.65 g (10.0 mmol) of sodium azide (NaN$_3$). After work-up, the crude material was purified by silica gel column chromatography using a mixture of ethyl acetate (EtOAc) and hexane (Hxn) (EtOAc/Hxn=1:4) as eluent to provide 1.1 g (65% yield) of the title compound (44b) as a colorless oil. $R_f$=0.30 (EtOAc/Hxn=1:4). $^1$H NMR (400 MHz, CDCl$_3$, both diastereomers): δ=1.04-1.06 (m, 6H), 1.19-1.30 (br. m, 3H), 1.40-1.49 (br. m, 2H), 1.51 (d, J=5.6 Hz, 3H), 1.62-1.66 (br. m, 1H), 1.70-1.78 (br. m, 2H), 1.85-1.94 (br. m, 2H), 2.01-2.08 (m, 2H), 2.24-2.37 (m, 1H), 3.09-3.15 (m, 2H), 3.43-3.47 (m, 2H), 3.81-3.83 (2s, 1H), 3.93 (d, J=8.8 Hz, 1H), 4.17-4.22 (m, 1H), 4.32-4.36 (2d, J=11.6, 11.2 Hz, 1H), 4.56-4.65 (2d, J=11.6, 11.6 Hz, 1H), 6.91-6.95 (m, 1H), 7.32-7.37 (m, 5H) ppm. MS (ESI) m/z 562.13 (M+Na)$^+$. The analytical data was consistent with the proposed structure.

Step C: (Cyclohexylcarbonyloxy)ethyl (2R)-4-{[(3-acetylamino)propyl]sulfonyloxy}-3,3-dimethyl-2-(phenylmethoxy)butanoate (44c)

Following the general procedure for the reduction of azides by hydrogenation of Description 17, a mixture of (cyclohexylcarbonyloxy)ethyl (2R)-4-[(3-azidopropyl)sulfonyloxy]-3,3-dimethyl-2-(phenylmethoxy)butanoate (44b) (1.1 g, 2.0 mmol), 0.38 mL (0.40 g, 4.0 mmol) of acetic anhydride ($Ac_2O$), and 1.5 g of 10 wt-% palladium on activated carbon in 16 mL of a mixture of methanol (MeOH) and ethyl acetate (EtOAc) (MeOH/EtOAc=1:1), was stirred overnight under a hydrogen atmosphere. After work-up, the crude material was purified by silica gel column chromatography using a mixture of ethyl acetate (EtOAc) and n-heptane (Hptn) (EtOAc/Hptn=9:1) as eluent to provide 0.79 g (77% yield) of the title compound (44c) as a colorless oil. $R_f$=0.40 (EtOAc/Hptn=9:1). $^1$H NMR (400 MHz, $CDCl_3$, both diastereomers): δ=1.04-1.06 (m, 6H), 1.22-1.46 (br. m, 5H), 1.51 (d, J=5.2 Hz, 3H), 1.68-1.80 (br. m, 5H), 1.97 (s, 3H), 2.24-2.37 (m, 3H), 3.06-3.11 (m, 2H), 3.33-3.38 (m, 2H), 3.79-3.82 (2s, 1H), 3.93-3.95 (2d, J=9.2, 9.2 Hz, 1H), 4.13-4.18 (dd, J=9.2 Hz, 9.6 Hz, 1H), 4.32-4.36 (2d, J=10.8, 11.2 Hz, 1H), 4.58-4.64 (2d, J=11.6, 11.2 Hz, 1H), 5.73-5.79 (br. m, 1H), 6.91-6.96 (m, 1H), 7.30-7.37 (m, 5H) ppm. MS (ESI) m/z 555.09 $(M+H)^+$, 578.09 $(M+Na)^+$. The analytical data was consistent with the proposed structure.

Step D: (Cyclohexylcarbonyloxy)ethyl (2R)-4-{[3-(acetylamino)propyl]sulfonyloxy}-2-hydroxy-3,3-dimethylbutanoate (44)

Following the general procedure for the hydrogenolysis of benzyl ethers of Description 18, a mixture of (cyclohexylcarbonyloxy)ethyl (2R)-4-{[3-(acetylamino)propyl]sulfonyloxy}-3,3-dimethyl-2-(phenylmethoxy)butanoate (44c) (0.79 g, 1.4 mmol), 0.4 g of 10 wt.-% of palladium on activated carbon in 20 mL of methanol (MeOH), and 30 μL of one molar (1.0 M) of hydrochloric acid (HCl) was stirred overnight under a hydrogen atmosphere. Upon the completion of reaction and following aqueous work-up, 0.62 g (94% yield) of the title compound (44) was obtained as a colorless, viscous oil. $^1$H NMR (400 MHz, DMSO-$d^6$, both diastereomers): δ=0.92-0.94 (2s, 3H), 0.97-0.98 (2s, 3H), 1.20-1.42 (br. m, 5H), 1.46-1.48 (2d, J=5.6, 5.6 Hz, 3H), 1.55-1.62 (br. m, 1H), 1.66-1.70 (br. m, 2H), 1.80-1.87 (m, 7H), 2.33-2.40 (m, 1H), 3.14-3.19 (m, 2H), 3.34-3.37 (m, 2H), 3.92-3.96 (m, 2H), 4.09-4.12 (2d, J=9.2, 9.6 Hz, 1H), 5.50-6.87 (2d, J=5.2, 5.6 Hz, 1H), 6.81-6.87 (m, 1H), 7.95-7.98 (br. m, 1H) ppm. MS (ESI) m/z: 466.10 $(M+H)^+$, 488.07 $(M+Na)^+$. The analytical data was consistent with the proposed structure.

Example 45

(2-Hydroxyacetyloxy)ethyl (2R)-4-{[3-(acetylamino)propyl]sulfonyloxy}-2-hydroxy-3,3-dimethylbutanoate (45)

Step A: [2-(phenylmethoxy)acetyloxy]ethyl (2R)-4-{[3-(acetylamino)propyl]sulfonyloxy}-3,3-dimethyl-2-(phenylmethoxy)butanoate (45a)

Following the general procedure for the preparation of acyloxyalkyl/alkoxycarbonyloxyalkyl carboxylic esters from carboxylic acids of Description 22, (2R)-4-{[3-(acetylamino)propyl]sulfonyloxy}-3,3-dimethyl-2-(phenylmethoxy)butanoic acid (17) (0.8 g, 2.0 mmol) dissolved in 12 mL of anhydrous toluene was reacted with 1.4 g (6.0 mmol) of 1-chloroethyl 2-(phenylmethoxy)acetate (25) in the presence of 1.1 g (4.0 mmol) of silver carbonate ($Ag_2CO_3$). After work-up and further purification by mass-guided preparative HPLC, 0.1 g (8.4% yield) of the title compound (45a) was obtained as a colorless, viscous oil. MS (ESI) m/z 594.15 $(M+H)^+$, 616.20 $(M+Na)^+$.

Step B: (2-Hydroxyacetyloxy)ethyl (2R)-4-{[3-(acetylamino)propyl]sulfonyloxy}-2-hydroxy-3,3-dimethylbutanoate (45)

Following the general procedure of hydrogenolysis of benzyl ethers of Description 18, a mixture of [2-(phenylmethoxy)acetyloxy]ethyl (2R)-4-{[3-(acetylamino)propyl]sulfonyloxy}-3,3-dimethyl-2-(phenylmethoxy)butanoate (45a) (0.10 g, 0.17 mmol) and 0.1 g of 10 wt.-% of palladium on activated carbon in 6 mL of a mixture of methanol (MeOH) and ethyl acetate (EtOAc) was stirred overnight under a hydrogen atmosphere. After work-up and further purification by mass-guided preparative HPLC, 51 mg (73% yield) of the title compound (45) was obtained as a colorless, viscous oil after lyophilization of the solvents. $^1$H NMR (400 MHz, $CDCl_3$, both diastereomers): δ=1.02-1.05 (2s, 3H), 1.10-1.13 (2s, 3H), 1.60 (t, J=5.2 Hz, 3H), 2.01 (s, 3H), 2.05-2.12 (m, 2H), 2.84-3.03 (br. m, 1H), 3.14-3.26 (m, 2H), 3.34-3.46 (m, 2H), 3.97-4.16 (m, 3H), 4.22 (s, 2H), 5.56-5.96 (br. m, 1H), 7.00-7.08 (m, 1H) ppm. MS (ESI) m/z: 414.02 $(M+H)^+$, 435.96 $(M+Na)^+$. The analytical data was consistent with the proposed structure.

Example 46

(3-Hydroxy-2,2-dimethylpropanoyloxy)ethyl (2R)-4-{[3-(acetylamino)propyl]sulfonyloxy}-2-hydroxy-3,3-dimethylbutanoate (46)

Step A: [2,2-Dimethyl-3-(phenylmethoxy)propanoyloxy]ethyl (2R)-4-[(3-chloropropyl)sulfonyloxy]-3,3-dimethyl-2-(phenylmethoxy)butanoate (46a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(phenylmethoxy)butanoic acid (11) (0.38 g, 1.0 mmol) dissolved in 3 mL of anhydrous toluene was reacted with 0.21 g (0.78 mmol) of 1-chloroethyl 2,2-dimethyl-3-(phenylmethoxy)propanoate (26) in the presence of 0.27 g (1.0 mmol) of silver carbonate ($Ag_2CO_3$). After work-up, the crude material was purified by silica gel column chromatography using a mixture of ethyl acetate (EtOAc) and n-heptane (Hptn) (EtOAc/Hptn=1:4) as eluent to provide a mixture of 0.47 g of the title compound (46a). $R_f$=0.37 (EtOAc/Hptn=1:4). MS (ESI) m/z 635.15 $(M+Na)^+$.

Step B: [2,2-Dimethyl-3-(phenylmethoxy)propanoyloxy]ethyl (2R)-4-[(3-azidopropyl)sulfonyloxy]-3,3-dimethyl-2-(phenylmethoxy)butanoate (46b)

Following the general procedure for the preparation of azides of Description 16, [2,2-dimethyl-3-(phenylmethoxy)propanoyloxy]ethyl (2R)-4-[(3-chloropropyl)sulfonyloxy]-3,3-dimethyl-2-(phenylmethoxy)butanoate (46a) (0.47 g, 0.77 mmol, max.) dissolved in 4 mL of anhydrous dimethyl sulfoxide (DMSO) was reacted with 90 mg (1.4 mmol) of sodium azide ($NaN_3$). After work-up, the crude material was purified by silica gel column chromatography using a mixture of ethyl acetate (EtOAc) and n-heptane (Hptn) (EtOAc/Hptn=1:4) as eluent to provide a mixture of 0.13 g (27%

151 yield) of the title compound (46b). $R_f$=0.17 (EtOAc/Hept=1:4). MS (ESI) m/z 642.20 (M+Na)$^+$.

Step C: [2,2-Dimethyl-3-(phenylmethoxy)propanoyloxy]ethyl (2R)-4-{[(3-acetylamino)propyl]sulfonyloxy}-3,3-dimethyl-2-(phenylmethoxy)butanoate (46c)

Following the general procedure for the reduction of azides by hydrogenation of Description 17, a mixture of [2,2-dimethyl-3-(phenylmethoxy)propanoyloxy]ethyl (2R)-4-[(3-azidopropyl)sulfonyloxy]-3,3-dimethyl-2-(phenylmethoxy)butanoate (46b) (0.13 g, 0.21 mmol), 0.1 mL (93 mg, 0.91 mmol) of acetic anhydride (Ac$_2$O), and 72 mg of 10 wt-% palladium on activated carbon in 6 mL of a mixture of methanol (MeOH) and ethyl acetate (EtOAc) (MeOH/EtOAc=1:1), was stirred overnight under a hydrogen atmosphere. After work-up, the crude title compound (46c) was obtained and used in the next step without further purification. MS (ESI) m/z 636.25 (M+H)$^+$.

Step D: (3-Hydroxy-2,2-dimethylpropanoyloxy)ethyl (2R)-4-{[3-(acetylamino)propyl]sulfonyloxy}-2-hydroxy-3,3-dimethylbutanoate (46)

Following the general procedure of hydrogenolysis of benzyl ethers of Description 18, a mixture of [2,2-dimethyl-3-(phenylmethoxy)propanoyloxy]ethyl (2R)-4-{[3-(acetylamino)propyl]sulfonyloxy}-3,3-dimethyl-2-(phenylmethoxy)butanoate (46c) (0.13 g, 0.21 mmol) and 75 mg of 10 wt.-% of palladium on activated carbon in 6 mL of methanol (MeOH) was stirred overnight under a hydrogen atmosphere. After work-up and further purification by mass-guided preparative HPLC, 24 mg (25% yield) of the title compound (46) was obtained as a colorless, viscous oil. $^1$H NMR (400 MHz, CDCl$_3$, both diastereomers): δ=0.96-0.99 (2s, 3H), 1.10-1.11 (2s, 3H), 1.18 (s, 3H), 1.20-1.21 (2s, 3H), 1.55-1.57 (2d, J=5.2, 5.6 Hz, 3H), 1.98-1.99 (2s, 3H), 2.03-2.12 (m, 2H), 2.54-2.68 (br. m, 1H), 3.11-3.29 (m, 2H), 3.30-3.51 (m, 3H), 3.51-3.63 (m, 2H), 3.93-3.96 (2d, J=8.8, 9.2 Hz, 1H), 4.05-4.07 (m, 1H), 4.14-4.17 (2d, J=9.6, 9.6 Hz, 1H), 5.92-5.98 (br. m, 1H), 6.91-6.98 (m, 1H) ppm. MS (ESI) m/z: 456.07 (M+H)$^+$, 478.02 (M+Na)$^+$. The analytical data was consistent with the proposed structure.

Example 47

2-Methyl-1-(methylethoxycarbonyloxy)propyl (2R)-4-{[3-(acetylamino)propyl]sulfonyloxy}-2-hydroxy-3,3-dimethylbutanoate (47)

Step A: 2-Methyl-1-(methylethoxycarbonyloxy)propyl (2R)-4-[(3-chloropropyl)sulfonyloxy]-3,3-dimethyl-2-(1,1,2,2-tetramethyl-1-silapropoxy)butanoate (47a)

Following the general procedure for the preparation of acyloxyalkyl/alkoxycarbonyloxyalkyl carboxylic esters from carboxylic acids of Description 22, (2R)-4-[(3-chloropropyl)sulfonyloxy]-3,3-dimethyl-2-(1,1,2,2-tetramethyl-1-silapropoxy)butanoic acid (15) (0.4 g, 0.99 mmol) dissolved in 5 mL of anhydrous toluene was reacted with 0.57 g (3.0 mmol) of 1-chloro-(2-methylpropyl)(methylethoxy)formate in the presence of 0.33 g (1.1 mmol) of silver carbonate (Ag$_2$CO$_3$). After work-up, the crude material was purified by silica gel column chromatography using a mixture of ethyl acetate (EtOAc) and hexane (Hxn) (EtOAc/Hxn=1:2) as eluent to provide 0.37 g of a mixture of the title compound (47a) and (3R)-4,4-dimethyl-3-(1,1,2,2-tetramethyl-1-silapropoxy)-3,4,5-trihydrofuran-2-one (4a). MS (ESI) m/z 583.12 (M+Na)$^+$.

Step B: 2-Methyl-1-(methylethoxycarbonyloxy)propyl (2R)-4-[(3-azidopropyl)sulfonyloxy]-3,3-dimethyl-2-(1,1,2,2-tetramethyl-1-silapropoxy)butanoate (47b)

Following the general procedure for the preparation of azides of Description 16, a mixture of 2-methyl-1-(methylethoxycarbonyloxy)propyl (2R)-4-[(3-chloropropyl)sulfonyloxy]-3,3-dimethyl-2-(1,1,2,2-tetramethyl-1-silapropoxy)butanoate (47a) (0.6 g max.) dissolved in 5 mL of anhydrous dimethyl sulfoxide (DMSO) was reacted with 69 mg (1.1 mmol) of sodium azide (NaN$_3$). After work-up, the crude title compound (47b) was used in the next step without further purification. MS (ESI) m/z 590.22 (M+Na)$^+$.

Step C: 2-Methyl-1-(methylethoxycarbonyloxy)propyl (2R)-4-{[(3-acetylamino)propyl]sulfonyloxy}-3,3-dimethyl-2-(1,1,2,2-tetramethyl-1-silapropoxy)butanoate (47c)

Following the general procedure for the reduction of azides by hydrogenation of Description 17, a mixture of 2-methyl-1-(methylethoxycarbonyloxy)propyl (2R)-4-[(3-azidopropyl)sulfonyloxy]-3,3-dimethyl-2-(1,1,2,2-tetramethyl-1-silapropoxy)butanoate (47b) (0.6 g maximum), 0.3 mL (0.32 g, 0.32 mmol) of acetic anhydride (Ac$_2$O), and 100 mg of 10 wt-% palladium on activated carbon in 10 mL of a mixture of methanol (MeOH) and ethyl acetate (EtOAc) was stirred overnight under a hydrogen atmosphere. After work-up, the crude material was purified by silica gel column chromatography using of a mixture of methanol (MeOH) and ethyl acetate (EtOAc) (MeOH/EtOAC=1:19) as eluent to provide 80 mg (14% yield over three steps) of the title compound (47c) as a colorless oil. $^1$H NMR (400 MHz, CDCl$_3$, both diastereomers): δ=0.04-0.05 (m, 3H), 0.06-0.07 (m, 3H), 0.89-0.92 (m, 12H), 1.01-1.05 (m, 9H), 1.29-1.32 (m, 6H), 1.78-1.84 (m, 1H), 2.06 (s, 3H), 2.08-2.10 (m, 2H), 3.14-3.19 (m, 2H), 3.39-3.44 (m, 2H), 3.99-4.09 (m, 3H), 4.84-4.92 (m, 1H), 6.04-6.07 (br. m, 1H), 6.53-6.60 (d, J=4.8, 4.0 Hz, 1H) ppm. MS (ESI) m/z 584.29 (M+H)$^+$, 606.28 (M+Na)$^+$. The analytical data was consistent with proposed structure.

Step D: 2-Methyl-1-(methylethoxycarbonyloxy)propyl (2R)-4-{[3-(acetylamino)propyl]sulfonyloxy}-2-hydroxy-3,3-dimethylbutanoate (47)

Following the general procedure for the cleavage of silyl ethers with triethylamine trihydrofluoride of Description 20, a mixture of 2-methyl-1-(methylethoxycarbonyloxy)propyl (2R)-4-{[(3-acetylamino)propyl]sulfonyloxy}-3,3-dimethyl-2-(1,1,2,2-tetramethyl-1-silapropoxy)butanoate (47c) (80 mg, 0.14 mmol) and triethylamine trihydrofluoride (Et$_3$N.3HF) 89 μL (88 mg, 0.55 mmol) in 2 mL tetrahydrofuran (THF) was stirred overnight at ca. 50-60° C. (oil bath). After work-up and isolation, the crude material was purified by silica gel column chromatography using ethyl acetate (EtOAc) and methanol (MeOH) mixtures (EtOAc/MeOH=19:1) as eluent to provide 20 mg (30% yield) of the title compound (47) as a colorless oil. $^1$H NMR (400 MHz, CDCl$_3$, both diastereomers): δ=0.96-1.00 (2s, 3H), 1.01-1.05 (m, 6H), 1.14-1.16 (2s, 3H), 1.30-1.34 (m, 6H), 1.99-2.01 (m, 4H), 2.03-2.15 (m, 2H), 3.13-3.24 (m, 2H), 3.33 (d, J=6.8 Hz, 1H), 3.35-3.45 (m, 2H), 3.90-3.96 (2d, J=9.2, 9.6 Hz, 1H), 4.07-4.10 (2d, J=6.8, 6.8 Hz, 1H), 4.16-4.21 (2d, J=9.2, 9.2 Hz, 1H), 4.85-4.94 (m, 1H), 5.98-6.03 (br. m, 1H), 6.58-6.63 (dd, J=4.4 Hz, 4.8 Hz, 1H) ppm. MS (ESI) m/z 470.07 $(M+H)^+$, 492.06 $(M+Na)^+$. The analytical data was consistent with proposed structure.

Example 48

(5-Methyl-2-oxo-1,3-dioxolen-4-yl)methyl (2R)-4-{[3-(acetylamino)propyl]sulfonyloxy}-2-hydroxy-3,3-dimethylbutanoate (48)

Step A: (5-Methyl-2-oxo-1,3-dioxolen-4-yl)methyl (2R)-4-{[3-(acetylamino)propyl]sulfonyloxy}-3,3-dimethyl-2-(1,1,2,2-tetramethyl-1-silapropoxy)butanoate (48a)

Following the general procedure for the preparation of acyloxyalkyl/alkoxycarbonyloxyalkyl carboxylic esters from carboxylic acids of Description 22, (2R)-4-{[3-(acetylamino)propyl]sulfonyloxy}-3,3-dimethyl-2-(1,1,2,2-tetramethyl-1-silapropoxy)butanoic acid (19) (1.5 g, 3.5 mmol) dissolved in 15 mL of anhydrous toluene was reacted with 1.4 g (7.0 mmol) of commercially available 5-bromomethyl-4-methyl-1,3-dioxolen-2-one in the presence of 1.4 g (5.3 mmol) of silver carbonate ($Ag_2CO_3$). After work-up and further purification by mass-guided preparative HPLC, 0.1 g (5.3% yield) of the title compound (48a) was obtained as a colorless, viscous oil. $R_f$=0.62 (EtOAc/MeOH=19:1). MS (ESI) m/z 538.14 $(M+H)^+$, 560.13 $(M+Na)^+$. The analytical data was consistent with the proposed structure.

Step B: (5-Methyl-2-oxo-1,3-dioxolen-4-yl)methyl (2R)-4-{[3-(acetylamino)propyl]sulfonyloxy}-2-hydroxy-3,3-dimethylbutanoate (48)

Following the general procedure for the cleavage of silyl ethers with triethylamine trihydrofluoride of Description 20, a mixture of (5-methyl-2-oxo-1,3-dioxolen-4-yl)methyl (2R)-4-{[(3-acetylamino)propyl]sulfonyloxy}-3,3-dimethyl-2-(1,1,2,22-tetramethyl-1-silapropoxy)butanoate (48a) (100 mg, 0.18 mmol) and triethylamine trihydrofluoride ($Et_3N.3HF$) 150 μL (149 mg, 0.93 mmol) in 2 mL of tetrahydrofuran (THF) was stirred overnight at ca. 50-60° C. (oil bath). After work-up and further purification by mass-guided preparative HPLC and lyophilization of the solvents, 6.2 mg (8.1% yield) of the title compound (48) was obtained as a colorless, viscous oil. $^1H$ NMR (400 MHz, $CDCl_3$): δ=1.03 (s, 3H), 1.11 (s, 3H), 2.01 (s, 3H), 2.04-2.11 (m, 2H), 2.22 (s, 3H), 3.10-3.23 (m, 2H), 3.31-3.46 (m, 2H), 4.00 (d, J=9.2 Hz, 1H), 4.07-4.10 (m, 2H), 4.93 (d, J=14.0 Hz, 1H), 5.03 (d, J=13.6 Hz, 1H), 5.86-5.88 (br. m, 1H) ppm. MS (ESI) m/z 424.01 $(M+H)^+$, 446.01 $(M+Na)^+$. The analytical data was consistent with the proposed structure.

Description 23

General Procedure for O-Phosphorylation

Adapting procedures, or variations thereof, according to Barlett et al., *J. Am. Chem. Soc.,* 1984, 106, 7854-7860; and Aaki et al., *J. Org. Chem.,* 1986, 51, 2126-2128, a round-bottomed flask equipped with a magnetic stirring bar and a rubber septum was charged with 1.0 mol-eq. of a functionalized neopentylalcohol, i.e., (2-methylpropanoyloxy)ethyl (2R)-4-{[3-(acetylamino)propyl]sulfonyloxy}-3,3-dimethyl-2-hydroxy-butanoate (29), (ethoxycarbonyloxy)ethyl (2R)-4-{[3-(acetylamino)propyl]sulfonyloxy}-3,3-dimethyl-2-hydroxy-butanoate (32), or others. The neopentylalcohol was dissolved in dichloromethane (DCM) (ca. 0.5-1.0 M). The solution was cooled to ca. 0° C. (ice-bath) and 2.0-3.0 mol-eq. of commercially available) diphenyl chlorophosphate [$(PhO)_2POCl$] was added. To the cooled solution was added 0.1-0.5 mol-eq. of 4-(N,N-dimethylamino)pyridine (DMAP) followed by slow addition of 1.0-1.2 mol-eq. of triethylamine ($Et_3N$, TEA). The solution was stirred and gradually warmed to room temperature overnight. Upon completion of the reaction, the solvent was evaporated under reduced pressure. The residue was diluted with ethyl acetate (EtOAc) or methyl tert-butyl ether (MTBE) and washed with a one molar (1.0 M) of hydrochloric acid (HCl). The aqueous phase was extracted several times with ethyl acetate (EtOAc) or methyl tert-butyl ether (MTBE) and the combined organic extracts were washed with a saturated aqueous solution of sodium hydrogen carbonate ($NaHCO_3$), then brine, and dried over anhydrous magnesium sulfate ($MgSO_4$). After filtration, the solvent was removed under reduced pressure using a rotary evaporator. The isolated material was further purified by silica gel column chromatography using mixtures or gradients thereof of hexane (Hxn) and ethyl acetate (EtOAc) or methyl tert-butyl ether (MTBE) as eluent to yield the target compounds usually as colorless, viscous oils.

Description 24

General Procedure for the Removal of a Phenyl Protecting Group via Catalytic Hydrogenolysis Adapting procedures or variations thereof according to Kuijpers et al., *Nucleic Acids Res.* 1990, 18, 5197; and Perich et al., *Aust. J. Chem.* 1991, 44, 233, in a representative synthesis a suitable-sized round-bottomed flask equipped with a magnetic stirring bar and a three-way adapter connected to a hydrogen-filled balloon was charged with 1.0 mol-eq. of the diphenyl phosphate conjugate in methanol (0.25-0.5 M). Platinum(IV) oxide ($PtO_2$, Adam's catalyst) or platinum(IV) oxide hydrate ($PtO_2H_2O$) (10 mol-%) was added to the solution. The atmosphere was exchanged to hydrogen using three evacuation and refill cycles and the reaction mixture was stirred overnight under a hydrogen atmosphere at a pressure of approximately 15 psi and at room temperature. The reaction was monitored by LC/MS. Upon completion of the reaction, the solids (heterogeneous catalyst) were filtered off using a short plug of Celite® and the solvent removed under reduced pressure using a rotary evaporator. The residue was dissolved in a mixture of ca. 60% (v/v) acetonitrile/water, the solution filtered through a 0.2-μm nylon syringe filter, and purified by mass-guided preparative HPLC. After lyophilization of the solvents, the desired product was obtained, typically as a colorless solid.

Example 49

(2-Methylpropanoyloxy)ethyl (2R)-4-{[3-(acetylamino)propyl]sulfonyloxy}-3,3-dimethyl-2-(oxyphosphinyloxyphosphinyl)butanoate (49)

Step A: (2-Methylpropanoyloxy)ethyl (2R)-4-{[3-(acetylamino)propyl]sulfonyloxy}-3,3-dimethyl-2-(phenoxyphosphinyl)butanoate (49a)

Following the general procedure for phosphorylation of Description 23, (2-methylpropanoyloxy)ethyl (2R)-4-{[3-

(acetylamino)propyl]sulfonyloxy}-3,3-dimethyl-2-hydroxy-butanoate (29) (1.0 g, 2.4 mmol) dissolved in 20 mL of anhydrous dichloromethane (DCM) was reacted with 1.46 mL (1.9 g, 7.0 mmol) of diphenyl chlorophosphate [(PhO)$_2$POCl] in the presence of 4-(N,N-dimethylamino)pyridine (DMAP) (0.17 g, 1.4 mmol) and triethylamine (TEA) (0.97 mL, 0.71 g, 7.0 mmol). The reaction was monitored by TLC. After aqueous work-up, the crude material was further purified by silica gel column chromatography using ethyl acetate (EtOAc) as eluent to provide 1.2 g (80% yield) of the title compound (49a) as a colorless oil. $R_f$=0.55 (EtOAc). $^1$H NMR (400 MHz, CDCl$_3$, both diastereomers): δ=1.06-1.15 (m, 12H), 1.40-1.46 (2d, J=5.6, 5.6 Hz, 3H), 1.85 (s, 3H), 2.01-2.08 (m, 2H), 2.45-2.55 (m, 1H), 3.13-3.17 (m, 2H), 3.28-3.33 (m, 2H), 3.97-4.04 (m, 2H), 4.84-4.88 (2d, J=7.2, 7.6 Hz, 1H), 6.32-6.36 (br. m, 1H), 6.88-6.93 (m, 1H), 7.18-7.26 (m, 6H), 7.31-7.38 (m, 4H) ppm. MS (ESI) m/z 658.25 (M+H)$^+$. The analytical data was consistent with proposed structure.

Step B: (2-Methylpropanoyloxy)ethyl (2R)-4-{[3-(acetylamino)propyl]sulfonyloxy}-3,3-dimethyl-2-(oxyphosphinyloxyphosphinyl)butanoate (49)

Following the general procedure for the removal of a phenyl protecting group via catalytic hydrogenolysis of Description 24, a mixture of (2-methylpropanoyloxy)ethyl (2R)-4-{[3-(acetylamino)propyl]sulfonyloxy}-3,3-dimethyl-2-(phenoxyphosphinyl)butanoate (49a) (1.0 g, 1.5 mmol) and 150 mg (0.66 mmol) of platinum oxide (PtO$_2$) in 20 mL of methanol was stirred overnight under a hydrogen atmosphere. After purification by mass-guided preparative HPLC and lyophilization of the solvents, 700 mg (92% yield) of the title compound (49) was obtained as a colorless solid. $^1$H NMR (400 MHz, CDCl$_3$, both diastereomers): δ=1.01-1.02 (2s, 3H), 1.07 (s, 3H), 1.13-1.16 (m, 6H), 1.51-1.53 (m, 3H), 2.11-2.13 (m, 5H), 2.49-2.61 (m, 1H), 3.27-3.43 (m, 4H), 3.94-3.97 (m, 1H), 4.09-4.13 (m, 1H), 4.51 (d, J=8.4 Hz, 1H), 6.88-6.94 (m, 1H), 7.64-7.70 (br. m, 1H), 7.85-8.15 (br. m, 2H) ppm. MS (ESI) m/z 506.04 (M+H)$^+$, 528.04 (M+Na)$^+$. The analytical data was consistent with the proposed structure.

Example 50

(Cyclohexylcarbonyloxy)ethyl (2R)-4-{[3-(acetylamino)propyl]sulfonyloxy}-3,3-dimethyl-2-(oxyphosphinyloxyphosphinyl)butanoate (50)

Step A: (Cyclohexylcarbonyloxy)ethyl (2R)-4-{[3-(acetylamino)propyl]sulfonyloxy}-3,3-dimethyl-2-(phenoxyphosphinyl)butanoate (50a)

Following the general procedure for phosphorylation of Description 23, (cyclohexylcarbonyloxy)ethyl (2R)-4-{[3-(acetylamino)propyl]sulfonyloxy}-3,3-dimethyl-2-hydroxy-butanoate (43) (0.47 g, 1.0 mmol) dissolved in 25 mL of anhydrous dichloromethane (DCM) was reacted with 0.62 mL (0.80 g, 3.0 mmol) of diphenyl chlorophosphate [(PhO)$_2$POCl] in the presence of 4-(N,N-dimethylamino)pyridine (DMAP) (0.12 g, 1.0 mmol) and triethylamine (TEA) (0.42 mL, 0.30 g, 3.0 mmol). The reaction was monitored by TLC. After aqueous work-up, the crude material was further purified by silica gel column chromatography using ethyl acetate (EtOAc) as eluent to provide 0.59 g (85% yield) of the title compound (50a) as a colorless oil. $R_f$=0.56 (EtOAc). $^1$H NMR (400 MHz, CDCl$_3$, both diastereomers): δ=0.97-0.99 (br. m, 1H), 1.06-1.07 (ss, 3H), 1.09-1.10 (2s, 3H), 1.18-1.24 (br. m, 3H), 1.34-1.46 (m, 5H), 1.67-1.72 (br. m, 2H), 1.82-1.85 (m, 5H), 2.00-2.05 (m, 2H), 2.19-2.28 (m, 1H), 3.13-3.17 (m, 2H), 3.28-3.33 (m, 2H), 3.97-4.04 (m, 2H), 4.84-4.88 (2d, J=8.0, 8.0 Hz, 1H), 6.34-6.38 (br. m, 1H), 6.89-6.94 (m, 1H), 7.18-7.24 (m, 6H), 7.33-7.38 (m, 4H) ppm. MS (ESI) m/z 698.26 (M+H)$^+$, 720.22 (M+Na)$^+$. The analytical data was consistent with proposed structure.

Step B: (Cyclohexylcarbonyloxy)ethyl (2R)-4-{[3-(acetylamino)propyl]sulfonyloxy}-3,3-dimethyl-2-(oxyphosphinyloxyphosphinyl)butanoate (50)

Following the general procedure for the removal of a phenyl protecting group via catalytic hydrogenolysis of Description 24, a mixture of (cyclohexylcarbonyloxy)ethyl (2R)-4-{[3-(acetylamino)propyl]sulfonyloxy}-3,3-dimethyl-2-(phenoxyphosphinyl)butanoate (50a) (0.60 g, 0.85 mmol) and 125 mg (0.55 mmol) of platinum oxide (PtO$_2$) in 20 mL of methanol was stirred overnight under a hydrogen atmosphere. After purification by mass-guided preparative HPLC, 0.28 g (60% yield) of the title compound (50) was obtained as a colorless solid after lyophilization of the solvent. $^1$H NMR (400 MHz, CD$_3$OD, both diastereomers): δ=1.09 (s, 3H), 1.10-1.11 (s, 3H), 1.26-1.49 (br. m, 5H), 1.53-1.54 (2d, J=5.2, 5.6 Hz, 3H), 1.66-1.69 (br. m, 1H), 1.75-1.79 (br. m, 2H), 1.90-1.94 (br. m, 2H), 1.98 (s, 3H), 2.01-2.08 (m, 2H), 2.34-2.42 (m, 1H), 3.29-3.35 (m, 4H), 4.06-4.13 (m, 2H), 4.51-4.54 (2d, J=8.0, 8.0 Hz, 1H), 6.92-6.98 (m, 1H) ppm. MS (ESI) m/z 546.04 (M+H)$^+$, 567.99 (M+Na)$^+$. The analytical data was consistent with proposed structure.

Example 51

(Ethoxycarbonyloxy)ethyl (2R)-4-{[3-(acetylamino)propyl]sulfonyloxy}-3,3-dimethyl-2-(oxyphosphinyloxyphosphinyl)butanoate (51)

Step A: (Ethoxycarbonyloxy)ethyl (2R)-4-{[3-(acetylamino)propyl]sulfonyloxy}-3,3-dimethyl-2-(phenoxyphosphinyl)butanoate (51a)

Following the general procedure for phosphorylation of Description 23, (ethoxycarbonyloxy)ethyl (2R)-4-{[3-(acetylamino)propyl]sulfonyloxy}-3,3-dimethyl-2-hydroxy-butanoate (32) (0.43 g, 1.0 mmol) dissolved in 10 mL of anhydrous dichloromethane (DCM) was reacted with 0.58 mL (0.67 g, 2.5 mmol) of diphenyl chlorophosphate [(PhO)$_2$POCl] in the presence of 4-(N,N-dimethylamino)pyridine (DMAP) (0.12 g, 1.0 mmol) and triethylamine (TEA) (0.35 mL, 0.25 g, 2.5 mmol). The reaction was monitored by TLC. After aqueous work-up, the crude material was further purified by silica gel column chromatography using ethyl acetate (EtOAc) as eluent to provide 0.43 g (65% yield) of the title compound (51a) as a colorless oil. $R_f$=0.45 (EtOAc). $^1$H NMR (400 MHz, CDCl$_3$, both diastereomers): δ=1.09-1.10 (2s, 3H), 1.12-1.13 (2s, 3H), 1.26-1.32 (m, 3H), 1.45-1.52 (2d, J=5.6, 5.6 Hz, 3H), 1.86-1.87 (2s, 3H), 2.01-2.06 (m, 2H), 3.15-3.17 (m, 2H), 3.39-3.34 (m, 2H), 3.98-4.05 (m, 2H), 4.15-4.22 (m, 3H), 4.87-4.91 (2d, J=7.6, 7.6 Hz, 1H), 6.30-6.34 (br. m, 1H), 6.81-6.83 (m, 1H), 7.18-7.26 (m, 6H), 7.33-7.38 (m, 4H) ppm. MS (ESI) m/z 660.11 (M+H)$^+$, 681.94 (M+Na)$^+$. The analytical data was consistent with the proposed structure.

Step B: (Ethoxycarbonyloxy)ethyl (2R)-4-{[3-(acetylamino)propyl]sulfonyloxy}-3,3-dimethyl-2-(oxyphosphinyloxyphosphinyl)butanoate (51)

Following the general procedure for the removal of a phenyl protecting group via catalytic hydrogenolysis of Description 24, a mixture of (ethoxycarbonyloxy)ethyl (2R)-4-{[3-(acetylamino)propyl]sulfonyloxy}-3,3-dimethyl-2-(phenoxyphosphinyl)butanoate (51a) (0.49 g, 0.73 mmol) and 62 mg (0.27 mmol) of platinum oxide (PtO$_2$) in 25 mL of methanol was stirred overnight under a hydrogen atmosphere. After purification by mass-guided preparative HPLC, 0.13 g (35% yield) of the title compound (51) was obtained as a white solid. $^1$H NMR (400 MHz, CD$_3$OD, both diastereomers): δ=0.97-0.98 (2s, 3H), 1.01 (s, 3H), 1.20 (t, J=7.2 Hz, 3H), 1.43-1.45 (2d, J=5.2, 4.8 Hz, 3H), 1.86 (s, 3H), 1.89-1.96 (m, 2H), 3.16-3.23 (m, 4H), 3.94-4.00 (m, 2H), 4.08-4.14 (m, 2H), 4.40-4.42 (2d, J=8.4, 8.0 Hz, 1H), 6.68-6.73 (m, 1H) ppm. MS (ESI) m/z 507.76 (M+H)$^+$, 529.71 (M+Na)$^+$. The analytical data was consistent with proposed structure.

Example 52

(Methylethoxycarbonyloxy)ethyl (2R)-4-{[3-(acetylamino)propyl]sulfonyloxy}-3,3-dimethyl-2-(oxyphosphinyloxyphosphinyl)butanoate (52)

Step A: (Methylethoxycarbonyloxy)ethyl (2R)-4-{[3-(acetylamino)propyl]sulfonyloxy}-3,3-dimethyl-2-(phenoxyphosphinyl)butanoate (52a)

Following the general procedure for phosphorylation of Description 23, (methylethoxycarbonyloxy)ethyl (2R)-4-{[3-(acetylamino)propyl]sulfonyloxy}-3,3-dimethyl-2-hydroxy-butanoate (40) (0.88 g, 2.0 mmol) dissolved in 10 mL of anhydrous dichloromethane (DCM) was reacted with 0.58 mL (1.6 g, 6.0 mmol) of diphenyl chlorophosphate [(PhO)$_2$POCl] in the presence of 4-(N,N-dimethylamino)pyridine (DMAP) (0.12 g, 1.0 mmol) and triethylamine (TEA) (0.84 mL, 0.61 g, 6.0 mmol). The reaction was monitored by TLC. After aqueous work-up, the crude material was further purified by silica gel column chromatography using ethyl acetate (EtOAc) as eluent to provide 1.1 g (81% yield) of the title compound (52a) as a colorless oil. R$_f$=0.45 (EtOAc). $^1$H NMR (400 MHz, CDCl$_3$, both diastereomers): δ=1.08-1.09 (2s, 3H), 1.12-1.13 (2s, 3H), 1.25-1.32 (m, 6H), 1.44-1.50 (2d, J=5.6, 5.6 Hz, 3H), 1.85 (s, 3H), 1.99-2.06 (m, 2H), 3.13-3.18 (m, 2H), 3.28-3.32 (m, 2H), 3.98-4.05 (m, 2H), 4.82-4.91 (m, 2H), 6.38-6.42 (br. m, 1H), 6.79-6.85 (m, 1H), 7.15-7.23 (m, 6H), 7.30-7.38 (m, 4H) ppm. MS (ESI) m/z 674.19 (M+H)$^+$, 696.09 (M+Na)$^+$. The analytical data was consistent with the proposed structure.

Step B: (Methylethoxycarbonyloxy)ethyl (2R)-4-{[3-(acetylamino)propyl]sulfonyloxy}-3,3-dimethyl-2-(oxyphosphinyloxyphosphinyl)butanoate (52)

Following the general procedure for the removal of a phenyl protecting group via catalytic hydrogenolysis of Description 24, a mixture of (methylethoxycarbonyloxy)ethyl (2R)-4-{[3-(acetylamino)propyl]sulfonyloxy}-3,3-dimethyl-2-(phenoxyphosphinyl)butanoate (52a) (0.60 g, 0.90 mmol) and 45 mg (0.20 mmol) of platinum oxide (PtO$_2$) in 30 mL of methanol was stirred overnight under a hydrogen atmosphere. After purification by mass-guided preparative HPLC, 54 mg (11% yield) of the title compound (52) was obtained as colorless solid. $^1$H NMR (400 MHz, CD$_3$OD, both diastereomers): δ=1.07 (s, 3H), 1.09-1.10 (2s, 3H), 1.28-1.30 (2d, J=6.4, 6.0 Hz, 6H), 1.52-1.54 (2d, J=5.6, 5.6 Hz, 3H), 1.99 (s, 3H), 1.99-2.06 (m, 2H), 3.26-3.23 (m, 4H), 4.03-4.10 (m, 2H), 4.49-4.52 (2d, J=8.4, 8.0 Hz, 1H), 4.83-4.88 (m, 1H), 6.76-6.83 (m, 1H) ppm. MS (ESI) m/z 521.94 (M+H)$^+$, 543.93 (M+Na)$^+$. The analytical data was consistent with the proposed structure.

Example 53

[2-(Oxyphosphinyloxyphosphinyl)acetyloxy]ethyl (2R)-4-{[3-(acetylamino)propyl]sulfonyloxy}-2-hydroxy-3,3-dimethylbutanoate (53)

Step A: [2-(Phenoxyphosphinyl)acetyloxy]ethyl (2R)-4-{[3-(acetylamino)propyl]sulfonyloxy}-2-hydroxy-3,3-dimethylbutanoate (53a)

Following the general procedure for phosphorylation of Description 23, (2-hydroxyacetyloxy)ethyl (2R)-4-{[3-(acetylamino)propyl]sulfonyloxy}-3,3-dimethyl-2-hydroxy-butanoate (45) (40 mg, 0.10 mmol) dissolved in 2 mL of anhydrous dichloromethane (DCM) was reacted with 60 L (78 mg, 0.29 mmol) of diphenyl chlorophosphate [(PhO)$_2$POCl] in the presence of pyridine (15.6 μL, 15.3 mg, 0.19 mmol) and triethylamine (TEA) (13.5 μL, 9.8 mg, 0.10 mmol). The reaction was monitored by TLC. After aqueous work-up, the crude title compound (53a) was obtained and used in the next step without purification. MS (ESI) m/z 646.05 (M+H)$^+$, 668.02 (M+Na)$^+$.

Step B: [2-(Oxyphosphinyloxyphosphinyl)acetyloxy]ethyl (2R)-4-{[3-(acetylamino)propyl]sulfonyloxy}-2-hydroxy-3,3-dimethylbutanoate (53)

Following the general procedure for the removal of a phenyl protecting group via catalytic hydrogenolysis of Description 24, a mixture of [2-(phenoxyphosphinyl)acetyloxy]ethyl (2R)-4-{[3-(acetylamino)propyl]sulfonyloxy}-2-hydroxy-3,3-dimethylbutanoate (53a) (0.10 mmol, maximum) and 25 mg (0.11 mmol) of platinum oxide (PtO$_2$) in 3 mL of methanol was stirred overnight under a hydrogen atmosphere. After purification by mass-guided preparative HPLC, 7.1 mg (15% yield over two steps) of the title compound (53) was obtained as a white solid. MS (ESI) m/z 493.94 (M+H)$^+$, 515.93 (M+Na)$^+$.

Example 54

Bioavailability of Acamprosate Following Administration of Acamprosate Prodrugs to Rats Rats were obtained commercially and were pre-cannulated in the jugular vein. Animals were conscious at the time of the experiment. All animals were fasted overnight and until 4 hours post-dosing of a prodrug of Formula (I).

Rat blood samples (0.3 mL/sample) were collected from all animals prior to dosing and at different time-points up to 24 h post-dose into tubes containing EDTA. Two aliquots (100 μL each) were quenched with 300 μL methanol and stored at −20° C. prior to analysis.

To prepare analysis standards, 90 μL of rat blood was quenched with 300 μL methanol followed by 10 μL of spiking standard and/or 20 μL of internal standard. The sample tubes were vortexed for at least 2 min and then centrifuged at 3400 rpm for 20 min. The supernatant was then transferred to an injection vial or plate for analysis by LC-MS-MS.

To prepare samples for analysis, 20 μL of internal standard was added to each quenched sample tube. The sample tubes were vortexed for at least 2 min and then centrifuged at 3400 rpm for 20 min. The supernatant was then transferred to an injection vial or plate for analysis by LC-MS-MS.

LC-MS-MS analysis was performed using an API 4000 equipped with Agilent 1100 HPLC and a Leap Technologies autosampler. The following HPLC column conditions were used: HPLC column: Thermal-Hypersil-Keystone C18, 4.6× 100 mm, 5 µm; mobile phase A: 0.1% formic acid in water; mobile phase B: 0.1% formic acid in acetonitrile; flow rate: 1.2 mL/min; gradient: 99% A/1% B at 0.0 min; 99% A/1% B at 0.5 min; 5% A/95% B at 1.8 min; 5% A/95% B at 3.5 min; 99% A/1% B at 3.6 min; and 99% A/1% B at 9.0 min. Acamprosate was monitored in negative ion mode. The LOQ was 0.004 µg/mL. The standard curve range was 0.004 to 10 µg/mL. Prodrug was monitored in positive ion mode. The LOQ and standard curve range was the same as for acamprosate.

Non-compartmental analysis was performed using Win-Nonlin software (v.3.1 Professional Version, Pharsight Corporation, Mountain View, Calif.) on individual animal profiles. Summary statistics on major parameter estimates was calculated for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

Acamprosate or acamprosate prodrug was administered by oral gavage to groups of four to six adult male Sprague-Dawley rats (about 250 g). Animals were conscious at the time of the experiment. Acamprosate or acamprosate prodrug was orally or colonically administered in 5% Phosal (53 MCT in 7.5% Tween 80 in 50 mM sodium phosphate buffer at pH 6.8) at a dose of 70 mg-equivalents acamprosate per kg body weight.

The percent relative bioavailability (F %) of acamprosate was determined by comparing the area under the acamprosate concentration vs time curve (AUC) following oral or colonic administration of an acamprosate prodrug or acamprosate with the AUC of the acamprosate concentration vs time curve following intravenous administration of acamprosate on a dose normalized basis. Compounds (29), (40), and (32) exhibited an acamprosate oral bioavailability at least about 5 times greater than the acamprosate oral bioavailability of an equivalent dose of acamprosate itself. Compounds (37), (29), (32), and (40) exhibited an acamprosate colonic bioavailability at least about 5 times greater than the acamprosate colonic bioavailability of an equivalent dose of acamprosate itself.

Description 25

Use of Clinical Trials to Assess the Efficacy of Acamprosate Prodrugs for Maintaining Abstinence from Alcohol The efficacy of an acamprosate prodrug for treating alcoholism can be assessed using a randomized, double-blind, double-dummy, placebo-controlled trial. Patients aged 18 to 65 years meeting DSM IV criteria for alcohol dependence and having a history of alcohol dependence for at least 12 months are selected for the study. Patients are required to have undergone detoxification and have had five or more days of abstinence from alcohol before commencing treatment. Patients having a body weight of less than 60 kg receive an equivalent of 1332 mg/day (two 333 mg tablets in the morning and one at midday and in the evening) or placebo, and patients having a bodyweight of greater than 50 kg receive an acamprosate equivalent of 1998 mg/day (two 333 mg tablets in the morning, midday and evening) or placebo. Other acamprosate equivalent doses may be appropriate depending upon the pharmacokinetics of a particular acamprosate prodrug.

Primary and secondary outcome measures include commonly accepted subjective measures (based mainly on self-reported data) of continuous abstinence rate (CAR, i.e., the percentage of patients completely abstinent throughout the entire treatment and/or follow-up period), cumulative abstinence duration (CAD), the proportion of the total time that CAD represented (CADP, i.e. CAD as a proportion of the total treatment duration) and/or time to first drink (TFD). Surrogate biological markers of relapse such as γ-glutamyl transferase, carbohydrate-deficient transferrin, AST and ALT levels, and mean corpuscular volume can also be determined. Efficacy of acamprosate prodrugs in the maintenance of abstinence in patients with alcohol dependence is reflected in an increased CAR, CADP, and TFD compared to patients receiving placebo.

Description 26

Use of Animal Models to Assess the Efficacy of Acamprosate Prodrugs for Treating Alcohol Withdrawal Withdrawal Seizure-Prone (WSP) and Withdrawal Seizure-Resistant (WSR) mice are used to assess the efficacy of acamprosate prodrugs for treating alcohol withdrawal. Mice are made dependent on ethanol via 72 h of chronic ethanol vapor inhalation. On day 1, mice are weighted, injected with a loading dose of ethanol and pyrazole HCl (Pyr), an alcohol dehydrogenase inhibitor, and placed into ethanol vapor chambers. Controls are placed into air chambers and receive Pyr only. At 24 and 48 h, Pyr boosters are administered to both the experimental and control groups. Blood ethanol concentrations (BECs) for ethanol groups are measured and the ethanol vapor concentrations adjusted to equate ethanol exposure between lines. Mean BECs are maintained between approximately 1.0-2.0 mg/mL, depending upon the effects of the test compound being studied. After 72 h, all mice are removed from the chambers to initiate withdrawal, and ethanol treated mice have blood samples drawn for BEC determinations.

Following removal from the ethanol or air chambers, mice are scored hourly for handling-induced convulsion (HIC). Scoring is initiated 1 h after removal from ethanol and hourly over the next 12-15 h and again at 24 h. If animals do not return to baseline HIC levels by 25 h, an additional score is obtained at 48 h. The scale such as the following is used (0—no convulsion after a gently 180° spin; 1—only facial grimace after gentle 180° spin; 2—tonic convulsion elicited by gently 180° spin; 3—tonic-clonic convulsion after 180° spin; 4—tonic convulsion when lifted by tail, no spin; 5—tonic-clonic convulsion when lifted by tail, no spin; 6—severe tonic-clonic convulsion when lifted by tail, no spin; and 7—severe tonic-clonic convulsion elicited before lifting by the tail). The area under the curve is calculated and used to quantitatively evaluate withdrawal severity. An additional index of withdrawal severity is the peak HIC score, calculated by identifying the highest HIC for each individual mouse and averaging this score with the two adjacent scores. Data are analyzed by appropriate statistical methods.

Description 27

Animal Model for Assessing Therapeutic Efficacy of Acamprosate Prodrugs for Treating Tinnitus Unilateral Noise Trauma The efficacy of acamprosate prodrugs of Formula (I) for treating tinnitus can be assessed using animal models of tinnitus in which unilateral noise trauma is used to induce tinnitus (Bauer and Brozoski, *J Assoc Res Otolarynology* 2001, 2(1), 54-64; and Guitton et al., US 2006/0063802).

Long-Evans rats are first behaviorally acclimated to lever-press for food pellets and then conditioned to respond in a distinctive and standard way to auditory test stimuli. After conditioning, the animals are separated into groups and exposed to unilateral noise trauma for 0, 1, or 2 hours. Animals are anesthetized, placed in a stereotaxic head frame, and unilaterally exposed once to narrowband noise with a peak intensity of 105 dB centered at 16 kHz for 0, 1, or 2 hours before or after behavioral training and testing. The animals are then administered an acamprosate prodrug and suppression of the conditioned response determined and compared to a control group not exposed to noise trauma.

Sodium Salicylate-Induced Sound Experience

An animal model developed for short-term, acute induced phantom auditory sensations in rats can be used to evaluate acamprosate prodrugs for treating tinnitus. Salicylate-induced animal models of tinnitus are known.

Female albino rats (Wistar, aged 8-20 weeks) are trained and tested on five consecutive days per week. Training and testing takes place in a commercial conditioning chamber (rat shuttle box, TSE) adapted for the study. Electrical stimuli (0.1-0.5 mA, 100 V, 0.5 s) can be supplied via a shockable floor ground. A resting platform with a mechanical sensor is mounted on one side of the cage, covering the shockable floor and serving as a resting location for the animal. The cage is separated by a wall into two short hallways. At both ends of the hallways, within a recess, small amounts of fluid can be given to an animal, gravity-advanced and controlled by flow resistance- and vibration-muted magnetic shutter valves. A typical open time is 0.5 s, resulting in a reward drop of ca. 20 μL, supplied to an animal via a curved metal drinking cannula. Reward drops not taken up by the animal are drained off into a reservoir unreachable by the rat. Photo sensors registered the visits of an animal at the feeder recesses. All sensors are monitored on a computer screen and a top-mounted USB camera provided pictures of the entire floor dimensions of the cage interior.

Auditory stimuli are generated and presented over three broadened speakers mounted vertically in the cage. A continuous white noise can be plated on the central loudspeaker switched off and on with a 100 ms ramp. In parallel to the white noise sound, a pure tone (cue tone, 8 kHz, 70 dB SPL, 200 ms length, 25 ms ramp, repeated five times with 300 ms pause) could be presented over loudspeakers mounted directly over the left and right feeder recesses.

Animals are trained on auditory stimuli for 30-60 min/day for 5 days/week. Training session length is adapted to the animal's activity. Always 15-18 h prior to behavioral testing (experimental session), the drinking water is withdrawn. The conditioned rats are divided into two groups (one animal per cage for either group). Animals from the first group receive an intraperitoneal injection of sodium salicylate (350 mg/kg bw) while animals from the second group receive an intraperitoneal injection of an equivalent volume of saline. Animals from either group are tested on the same day in a semi-random order exactly 3 h after injection. During the experimental session electrical stimuli are omitted. Four minutes after the start of a session the sugar water reward is stopped and the behavioral performances are recorded from 12-16 min and subsequently analyzed. Within the next 2-5 days rats receive the same training as before the experiment. On the next experimental day animals from the group previously treated with salicylate are injected with saline or test compound and tested again.

Frequencies of feeder access action of a rat are calculated for periods of sound and periods of silence separately (accesses/min) and normalized (SA activity ratio). The difference of silence activity ratios (ΔSA ratio) is determined as the silence activity ratio of an animal tested after salicylate injection less the silence activity ratio of the same animal after saline injection. Data is analyzed using appropriate statistical methods.

During the training procedure, animals are conditioned to discriminate between periods of sound and periods of silence using auditory cues.

To induce phantom auditory sensations, animals are injected with salicylate (350 mg/kg bw) or an equivalent volume of saline and tested 3 h later. The SA ratio of animals treated with salicylate is significantly higher than the SA ratio for animals treated with saline.

Test compounds can be administered and their ability to reverse the effects of the salicylate induced phantom auditory sensations determined. Compounds that reduce the increase in the SA ratio following in the salicylate treated animals can have potential in treating tinnitus.

Description 28

Method for Assessing Therapeutic Efficacy of Acamprosate Prodrugs for Treating Tinnitus in Humans The efficacy of acamprosate prodrugs of Formula (I) for treating tinnitus in humans can be assessed using methods known in the art.

Patients are screened using pre-established inclusion and exclusion criteria and selected for their ability to perform a psychophysical loudness matching task using pure tones and broad-band noise (BBN). Examples of inclusion criteria include, for example, age, type of tinnitus, e.g., continuous or pulsed, duration of tinnitus, Tinnitus Handicap Questionnaire (THQ) score >30, Beck Depression Index (BDI)<13, and criterion performance on loudness matching task using a 1 KHz standard.

Following screening, selection and enrollment, tinnitus is evaluated before and after an acamprosate prodrug is administered to a patient. Hearing thresholds are evaluated using an objective stimulus loudness match and a tinnitus loudness matching procedure.

Prior to enrollment, subjects are screened for proficiency in a psychophysical matching task. In the objective stimulus loudness matching procedure, subjects match a binaural 1 KHz standard tone at 20 dB sensation levels to each of five binaural comparison stimuli (BBN, 0.5, 1, 2, and 4 KHz). The loudness match is obtained using a forced two-choice procedure. Each trial begins with the simultaneous presentation of a visual cue and the 1 KHz standard followed by the presentation of the second visual cue and the comparison stimulus. Subjects are instructed to indicate whether the standard and comparison stimuli sound the "same" or "different" in loudness by clicking an on-screen button. An ascending-descending method of limits procedure is used. Subjects are screened using this loudness-matching test and are required to meet inclusion criteria of efficiency (completion time ≦1 h) and reliability (standard deviation of match levels ≦5 dB).

The tinnitus loudness matching procedure differs from the objective stimulus loudness matching procedure in that the initial presentation on each trial is a null presentation during which an on-screen message instructs subjects to listen closely to their tinnitus. During this initial 1-sec cue subjects are instructed to use their perception of tinnitus as the standard stimulus. Subjects are instructed to click a "same loudness" button when the loudness of the comparison stimulus matches the loudness of their tinnitus. The presentation order of the comparison stimuli (BBN, 0.5, 1, 2, and 4 KHz) is randomized, and each ascending and descending stimulus series is repeated once, for a total of four tinnitus loudness matches at each of the five comparison stimuli. The intensities of the loudness-match points are recorded and converted to sensation levels of tinnitus loudness using the hearing threshold determined in each session for the comparison stimuli. Psychoacoustically determined tinnitus loudness is reported as dB HL of the maximum sensation-level match obtained within a session.

Assessment sessions are performed at the initiation of the study and at intervals during the study. Subjects can be given placebo only, an acamprosate prodrug only, a variable including escalating or deescalating dose of an acamprosate prodrug, or a combination of placebo and acamprosate prodrug during the course of a study. The duration of the study can be a few hours, days, weeks, months, or years.

Primary outcome measures are psychoacoustically determined tinnitus loudness and perceived tinnitus handicap. Tinnitus handicap can be determined using the Tinnitus Handicap Questionnaire, which provides a global score and subscores related to emotional, functional, and cognitive aspects of tinnitus. Secondary outcome measures include general health and quality of life factors determined using, for example, the General Health Survey Short form (RAND 36-Item Health Survey, 1.0, Rand Health, Santa Monica, Calif.) and the Tinnitus Experience Questionnaire, a set of seven scaled questions that evaluate the experiential sensory features of tinnitus. Other questionnaires for assessing tinnitus can be used.

Description 29

Animal Model for Assessing Therapeutic Efficacy of Acamprosate Prodrugs for Treating Sleep Apnea Sprague-Dawley rats are anesthetized and a surgical incision of the scalp is made to allow bilateral implantation of stainless steel screws into the frontal and parietal bones of the skull for electroencephalogram (EEG) recording. Bilateral wire electrodes are placed into the nuchal muscles for electromyogram (EMG) recording. The skin is then sutured and the animals allowed at least 7 days for recovery. Respirations are recorded by placing each rat inside a single chamber plethysmograph. The plethysmograph chamber is flushed with room air at a constant regulated flow rate of 2 L/min. EEG, EMG and respirations are continuously recorded. Sleep apneas are defined as cessation of respiratory effort for at least 2.5 s. The effects of recording hour, sleep state, and acamprosate prodrug administration are analyzed using appropriate statistical methods.

Description 30

Study for Assessing the Therapeutic Efficacy of Acamprosate Prodrugs for Treating Sleep Apnea in Humans Inclusion criteria are an apnea-hypopnea index (AHI) exceeding 20 based on self-rated sleep duration at previous unattended ventilatory screening or an AHI exceeding 25 in a previous polysomnographic (PSG) recording. A double blind, randomized, placebo-controlled cross-over study comparing the effects of an acamprosate prodrug and placebo is used. Each patient undergoes a complete PSG recording for habituation at night 1. Patients are randomized to receive acamprosate prodrug on night 2 and placebo on night 3, or vice versa. Night 2 is scheduled within 1-21 days after night 1 and night 3 within 7-28 days after night 1 to provide a minimum of 7 days between night 2 and night 3 washout. A complete PSG recording, physical examination, and recording of ECG is performed in an identical manner at all study nights. Blood samples are obtained in the morning after study nights for hematology and clinical chemistry. Adverse events are determined by active questioning. AHI, the number of obstructive apneic/hyponeic events per time, is the primary efficacy variable. Secondary efficacy variables are REM AHI, non-REM AHI, apnea index (AI), hypopnea index (HI), oxygen desaturation index (ODI), minimum overnight oxygen saturation, sleep stage distribution arousal index, REM sleep and slow wave sleep latency, safety and tolerability. An obstructive apnea is defined as loss of nasal pressure accompanied by paradoxical respiratory movements for >10 s. An obstructive hypopnea is defined as a >50% reduction of the nasal pressure signal, but accompanied by chest wall paradoxical motion through most of inspiration for >10 s. Events without respiratory movements are classified as central apneas.

Description 31

Animal Models for Assessing Therapeutic Efficacy of Acamprosate Prodrugs for Treating Parkinson's Disease MPTP Induced Neurotoxicity MPTP, or 1-methyl-4-phenyl-1,2,3,6-tetrahydropyridine is a neurotoxin that produces a Parkinsonian syndrome in both man and experimental animals. Studies of the mechanism of MPTP neurotoxicity show that it involves the generation of a major metabolite, MPP$^+$, formed by the activity of monoamine oxidase on MPTP. Inhibitors of monoamine oxidase block the neurotoxicity of MPTP in both mice and primates. The specificity of the neurotoxic effects of MPP$^+$ for dopaminergic neurons appears to be due to the uptake of MPP$^+$ by the synaptic dopamine transporter. Blockers of this transporter prevent MPP$^+$ neurotoxicity. MPP$^+$ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that MPP$^+$ administered intrastriatally to rats produces significant depletion of ATP as well as increased lactate concentration confined to the striatum at the site of the injections. Compounds that enhance ATP production can protect against MPTP toxicity in mice.

A prodrug of Formula (I) is administered to mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Prodrugs of Formula (I) that protect against DOPAC depletion induced by MPTP, HVA, and/or dopamine depletion are neuroprotective and therefore can be useful for the treatment of Parkinson's disease.

Haloperidol-Induced Hypolocomotion

The ability of a compound to reverse the behavioral depressant effects of dopamine antagonists such as haloperidol in rodents and is considered a valid method for screening drugs with potential antiparkinsonian effects. Hence, the ability of prodrugs of Formula (I) to block haloperidol-induced deficits in locomotor activity in mice can be used to assess both in vivo and potential anti-Parkinsonian efficacy.

Mice used in the experiments are housed in a controlled environment and allowed to acclimatize before experimental use. 1.5 h before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

A 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is closed, the animal removed from the stereoreotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a prodrug of Formula (I). Immediately prior to testing, animals are given a subcutaneous injection of a sub-threshold dose of apomorphine, and then placed in the harness and the number of rotations recorded for one hour. The total number of full contralateral rotations during the hour test period serves as an index of antiparkinsonian drug efficacy.

L-Dopa Induced Dyskinesia

The ability of acamprosate prodrugs to mitigate the effects of L-dopa induced dyskinesia can be assessed using animal models.

Male, Sprague-Dawley rats (250-300 g) are housed and maintained under standard conditions.

Reserpine (4 mg/kg) is administered under light isofluorane anesthesia. Eighteen hours following reserpine administration, the animals are placed into observation cages. Behavior is assessed using an automated movement detection system that includes dual layers of rectangular grids of sensors containing an array of 24 infrared beams surrounding the cage. Each beam break is registered as an activity count and contributes to the assessment of a variety of different behavioral parameters depending on the location of the event and the timing of successive beam breaks. These parameters include: (1) horizontal activity, a measure of the number of beams broken on the lower level; and (2) vertical activity, a measure of beams broken on the upper level.

In one experiment, immediately prior to commencing behavioral assessments, rats are injected with a combination of L-dopa methyl ester and carbidopa (or benserazide). In another study, to assess the effects of acamprosate prodrugs on L-dopa induced activity, animals are randomly assigned to groups. In each group, immediately following L-dopa/carbidopa administration, vehicle or acamprosate prodrug is administered. The behavior of normal, non-resperine-treated, animals is also assessed. Behavior of the animals in the different groups is monitored for at least 4 hours. Acamprosate prodrugs that reduce the L-dopa-induced locomotion in the reserpine-treated rats are potentially useful in treating Parkinson's disease and/or the symptoms associated with Parkinson's disease.

Description 32

Use of Clinical Trials to Assess the Efficacy of Acamprosate Prodrugs for Treating Parkinson's Disease The following clinical study may be used to assess the efficacy of a compound in treating Parkinson's disease.

Patients with idiopathic PD fulfilling the Queen Square Brain Bank criteria with motor fluctuations and a defined short duration GABA analog response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of L-Dopa, COMT inhibitors, selegiline, anticholinergic drugs, or other drugs that could potentially interfere with gastric absorption (e.g. antacids). Other exclusion criteria include patients with psychotic symptoms or those on antipsychotic treatment, patients with clinically relevant cognitive impairment, defined as MMS (Mini Mental State) score of less than 24, risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double blind, and cross-over study design is used. Each patient is randomized to the order in which either L-dopa or one of the two dosages of test compound, e.g., an acamprosate prodrug, is administered in a single-dose challenge in double-dummy fashion in three consecutive sessions. Randomization is by computer generation of a treatment number, allocated to each patient according to the order of entry into the study. All patients give informed consent.

Patients are admitted to a hospital for an overnight stay prior to administration of test compound the next morning on three separate occasions at weekly intervals. After withdrawal of all antiparkinsonian medication from midnight the previous day, test compound is administered at exactly the same time in the morning in each patient under fasting conditions.

Patients are randomized to the order of the days on which they receive placebo or test compound. The pharmacokinetics of a test compound can be assessed by monitoring plasma acamprosate concentration over time. Prior to administration, a 22 G intravenous catheter is inserted in a patient's forearm. Blood samples of 5 ml each are taken at baseline and 15, 30, 45, 60, 75, 90, 105, 120, 140, 160, 180, 210, and 240 minutes after administering a test compound or until a full off state has been reached if this occurs earlier than 240 minutes after drug ingestion. Samples are centrifuged immediately at the end of each assessment and stored deep frozen until assayed. Plasma acamprosate levels are determined by high-pressure liquid chromatography (HPLC). On the last assessment additional blood may be drawn for routine hematology, blood sugar, liver, and renal function.

For clinical assessment, motor function is assessed using the United Parkinson's Disease Rating Scale motor score and BrainTest, which is a tapping test performed with a patient's more affected hand on the keyboard of a laptop computer. These tests are carried out at baseline and then immediately following each blood sample until patients reach their full on-stage, and thereafter at 3 intervals of 20 min, and 30 min intervals until patients reach their baseline off-status. Once patients reach their full on-state, video recordings are performed three times at 20 min intervals. The following mental and motor tasks, which have been shown to increase dyskinesia, are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Occurrence and severity of dyskinesia is measured with a Dyskinesia Monitor. The device is taped to a patient's shoulder on their more affected side. The monitor records during the entire time of a challenging session and provides a measure of the frequency and severity of occurring dyskinesias.

Results can be analyzed using appropriate statistical methods.

Description 33

Use of Clinical Trials to Assess the Efficacy of Acamprosate Prodrugs for Treating Levodopa-Induced Dyskinesias in Parkinson's Disease A double-blind placebo-controlled clinical trial such as that described by Goetz et al., *Movement Disorders* 2007, 22(2), 179-186 can be used to assess the efficacy of an acamprosate prodrug for treating levodopa-induced dyskinesias in Parkinson's disease.

Patients are 30 years of age or older with Parkinson's disease and received levodopa treatment at a stable (at least 4 weeks) and optimized dose. Following enrollment, patients are randomized and receive either placebo or an appropriate dose and regimen of acamprosate prodrug. Levodopa doses are maintained at the baseline level. At appropriate intervals during the study, patients are evaluated for periods during the day characterized by sleep, off, on-without dyskinesias, on-with non-troublesome dyskinesias, and on-with troublesome dyskinesia. The primary outcome is change from baseline in on-time without dyskinesia. Various dyskinesia rating scales such as, for example, the Abnormal Involuntary Movement Scale, Unified Parkinson's Disease Rating Scale (UPDRS) Motor examination (Part III), or UPDRS Activities of Daily Living assessment (Part III) can also be used. Measures of safety such as frequency and severity of reported adverse events, changes in vital signs, laboratory test results, including ACTH-suppression testing of cortisol levels and electrocardiogram can also be determined.

Description 34

Animal Model for Assessing Therapeutic Efficacy of Acamprosate Prodrugs for Treating Alzheimer's Disease Heterozygous transgenic mice expressing the Swedish AD mutant gene, hAPPK670N, M671L (Tg2576) are used as an animal model of Alzheimer's disease. Beginning at 9 months of age, mice are divided into two groups. The first two groups of animals receive increasing doses of an acamprosate prodrug, over six weeks. The remaining control group receives daily saline injections for six weeks.

Behavioral testing is performed at each drug dose using the same sequence over two weeks in all experimental groups: (1) spatial reversal learning, (2) locomotion, (3) fear conditioning, and (4) shock sensitivity. This order is selected to minimize interference among testing paradigms.

Acquisition of the spatial learning paradigm and reversal learning are tested during the first five days of test compound administration using a water T-maze. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criterion and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of the animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined. On day 12, the animals are tested to assess their sensitivity to the conditioning stimulus, i.e., foot shock. Following the last day of behavioral testing, animals are anesthetized and the brains removed, post-fixed overnight, and sections cut through the hippocampus. The sections are stained to image β-amyloid plaques.

Data are analyzed using appropriate statistical methods.

Description 35

Animal Model for Assessing Therapeutic Efficacy of Acamprosate Prodrugs for Treating Huntington's Disease Neuroprotective Effects in a Transgenic Mouse Model of Huntington's Disease Transgenic HD mice of the N171-82Q strain and non-transgenic littermates are treated with a prodrug of Formula (I) or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered prodrugs of Formula (I) that are neuroprotective in the N171-82Q transgenic HD mouse model remain on the rotarod for a longer period of time and travel further than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease. The enzyme succinate dehydrogenase plays a central role in both the tricarboxylic acid cycle as well as the electron transport chain in mitochondria. Malonate is a reversible inhibitor of succinate dehydrogenase. Intrastriatal injections of malonate in rats have been shown to produce dose dependent striatal excitotoxic lesions that are attenuated by both competitive and noncompetitive NMDA antagonists. For example, the glutamate release inhibitor, lamotrigine, also attenuates the lesions. Co-injection with succinate blocks the lesions, consistent with an effect on succinate dehydrogenase. The lesions are accompanied by a significant reduction in ATP levels as well as a significant increase in lactate levels in vivo as shown by chemical shift resonance imaging. The lesions produce the same pattern of cellular sparing, which is seen in Huntington's disease, supporting malonate challenge as a useful model for the neuropathologic and neurochemical features of Huntington's disease.

To evaluate the effect of acamprosate prodrugs of Formula (I) in this malonate model for Huntington's disease, a prodrug of Formula (I) is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 µL of 3 µmol malonate are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-tiphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections. Compounds exhibiting a neuroprotective effect and therefore potentially useful in treating Huntington's disease show a reduction in malonate-induced lesions.

Description 36

Animal Model for Assessing Therapeutic Efficacy of Acamprosate Prodrugs for Treating Amyotrophic Lateral Sclerosis A murine model of SOD1 mutation-associated ALS has been developed in which mice express the human superoxide dismutase (SOD) mutation glycine-alanine at residue 93 (SOD1). These SOD1 mice exhibit a dominant gain of the adverse property of SOD, and develop motor neuron degeneration and dysfunction similar to that of human ALS. The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and, as the disease progresses, motor neuron loss.

Studies are performed on transgenic mice overexpressing human Cu/Zn-SOD G93A mutations ((B6SJL-TgN (SOD1-G93A) 1 Gur)) and non-transgenic B6/SJL mice and their wild litter mates. Mice are housed on a 12-hr day/light cycle and (beginning at 45 d of age) allowed ad libitum access to either test compound-supplemented chow, or, as a control, regular formula cold press chow processed into identical pellets. Genotyping can be conducted at 21 days of age. The SOD1 mice are separated into groups and treated with a test compound, e.g., an acamprosate prodrug, or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0—normal reflex on the hind limbs (animal will splay its hind limbs when lifted by its tail); 1—abnormal reflex of hind limbs (lack of splaying of hind limbs weight animal is lifted by the tail); 2—abnormal reflex of limbs and evidence of paralysis; 3—lack of reflex and complete paralysis; and 4—inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the rod without falling. The test can be stopped after an arbitrary limit of 120 sec. Should the animal fall down before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 cm$^2$) situated above a plane support. The number of times the mice put their paws through the grid is counted and serves as a measure for motor coordination.

The hanging test evaluates the ability of an animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD1 mice during the onset of motor impairment, samples of lumbar spinal cord (protein extracts) are applied to ProteinChip Arrays with varying surface chemical/biochemical properties and analyzed, for example, by surface enhanced laser desorption ionization time of flight mass spectrometry. Then, using integrated protein mass profile analysis methods, data is used to compare protein expression profiles of the various treatment groups. Analysis can be performed using appropriate statistical methods.

Description 37

Assessing Therapeutic Efficacy of Acamprosate Prodrugs for Treating Cortical Spreading Depression It has been hypothesized that cortical spreading depression emanating from a site of injury causes secondary damage in the "penumbra" by disrupting ion homeostasis and producing demands on neurons already in a compromised state. Focal CNS injury or ischemia also results in an induction of the immediate early gene c-fos. c-fos induction spreads throughout the injured hemisphere by a process that appears to be dependent on cortical spreading depression. c-fos induction is inhibited by NMDA receptor antagonists. Thus, both cortical spreading depression and c-fos induction are NMDA receptor activated processes associated with CNS injury and may be components of the cascade leading to neuron death.

NMDA-induced increase in fos immunoreactivty in mice is determined according to the following protocol. Male CF-1 mice (20 to 25 g) are administered varying doses of an acamprosate prodrug or vehicle. Thirty min later, animals receive intraperitoneal administration of NMDA (75 mg/kg) or vehicle. Sixty min later, animals are terminally anesthetized, brains are removed to ice and immersed for 1 h in 2% paraformaldehyde in phosphate buffered saline, and transferred to 15% sucrose in phosphate buffered saline, incubated overnight, and then frozen at −80° C. Coronal sections through the hippocampal region are taken, washed, and incubated with a sheep anti-fos polyclonal antibody (OA-11-824) for 18 h at 4° C. Sections are washed with phosphate buffered saline and then incubated with biotinylated rabbit anti-sheep antibody for 2 h. After 3 washes in phosphate buffered saline, sections are incubated in Vector ABC solution for 1 h at 25° C., washed 3 times, stained for glucose oxidase, and mounted. Each section is photographed and the intensity of fos-like immunoreactivity in the dentate gyrus is analyzed.

CNS trauma-induced c-fos mRNA induction in rats is determined according to the following protocol. Male Sprague-Dawley rats (200-250 g) are administered different doses of an acamprosate prodrug or vehicle. After 30 min, animals are anesthetized and a burr hole drilled over the right frontal parietal cortex 3 mm anterior and 3 mm lateral to bregma. An 18-gauge needle is inserted through the hole for 2 min to a depth of about 3 mm into the cortex. After a 60 min recovery animals are sacrificed, the brains removed, and cortices dissected and frozen in liquid nitrogen. Changes in c-fos mRNA expression following needle injury are quantified using procedures known in the art.

To assess the effects of acamprosate prodrugs on electrically-induced cortical spreading depression in rats, male Sprague-Dawley rats (275-325 g) are anaesthetized. The spontaneously breathing animals are fixed in a stereotaxic frame, a craniotomy is drilled over the parietal cortex, and the dura is removed. Two saline-filled glass recording microelectrodes each containing a Ag/AgCl wire are inserted into the parietal cortex at a depth of about 1 mm and 1.5-2.0 mm apart along the sagital plane using a micromanipulator. Two saline filled cannulae each containing a Ag/AgCl wire are inserted under the skin of the animal to serve as reference electrodes. Cortical spreading depression is induced in the parietal cortex using a bipolar stimulating electrode placed at 90° to the frontal recording electrode and positioned so that the electrode visibly touches but does not depress the cortex. Electrocortical stimulation consists of a train of 5 ms pulses at 40 Hz lasting for 2 s. The threshold stimulation for cortical spreading depression determined by varying the current. Once the threshold current has been determined, the current is increased by 20% for experimental measurements. DC potentials are recorded at 10 min intervals for four control stimulations. An acamprosate prodrug is then administered. DC potentials are again recorded at 10 min intervals. The speed of cortical spreading depression expansion is calculated from the latency difference of the negative DC shift at the rostral and caudal electrodes.

Description 38

Animal Models to Assess the Efficacy of Acamprosate Prodrugs for Treating Migraine Therapeutic activity of acamprosate prodrugs provided by the present disclosure may be determined in various animal models of neuropathic pain or in clinically relevant studies of different types of neuropathic pain. Animal models for neuropathic pain are known in the art and include animal models that determine analgesic activity or compounds that act on the CNS to reduce the phenomenon of central sensitization that results in pain from nonpainful or nonnoxious stimuli. Other animal models that are known in the art, such as hot plate tests, model acute pain, are useful for determining analgesic properties of compounds that are effective when painful or noxious stimuli are present. The progression of migraines is believed to be similar to the progression of epilepsy (because an episodic phenomenon underlies the initiation of the epileptic episode) and, as such, it is believed that epilepsy animal models may be useful in determining efficacy in treating migraine.

Analgesic Activity

The following test can be used to evaluate the analgesic activity of an acamprosate prodrug. Test compound is administered orally to mice. Morphine is administered as a reference substance at 64 mg/kg to mice under the same experimental conditions. A vehicle is administered to mice as a control substance under the same experimental conditions. Test compound, morphine, or vehicle is administered to the mice in a blind study. Sixty minutes after the test compound, morphine, or vehicle is administered, the mice are placed onto a hot metal plate maintained at 54° C. and surrounded by a Plexiglass cylinder. The time taken for the mice to lick their feet is an index of analgesic activity. Effective analgesics increase the latency or amount of time to licking. Latency to the first foot lick is measured, up to a maximum time of 30 sec to prevent tissue damage to the mice.

Hyperreflexia and Flexor Reflex Tests

Assessment of hyperreflexia, pain, and muscle tone in chronic spinally transected rats is performed using male albino Holtzman-derived rats weighing 270-530 gm. The rats are housed independently and have continuous access to food and water throughout the experiments. Animals are anesthetized. Rats are placed in a stereotaxic frame and anesthesia is maintained. An incision is made so that the paraspinal muscles can be retracted and a laminectomy performed between T6-T9. A one- to two-millimeter portion of the spinal cord is removed by evacuation and replaced with gel foam to reduce bleeding, after which the incision is closed in layers.

Following the transection, rats are placed in a room in which the ambient temperature is raised to about 27° C. to maintain body temperature. On the following morning post-surgery, the hindquarters of the spinalized rats are bathed and their urine expressed manually by applying pressure to their bladders. Experiments are conducted between 21 and 28 days after surgery. For the first two weeks post-surgery, 0.25 mL of an antibiotic is administered to the rats to prevent bladder infection. A topical antibiotic is applied to any part of the skin that shows signs of decubitus lesions. Within approximately two weeks, all animals regain bladder control and are no longer given antibiotic treatment. Assessment of hyperreflexia and flexor reflex is performed before and after treatment with test compound so that each animal serves as its own control.

Initial assessment of hyperreflexia is performed by rating the hyperreflexia response elicited with an innocuous stimulus, such as a metal probe. A metal probe is pressed against the lower abdomen at four specific sites. The response is evaluated for each of four trials using a scale ranging from zero (no response in all four trials) to four (a maximum, tonic-clonic reaction elicited in all four trials). All scores, pre- and post-treatment, are transformed to indicate the percent of hyperreflexia, pain, or muscle tone. The data is analyzed using appropriate statistical methods.

After determining hyperreflexia before drug treatment, test compound is administered to the rats.

Polysynaptic flexor-reflex responses, elicited by stimuli that activate high-threshold afferents, are recorded as EMG activity from the ipsilateral hamstring muscle. Supramaximal electric shocks are applied to the hindpaw and recording electrodes are placed in the biceps femoris semitendinosus muscle. Five sets of stimuli are made at each time point. The flexor reflex is recorded, in periods with and without test compound, every 30 min once a stable baseline response is achieved. The data at time zero represent pre-treatment control values. The responses are determined in spinalized rats by observing the flexor-reflex response before treatment and at each of 30, 60, 90, and 120 min following administration of test compound, baclofen (10 mg/kg sc), or vehicle (water, 12 ml/kg po). Efficacy is indicated when a test compound is shown to reduce the magnitude of the flexor-reflex responses in a chronic spinalized rat at all time points with similar efficacy to baclofen, the positive control.

Cutaneous Hypersensitivity Test

The effects of a test compound on nociceptive activation of the trigeminovascular system is determined using an animal model of migraine. A pharmaceutical composition comprising a test compound is administered to cats. To serve as positive and negative controls, a vehicle control is administered to the cats. Efficacy is indicated for compounds that inhibit trigeminovascular activation compared to the trigeminovascular activation in the cats that receive the vehicle.

Yawning

Yawning is a behavior that has been linked to activation of dopaminergic neurotransmission. Yawning is part of a behavioral syndrome occurring in most patients during a migraine attack. Blockage of quinipirole-induced yawning in rats has been used as an animal model to study the potential antagonism of migraine symptoms.

Male Sprague Dawley rats are acclimatized for 12 days before testing and at the time of the study. The rats are housed in standard size steel cages with four animals per cage and are maintained on a 12 hour light/dark schedule. Test compound or vehicle is administered 15 min before the dopamine D2 agonist quinipirole in vehicle or the vehicle alone is administered to the animals. The animals are then placed individually in 6 in×6 in plexiglass observation cages and the number of yawns is counted for the subsequent 30 min. The data is analyzed by an appropriate statistical method.

The dopamine D2 agonist quinipirole can produce an average of 13-15 yawns per 30 minutes while no yawning behavior is typically observed in vehicle treated animals. Compounds that inhibit quinipirole-induced yawning may be efficacious in treating migraine.

Animal Model of Dural Protein Extravasation

The following animal model can be employed to determine the ability of an acamprosate prodrug to inhibit protein extravasation, an exemplary functional assay of the neuronal mechanism of migraine.

Rats or guinea pigs are anesthetized and placed in a stereotaxic frame with the incisor bar set at −3.5 mm for rats or −4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, with all coordinates referenced to bregma). Pairs of stainless steel stimulating electrodes, insulated except at the tips are lowered through the holes in both hemispheres to a depth of 9 mm (rats) or 10.5 mm (guinea pigs) from dura.

Test compound is administered. About 7 min later a fluorescent dye (e.g., Evans Blue) is administered. The fluorescent dye complexes with proteins in the blood and functions as a marker for protein extravasation. Ten (10) min post-injection of the test compound, the left trigeminal ganglion is stimulated for 3 minutes at a current intensity of 1.0 mA (5 Hz, 4 msec duration) with a potentiostat/galvanostat. Fifteen minutes following stimulation, the animals are killed and exsanguinated with 20 mL of saline. The top of the skull is removed to facilitate collection of the dural membranes. Dural membrane samples are removed from both hemispheres, rinsed with water, and spread flat on microscopic slides. Once dried, the tissues are coverslipped with a 70% glycerol/water solution. A fluorescence microscope equipped with a grating monochromator and a spectrophotometer is used to quantify the amount of fluorescent dye in each sample.

The extravasation induced by the electrical stimulation of the trigeminal ganglion is an ipsilateral effect (i.e. occurs only on the side of the dura in which the trigeminal ganglion is stimulated). This allows the other (unstimulated) half of the dura to be used as a control. The ratio of the amount of extravasation in the dura from the stimulated side, over the amount of extravasation in the unstimulated side, is calculated. Control animals dosed with only saline, yield, for example, a ratio of about 2.0 in rats and about 1.8 in guinea pigs. In contrast, a compound that effectively prevents the extravasation in the dura from the stimulated side yields a ratio of about 1.0. Dose-response curves can be generated for a test compound and the dose that inhibits the extravasation by 50% ($ID_{50}$) or 100% ($ID_{100}$) can be determined.

Amygdala Kindling Model

A relationship has been reported between migraine, affective illness and epilepsy. Although the three disorders are distinct, they all are paroxysmal dysregulations of the nervous system that partially overlap in their pharmacology. The kindling model for complex-partial seizures is based on the progressive development of seizures combined with electroencephalographic (EEG) paroxysmal patterns induced by repeated initially subconvulsive electrical stimulation of limbic structures, e.g., the basolateral nucleus of the amygdala. Once established, the phenomenon persists for months. Since the amygdala-kindled seizures in animals share numerous characteristics with complex-partial seizures in humans, it is a useful animal model of complex partial seizures. An advantage of using the amygdala kindling model is that both behavioral and EEG parameters of the partial and generalized seizures can be measured. Furthermore, the amygdala kindling model is reported to be appropriate for studying diseases such as migraine, affective illness, and epilepsy which increase in severity over time and in a manner which is related to the number of symptomatic episodes.

Rats are obtained at an age of 11-12 weeks (body weight 180-200 gm). Rats are maintained separately in plastic cages at controlled temperature (23° C.) and humidity (about 50% RH) with a 12-h light cycle. The rats receive standard diet and tap water ad libitum.

For implantation of stimulation and recording electrodes, rats are anesthetized and receive stereotaxic implantation of one bipolar electrode in the right basolateral amygdala. Coordinates for electrode implantation are AP-2.2 mm, L-4.8 mm, V-8.5 mm. All coordinates are measured from bregma. Skull screws serve as the reference electrode. The electrode assembly is attached to the skull by dental acrylic cement. After a postoperative period of 2 weeks, constant current stimulations (500 µA, 1 ms, monophasic square-wave pulses, 50/sec for 1 sec) are delivered to the amygdala at intervals of 1/day until ten stage 5 seizures are elicited. The electrical susceptibility of the stimulated region (threshold for induction of afterdischarges) is recorded on the first day of the experiment (initial afterdischarge threshold) as well as after kindling acquisition (with an interval of at least 4 days after the tenth stage 5 seizure) using an ascending staircase procedure. The initial current intensity is 1 µA, and the current intensity is increased in steps of about 20% of the previous current at intervals of 1 min until an afterdischarge of at least 3 sec duration is elicited. In addition to afterdischarge threshold, the following parameters of kindled seizures are measured in fully-kindled rats after stimulation with the afterdischarge threshold current: seizure severity is classified as follows: 1—immobility, eye closure, twitching of vibrissae, sniffing, facial clonus; 2—head nodding associated with more severe facial clonus; 3—clonus of one forelimb; 4—rearing, often accompanied by bilateral forelimb clonus; and 5—rearing with loss of balance and falling accompanied by generalized clonic seizures. Seizure duration 1 is the duration of limbic (stage 1-2) and/or motor seizures (stage 3-5). Seizure duration 2 includes the time of limbic and/or motor seizures plus the adjacent time of immobility. After discharge duration 1 (ADD 1) is the time of spikes in the EEG recorded from the site of stimulation with a frequency of at least 1/sec. Afterdischarge duration 2 (ADD 2) is the total time of spikes occurring in the EEG including those, which followed the ADD I with lower frequency and amplitude.

Test compound is administered to the prepared animals. Control experiments are performed 2-3 days before each test compound experiment. For control determinations, rats receive vehicle (e.g., saline) with the pretreatment time of the respective test compound experiment. For all test compound experiments, at least 4 days are interposed between successive administrations in order to avoid alterations in drug potency due to cumulation or tolerance. Data is analyzed using appropriate statistical methods.

In addition to recordings of anticonvulsant parameters, kindled rats can be observed for adverse effects in order to estimate a therapeutic index. Tests include open field observations, rotarod test, and body temperature. Tests used to evaluate adverse effects are performed in the same manner in control and test compound experiments at two different times, immediately before application of a test compound or vehicle and 13 min after application.

The rotarod test is carried out with a rod of 6 cm diameter and rotation speed of 8 rpm. Neurological deficit is indicated by inability of the animals to maintain their equilibrium for at least 1 min on the rotating rod. Rats are trained prior to the rotarod evaluation to maintain their balance on the rod. After treatment with a test compound or vehicle, rats that are not able to maintain their equilibrium on the rod for three subsequent 1 min attempts are considered to exhibit neurological deficit.

In addition to these quantitative estimations of neurological deficit, behavioral alterations after administration of test compound are noted in the cage and after placing the animals in an open field of 90-100 cm diameter. Muscle tone is estimated by palpation of the abdomen. The extent of deficits in behavior after administration of a test compound is determined by a rating system. Animals are taken out of the cage, placed in an open field, observed for about 1 minute and rated separately for ataxia, abducted hindlimbs, reduced righting, flat body posture, circling, Straub tail, piloerection, hypolocomotion and hyperlocomotion (abdominal muscle tone is evaluated by palpation at the end of the period of observation). All other parameters except ataxia are scored from 0 to 3: 0—absent; 1—equivocal; 2—present; 3—intense. For ataxia: 1—slight ataxia in hind-legs (tottering of the hind quarters); 2—more pronounced ataxia with dragging of hind legs; 3—further increase of ataxia and more pronounced dragging of hind legs; 4—marked ataxia, animals lose balance during forward locomotion; 5—very marked ataxia with frequent loss of balance during forward locomotion; and 6—permanent loss of righting reflexes, but animal still attempts to move forward. Rectal body temperature is measured. Body weight of the animals is recorded once daily before a test compound is administered. Data is analyzed by an appropriate statistical method. The ability of a test compound to increase the electrical threshold for induction of afterdischarges, decrease the severity of seizures, reduce seizure duration, and reduce total afterdischarge duration suggests efficacy in treating migraine.

Description 39

Use of Clinical Trials to Assess the Efficacy of Acamprosate Prodrugs for Treating Migraine The efficacy of a compound of Formula (I) in treating migraine may be assessed using a randomized, double blind, placebo-controlled, parallel group, clinical trial. The primary objective of the study is to evaluate the safety and efficacy of a test compound vs placebo in the treatment of recurrent episodes of migraine based on change from the baseline phase to the double-blind phase in the monthly (28 days) migraine episode rate. The secondary objectives are to evaluate the effect of treatment with a test compound versus placebo in migraine patients on percentage of subjects responding to treatment (50% or more reduction in monthly migraine episode rate) and change from the baseline phase to the double-blind phase in migraine days per month, average migraine duration, rescue medication use, average severity of migraine headache, average severity of migraine associated symptoms (nausea, vomiting, photophobia, phonophobia), to provide safety and efficacy data for the comparison a dose of a test compound in the treatment of migraine, and to evaluate the effect of treatment with a dose of a test compound versus placebo in migraine patients on migraine-specific measures of health-related quality of life (HRQL) and SF-36 quality-of-life measures, as well as the correlation between HRQL and migraine frequency.

The clinical trial is a randomized, double blind, placebo controlled, parallel-group, multicenter study to evaluate the efficacy and safety of one or more doses of a test compound versus placebo in migraine prophylaxis. Patients are randomized into treatment groups. The patients must have been diagnosed with migraine for at least twelve months, with or without aura, as defined by the International Headache Society (IHS). The IHS diagnostic criteria differ from the definition of a migraine period utilized in this study for evaluation of efficacy. For the purposes of this study a migraine period is defined as the twenty-four hour period starting with the onset of painful migraine symptoms, or aura with successful abortive/rescue treatment. Any recurrence during the twenty-four hour period is considered part of the initial episode. If the migraine pain persists beyond the twenty-four hour period, for the purposes of this study, this is considered a new episode.

There are four phases in the clinical trial: Baseline, Core Double-Blind, Blinded Extension, and Taper/Exit. The Baseline Phase lasts up to 42 days and includes two periods: Washout and Prospective Baseline. At Baseline Visit 1 (screening), patients are evaluated to ensure that they meet inclusion/exclusion criteria. In addition, a three-month retrospective headache history is recorded. During each of the three months prior to Visit 1, patients should have had no more than 8 migraines and no more than 15 total headache days (migraine plus other headache types). Eligible patients then undergo other study procedures and are given a headache/rescue medication record. Patients maintain this record from Visit 1 throughout their participation in the clinical trial, documenting the occurrence of any headaches, or auras, as well as the duration, severity, and symptomatology of any migraine attacks. Patients also record the use of any abortive/rescue medication taken for the relief of migraine pain and associated symptoms, or during an aura to prevent migraine pain or relieve symptoms. In addition, for each migraine attack, patients answer the questions on the headache record regarding work loss and productivity. If at the start of the trial, eligible patients are on any prophylactic medication to treat their migraines, they enter a Washout Period of up to 14 days to taper from these medications. This washout is concluded by the time the patient enters the Prospective Baseline Period, 28 days prior to Visit 2 (randomization).

At Baseline Visit 2 (Day 1), headache/rescue medication record information is reviewed. To be eligible for randomization into the trial a patient must have had 3 to 12 migraine episodes but no greater than 15 (migraine and non-migraine), headache days during the 28 days prior to Visit 2.

In the Core Double-Blind Phase, patients who complete the Baseline Phase and meet the entry criteria (including Prospective Baseline Period migraine/headache rate) are randomized into treatment groups representing one or more doses of test compound or placebo. The Core Double-Blind Phase has two periods: Titration and Maintenance.

The Titration Period immediately follows the Baseline Phase and extends for eight weeks (56 days). During this period, patients randomized to test compound are started at an initial dose and the daily dose is increased weekly until the assigned dose is achieved (or maximum tolerated dose, whichever is less). From the third week of Titration until the end of the Maintenance Period, a maximum of two dose level reductions are permitted for unacceptable tolerability problems. If a patient is still in the Titration Period, after a dose reduction, rechallenge is attempted to approach the patient's assigned dose, and, if unsuccessful, the dose is reduced again to the original reduced dose. Patients who have already had their study medication dose decreased by two levels, and are still experiencing unacceptable tolerability problems, which warrant additional dose reductions, exit the study, or enter the Open Label Extension Phase, where their dose is further adjusted. Clinic visits occur on, for example, Day 29 (Visit 3) and Day 57 (Visit 4/End of Titration).

During the 18-week Maintenance Period, patients remain on the dose of test compound reached at the end of the Titration Period (the assigned dose or the maximum tolerated dose). If a patient experiences unacceptable tolerability problems, the dose is reduced, but only to the point that there are no more than two dose reductions for the entire Core Phase (Titration plus Maintenance). No rechallenge is permitted during the Maintenance Period, so a patient continues on the reduced dose for the remainder of the period. Patients who have already had their study medication dose decreased by two levels, and are still experiencing unacceptable tolerability problems, which would warrant additional dose reductions, exit the study. Clinic visits occur, for example, on Day 83 (Visit 5), Day 113 (Visit 6), Day 141 (Visit 7) and Day 183 (Visit 8/Core Double-Blind Final Visit or Early Withdrawal).

Patients are considered to have completed the Core Double-Blind Phase if they complete all 26 weeks of the Phase (8 weeks of Titration and 18 weeks of Maintenance) without prematurely discontinuing study medication. Only patients who complete all 26 weeks of the Core Phase have the option of entering the Blinded Extension Phase.

During the Blinded Extension Phase, patients remain on test compound at the same dose they achieve during the Core Phase for six months, or until they withdraw. During this phase, patients are not permitted to adjust the dose of test compound. Patients are seen quarterly during this phase (Visits 10 and 11/Blinded Extension Final Visit). Patients are considered to have completed the Blinded Extension Phase if they complete all six months of the Phase without prematurely discontinuing the test compound.

In the Taper/Exit Phase, patients exiting the study are tapered from study medication. If a patient exits the study during the Core Double-Blind Phase (Titration or Maintenance Period), he or she is tapered from study medication in a blinded fashion. The length of the taper is as long as seven weeks, but varied according to the dose the patient achieves. Patients who exit the study during the Blinded Extension Phase are tapered from their medication following the recommended taper schedule.

Physical examinations (including height) and neurologic examinations are performed at the beginning and end of the study. A baseline electrocardiogram is performed at the beginning of the study. Vital signs and weight are recorded at each clinic visit. Adverse events are recorded. Quality of Life assessments are performed at intervals, for example, Visits 2 (Day 1), 4 (Day 57/Exit from Titration), 6 (Day 113) and 8 (Day 183/Core Double-Blind Final Visit/Early Withdrawal). Health Care Resource Use information is recorded at intervals, for example, Visits 3 through 8. The occurrence of any headaches or auras, severity and symptomatology of any migraine headaches, and the use of rescue medication is transcribed from a patient's headache record to their case record form at each visit.

Efficacy evaluations are based on information recorded on the subject's headache/rescue medication record and Health-Related Quality of Life assessments. On the headache/rescue medication record the patients documented the following throughout his/her study participation: occurrence and duration of headaches (and auras if no headache pain develops), severity of migraine pain and associated symptoms, as well as the use of medication taken to relieve migraine pain or symptoms (or taken during an aura to relieve symptoms or prevent migraine pain). Health-Related Quality of Life (HRQL) assessments are completed at specified intervals throughout the study. The Migraine-Specific Quality of Life questionnaire (MSQ), and the Medical Outcomes Study Short Form-36 (SF-36) can be used to assess HRQL.

The primary efficacy criterion is the reduction in migraine episodes per month (28 days) during the Core Double-Blind Phase compared to the 28 day Prospective Baseline Period. Secondary efficacy criteria include the percentage of patients responding to treatment (50% or more reduction in the monthly (28 day) migraine episode rate) and reduction from the Prospective Baseline Period to the Core Double-Blind Phase in migraine days per month, monthly rate of all types of headaches, average migraine duration, rescue medication use, average severity of migraine headache, and average severity of migraine-associated symptoms (nausea, vomiting, photophobia, phonophobia). Also included in the secondary efficacy criteria is the effect of treatment with test compound versus placebo on migraine-specific measures of health-related quality of life (HRQL) and SF-36 quality-of-life measures, as well as the correlation between HRQL and migraine frequency. The Medical Outcomes Study Short Form-36 (SF-36) is the most frequently used generic measure of HRQL in migraine patients and has been used in studies of migraine. The SF-36 is a 36-item questionnaire measuring eight domains. The SF-36 has been shown to be reliable and valid in a wide variety of patient populations as well as for migraine patients. The migraine specific quality of life questionnaire (MSQ) can also be administered. The MSQ is a disease-specific instrument developed to assess quality of life relating to migraine. The MSQ has been used in published clinical trials of migraine therapy and has demonstrated evidence of reliability, validity, and responsiveness.

Description 40

Animal Model for Assessing Therapeutic Efficacy of Acamprosate Prodrugs for Treating Schizophrenia Morris Water Maze The Morris Water Maze (MWM) is used as a well-validated hippocampus dependent test of visual-spatial memory. The MWM tests the ability of an animal to locate a hidden platform submerged under water by using extra-maze cues from the test environment. Rats are trained in a pool 1.8 m in diameter and 0.6 m high, containing water at about 26° C. A 10 cm square transparent platform is hidden in a constant position 1 cm below the water level in the pool. Only distal visuo-spatial cues are available to the rats for location of the submerged platform. The rats are given trials to find the hidden platform. The escape latency, i.e., the time required by the rats to find and climb onto the platform, is recorded for up to 120 s. Each rat is allowed to remain on the platform for 30 s, after which it is removed to its home cage. If the rat did not find the platform within 120 s, it is manually placed on the platform and returned to its home cage after 30 s.

Male Sprague-Dawley rats weighing 150-200 g are used. Ten days before the beginning of the experiments, the rats are handled once daily to reduce experimental stress. Acamprosate prodrug or control is administered to the rats for three consecutive days before behavioral testing. On each day of behavioral testing the rats are injected with either haloperidol or saline 30 min before behavioral assessment.

PCP-Induced Hyperactivity Model

Male C57Bl/6J mice are used. Mice are received at 6-weeks of age. Upon receipt, mice are assigned unique identification numbers (tail marked) and are group housed with 4 mice/cage in OPTI mouse ventilated cages. All animals remain housed in groups of four during the study. All mice are acclimated to the colony room for at least two weeks prior to testing and are subsequently tested at an average age of 8 weeks of age. During the period of acclimation, mice and rats are examined on a regular basis, handled, and weighed to assure adequate health and suitability.

Test compounds are prepared and administered according to the following procedures. An acamprosate prodrug is dissolved in sterile injectable water and administered i.p. at a dose volume of 10 mL/kg at 60 min prior to PCP injection. The amount of acamprosate prodrug administered can range, for example, from 0.01 mg/kg to 100 mg/kg. As a positive control, clozapine (1 mg/kg) is dissolved in 10% DMSO and administered i.p. at a dose volume of 10 mL/kg at 30 min prior to PCP injection. PCP (5 mg/kg) is dissolved in sterile injectable water and administered i.p. at a dose volume of 10 mL/kg.

The Open Filed (OF) test is used to assess both anxiety and locomotor behavior. The open field chambers are Plexiglas square chambers (27.3×27.3×20.3 cm) surrounded by infrared photobeams (16×16×16) to measure horizontal and vertical activity. The analysis is configured to divide the open field into a center and periphery zone. Distance traveled is measured from horizontal beam breaks as a mouse moves, and rearing activity is measured from vertical beam breaks.

Mice are acclimated to the activity experimental room for at least 1 h to prior to testing. Eight animals are tested in each run. Mice are injected with water or acamprosate prodrug, placed in holding cages for 30 min, and then in the OF chamber for 30 min, removed from the OF chamber and injected with either water or PCP and returned to the OF chambers for a 60-minute session. A different group of mice are injected with either 10% DMSO or clozapine and placed in the OF chamber for 30 min, removed from the OF chamber and injected with PCP (5 mg/kg), and returned to the OF chambers for a 60-minute session.

Data is analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fall above or below 2 standard deviations from the mean are removed from the final analysis. An effect is considered significant if $p<0.05$.

Auditory Startle and Prepulse Inhibition of Startle (PPI)

Young, adult male C57Bl/6J mice are used in this study. Mice are received at 6-weeks of age. Upon receipt, mice are assigned unique identification numbers (tail marked) and are group housed in standard mouse cages. For testing, animals are randomly assigned across treatment groups and balanced by PPI chamber.

Acoustic startle measures an unconditioned reflex response to external auditory stimulation. PPI consisting of an inhibited startle response (reduction in amplitude) to an auditory stimulation following the presentation of a weak auditory stimulus or prepulse, has been used as a tool for the assessment of deficiencies in sensory-motor gating, such as those seen in schizophrenia. Mice are placed in the PPI chamber (Med Associates) for a 5 min session of white noise (70 dB) habituation. A test session begins immediately after the 5 min acclimation period. The session starts with a habituation block of 6 presentations of the startle stimulus alone, followed by 10 PPI blocks of 6 different types of trials. Trial types are: null (no stimuli), startle (120 dB), startle plus prepulse (4, 8 and 12 dB over background noise i.e., 74, 78 or 82 dB) and prepulse alone (82 dB). Trial types are presented at random within each block. Each trial begins with a 50 ms null period during which baseline movements are recorded. There is a subsequent 20 ms period during which prepulse stimuli are presented and responses to the prepulse measured. Following a 100 ms pause, the startle stimuli are presented for 40 ms and responses are recorded for 100 ms from startle onset. Responses are sampled every ms. The inter-trial interval is variable with an average of 15 s (range from 10 to 20 s). In startle alone trials the basic auditory startle is measured and in prepulse plus startle trials the amount of inhibition of the normal startle is determined and expressed as a percentage of the basic startle response (from startle alone trials), excluding the startle response of the first habituation block.

For the normal mouse-PPI portion of the study, C57BL/6J mice are treated with vehicle, haloperidol or acamprosate prodrug and placed back in their holding cages. Thirty min following administration of vehicle or haloperidol and 60 min following injection of vehicle or acamprosate prodrug, normal mouse-PPI testing commences.

For the PCP-PPI portion of the study, C57BL/6J mice are treated with vehicle, clozapine, or acamprosate prodrug and returned to their holding cages. Thirty min later, all treatment groups are injected with vehicle or PCP. Thirty min following vehicle or PCP injection, PPI testing commences.

Description 41

Animal Model for Assessing Therapeutic Efficacy of Acamprosate Prodrugs for Treating Anxiety The elevated plux-maze test can be used to assess the effects of test compounds on anxiety. A plus-maze is consists of two open arms (50×10 cm) and two closed arms (50×10× 40 cm). The arms extend from a central platform (10×10 cm) and are raised 50 cm. Each mouse is placed at the center of the maze facing a closed arm and is allowed to explore the maze for 5 min. The time spent in the open arms and the time spent in the closed arms is monitored, and the percent of time spent in the open arms determined. Increased time spent in the open arms indicates an anxiolytic effect for the test condition. A test that measures spontaneous locomotor activity such as measurement in an activity cage can be used to determine whether the test compound also affects locomotor activity. It is desirable that a compound exhibiting an anxiolytic effect not decrease locomotor activity.

Description 42

Animal Models of Depression

Forced Swim Test in Rats

Male Wistar rats weighting 230-270 g are acclimated to the colony room for a minimum of 1 week, handled daily for at least 4 days and habituated to saline injections for 2 days before the experiments.

Two glass cylinders (20 cm dia×40 cm height) are separated by black opaque partitions and filled with water at about 24° C. to a depth of 30 cm. At this depth a rat cannot stand on the cylinder bottom. The water level is 10 cm from the top. Water is changed before each animal is placed into the water tank. An experimental session consists of two trials. During the conditioning trial, rats are gently placed into the cylinders for 15 min. After the trial, rats are dried and placed into a warm cage with the paper towels for 10-15 min before being returned to their home cages. Twenty-four hours later, for the test trial, animals are placed again into the cylinders for a 5-min test session. Tests are video taped for subsequent quantitative behavioral analysis. The frequency and/or total duration are calculated for each of the following categories: passive/immobile behavior (floating is scored when an animal remains in the water with all four limbs motionless, except for occasional alternate movements of paws and tail necessary to prevent sinking and to keep head/nose above the water); active/mobile behaviors (swimming characterized by rigorous movements with all four legs; paddling characterized by floating with rhythmical simultaneous kicks and occasional pushes off the wall to give speed and direction to the drift), including escape-oriented behaviors (climbing characterized by intense movements with all four limbs, with the two forepaws breaking the surface of the water and being directed against the walls of the cylinder; diving characterized by movements towards the bottom of the cylinder with the head of the rat below its hind limbs), and self-directed behaviors (headshakes, vigorous headshakes to get water off the snout and eyes; wiping, rubbing water away from the snout). In addition, at the end of each test trial, fecal boli are counted. A test compound, control, or positive control (e.g., imipramine) is administered prior to the test.

Tail Suspension Test in Mice

Mice are housed in standard laboratory cages and acclimated. Mice are moved from the housing room to the testing area in their home cages and allowed to adapt to the new environment for at least 1 h before testing. Immobility is induced by tail suspension. Mice are hung individually on a paper adhesive tape, 65 cm above a tabletop. Tape is placed approximately 1 cm from the tip of the tail. Animals are allowed to hang for 6 min and the duration of immobility is recorded. Mice are considered immobile only when hanging passively and completely motionless. Mice from these experiments are used one week later in locomotor activity studies. A test compound, control, or positive control (e.g., imipramine) is administered prior to the test.

Locomotor Activity

The spontaneous locomotor activity of mice is measured in photoresistor actometers (circular cages, 25 cm in dia, 15 cm high, two light sources, two photoresistors), in which the animals are placed individually 1 h after administration of a test compound. The number of crossings of light beams is measured during the first 30 min of the experimental session. The first measurement is performed 6 min after placing an animal into the actometer.

Description 43

Animal Model for Assessing Therapeutic Efficacy of Acamprosate Prodrugs for Treating Tardive Dyskinesia Vacuous chewing movements (VCM) are a rodent model of TD. In this model, animals are treated chronically with antipsychotics and their vacuous chewing motions are assessed by observation. The model has been shown to be sensitive to differential effects of typical and atypical antipsychotics and potential anti-dyskinetic agents.

Rats are housed in a controlled environment and allowed to acclimatize prior to testing. In order to limit neuroleptic-induced weight gain, food consumption is restricted to 15 g per animal per day. Rats are weighed biweekly throughout the study.

For two weeks prior to administration of test compound, animals are handled daily and habituated to the animal colony and the procedures related to drug administration and video recording. Subsequently (week 0), rats undergo a behavior video recording session following which they are randomized to a haloperidol treatment and a control group. The rats in the treatment group receive an intramuscular injection in the thigh muscles with haloperidol decanoate. The control rats are similarly injected with an equal volume of phosphate buffered saline (PBS). The haloperidol decanoate and saline injections are repeated every four weeks, for 20 weeks. Additional behavior video recording sessions are performed at weeks 12, 20 and 24 (i.e., 4 weeks after the last (fifth) injection). During the injection procedures, rats are handheld with minimal restraint.

On the basis of the results of the behavior assessment performed 24 weeks after the first haloperidol injection (i.e., baseline day), the haloperidol-treated rats are assigned to 10 subject-each treatment groups having an equal mean frequency of observed VCM episodes. One week later (i.e., test day), the groups are randomized to receive either 0.5 mL PBS (vehicle) or acamprosate prodrug in 0.5 mL PBS. Rats undergo a 30-150 min video recorded behavior assessment session following administration. Two weeks after the test day (i.e., post-test day), the video recorded behavior assessment session is repeated to investigate longer-term effects of the experimental treatments.

The videotapes are scored. A VCM episode is defined as a bout of vertical deflections of the lower jaw, which may be accompanied by contractions of the jaw musculature.

Description 44

Animal Model for Assessing Therapeutic Efficacy of Acamprosate Prodrugs for Treating Spasticity The mutant spastic mouse is a homozygous mouse that carries an autosomal recessive trait of genetic spasticity characterized by a deficit of glycine receptors throughout the central nervous system. The mouse is normal at birth and subsequently develops a coarse tremor, abnormal gait, skeletal muscle rigidity, and abnormal righting reflexes at two to three weeks of age. Assessment of spasticity in the mutant spastic mouse can be performed using electrophysiological measurements or by measuring the righting reflex (any righting reflex over one second is considered abnormal), tremor (holding mice by their tails and subjectively rating tremor), and flexibility.

Models of acute spasticity including the acute decerebrate rat, the acute or chronic spinally transected rat, and the chronically spinal cord-lesioned rat. The acute models, although valuable in elucidating the mechanisms involved in the development of spasticity, have come under criticism due to the fact that they are acute. The animals usually die or have total recovery from spasticity. The spasticity develops immediately upon intervention, unlike the spasticity that evolves in the human condition of spasticity, which most often initially manifests itself as a flaccid paralysis. Only after weeks and months does spasticity develop in humans. Some of the more chronic-lesioned or spinally transected models of spasticity do postoperatively show flaccid paralysis. At approximately four weeks post-lesion/transection, the flaccidity changes to spasticity of variable severity. Although all of these models have their own particular disadvantages and lack of true representation of the human spastic condition, they are shown useful in developing treatments for spasticity in humans. Many of these models have also made use of different species, such as cats, dogs, and primates. Baclofen, diazepam, and tizanidine, effective antispastic agents in humans, are effective on different parameters of electrophysiologic assessment of muscle tone in these models.

The Irwin Test is used to detect physiological, behavioral, and toxic effects of a test substance, and indicates a range of dosages that can be used for later experiments. Typically, rats (three per group) are administered the test substance and are then observed in comparison with a control group given vehicle. Behavioral modifications, symptoms of neurotoxicity, pupil diameter, and rectal temperature are recorded according to a standardized observation grid derived from that of Irwin. The grid contains the following items: mortality, sedation, excitation, aggressiveness, Straub tail; writhes, convulsions, tremor, exopthalmos, salivation, lacrimation, piloerection, defecation, fear, traction, reactivity to touch, loss of righting reflexes, sleep, motor incoordination, muscle tone, stereotypes, head-weaving, catalepsy, grasping, ptosis, respiration, corneal reflex, analgesia, abnormal gait, forepaw treading, loss of balance, head twitches, rectal temperature, and pupil diameter. Observations are performed at 15, 30, 60, 120, and 180 minutes following administration of a test compound, and also 24 hours later.

In the Rotarod Test rats or mice are placed on a rod rotating at a speed of eight turns per minute. The number of animals that drop from the rod before three minutes is counted and the drop-off times are recorded (maximum: 180 sec). Diazepam, a benzodiazepine, can be administered at 8 mg/kg, i.p., as a reference substance.

Description 45

Animal Model for Assessing Therapeutic Efficacy of Acamprosate Prodrugs for Treating Multiple Sclerosis Experiments are conducted on female C57BL/6 mice aged 4-6 weeks weighing 17-20 g. Experimental autoimmune encephalomyelitis (EAE) is actively induced using ≧95% pure synthetic myelin oligodendrocyte glycoprotein peptide 35-55 (MOG35-55, MEVGWYRSPFSRVVHLYRNGK). Each mouse is anesthetized and receives 200 μg of MOG peptide and 15 μg of Saponin extract from Quilija bark emulsified in 100 μL of phosphate-buffered saline. A 25 μL volume is injected subcutaneously over four flank areas. Mice are also intraperitoneally injected with 200 ng of pertussis toxin in 200 μL of PBS. A second, identical injection of pertussis toxin is given after 48 h.

An acamprosate prodrug is administered at varying doses. Control animals receive 25 μL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hindlimbs); 2, unitlateral partial hindlimb paralysis; 2.5, bilateral hindlimb paralysis; 3, complete bilateral hindlimb paralysis; 3.5, complete hindlimb paralysis and unilateral forelimb paralysis; 4, total paralysis of hindlimbs and forelimbs.

Inflammation and demyelination are assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabelled with anti-CD3+ monoclonal antibody. After washing, sections are incubated with goat anti-rat HRP secondary antibody. Sections are then washed and counterstained with methyl green. Spenocytes isolated from mice at 30 and 60 days post-immunization are treated with lysis buffer to remove red blood cells. Cells are then resuspended in PBS and counted. Cells at a density of about 3×106 cells/mL are incubated overnight with 20 μg/mL of $MOG_{35\text{-}55}$ peptide. Supernatants from stimulated cells are assayed for IFN-γ protein levels using an appropriate mouse IFN-γ immunoassay system.

Description 46

Animal Models of Pain

Inflammatory Pain—Formalin Test

A formalin assessment test is used. Fifty μL of a 5% formalin solution is injected subcutaneously into the dorsal aspect of the right hind paw and the rats are then individually placed into clear observation cages. Rats are observed for a continuous period of 60 min or for periods of time corresponding to phase I (from 0 to 10 min following formalin injection) and phase II (from 30 to 50 min following formalin injection) of the formalin test (Abbott et al., *Pain* 1995, 60, 91-102). The number of flinching behaviors of the injected paw is recorded using a sampling technique in which each animal is observed for one 60-sec period during each 5-min interval. Test compound is administered 30 min or other appropriate interval prior to formalin injection.

Inflammatory Pain—Carrageenan-Induced Acute Thermal Hyperalgesia and Edema

Paw edema and acute thermal hyperalgesia are induced by injecting 100 μL of a 1% solution of λ-carrageenan in physiological saline into the plantar surface of the right hind paw. Thermal hyperalgesia is determined 2 h following carrageenan injection, using a thermal paw stimulator. Rats are placed into plastic cubicles mounted on a glass surface maintained at 30° C. and a thermal stimulus in the form of radiant heat emitted form a focused projection bulb is then applied to the plantar surface of each hind paw. The stimulus current is maintained at 4.50±0.05 amp, and the maximum time of exposure is set at 20.48 sec to limit possible tissue damage. The elapsed time until a brisk withdrawal of the hind paw from the thermal stimulus is recorded automatically using photodiode motion sensors. The right and left hind paw of each rat is tested in three sequential trials at about 5-min intervals. Carrageenan-induced thermal hyperalgesia of paw withdrawal latency ($PWL_{thermal}$) is calculated as the mean of the two shortest latencies. Test compound is administered 30 min before assessment of thermal hyperalgesia.

The volume of paw edema is measured using water displacement with a plethysmometer 2 h following carrageenan injection by submerging the paw up to the ankle hairline (approx. 1.5 cm). The displacement of the volume is measured by a transducer and recorded. Test compound is administered at an appropriate time following carrageenan injection, such as for example, 30 min or 90 min.

Visceral Pain

Thirty min following administration of test compound, mice receive an injection of 0.6% acetic acid in sterile water (10 mL/kg, i.p.). Mice are then placed in table-top Plexiglass observation cylinders (60 cm high×40 cm diameter) and the number of constrictions/writhes (a wave of mild constriction and elongation passing caudally along the abdominal wall, accompanied by a slight twisting of the trunk and followed by bilateral extension of the hind limbs) is recorded during the 5-20 min following acetic acid injection for a continuous observation period of 15 min.

Neuropathic Pain—Spinal Nerve Ligation

Rats receive unilateral ligation of the lumbar 5 (L5) and lumbar 6 (L6) spinal nerves. The left L5 and L6 spinal nerves of the rat are isolated adjacent to the vertebral column and tightly ligated with a 5-0 silk suture distal to the dorsal root ganglia, and care is taken to avoid injury of the lumbar 4 (L4) spinal nerve. Control rats undergo the same procedure but without nerve ligation. All animals are allowed to recover for at least 1 week and not more than 3 weeks prior to assessment of mechanical allodynia. Mechanical allodynia is measure using calibrated von Frey filaments. Rats are placed into inverted plastic containers (20×12.5×20 cm) on top of a suspended wire mesh grid and acclimated to the test chamber for 20 min. The von Frey filaments are presented perpendicularly to the plantar surface of the selected hind paw, and then held in this position for approximately 8 s with enough force to cause a slight bend in the filament. Positive responses include an abrupt withdrawal of the hind paw from the stimulus or flinching behavior immediately following removal of the stimulus. A 50% paw withdrawal threshold (PWT) is determined. Rats with a PWT $\leq 5.0$ g are considered allodynic and utilized to test the analgesic activity of a test compound. The test compound can be administered 30 min prior to the assessment of mechanical allodynia.

Neuropathic Pain—Chronic Constriction Injury of the Sciatic Nerve

A model of chronic constriction injury of the sciatic nerve-induced neuropathic pain is used. The right common sciatic nerve is isolated at mid-thigh level and loosely ligated by four chromic gut (4-0) ties separated by an interval of 1 mm. Control rats undergo the same procedure but without sciatic nerve constriction. All animals are allowed to recover for at least 2 weeks and for no more than 5 weeks prior to testing of mechanical allodynia. Allodynic PWT is assessed in the animals as described for animals with spinal nerve ligation. Only rats with a PWT $\leq 5.0$ g are considered allodynic and utilized to evaluate the analgesic activity of a test compound. Test compound is administered 30 min or other appropriate time prior to the assessment of mechanical allodynia.

Neuropathic Pain—Vincristine-Induced Mechanical Allodynia

A model of chemotherapy-induced neuropathic pain is produced by continuous intravenous vincristine infusion (Nozaki-Taguchi et al., *Pain* 2001, 93, 69-76). Anesthetized rats undergo a surgical procedure in which the jugular vein is catheterized and a vincristine-primed pump is implanted subcutaneously. Fourteen days of intravenous infusion of vincristine (30 µg/kg/day) results in systemic neuropathic pain of the animal. Control animals undergo the same surgical procedure, with physiological saline infusion. PWT of the left paw is assessed in the animals 14 days post-implantation as described for the spinal nerve ligation model. Test compound is administered 30 min prior to the test for mechanical allodynia in rats with PWT $\leq 5.00$ g before treatment.

Post-Operative Pain

A model of post-operative pain is performed in rats. The plantar aspect of the left hind paw is exposed through a hole in a sterile plastic drape, and a 1-cm longitudinal incision is made through the skin and fascia, starting 0.5 cm from the proximal edge of the heel and extending towards the toes. The plantaris muscle is elevated and incised longitudinally leaving the muscle origin and insertion points intact. After hemostasis by application of gently pressure, the skin is apposed with two mattress sutures using 5-0 nylon. Animals are then allowed to recover for 2 h following surgery, at which time mechanical allodynia and thermal hyperalgesia are assessed.

Effects of test compound on mechanical allodynia are assessed 30 min following administration, with PWT being examined in these animals for both the injured and non-injured paw as described for the spinal nerve ligation model with the von Frey filament systematically pointing towards the medial side of the incision. In a separate experiment, the effects of test compound on thermal hyperalgesia are assessed 30 min following administration of test compound, with $PWL_{thermal}$ being determined as described for the carrageen-induced thermal hyperalgesia model with the thermal stimulus applied to the center of the incision of the paw planter aspect.

Description 47

Animal Model for Assessing Therapeutic Efficacy of Acamprosate Prodrugs for Treating Binge Eating Thirty 2-month old male Sprague Dawley rats are individually housed in a temperature- and humidity-controlled vivarium under a 12:12 light:dark cycle. Three days after being introduced into the vivarium, rats are given overnight access to a bowl of vegetable shortening. The rats are then divided into three groups of ten matched for two-day average chow intake, overnight shortening intake, and body weight.

The groups and different test phases are designed to test the effects of acamprosate prodrug under different shortening access conditions. In phase 1, rats maintained on a feeding protocol that promotes infrequent, large binges (B group) are compared to rats maintained on feeding protocols that promote no binges (FM and C groups). In phase 2, rats maintained for an extended period of time on the infrequent, large binge protocol (B group) are compared to rats that have just started the same binge protocol (FM and C groups). In phase 3, rats maintained on the feeding protocol that promotes infrequent, large binges (B group) are compared to rats on a feeding protocol that promotes more frequent, smaller binges (FM and C groups).

The three groups are maintained as follows: Binge (B): The (B) rats have continuous access to chow and water. In addition, they are given 2-h access to a separate bowl of vegetable shortening every Monday, Wednesday, and Friday (MWF), during the 2 h prior to no light. During the 2-h shortening access period, the chow and water remain available. This protocol results in infrequent, large episodes of binge-type eating in male rats. This protocol models the intermittent excessive eating behavior that characterizes binge eating. The B rats are maintained on this protocol throughout all phases of the study. Fat-Matched (FM): The rats in group FM are given the same proportions of chow and shortening that the Binge (B) groups consume except that the shortening is mixed into the chow, which is provided continuously. The proportions of chow and shortening consumed by the Binge group each week are determined, and the FM group is provided with a fat-matched chow mixed to that proportion the following week. The FM group has free access to the FM chow and water. The FM group is included to control for possible neural or behavioral effects of dietary fat. The FM group is maintained on the FM chow throughout all phases of the study. During phase 1, the FM group only has access to the FM chow. During phase 2, the FM group has access to a separate bowl of vegetable shortening for 2-h on MWF each week, in addition to the continuously available FM chow. During phase 3, the FM group has 2-h access to the vegetable shortening every day, in addition to the continuously available FM chow. This daily protocol results in more frequent, smaller episodes of binge-type eating. Chow/change (C): The rats in group C have continuous access to the regular chow and water through all phases of the study. During the first phase, the C group only has access to the regular chow diet. During the second phase, the C group has access to a separate bowl of vegetable shortening for 2-h on MWF each week in addition to the continuously available regular chow. During the third phase, the C group has 2-h access to the vegetable shortening every day in addition to the continuously available regular chow.

The effects of acamprosate prodrugs effects are determined during each of the three phases of the study. In phase 1, the effects of acamprosate prodrug are determined on binge-type consumption of vegetable shortening and on consumption of the regular and FM chow diets. Rats are on their respective diets for about 6 weeks prior to the initiation of acamprosate prodrug testing. In phase 2, the effects of acamprosate prodrug are assessed in rats that are bingeing for a relatively long (B group: three months) or short (FM and C groups: 1 day) period of time (all groups have MWF 2-h access to shortening in addition to their assigned regular or FM chow). In phase 3, the effects of acamprosate prodrug are assessed under conditions of infrequent (B: 2-h MWF) and more frequent (FM and C groups: 2-h daily) shortening access. The FM and C rats are on the daily shortening access schedule for ten days before the first acamprosate prodrug administration in phase 3. Acamprosate prodrug is not tested in rats with continuous access to a bowl of shortening due to the low 2-h intakes that are generated on that protocol under non-food-deprived conditions. A dose and regimen of acamprosate prodrug is administered as appropriate for the objectives of the study.

Acamprosate prodrug is administered at an appropriate time prior to the shortening access period. Chow is removed during the 30-min pretreatment period. Shortening and/or chow are weighted and placed into the cage at the beginning of the test period, e.g., 2-h, and then re-weighted at the end of the test period. The data is analyzed using appropriate statistical methods.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A compound of Formula (I):

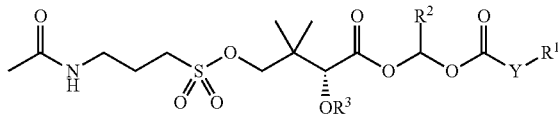

(I)

or a pharmaceutically acceptable salt thereof, wherein:

Y is chosen from —O— and a bond;

$R^1$ is chosen from $C_{1-6}$ alkyl, substituted $C_{1-6}$ alkyl, $C_{3-6}$ cycloalkyl, substituted $C_{3-6}$ cycloalkyl, phenyl, substituted phenyl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{3-6}$ heterocycloalkyl, substituted $C_{3-6}$ heterocycloalkyl, $C_{5-6}$ heteroaryl, substituted $C_{5-6}$ heteroaryl, $C_{4-12}$ heterocycloalkylalkyl, substituted $C_{4-12}$ heterocycloalkylalkyl, $C_{6-12}$ heteroarylalkyl, substituted $C_{6-12}$ heteroarylalkyl, and —$(CH^{R6})_n$—OPO(OH)$_2$ wherein n is chosen from 1, 2, and 3, and each $R^6$ is independently chosen from hydrogen and methyl;

$R^2$ is chosen from hydrogen, $C_{1-6}$ alkyl, substituted $C_{1-6}$ alkyl, $C_{3-6}$ cycloalkyl, substituted $C_{3-6}$ cycloalkyl, phenyl, and substituted phenyl; and $R^3$ is chosen from hydrogen, —PO(OH)$_2$, and —C(O)$R^4$ wherein $R^4$ is $C_{1-4}$ alkyl.

2. The compound of claim 1, wherein:

Y is —O—; and $R^1$ is chosen from $C_{1-4}$ alkyl, substituted $C_{1-4}$ alkyl, $C_{5-6}$ cycloalkyl, substituted $C_{5-6}$ cycloalkyl, phenyl, substituted phenyl, $C_{6-10}$ cycloalkylalkyl, substituted $C_{6-10}$ cycloalkylalkyl, $C_{7-10}$ arylalkyl, substituted $C_{7-10}$ arylalkyl, $C_{1-4}$ heteroalkyl, substituted $C_{1-4}$ heteroalkyl, $C_{5-6}$ heterocycloalkyl, substituted $C_{5-6}$ heterocycloalkyl, $C_{5-6}$ heteroaryl, substituted $C_{5-6}$ heteroaryl, $C_{6-10}$ heterocycloalkylalkyl, substituted $C_{6-10}$ heterocycloalkylalkyl, $C_{6-10}$ heteroarylalkyl, substituted $C_{6-10}$ heteroarylalkyl, and —$(CH^{R6})_n$—OPO(OH)$_2$, wherein n is chosen from 1, 2 and 3.

3. The compound of claim 1, wherein:

Y is a bond; and $R^1$ is chosen from $C_{1-4}$ alkyl, substituted $C_{1-4}$ alkyl, $C_{5-6}$ cycloalkyl, substituted $C_{5-6}$ cycloalkyl, phenyl, substituted phenyl, $C_{6-10}$ cycloalkylalkyl, substituted $C_{6-10}$ cycloalkylalkyl, $C_{7-10}$ arylalkyl, substituted $C_{7-10}$ arylalkyl, $C_{1-4}$ heteroalkyl, substituted $C_{1-4}$ heteroalkyl, $C_{5-6}$ heterocycloalkyl, substituted $C_{5-6}$ heterocycloalkyl, $C_{5-6}$ heteroaryl, substituted $C_{5-6}$ heteroaryl, $C_{6-10}$ heterocycloalkylalkyl, substituted $C_{6-10}$ heterocycloalkylalkyl, $C_{6-10}$ heteroarylalkyl, substituted $C_{6-10}$ heteroarylalkyl, and —$(CH^{R6})_n$—OPO(OH)$_2$, wherein n is chosen from 1, 2 and 3, and each $R^6$ is independently chosen from hydrogen and methyl.

4. The compound of claim 1, wherein $R^1$ is chosen from $C_{1-4}$ alkyl, $C_{5-6}$ cycloalkyl, phenyl, $C_{6-10}$ cycloalkylalkyl, $C_{7-10}$ arylalkyl, $C_{1-4}$ heteroalkyl, $C_{5-6}$ heteroaryl, $C_{6-10}$ heterocycloalkylalkyl, $C_{6-10}$ heteroarylalkyl, and —$(CH^{R6})_n$—OPO(OH)$_2$, wherein n is chosen from 1, 2 and 3, and each $R^6$ is independently chosen from hydrogen and methyl.

5. The compound of claim 1, wherein each substituent group is independently chosen from halogen, —OH, $C_{1-4}$ alkyl, $C_{1-4}$ alkoxy, and —N($R^5$)$_2$, wherein each $R^5$ is independently chosen from hydrogen and $C_{1-2}$ alkyl.

6. The compound of claim 1, wherein $R^1$ is chosen from $C_{1-4}$ alkyl, phenyl, substituted phenyl, benzyl, substituted benzyl, cyclohexyl, substituted cyclohexyl, and —$(CH^{R6})_n$—OPO(OH)$_2$, wherein n is chosen from 1, 2 and 3, and each $R^6$ is independently chosen from hydrogen and methyl.

7. The compound of claim 1, wherein $R^1$ is chosen from methyl, ethyl, n-propyl, isopropyl, n-butyl, isobutyl, sec-butyl, tert-butyl, phenyl, o-tolyl, benzyl, cyclohexyl, and —$(CH^{R6})_n$—OPO(OH)$_2$, wherein n is chosen from 1, 2 and 3, and each $R^6$ is independently chosen from hydrogen and methyl.

8. The compound of claim 1, wherein $R^1$ is chosen from $C_{1-6}$ alkyl, benzyl, phenyl, cyclohexyl, hydroxymethyl, 3-hydroxy-2,2-dimethylpropyl, and —CH$_2$—OPO(OH)$_2$.

9. The compound of claim 1, wherein $R^2$ is chosen from hydrogen, $C_{1-4}$ alkyl, phenyl, and cyclohexyl.

10. The compound of claim 1, wherein $R^2$ is chosen from hydrogen, methyl, ethyl, n-propyl, and isopropyl.

11. The compound of claim 1, wherein $R^2$ is chosen from $C_{1-6}$ alkyl, substituted $C_{1-6}$ alkyl, $C_{3-6}$ cycloalkyl, substituted $C_{3-6}$ cycloalkyl, phenyl, and substituted phenyl; and the stereochemistry of the carbon atom to which $R^2$ is bonded is of the (S)-configuration.

12. The compound of claim 1, wherein $R^2$ is chosen from $C_{1-6}$ alkyl, substituted $C_{1-6}$ alkyl, $C_{3-6}$ cycloalkyl, substituted $C_{3-6}$ cycloalkyl, phenyl, and substituted phenyl; and the stereochemistry of the carbon atom to which $R^2$ is bonded is of the (R)-configuration.

13. The compound of claim 1, wherein $R^3$ is chosen from hydrogen and —PO(OH)$_2$.

14. The compound of claim 1, wherein $R^3$ is hydrogen.

15. The compound of claim 1, wherein Y is a bond.

16. The compound of claim 1, wherein Y is —O—.

17. The compound of claim 1, wherein:
Y is —O—;
$R^1$ is chosen from methyl, ethyl, n-propyl, isopropyl, n-butyl, isobutyl, sec-butyl, tert-butyl, phenyl, o-tolyl, benzyl, cyclohexyl, and —(CH$_2$)$_n$—OPO(OH)$_2$;
$R^2$ is chosen from hydrogen, methyl, ethyl, n-propyl, isopropyl, cyclohexyl, and phenyl; and
$R^3$ is chosen from hydrogen and —PO(OH)$_2$.

18. The compound of claim 1, wherein:
Y is a bond;
$R^1$ is chosen from methyl, ethyl, n-propyl, isopropyl, n-butyl, isobutyl, sec-butyl, tert-butyl, phenyl, o-tolyl, benzyl, cyclohexyl, and —(CH$_2$)$_n$—OPO(OH)$_2$;
$R^2$ is chosen from hydrogen, methyl, ethyl, n-propyl, isopropyl, cyclohexyl, and phenyl; and
$R^3$ is chosen from hydrogen and —PO(OH)$_2$.

19. The compound of claim 1, wherein the compound is chosen from:
(ethylethoxycarbonyloxy)methyl(2R)-4-{[3-(acetylamino)propyl]sulfonyloxy}-3,3-dimethyl-2-hydroxy-butanoate;
(2-phenylacetyloxy)methyl(2R)-4-{[3-(acetylamino)propyl]sulfonyloxy}-3,3-dimethyl-2-hydroxy-butanoate;
(2-methylpropanoyloxy)ethyl(2R)-4-{[3-(acetylamino)propyl]sulfonyloxy}-3,3-dimethyl-2-hydroxy-butanoate;
-(2-methylpropanoyloxy)ethyl(2R)-4-{[3-(acetylamino)propyl]sulfonyloxy}-3,3-dimethyl-2-hydroxy-butanoate;
(1R)-(2-methylpropanoyloxy)ethyl(2R)-4-{[3-(acetylamino)propyl]sulfonyloxy}-3,3-dimethyl-2-hydroxy-butanoate;
ethoxycarbonyloxyethyl(2R)-4-{[3-(acetylamino)propyl]sulfonyloxy}-3,3-dimethyl-2-hydroxy-butanoate;
(1R)-1-ethoxycarbonyloxyethyl(2R)-4-{[3-(acetylamino)propyl]sulfonyloxy}-3,3-dimethyl-2-hydroxy-butanoate;
ethoxycarbonyloxyethyl(2R)-4-{[3-(acetylamino)propyl]sulfonyloxy}-3,3-dimethyl-2-hydroxy-butanoate;
ethoxycarbonyloxyethyl(2R)-4-{[3-(acetylamino)propyl]sulfonyloxy}-3,3-dimethyl-2-(2-methylpropanoyloxy)-butanoate;
ethoxycarbonyloxyethyl 4-{[3-(acetylamino)propyl]sulfonyloxy}-3,3-dimethyl-2-hydroxy-butanoate;
benzoyloxyethyl(2R)-4-{[3-(acetylamino)propyl]sulfonyloxy}-3,3-dimethyl-2-hydroxy-butanoate;
benzoyloxyethyl 4-{[3-(acetylamino)propyl]sulfonyloxy}-3,3-dimethyl-2-hydroxy-butanoate;
(methylethoxycarbonyloxy)ethyl (2R)-4-{[3-(acetylamino)propyl]sulfonyloxy}-2-hydroxy-3,3-dimethylbutanoate;
(1R)-(methylethoxycarbonyloxy)ethyl(2R)-4-{[3-(acetylamino)propyl]sulfonyloxy}-2-hydroxy-3,3-dimethylbutanoate;
(1S)-(methylethoxycarbonyloxy)ethyl(2R)-4-{[3-(acetylamino)propyl]sulfonyloxy}-2-hydroxy-3,3-dimethylbutanoate;
cyclohexyloxycarbonyloxyethyl(2R)-4-{[3-(acetylamino)propyl]sulfonyloxy}-2-hydroxy-3,3-dimethylbutanoate;
cyclohexylcarbonyloxyethyl(2R)-4-{[3-(acetylamino)propyl]sulfonyloxy}-2-hydroxy-3,3-dimethylbutanoate;
(2-hydroxyacetyloxy)ethyl(2R)-4-{[3-(acetylamino)propyl]sulfonyloxy}-2-hydroxy-3,3-dimethylbutanoate;
(3-hydroxy-2,2-dimethylpropanoyloxy)ethyl(2R)-4-{[3-(acetylamino)propyl]sulfonyloxy}-2-hydroxy-3,3-dimethylbutanoate;
2-methyl-1-(methylethoxycarbonyloxy)propyl(2R)-4-{[3-(acetylamino)propyl]sulfonyloxy}-3,3-dimethyl-2-hydroxy-butanoate;
(2-methylpropanoyloxy)ethyl(2R)-4-{[3-(acetylamino)propyl]sulfonyloxy}-3,3-dimethyl-2-(oxyphosphinyloxyphosphinyl)butanoate;
cyclohexylcarbonyloxyethyl(2R)-4-{[3-(acetylamino)propyl]sulfonyloxy}-3,3-dimethyl-2-(oxyphosphinyloxyphosphinyl)butanoate;
ethoxycarbonyloxyethyl(2R)-4-{[3-(acetylamino)propyl]sulfonyloxy}-3,3-dimethyl-2-(oxyphosphinyloxyphosphinyl)butanoate;
(methylethoxycarbonyloxy)ethyl(2R)-4-{[3-(acetylamino)propyl]sulfonyloxy}-3,3-dimethyl-2-(oxyphosphinylphosphinyl)butanoate;
[2-(oxyphosphinyloxyphosphinyl)acetyloxy]ethyl(2R)-4-{[3-(acetylamino)propyl]sulfonyloxy}-2-hydroxy-3,3-dimethylbutanoate; and
a pharmaceutically acceptable salt of any of the foregoing.

20. A pharmaceutical composition comprising a compound of claim 1 and at least one pharmaceutically acceptable vehicle.

21. The pharmaceutical composition of claim 20, comprising an amount of the compound effective for treating a disease in a patient wherein the disease is chosen from alcohol dependence, binge eating, tinnitus, levodopa-induced dyskinesias in Parkinson's disease, Alzheimer's disease, Huntington's disease, amyotrophic lateral sclerosis, multiple sclerosis, schizophrenia, bipolar disorder, anxiety, tardive dyskinesia, spasticity, cortical spreading depression, sleep apnea, neuropathic pain, epilepsy, cognitive dysfunction, diabetes, and gastroesophageal reflux disease.

22. The pharmaceutical composition of claim 20, wherein the pharmaceutical composition is an oral dosage formulation.

23. The pharmaceutical composition of claim 22, wherein the pharmaceutical composition is a sustained release oral dosage formulation.

24. A method of treating a disease in a patient comprising administering to a patient in need of such treatment the compound of claim 1, wherein the disease is chosen from alcohol dependence, binge eating, tinnitus, levodopa-induced dyskinesias in Parkinson's disease, Alzheimer's disease, Huntington's disease, amyotrophic lateral sclerosis, multiple sclerosis, schizophrenia, bipolar disorder, anxiety, tardive dyskinesia, spasticity, cortical spreading depression, sleep apnea, neuropathic pain, epilepsy, cognitive dysfunction, diabetes, and gastroesophageal reflux disease.

25. A method of treating a disease in a patient comprising administering to a patient in need of such treatment the pharmaceutical composition of claim 20, wherein the disease is chosen from alcohol dependence, binge eating, tinnitus, levodopa-induced dyskinesias in Parkinson's disease, Alzheimer's disease, Huntington's disease, amyotrophic lateral sclerosis, multiple sclerosis, schizophrenia, bipolar disorder, anxiety, tardive dyskinesia, spasticity, cortical spreading depression, sleep apnea, neuropathic pain, epilepsy, cognitive dysfunction, diabetes, and gastroesophageal reflux disease.

* * * * *